(12) United States Patent
Eckelman et al.

(10) Patent No.: US 10,501,551 B2
(45) Date of Patent: Dec. 10, 2019

(54) MULTIVALENT AND MULTISPECIFIC 41BB-BINDING FUSION PROTEINS

(71) Applicant: Inhibrx, Inc., La Jolla, CA (US)

(72) Inventors: Brendan P. Eckelman, La Jolla, CA (US); John C. Timmer, La Jolla, CA (US); Chelsie Hata, La Jolla, CA (US); Kyle S. Jones, La Jolla, CA (US); Abraham Hussain, La Jolla, CA (US); Amir S. Razai, La Jolla, CA (US); Bryan Becklund, La Jolla, CA (US); Rajay Pandit, La Jolla, CA (US); Mike Kaplan, La Jolla, CA (US); Lucas Rascon, La Jolla, CA (US); Quinn Deveraux, La Jolla, CA (US)

(73) Assignee: Inhibrx, Inc., La Jolla, CA (US)

( * ) Notice: Subject to any disclaimer, the term of this patent is extended or adjusted under 35 U.S.C. 154(b) by 118 days.

(21) Appl. No.: 15/404,016

(22) Filed: Jan. 11, 2017

(65) Prior Publication Data
US 2017/0198050 A1    Jul. 13, 2017

Related U.S. Application Data

(60) Provisional application No. 62/277,028, filed on Jan. 11, 2016.

(51) Int. Cl.
| | | |
|---|---|---|
| *C12P 21/08* | (2006.01) | |
| *A61K 39/00* | (2006.01) | |
| *C07K 16/28* | (2006.01) | |

(52) U.S. Cl.
CPC ...... *C07K 16/2878* (2013.01); *C07K 16/2827* (2013.01); *C07K 2317/24* (2013.01); *C07K 2317/31* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| | | |
|---|---|---|
| 2004/0038307 A1 | 2/2004 | Lee et al. |
| 2005/0032174 A1 | 2/2005 | Peters et al. |
| 2008/0108070 A1 | 5/2008 | Xu et al. |
| 2011/0262348 A1 | 10/2011 | Movahedi et al. |
| 2012/0039906 A1 | 2/2012 | Olive |
| 2012/0237498 A1 | 9/2012 | Ahrens et al. |
| 2012/0269859 A1 | 10/2012 | Minato et al. |
| 2014/0079701 A1 | 3/2014 | Miller et al. |

FOREIGN PATENT DOCUMENTS

WO    2014028776 A1    2/2014

OTHER PUBLICATIONS

Holt et al., 2003, TRENDS biotech. vol. 21: 484-490.*
Zhang et al., 2017, Cell Disco. vol. 3: 1-12.*
He et al., 2017, Oncotarget, vol. 8: 67129-67139.*
Scott et al., 2012, Nat Rev. vol. 12: 278-287.*
Iezzi et al., 2018, Front. Immunol. vol. 9: 1-11.*
Cardoso, FM et al., "Single-Domain Antibodies Targeting Neuraminidase Protect against an H5N1 Influenza Virus Challenge," Journal of Virology, vol. 88, No. 15; pp. 8278-8296; May 14, 2014.
Chang, C et al., "The Development of Bispecific Hexavalent Antibodies as a Novel Class of Dock-and-LOCKTM (DNLTM) Complexes," Antibodies, vol. 2, No. 2; pp. 353-370; May 23, 2013.
Chen, S et al., "Combination of 4-1BB Agonist and PD-1 Antagonist Promotes Antitumor Effector/Memory CD8 T Cells in a Poorly Immunogenic Tumor Model," Cancer Immunology research, vol. 3, No. 2; pp. 149-160; Nov. 11, 2014.
Huang, SC et al., "Human B Cells Accumulate Immunoglobulin V Gene Somatic Mutations in a Cell Contact—Dependent Manner in Cultures Supported by Activated T cells But Not in Cultures Supported by CD40 Ligand," Clinical and Experimental Immunology, vol. 116, No. 3; pp. 441-448; Jun. 1999.
International Search Report and Written Opinion for International Application PCT/US17/13040 dated Jul. 20, 2017; 31 pages.
Lu, J et al., "Structure of FcyRI in Complex with Fc Reveals the Importance of Glycan Recognition for High-Affinity IgG Binding," Proceedings of the National Academy of Sciences of USA. vol. 112, No. 3; pp. 833-838; Genbank supplement pp. 1-2; DOI: 10.1073/pnas.1418812112, Jan. 5, 2015.
Raaphorst, FM et al., "Restricted Utilization of Germ-line VH3 genes and Short Diverse Third Complementarity—Determining Regions (CDR3) in Human Fetal B Lymphocyte Immunoglobulin Heavy Chain Rearrangements," European Journal of Immunology, vol. 22, No. 1; pp. 247-251; Jan. 1992.
Rossi et al., "The Dock-and-Lock Method Combines Recombinant Engineering with Site-Specific Covalent Conjugation to Generate Multifunctional Structures," American Chemical Society; pp. 309-323; 2011.
Tran, M et al., "Production of Anti-cancer Immunotoxins in Algae: Ribosome Inactivating Proteins as Fusion Partners," Biotechnology and Bioengineering, vol. 110, No. 11; pp. 2826-2835; Jun. 25, 2013.

(Continued)

*Primary Examiner* — Amy E Juedes
(74) *Attorney, Agent, or Firm* — McNeill Baur PLLC

(57) ABSTRACT

This invention relates generally to molecules that specifically engage 41BB, a member of the TNF receptor superfamily (TNFRSF). More specifically, this invention relates to multivalent and multispecific molecules that bind at least 41BB.

64 Claims, 28 Drawing Sheets
Specification includes a Sequence Listing.

(56) References Cited

OTHER PUBLICATIONS

Williams, JV et al., "The Human Neonatal B Cell Response to Respiratory Syncytial Virus uses a Biased Antibody Variable Gene Repertoire that Lacks Somatic Mutations," Molecular Immunology, vol. 47, No. 2-3; pp. 407-414, Oct. 4, 2009.

Extended European Search Report dated Aug. 19, 2019, for European Application No. 17738869.1; 7 pages.

Fisicaro et al., "Combined Blockade of Programmed Death-1 and Activation of CD137 Increase Responses of Human Liver T Cells Against HBV, But Not HCV," Gastroenterology, 2012, 143(6): 1576-1585.

Inman et al, "Utomilumab/Pembrolizumab Combo Shows responses in Different Solid Tumors", downloaded from www.targetedonc.com/conference/asco-immune-2016/utomiluma/pembrolizumab; Jun. 14, 2016; 2 pages.

Pardon et al., "A general protocol for the generation of Nanobodies for structural biology," Nature Protocols, 2014, 9(3) 674-693.

Rahbarizadeh et al., "Nanobody; an Old Concept and New Vehicle for Immunotargeting," Immunological Investigations, 2011, 40(3): 299-338.

Sanmamed et al., "Nivolumab and Urelumab Enhance Antitumor Activity of Human T Lymphocytes Engrafted in Rag2-/-IL2Rynull Immunodeficient Mice", Cancer Research, 2015, 75(17): 3466-3478.

\* cited by examiner

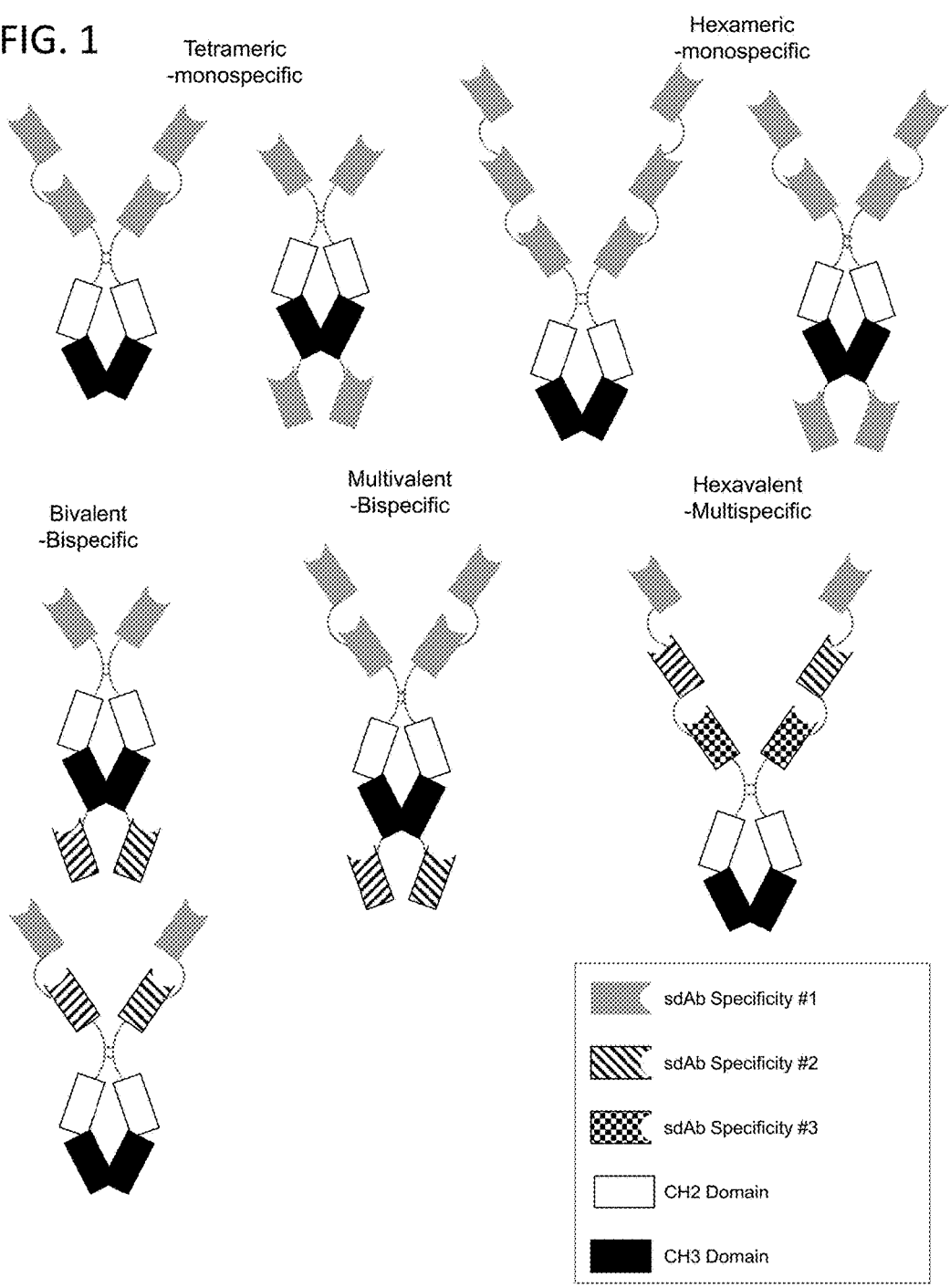

FIG. 8A
FIG. 8B
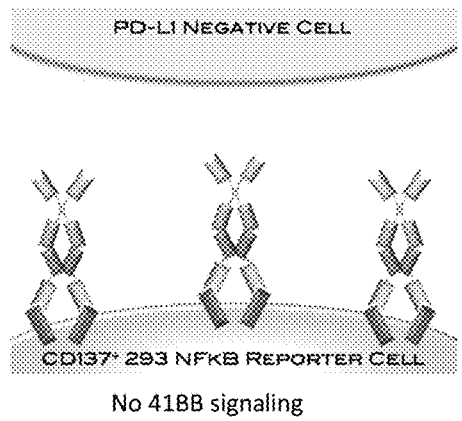
No 41BB signaling
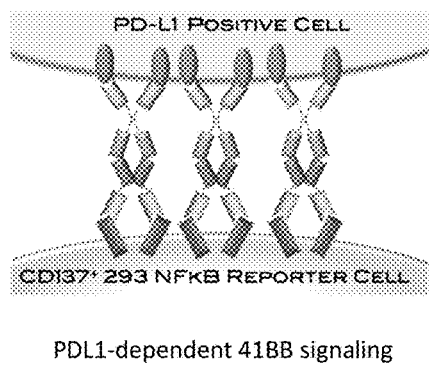
PDL1-dependent 41BB signaling
FIG. 8C
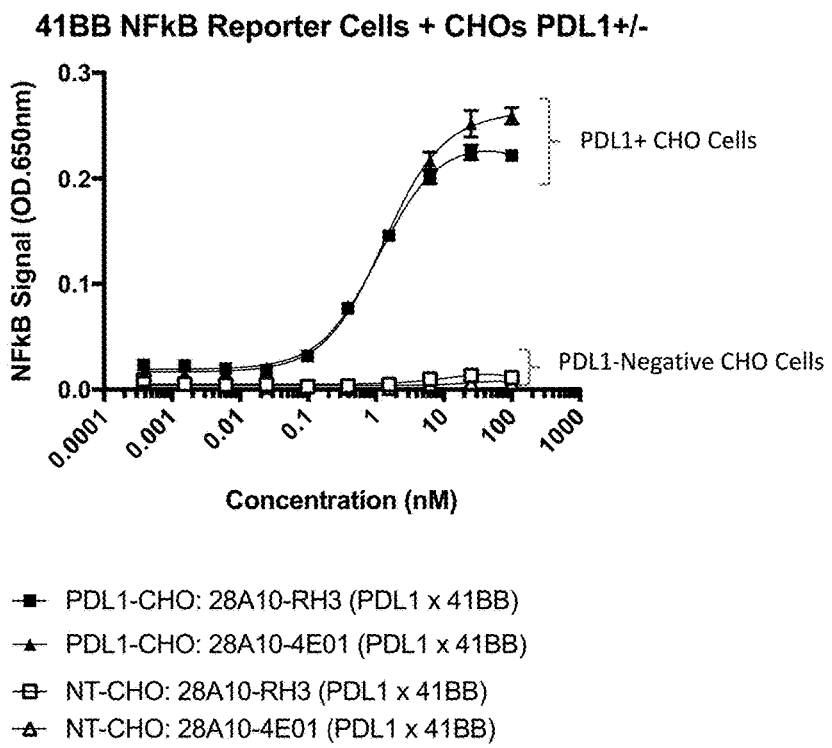
- ■ PDL1-CHO: 28A10-RH3 (PDL1 x 41BB)
- ▲ PDL1-CHO: 28A10-4E01 (PDL1 x 41BB)
- □ NT-CHO: 28A10-RH3 (PDL1 x 41BB)
- △ NT-CHO: 28A10-4E01 (PDL1 x 41BB)

MULTIVALENT AND MULTISPECIFIC 41BB-BINDING FUSION PROTEINS

RELATED APPLICATIONS

This application claims the benefit of U.S. Provisional Application No. 62/277,028, filed Jan. 11, 2016; the contents of each of which are incorporated herein by reference in their entirety.
The contents of the text file named "INHI027001USSeqList", which was created on Mar. 23, 2017 and is 475 KB in size, are hereby incorporated by reference in their entirety.

FIELD OF THE INVENTION

This invention relates generally to molecules that specifically engage 41BB, a member of the TNF receptor superfamily (TNFRSF). More specifically, this invention relates to multivalent and/or multispecific molecules that bind at least 41BB.

BACKGROUND OF THE INVENTION

The tumor necrosis factor receptor superfamily consists of several structurally related cell surface receptors. Activation by multimeric ligands is a common feature of many of these receptors. Many members of the TNFRSF have therapeutic utility in numerous pathologies, if activated properly. Agonism of this receptor family often requires higher order clustering, and conventional bivalent antibodies are not ideal for this purpose. Therefore, there exists a therapeutic need for more potent agonist molecules of the TNFRSF.

SUMMARY OF THE INVENTION

The disclosure provides multivalent and multispecific TNF receptor superfamily (TNFRSF) binding fusion polypeptides that bind at least 41BB (also known as tumor necrosis factor receptor superfamily, member 4 (TNFRSF9) and/or CD137)). The use of the term "41BB" is intended to cover any variation thereof, such as, by way of non-limiting example, 41-BB and/or 4-1BB, and all variations are used herein interchangeably. These molecules that bind at least 41BB are referred to herein as "41BB-targeting molecules" or "41BB-targeting fusions" or "41BB-targeting proteins" or "41BB-targeting fusion polypeptides" or "41BB-targeting fusion proteins." In some embodiments, the 41BB-targeting molecule is a multivalent molecule, for example, a multivalent 41BB-targeting fusion protein. In some embodiments, the 41BB-targeting molecule is a multispecific molecule, for example, a multispecific 41BB-targeting fusion protein. In some embodiments, the 41BB-targeting molecule is a multivalent and multispecific molecule, for example, a multivalent and multispecific 41BB-targeting fusion protein. As used herein, the term "fusion protein" or "fusion polypeptide" or "41BB-targeting fusion protein" or "41BB-targeting fusion polypeptide," unless otherwise specifically denoted, refers to any fusion protein embodiment of the disclosure, including, but not limited to, multivalent fusion proteins, multispecific fusion proteins, or multivalent and multispecific fusion proteins.

The disclosure also provides multivalent and multispecific fusion polypeptides that bind at least programmed death ligand 1 (PDL1), also known as PD-L1, CD274, B7 homolog 1 and/or B7-H1. The use of the term "PDL1" is intended to cover any variation thereof, such as, by way of non-limiting example, PD-L1 and/or PDL-1, all variations are used herein interchangeably. These molecules that bind at least PDL1 are referred to herein as "PDL1-targeting molecules" or "PDL1-targeting fusions" or "PDL1-targeting proteins" or "PDL1-targeting fusion polypeptides" or "PDL1-targeting fusion proteins." In some embodiments, the PDL1-targeting molecule is a multivalent molecule, for example, a multivalent PDL1-targeting fusion protein. In some embodiments, the PDL1-targeting molecule is a multispecific molecule, for example, a multispecific PDL1-targeting fusion protein. In some embodiments, the PDL1-targeting molecule is a multivalent and multispecific molecule, for example, a multivalent and multispecific PDL1-targeting fusion protein. As used herein, the term "fusion protein" or "fusion polypeptide" or "PDL1-targeting fusion protein" or "PDL1-targeting fusion polypeptide," unless otherwise specifically denoted, refers to any fusion protein embodiment of the disclosure, including, but not limited to, multivalent fusion proteins, multispecific fusion proteins, or multivalent and multispecific fusion proteins.

The disclosure also provides multivalent and multispecific fusion polypeptides that bind at least PDL1 and 41BB. These molecules that bind at least PDL1 are referred to herein as "PDL1x41BB-targeting molecules" or "PDL1x41BB-targeting fusions" or "PDL1x41BB-targeting proteins" or "PDL1x41BB-targeting fusion polypeptides" or "PDL1x41BB-targeting fusion proteins." In some embodiments, the PDL1x41BB-targeting molecule is a multivalent molecule, for example, a multivalent PDL1x41BB-targeting fusion protein. In some embodiments, the PDL1x41BB-targeting molecule is a multispecific molecule, for example, a multispecific PDL1x41BB-targeting fusion protein. In some embodiments, the PDL1x41BB-targeting molecule is a multivalent and multispecific molecule, for example, a multivalent and multispecific PDL1-targeting fusion protein. As used herein, the term "fusion protein" or "fusion polypeptide" or "PDL1x41BB-targeting fusion protein" or "PDL1x41BB-targeting fusion polypeptide," unless otherwise specifically denoted, refers to any fusion protein embodiment of the disclosure, including, but not limited to, multivalent fusion proteins, multispecific fusion proteins, or multivalent and multispecific fusion proteins.

In some embodiments, the multivalent and/or multispecific fusion protein binds at least 41BB. Conventional antibodies targeting members of the TNF receptor superfamily (TNFRSF) have been shown to require exogenous cross-linking to achieve sufficient agonist activity, as evidenced by the necessity for Fc-gamma Receptor (FcγRs) for the activity of antibodies to DR4, DR5, GITR and OX40 (Ichikawa et al 2001 al Nat. Med. 7, 954-960, Li et al 2008 Drug Dev. Res. 69, 69-82; Pukac et al 2005 Br. J. Cancer 92, 1430-1441; Yanda et al 2008 Ann. Oncol. 19, 1060-1067; Yang et al 2007 Cancer Lett. 251:146-157; Bulliard et al 2013 JEM 210(9): 1685; Bulliard et al 2014 Immunol and Cell Biol 92: 475-480). In addition to crosslinking via FcγRs other exogenous agents including addition of the oligomeric ligand or antibody binding entities (e.g. protein A and secondary antibodies) have been demonstrated to enhance anti-TNFRSF antibody clustering and downstream signaling. For example, the addition of the DR5 ligand TRAIL enhanced the apoptosis inducing ability of an anti-DR5 antibody (Graves et al 2014 Cancer Cell 26: 177-189). These findings suggest the need for clustering of TNFRSFs beyond a dimer.

The present disclosure provides multivalent TNFRSF binding fusion proteins, which comprise 2 or more TNFRSF binding domains (TBDs) where at least one TBD binds 41BB. In some embodiments, the fusion proteins of the present disclosure have utility in treating neoplasms.

In some embodiments, the fusion protein contains two or more different TBDs, where each TBD binds 41BB. In some embodiments, the fusion protein contains multiple copies of a TBD that binds 41BB. For example, in some embodiments, the fusion protein contains at least two copies of a TBD that binds 41BB. In some embodiments, the fusion protein contains at least three copies of a TBD that binds 41BB. In some embodiments, the fusion protein contains at least four copies of a TBD that binds 41BB. In some embodiments, the fusion protein contains at least five copies of a TBD that binds 41BB. In some embodiments, the fusion protein contains at least six copies of a TBD that binds 41BB. In some embodiments, the fusion protein contains six or more copies of a TBD that binds 41BB.

In other embodiments, the fusion proteins of the present disclosure bind 41BB and a second TNFRSF member for example GITR, OX40, CD27, TNFR2 and/or CD40. In these embodiments, the fusion proteins of the present disclosure modulate immune cells leading to enhanced tumor destruction. In other embodiments, the fusion proteins of the present disclosure have utility in treating inflammatory conditions. In these embodiments, the fusion proteins of the present disclosure modulate immune cells leading to dampening of the inflammatory insult. For example, specifically agonizing TNFR2 can enhance Treg proliferation leading to immune suppression.

The fusion proteins of the present disclosure are capable of enhanced clustering of TNFRSF members compared to non-cross-linked bivalent antibodies. The enhanced clustered of TNFRSF members mediated by the fusion proteins of the present disclosure induce enhanced TNFRSF-dependent signaling compared to non-cross-linked bivalent antibodies. In most embodiments, the fusion protein will incorporate more than 2 TBDs, for example, three, four, five, or six.

In some embodiments, the fusion proteins are multispecific containing a TBD and a binding domain directed toward a second antigen. In these, embodiments, the binding to the second antigen is capable of providing the additional crosslinking function and TNFRSF activation can be achieved with only one or two TBDs. In these embodiments, the TNFRSF signaling is enhanced and focused by the presence of the second antigen. These multispecific TBD containing fusion proteins are useful means to achieve conditional signaling of a given TNFRSF member.

In these embodiments, binding to the TNFRSF member by the TBD induces minimal signaling unless the second antigen is co-engaged. For example, the multispecific fusion proteins of the present disclosure are capable binding 41BB and PD-L1 and 41BB-dependent signaling is greatly enhanced when the fusion protein is bound to a PD-L1 expressing cell. In another example, the multispecific fusion proteins of the present disclosure are capable binding 41BB and Folate Receptor Alpha (FRα) and 41BB-dependent signaling is greatly enhanced when the fusion protein is bound to a FRα expressing cell.

The present disclosure provides isolated polypeptides that specifically bind 41BB. In some embodiments, the isolated polypeptide is derived from antibodies or antibody fragments including scFv, Fabs, single domain antibodies (sdAb), $V_{NAR}$, or VHHs. In some embodiments, the isolated polypeptide is human or humanized sdAb. The sdAb fragments can be derived from VHH, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the isolated polypeptides are derived from non-antibody scaffold proteins for example but not limited to designed ankyrin repeat proteins (darpins), avimers, anticalin/lipocalins, centyrins and fynomers.

In some embodiments, the isolated polypeptide includes an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83. In some embodiments, the isolated polypeptide includes an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83.

In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83. In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83.

In some embodiments, the isolated polypeptide comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57.

The present disclosure provides multivalent fusion proteins, which comprise two or more binding domains (BDs) where at least one BD binds PDL1. In some embodiments, the fusion proteins of the present disclosure have utility in treating neoplasms.

In some embodiments, the fusion protein contains two or more different BDs, where each BD binds PDL1. In some embodiments, the fusion protein contains multiple copies of a BD that binds PDL1. For example, in some embodiments, the fusion protein contains at least two copies of a BD that binds PDL1. In some embodiments, the fusion protein contains at least three copies of a BD that binds PDL1. In some embodiments, the fusion protein contains at least four copies of a BD that binds PDL1. In some embodiments, the fusion protein contains at least five copies of a BD that binds PDL1. In some embodiments, the fusion protein contains at least six copies of a BD that binds PDL1. In some embodiments, the fusion protein contains six or more copies of a BD that binds PDL1.

The present disclosure provides isolated polypeptides that specifically bind 41BB. In some embodiments, the isolated polypeptide is derived from antibodies or antibody fragments including scFv, Fabs, single domain antibodies (sdAb), $V_{NAR}$, or VHHs. In some embodiments, the isolated polypeptide is human or humanized sdAb. The sdAb fragments can be derived from VHH, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the isolated polypeptides are derived from non-antibody scaffold proteins for example but not limited to designed ankyrin repeat proteins (darpins), avimers, anticalin/lipocalins, centyrins and fynomers.

In some embodiments, the isolated polypeptide includes an amino acid sequence selected from the group consisting of SEQ ID NO: 100, 104, 108, 112, 114, 116, and 119-124. In some embodiments, the isolated polypeptide includes an amino acid sequence selected from the group consisting of SEQ ID NO: 119-124.

In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 100, 104, 108, 112, 114, 116, and 119-124. In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 119-124.

In some embodiments, the isolated polypeptide comprises a complementarity determining region 1 (CDR1) comprising an amino acid sequence selected from the group consisting of SEQ ID NO: 101, 105, and 109; a complementarity determining region 2 (CDR2) comprising an amino acid sequence selected from the group consisting of SEQ ID NO: 102, 106, 110, and 117; and a complementarity determining region 3 (CDR3) comprising an amino acid sequence selected from the group consisting of SEQ ID NO: 103, 107, 111, 113, 115, and 118.

In some embodiments, the present disclosure provides isolated polypeptides that specifically bind at least 41BB and PDL1. In some embodiments, each binding domain (BD) in the isolated polypeptide is derived from antibodies or antibody fragments including scFv, Fabs, single domain antibodies (sdAb), $V_{NAR}$, or VHHs. In some embodiments, each BD is human or humanized sdAb. The sdAb fragments can be derived from VHH, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the isolated polypeptides are derived from non-antibody scaffold proteins for example but not limited to designed ankyrin repeat proteins (darpins), avimers, anticalin/lipocalins, centyrins and fynomers.

In some embodiments, the isolated polypeptide includes a first amino acid sequence that binds 4B11 selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83, and a second amino acid sequence that binds PDL1 selected from the group consisting of SEQ ID NO: 100, 104, 108, 112, 114, 116, and 119-124.

In some embodiments, the isolated polypeptide includes a first amino acid sequence that binds 4B11 selected from the group consisting of SEQ ID NO: 33, 39, 33-41, 43, 45-47, 49, 51, 53, 54, 56, 58-60, 62, 65, 66, 68, 70, 72, 74, 76, 78, and 80-83, and a second amino acid sequence that binds PDL1 selected from the group consisting of SEQ ID NO: 119-124.

In some embodiments, the isolated polypeptide includes a first amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds 4B11 selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83, and a second amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds PDL1 selected from the group consisting of SEQ ID NO: 100, 104, 108, 112, 114, 116, and 119-124.

In some embodiments, the isolated polypeptide includes a first amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds 4B11 selected from the group consisting of SEQ ID NO: 33, 39, 33-41, 43, 45-47, 49, 51, 53, 54, 56, 58-60, 62, 65, 66, 68, 70, 72, 74, 76, 78, and 80-83, and a second amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds PDL1 selected from the group consisting of SEQ ID NO: 119-124.

In some embodiments, the isolated polypeptide includes (i) a first amino acid sequence that binds 4B11 and comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57; and (ii) a second amino acid sequence that binds PDL1 and comprises a CDR1 comprising an amino acid sequence selected from the group consisting of SEQ ID NO: 101, 105, and 109; a CDR2 comprising an amino acid sequence selected from the group consisting of SEQ ID NO: 102, 106, 110, and 117; and a CDR3 comprising an amino acid sequence selected from the group consisting of SEQ ID NO: 103, 107, 111, 113, 115, and 118.

In some embodiments, the binding domains (BDs) of the present disclosure, e.g., the 41BB-binding domains and/or the PDL1-binding domains, are derived from antibodies or antibody fragments including scFv, Fabs, single domain antibodies (sdAb), $V_{NAR}$, or VHHs. In some embodiments, the BDs are human or humanized sdAb. The sdAb fragments, can be derived from VHH, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the BDs are derived from non-antibody scaffold proteins for example but not limited to designed ankyrin repeat proteins (darpins), avimer, anticalin/lipocalins, centyrins and fynomers.

Generally, the fusion proteins of the present disclosure consist of at least two or more BDs operably linked via a linker polypeptide. The utilization of sdAb fragments as the specific BD within the fusion the present disclosure has the benefit of avoiding the heavy chain:light chain mis-pairing problem common to many bi/multispecific antibody approaches. In addition, the fusion proteins of the present disclosure avoid the use of long linkers necessitated by many bispecific antibodies.

In some embodiments, all of the BDs of the fusion protein are TBDs that recognize the same epitope on the given TNFRSF member. For example, the fusion proteins of present disclosure may incorporate 2, 3, 4, 5, or 6 TBDs with identical specificity to 41BB. In other embodiments, the fusion protein incorporates TBDs that recognize distinct epitopes on the given TNFRSF member. For example, the fusion proteins of present disclosure may incorporate 2, 3, 4, 5, or 6 TBDs with distinct recognition specificities toward various epitopes on 41BB. In these embodiments, the fusion proteins of the present disclosure contain multiple TBDs that target distinct regions of the particular TNFRSF member. In some embodiments, the TBDs may recognize different epitopes on the same TNFRSF member or recognize epitopes on distinct TNFRSF members. For example, the present disclosure provides multispecific fusion proteins incorporating TBDs that bind GITR and 41BB or OX40 and 41BB, or CD27 and 41BB.

In some embodiments, the multispecific fusion protein is a bispecific molecule that targets 41BB and PDL1. In some embodiments, the bispecific fusion protein includes a 41BB-targeting binding domain selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83, operably linked to a second binding domain (BD2) that binds PDL1. In some embodiments, the BD2 comprises an amino acid sequence that specifically binds PDL1. In some embodiments, the BD2 comprises a PDL1-targeting domain selected from the group consisting of SEQ ID NO: 100, 104, 108, 112, 114, 116, and 119-124. some embodiments, the BD2 comprises a PDL1-targeting domain selected from the group consisting of SEQ ID NO: 119-124. In some embodiments, the BD2 comprises an amino acid sequence that specifically binds PDL1 and is selected from the group consisting of SEQ ID NO: 126-408.

In some embodiments, the multispecific fusion protein is a bispecific molecule that targets 41BB and PDL1. In some embodiments, the bispecific fusion protein includes a 41BB-targeting binding domain selected from the group consisting of SEQ ID NO: 33-41, 43, 45-47, 49, 51, 53, 54, 56, 58-60, 62, 65, 66, 68, 70, 72, 74, 76, 78, and 80-83, operably linked to a second binding domain (BD2) that binds PDL1. In some embodiments, the BD2 comprises an amino acid sequence that specifically binds PDL1. In some embodiments, the BD2 comprises a PDL1-targeting domain selected from the group consisting of SEQ ID NO: 100, 104, 108, 112, 114, 116, and 119-124. In some embodiments, the BD2 comprises a PDL1-targeting domain selected from the group consisting of SEQ ID NO: 119-124. In some embodiments, the BD2 comprises an amino acid sequence that specifically binds PDL1 and is selected from the group consisting of SEQ ID NO: 126-408.

In some embodiments, the multispecific fusion protein is a bispecific molecule that targets 41BB and PDL1. In some embodiments, the bispecific fusion protein includes a PDL1-targeting binding domain selected from the group consisting of SEQ ID NO: 100, 104, 108, 112, 114, 116, and 119-124, operably linked to a second TBD (TBD2) that binds 41BB. In some embodiments, the TBD2 comprises an amino acid sequence that specifically binds 41BB. In some embodiments, the TBD2 comprises a 41BB-targeting domain selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83. In some embodiments, the TBD2 comprises an amino acid sequence that specifically binds 41BB and is selected from the group consisting of SEQ ID NO: 84-99.

In some embodiments, the multispecific fusion protein is a bispecific molecule that targets 41BB and PDL1. In some embodiments, the bispecific fusion protein includes a PDL1-targeting binding domain selected from the group consisting of SEQ ID NO: 119-124, operably linked to a second TBD (TBD2) that binds 41BB. In some embodiments, the TBD2 comprises an amino acid sequence that specifically binds 41BB. In some embodiments, the TBD2 comprises a 41BB-targeting domain selected from the group consisting of SEQ ID NO: 33, 39, 33-41, 43, 45-47, 49, 51, 53, 54, 56, 58-60, 62, 65, 66, 68, 70, 72, 74, 76, 78, and 80-83. In some embodiments, the TBD2 comprises an amino acid sequence that specifically binds 41BB and is selected from the group consisting of SEQ ID NO: 84-99.

In some embodiments, the multispecific fusion protein is a bispecific molecule that targets 41BB and PDL1 and comprises an amino acid sequence that is selected from the group consisting of SEQ ID NO: 448-456.

In some embodiments, the multispecific fusion protein is a bispecific molecule that targets 41BB and PDL1 and comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 448-456.

In some embodiments, all of the BDs of the fusion protein recognize the same epitope on PDL1. For example, the fusion proteins of present disclosure may incorporate 2, 3, 4, 5, or 6 BDs with identical specificity to PDL1. In other embodiments, the fusion protein incorporates BDs that recognize distinct epitopes on PDL1. For example, the fusion proteins of present disclosure may incorporate 2, 3, 4, 5, or 6 BDs with distinct recognition specificities toward various epitopes on PDL1. In these embodiments, the fusion proteins of the present disclosure contain multiple BDs that target distinct regions of the PDL1. In some embodiments, the BDs may recognize different epitopes on PDL1.

In some embodiments, the fusion protein of the present disclosure is composed of a single polypeptide. In other embodiments, the fusion protein of the present disclosure is composed of more than one polypeptide. For example, wherein a heterodimerization domain is incorporated into the fusion protein so as the construct an asymmetric fusion protein. For example, if an immunoglobulin Fc region is incorporated into the fusion protein the CH3 domain can be used as a homodimerization domain, or the CH3 dimer interface region can be mutated so as to enable heterodimerization.

In some embodiments, the fusion protein contains the BDs opposite ends. For example, the BDs are located on both the amino-terminal (N-terminal) portion of the fusion protein and the carboxy-terminal (C-terminal) portion of the fusion protein. In other embodiments, all the TBDs reside on the same end of the fusion protein. For example, BDs reside on either the amino- or carboxy-terminal portions of the fusion protein.

In some embodiments, the linker polypeptide contains an immunoglobulin Fc region. In some embodiments, the immunoglobulin Fc region is an IgG isotype selected from the group consisting of IgG1 subclass, IgG2 subclass, IgG3 subclass, and IgG4 subclass.

In some embodiments, the immunoglobulin Fc region or immunologically active fragment thereof is an IgG isotype. For example, the immunoglobulin Fc region of the fusion protein is of human IgG1 subclass, having an amino acid sequence:

```
                                            (SEQ ID NO: 1)
PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSRDELT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, the human IgG1 Fc region is modified at amino acid Asn297 (Boxed in SEQ ID NOs: 1-4, Kabat Numbering) to prevent to glycosylation of the fusion protein, e.g., Asn297Ala (N297A) or Asn297Asp (N297D). In some embodiments, the Fc region of the fusion protein is modified at amino acid Leu235 (Bold in SEQ ID NO: 1, Kabat Numbering) to alter Fc receptor interactions, e.g., Leu235Glu (L235E) or Leu235Ala (L235A). In some embodiments, the Fc region of the fusion protein is modified at amino acid Leu234 (Bold in SEQ ID NO: 1, Kabat Numbering) to alter Fc receptor interactions, e.g., Leu234Ala (L234A). In some embodiments, the Fc region of the fusion protein is modified at amino acid Leu234 (Boxed, Kabat Numbering) to alter Fc receptor interactions, e.g., Leu235Glu (L235E). In some embodiments, the Fc region of the fusion protein is altered at both amino acid 234 and 235, e.g., Leu234Ala and Leu235Ala (L234A/L235A) or Leu234Val and Leu235Ala (L234V/L235A). In some embodiments, the Fc region of the fusion protein is lacking an amino acid at one or more of the following positions to reduce Fc receptor binding: Glu233 (E233, Bold in SEQ ID NO: 1), Leu234 (L234), or Leu235 (L235). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 (Boxed in SEQ ID NO: 1) to enhance the interaction with CD32A, e.g., Gly236Ala (G236A). In some embodiments, the human IgG1 Fc region lacks Lys447 (EU index of Kabat et al 1991 *Sequences of Proteins of Immunological Interest*).

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the Fc region of the fusion protein is lacking an amino acid at one or more of the following positions to reduce Fc receptor binding: Glu233 (E233), Leu234 (L234), or Leu235 (L235). In these embodiments, Fc deletion of these three amino acids reduces the complement protein C1q binding. These modified Fc region polypeptides are referred to herein as "Fe deletion" polypeptides.

```
                                            (SEQ ID NO: 2)
PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the immunoglobulin Fc region or immunologically active fragment of the fusion protein is of human IgG2 subclass, having an amino acid sequence:

```
                                            (SEQ ID NO: 3)
PAPPVAGPSV FLFPPKPKDT LMISRTPEVT CVVVDVSHED

PEVQFNWYVD GVEVHNAKTK PREEQFNSTF RVVSVLTVVH

QDWLNGKEYK CKVSNKGLPA PIEKTISKTK GQPREPQVYT

LPPSREEMTK NQVSLTCLVK GFYPSDISVE WESNGQPENN

YKTTPPMLDS DGSFFLYSKL TVDKSRWQQG NVFSCSVMHE

ALHNHYTQKS LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG2 Fc region is modified at amino acid Asn297 (Boxed in SEQ ID NOs: 1, 3, 4, and 5), to prevent to glycosylation of the antibody, e.g., Asn297Ala (N297A). In some embodiments, the human IgG2 Fc region lacks Lys447, which corresponds to residue 217 of SEQ ID NO: 3 (EU index of Kabat et al 1991 *Sequences of Proteins of Immunological Interest*).

In some embodiments, the immunoglobulin Fc region or immunologically active fragment of the fusion protein is of human IgG3 subclass, having an amino acid sequence:

```
                                            (SEQ ID NO: 4)
PAPELLGGPS VFLFPPKPKD TLMISRTPEV TCVVVDVSHE

DPEVQFKWYV DGVEVHNAKT KPREEQYNST FRVVSVLTVL
```

```
HQDWLNGKEY KCKVSNKALP APIEKTISKT KGQPREPQVY

TLPPSREEMT KNQVSLTCLV KGFYPSDIAV EWESSGQPEN

NYNTTPPMLD SDGSFFLYSK LTVDKSRWQQ GNIFSCSVMH

EALHNRFTQK SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In some embodiments, the human IgG3 Fc region is modified at amino acid Asn297 (Boxed in SEQ ID NOs: 1-4, Kabat Numbering) to prevent to glycosylation of the antibody, e.g., Asn297Ala (N297A). In some embodiments, the human IgG3 Fc region is modified at amino acid 435 to extend the half-life, e.g., Arg435His (R435H, Boxed in SEQ ID NO: 3). In some embodiments, the human IgG3 Fc region lacks Lys447, which corresponds to residue 218 of SEQ ID NO: 4 (EU index of Kabat et al 1991 *Sequences of Proteins of Immunological Interest*).

In some embodiments, the immunoglobulin Fc region or immunologically active fragment of the fusion protein is of human IgG4 subclass, having an amino acid sequence:

```
                                                  (SEQ ID NO: 5)
PAPEFLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 5.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Boxed in SEQ ID NOs: 1-4, Kabat Numbering) to prevent to glycosylation of the antibody, e.g., Asn297Ala (N297A). In some embodiments, the human IgG4 Fc region lacks Lys447, which corresponds to residue 218 of SEQ ID NO: 5 (EU index of Kabat et al 1991 *Sequences of Proteins of Immunological Interest*).

In some embodiments, the immunoglobulin Fc region or immunologically active fragment of the fusion protein is of human IgG4 isotype, having an amino acid sequence:

```
                                                  (SEQ ID NO: 6)
PAPELLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 6.

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, *J. Biol Chem* Vol. 281(33) 23514-23524), Met428Leu and Asn434Ser (M428L, N434S) (Zalevsky et al 2010 *Nature Biotech*, Vol. 28(2) 157-159), or Met252Ile, Thr256Asp, Met428Leu (M252I, T256D, M428L, respectively), (EU index of Kabat et al 1991 *Sequences of Proteins of Immunological Interest*). Met252 corresponds to residue 23 in SEQ ID NOs: 1, 4, and 5 and residue 22 in SEQ ID NO: 3. Ser254 corresponds to corresponds to residue 25 in SEQ ID NOs: 1, 4, and 5 and residue 24 in SEQ ID NO: 3. Thr256 corresponds to residue 27 in SEQ ID NOs: 1, 4, and 5 and residue 26 in SEQ ID NO: 3. Met428 corresponds to residue 199 in SEQ ID NOs: 1, 4, and 5 and residue 198 in SEQ ID NO: 3. Asn434 corresponds to residue 205 in SEQ ID NOs: 1, 4, and 5 and residue 204 in SEQ ID NO: 3. In some embodiments where the fusion protein of the disclosure includes an Fc polypeptide, the Fc polypeptide is mutated or modified. In these embodiments, the mutated or modified Fc polypeptide includes the following mutations: Met252Tyr and Met428Leu (M252Y, M428L) using the Kabat numbering system.

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11. Examples of mutations that enhance ADCC include modification at Ser239 and Ile332, for example Ser239Asp and Ile332Glu (S239D, I332E). Examples of mutations that enhance CDC include modifications at Lys326, which corresponds to residue 97 of SEQ ID NOs: 1, 4, and 5 and residue 96 of SEQ ID NO: 2, and Glu333, which corresponds to residue 104 of SEQ ID NOs: 1, 4, and 5 and residue 103 of SEQ ID NO: 3. In some embodiments the Fc region is modified at one or both of these positions, for example Lys326Ala and/or Glu333Ala (K326A and E333A).

In some embodiments, the human IgG Fc region is modified to induce heterodimerization. For example, having an amino acid modification within the CH3 domain at Thr366, which when replaced with a more bulky amino acid, e.g., Trp (T366W), is able to preferentially pair with a second CH3 domain having amino acid modifications to less bulky amino acids at positions Thr366, which corresponds to residue 137 of SEQ ID NOs: 1, 4, and 5 and residue 136 of SEQ ID NO: 3, Leu368, which corresponds to residue 139 of SEQ ID NOs: 1, 4, and 5 and residue 138 of SEQ ID NO: 2, and Tyr407, which corresponds to residue 178 of SEQ ID NOs: 1, 4, and 5 and residue 177 of SEQ ID NO: 3, e.g., Ser, Ala and Val, respectively (T366S/L368A/Y407V). Heterodimerization via CH3 modifications can be further stabilized by the introduction of a disulfide bond, for example by changing Ser354, which corresponds to residue 125 of SEQ ID NOs: 1, 4, and 5 and residue 124 of SEQ ID NO: 3, to Cys (S354C) and Tyr349, which corresponds to residue 120 of SEQ ID NOs: 1, 4, and 5 and residue 119 of SEQ ID NO: 3, to Cys (Y349C) on opposite CH3 domains (Reviewed in Carter, 2001 Journal of Immunological Methods, 248: 7-15). In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, which corresponds to residue 24 of SEQ ID NOs: 1, 4, and 5 and residue 23 of SEQ ID NO: 3, for example Ile253Arg (I253R). For example, the I253R modification maybe combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed.

In some embodiments, the human IgG Fc region is modified to prevent dimerization. In these embodiments, the fusion proteins of the present disclosure are monomeric. For example, modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTHTCPPC (SEQ ID NO: 7), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 8).

In some embodiments, the fusion protein has a modified hinge from IgG4, which is modified to prevent or reduce strand exchange, e.g., Ser228Pro (S228P), having the sequence ESKYGPPCPPC (SEQ ID NO: 9). In some embodiments, the fusion protein contains one or more linker polypeptides. In other embodiments, the fusion protein contains linker and hinge polypeptides.

In some embodiments, the fusion proteins of the present disclosure lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine, 2-deoxy-fucose, 2-flurofucose; the use of production cell lines with naturally reduced fucosylation pathways and metabolic engineering of the production cell line.

In some embodiments, the single domain antibody, VHH, or humanized single domain antibody, or human single domain antibody is engineered to eliminate recognition by pre-existing antibodies found in humans. In some embodiments, single domain antibodies of the present disclosure are modified by mutation of position Leu11, for example Leu11Glu (L11E) or Leu11Lys (L11K). In other embodiments, single domain antibodies of the present disclosure are modified by changes in carboxy-terminal region, for example the terminal sequence consists of GQGTLVTVKPGG (SEQ ID NO: 14) or GQGTLVTVEPGG (SEQ ID NO: 15) or modification thereof. In some embodiments, the single domain antibodies of the present disclosure are modified by mutation of position 11 and by changes in carboxy-terminal region.

In some embodiments, the BDs of the fusion proteins of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 10); GGSGGSGGS, i.e., $(GGS)_3$ (SEQ ID NO: 11); GGSGGSGGSGGS, i.e., $(GGS)_4$ (SEQ ID NO: 12); and GGSGGSGGSGGSGGS, i.e., $(GGS)_5$ (SEQ ID NO: 13).

In some embodiments, the multivalent binding fusion protein is tetravalent. In some embodiments, the tetravalent fusion protein has the following structure: BD-Linker-BD-Linker-Hinge-Fc. In some embodiments, the tetravalent fusion protein has the following structure: BD-Linker-Hinge-Fc-Linker-BD.

In some embodiments, the BD of the tetravalent fusion protein is a single domain antibody or VHH. In some embodiments, each BD of the tetravalent fusion protein is a single domain antibody or VHH. In some embodiments, the tetravalent fusion protein has the following structure: VHH-Linker-VHH-Linker-Hinge-Fc, where the VHH is a humanized or fully human VHH sequence. In some embodiments, the tetravalent fusion protein has the following structure: VHH-Linker-Hinge-Fc-Linker-VHH, where the VHH is a humanized or fully human VHH sequence.

In some embodiments, the multivalent TNFRSF binding fusion protein is tetravalent. In some embodiments, the tetravalent TNFRSF binding fusion protein has the following structure: TBD-Linker-TBD-Linker-Hinge-Fc. In some embodiments, the tetravalent TNFRSF binding fusion protein has the following structure: TBD-Linker-Hinge-Fc-Linker-TBD.

In some embodiments, the TBD of the tetravalent TNFRSF binding fusion protein is a single domain antibody or VHH. In some embodiments, each TBD of the multivalent TNFRSF binding fusion protein is single domain antibody or VHH. In some embodiments, the tetravalent TNFRSF binding fusion protein has the following structure: VHH-Linker-VHH-Linker-Hinge-Fc, where the VHH is a humanized or fully human VHH sequence. In some embodiments, the tetravalent TNFRSF binding fusion protein has the following structure: VHH-Linker-Hinge-Fc-Linker-VHH, where the VHH is a humanized or fully human VHH sequence.

In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

In some embodiments, the multivalent fusion protein is hexavalent. In some embodiments, the hexavalent fusion protein has the following structure: BD-Linker-TBD-Linker-BD-Linker-Hinge-Fc. In some embodiments, the hexavalent fusion protein has the following structure: BD-Linker-BD-Linker-Hinge-Fc-Linker-BD, or BD-Linker-Hinge-Fc-Linker-BD-Linker-BD.

In some embodiments, the BD of the hexavalent fusion protein is a single domain antibody or VHH. In some embodiments, each BD of the hexavalent fusion protein is a single domain antibody or VHH. In some embodiments, the hexavalent fusion protein has the following structure: VHH-Linker-VHH-Linker-VHH-Linker-Hinge-Fc, where the VHH is a humanized or fully human VHH sequence. In some embodiments, the hexavalent fusion protein has the following structure: VHH-Linker-VHH-Linker-Hinge-Fc-Linker-VHH, or VHH-Linker-Hinge-Fc-Linker-VHH-Linker-VHH where the VHH is a humanized or fully human VHH sequence.

In some embodiments, the multivalent TNFRSF binding fusion protein is hexavalent. In some embodiments, the hexavalent TNFRSF binding fusion protein has the following structure: TBD-Linker-TBD-Linker-TBD-Linker-Hinge-Fc. In some embodiments, the hexavalent TNFRSF binding fusion protein has the following structure: TBD-Linker-TBD-Linker-Hinge-Fc-Linker-TBD, or TBD-Linker-Hinge-Fc-Linker-TBD-Linker-TBD.

In some embodiments, the TBD of the hexavalent TNFRSF binding fusion protein is a single domain antibody or VHH. In some embodiments, each TBD of the hexavalent TNFRSF binding fusion protein is a single domain antibody or VHH. In some embodiments, the hexavalent TNFRSF binding fusion protein has the following structure: VHH-Linker-VHH-Linker-VHH-Linker-Hinge-Fc, where the VHH is a humanized or fully human VHH sequence. In some embodiments, the hexavalent TNFRSF binding fusion protein has the following structure: VHH-Linker-VHH-Linker-Hinge-Fc-Linker-VHH, or VHH-Linker-Hinge-Fc-Linker-VHH-Linker-VHH where the VHH is a humanized or fully human VHH sequence.

In some embodiments, the multivalent fusion protein lacks an Fc region. In some of these embodiments, the fusion protein is tetravalent and has the following structure BD-Linker-BD-Linker-BD-Linker-BD-Linker. In some of these embodiments, the fusion protein is pentavalent and has the following structure BD-Linker-BD-Linker-BD-Linker-BD-Linker-BD. In some of these embodiments, the fusion protein is hexavalent and has the following structure BD-Linker-BD-Linker-BD-Linker-BD-Linker-BD-Linker-BD.

In some embodiments, the multivalent TNFRSF binding fusion protein lacks an Fc region. In some of these embodiments, the TNFRSF binding fusion protein is tetravalent and has the following structure TBD-Linker-TBD-Linker-TBD-Linker-TBD-Linker. In some of these embodiments, the TNFRSF binding fusion protein is pentavalent and has the following structure TBD-Linker-TBD-Linker-TBD-Linker-TBD-Linker-TBD. In some of these embodiments, the TNFRSF binding fusion protein is hexavalent and has the following structure TBD-Linker-TBD-Linker-TBD-Linker-TBD-Linker-TBD-Linker-TBD.

In some embodiments, the BD of a multivalent fusion protein is a single domain antibody or VHH. In some embodiments, the multivalent fusion protein lacks an Fc region. In some of these embodiments, the fusion protein is tetravalent and has the following structure VHH-Linker-VHH-Linker-VHH-Linker-VHH-Linker. In some of these embodiments, the fusion protein is pentavalent and has the following structure VHH-Linker-VHH-Linker-VHH-Linker-VHH-Linker-VHH. In some of these embodiments, the fusion protein is hexavalent and has the following structure VHH-Linker-VHH-Linker-VHH-Linker-VHH-Linker-VHH-Linker-VHH. In any of these embodiments, the VHH is a humanized or fully human VHH sequence.

In some embodiments, the TBD of the a multivalent TNFRSF binding fusion protein is a single domain antibody or VHH. In some embodiments, the multivalent TNFRSF binding fusion protein lacks an Fc region. In some of these embodiments, the TNFRSF binding fusion protein is tetravalent and has the following structure VHH-Linker-VHH-Linker-VHH-Linker-VHH-Linker. In some of these embodiments, the TNFRSF binding fusion protein is pentavalent and has the following structure VHH-Linker-VHH-Linker-VHH-Linker-VHH-Linker-VHH. In some of these embodiments, the TNFRSF binding fusion protein is hexavalent and has the following structure VHH-Linker-VHH-Linker-VHH-Linker-VHH-Linker-VHH-Linker-VHH. In any of these embodiments, the VHH is a humanized or fully human VHH sequence.

In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

In some embodiments, the fusion proteins are multispecific containing a TBD and a binding domain directed toward a second antigen. In these embodiments, the second antigen binding domain can be positioned at numerous positions within the molecule relative to the TBD. In some embodiments, the second antigen binding domain is located N-terminal TBD. In other embodiments, the second antigen binding domain is located to C-terminal to the TBD. In other embodiments, the second antigen binding domain is located on a distinct polypeptide that associates with a first polypeptide containing the TBD.

In some embodiments, the fusion proteins are multispecific containing an anti-41BB binding domain and a binding domain directed toward a second antigen. In these embodiments, the second antigen binding domain can be positioned at numerous positions within the molecule relative to the an anti-41BB binding domain. In some embodiments, the second antigen binding domain is located N-terminal an anti-41BB binding domain. In other embodiments, the second antigen binding domain is located to C-terminal to the an anti-41BB binding domain. In other embodiments, the second antigen binding domain is located on a distinct polypeptide that associates with a first polypeptide containing the an anti-41BB binding domain.

In some embodiments, the fusion proteins are multispecific containing an anti-PDL1 binding domain and a binding domain directed toward a second antigen. In these embodiments, the second antigen binding domain can be positioned at numerous positions within the molecule relative to the an anti-PDL1 binding domain. In some embodiments, the second antigen binding domain is located N-terminal an anti-PDL1 binding domain. In other embodiments, the second antigen binding domain is located to C-terminal to the an anti-PDL1 binding domain. In other embodiments, the second antigen binding domain is located on a distinct polypeptide that associates with a first polypeptide containing the an anti-PDL1 binding domain.

In some embodiments, the TBD within the multispecific TNFRSF binding fusion protein is a single domain antibody or VHH. In some embodiments, the TBD within the multispecific TNFRSF binding fusion protein is a composed of antibody variable heavy (VH) chain and variable light (VL) chain region. In some embodiments, the VH and VL of the TBD are formatted as a single chain variable fragment (scFv) connected via a linker region. In some embodiments, the VH and VL of the TBD are formatted as a FAB fragment that associates via a constant heavy 1 (CH1) domain and a constant light chain (CL) domain. In some embodiments, non-antibody heterodimerization domains are utilized to enable the proper association of the VH and VL of the TBD. In some embodiments, the TBD within the multispecific TNFRSF binding fusion protein is derived from non-antibody scaffold proteins for example but not limited to designed ankyrin repeat proteins (darpins), avimer, anticalin/lipocalins, centyrins and fynomers.

In some embodiments, the TBD within the multispecific TNFRSF binding fusion protein is a single domain antibody or VHH that binds 41BB. In some embodiments, the anti-41BB binding domain within the multispecific TNFRSF binding fusion protein is a composed of antibody variable heavy (VH) chain and variable light (VL) chain region. In some embodiments, the VH and VL of the anti-41BB binding domain are formatted as a single chain variable fragment (scFv) connected via a linker region. In some embodiments, the VH and VL of the anti-41BB binding domain are formatted as a Fab fragment that associates via a constant heavy 1 (CH1) domain and a constant light chain (CL) domain. In some embodiments, non-antibody heterodimerization domains are utilized to enable the proper association of the VH and VL of the anti-41BB binding domain. In some embodiments, the anti-41BB binding domain within the multispecific TNFRSF binding fusion protein is derived from non-antibody scaffold proteins for example but not limited to designed ankyrin repeat proteins (darpins), avimer, anticalin/lipocalins, centyrins and fynomers.

In some embodiments, the binding domain within the multispecific fusion protein is a single domain antibody or VHH that binds PDL1. In some embodiments, the anti-PDL1 binding domain within the multispecific TNFRSF binding fusion protein is a composed of antibody variable heavy (VH) chain and variable light (VL) chain region. In some embodiments, the VH and VL of the anti-PDL1 binding domain are formatted as a single chain variable fragment (scFv) connected via a linker region. In some embodiments, the VH and VL of the anti-PDL1 binding domain are formatted as a Fab fragment that associates via a constant heavy 1 (CH1) domain and a constant light chain (CL) domain. In some embodiments, non-antibody heterodimerization domains are utilized to enable the proper association of the VH and VL of the anti-PDL1 binding domain. In some embodiments, the anti-PDL1 binding domain within the multispecific fusion protein is derived from non-antibody scaffold proteins for example but not limited to designed ankyrin repeat proteins (darpins), avimer, anticalin/lipocalins, centyrins and fynomers.

In some embodiments, the anti-41BB binding domain of the multispecific TNFRSF binding fusion protein is a bispecific antibody or antigen-binding fragment thereof.

In some embodiments, the anti-PDL1 binding domain of the multispecific fusion protein is a bispecific antibody or antigen-binding fragment thereof.

In any of these embodiments, the bispecific antibody or antigen-fragment thereof can be any suitable bispecific format known in the art, including, by way of non-limiting example, formats based on antibody fragments such as, e.g., X-Link Fab, cross-linked Fab fragments; tascFv/BiTE, tandem-scFv/Bispecific T cell Engager; Db, diabody; taDb, tandem diabody; formats based on Fc-fusions such as, e.g., Db-Fc, diabody-Fc fusion; taDb-Fc fusion, tandem diabody-Fc fusion; taDb-CH3, tandem diabody-CH3 fusion; (scFv) 4-Fc, tetra scFv-Fc fusion; DVD-Ig, dual variable domain immunoglobulin; IgG formats such as, e.g., knob-hole and SEED, strand exchange engineered domain; CrossMab, knob-hole combined with heavy and light chain domain exchange; bsAb, quadroma derived bispecific antibody; sdAb, single domain based antibody; and kappa-lambda bodies such as those described in PCT Publication No. WO 2012/023053.

In any of the above embodiments, at least one TBD comprises an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83.

In any of the above embodiments, at least one TBD comprises an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83.

In any of the above embodiments, at least one TBD comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57.

In any of the above embodiments, at least one BD comprises an amino acid sequence selected from the group consisting of SEQ ID NO: 100, 104, 108, 112, 114, 116, and 119-124.

In any of the above embodiments, at least one BD comprises an amino acid sequence selected from the group consisting of SEQ ID NO: 119-124.

In any of the above embodiments, at least one BD comprises a CDR1 comprising an amino acid sequence selected from the group consisting of SEQ ID NO: 101, 105, and 109; a CDR2 comprising an amino acid sequence selected from the group consisting of SEQ ID NO: 102, 106, 110, and 117; and a CDR3 comprising an amino acid sequence selected from the group consisting of SEQ ID NO: 103, 107, 111, 113, 115, and 118.

In any of the above embodiments, at least one TBD comprises an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83, and at least one BD comprises an amino acid sequence selected from the group consisting of SEQ ID NO: 100, 104, 108, 112, 114, 116, and 119-124.

In any of the above embodiments, at least one TBD comprises an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83, and at least one BD comprises an amino acid sequence selected from the group consisting of SEQ ID NO: 119-124.

In any of the above embodiments, at least one TBD comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57, and at least one BD comprises a CDR1 comprising an amino acid sequence selected from the group consisting of SEQ ID NO: 101, 105, and 109; a CDR2 comprising an amino acid sequence selected from the group consisting of SEQ ID NO: 102, 106, 110, and 117; and a CDR3 comprising an amino acid sequence selected from the group consisting of SEQ ID NO: 103, 107, 111, 113, 115, and 118.

BRIEF DESCRIPTION OF THE DRAWINGS

FIG. 1 is schematic of exemplary multivalent and multi-specific fusion proteins of the present disclosure.

FIGS. 8A, 8B, and 8C are a series of illustrations and a graph depicting PDL1-dependent 41BB agonism mediated by bispecific PDL1-41BB targeting fusion proteins of the present disclosure. FIGS. 8A and 8B are conceptual schematics, wherein the bispecific fusion proteins have minimal 41BB agonistic properties (FIG. 8A) unless bound by a PD-L1 expressing cell (FIG. 8B). FIG. 8C is a graph demonstrating the ability of a PDL1-positive cell (here PDL1 transfected CHO cells) to mediate 41BB signaling and the inability of PDL1-negative cell (here untransfected CHO cells) to mediate 41BB signaling. 41BB signaling was monitored using a NF-kB reporter 293 cell line expressing 41BB.

FIG. 9E is a graph demonstrating that the humanized variants hzRH3v5-1 and hzRH3v9 do not block binding of 41BBL to cell surface 41BB. Herein a recombinant fusion protein 41BBL-mFc, containing a mouse Fc region was used and bound 41BBL was detected using an anti-mouse IgG-Fc specific secondary antibody.

FIG. 11D is a graph demonstrating that the humanized variants hz4E01v16, hz4E01v18, hz4E01v21, hz4E01v22 and hz4E01v23 block binding of 41BBL to cell surface 41BB. In these studies, a recombinant fusion protein 41BBL-mFc, containing a mouse Fc region was used and bound 41BBL was detected using an anti-mouse IgG-Fc specific secondary antibody.

FIG. 14C is a graph that demonstrates that the bispecific fusion protein containing hzRh3v5-1 does not block 41BBL binding to cell surface 41BB. Herein a recombinant fusion protein of 41BBL and mouse Fc region was used and bound 41BBL was detected using an anti-mouse IgG-Fc specific secondary antibody.

FIG. 19A. is a graph showing the binding of INBRX-105-1 to the PDL1 expressing K562 cells. FIG. 19B is a graph showing the binding of recombinant 41BB to INBRX-105-1 on the PDL1 expressing cells.

DETAILED DESCRIPTION OF THE INVENTION

Figure 2A:
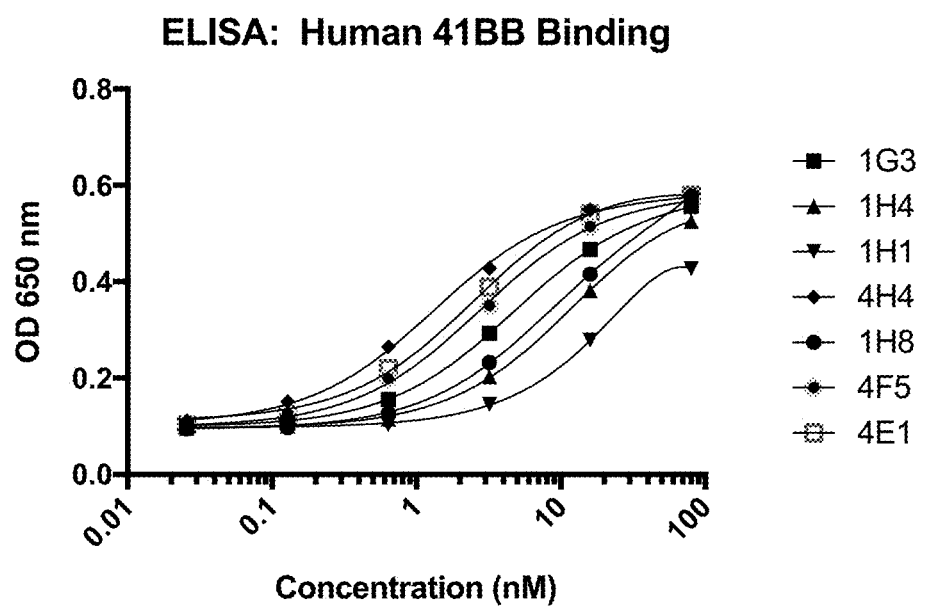
FIGS. 2A and 2B are a pair of graphs demonstrating the ability of 41BB single domain antibodies (sdAbs) to bind recombinant human 41BB (FIG. 2A) or cyno 41BB (FIG. 2B). Binding was assessed by ELISA wherein recombinant 41BB-mFc protein was immobilized on a Medisorp 96 well plate.

All patents and publications mentioned in this specification are herein incorporated by reference to the same extent as if each independent patent and publication was specifically and individually indicated to be incorporated by reference.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms "dual-targeting fusion protein" and "antibody" can be synonyms. As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d$>$10^{-6}$). Antibodies include, but are not limited to, polyclonal, monoclonal, chimeric, dAb (domain antibody), single chain, Fab, Fab' and F(ab')$_2$ fragments, Fv, scFvs, a Fab expression library, and single domain antibody (sdAb) fragments, for example V$_H$H, V$_{NAR}$, engineered V$_H$ or V$_K$.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses (also known as isotypes) as well, such as IgG$_1$, IgG$_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The single domain antibody (sdAb) fragments portions of the fusion proteins of the present disclosure are referred to interchangeably herein as targeting polypeptides herein.

As used herein, the term "epitope" includes any protein determinant capable of specific binding to/by an immunoglobulin or fragment thereof, or a T-cell receptor. The term "epitope" includes any protein determinant capable of specific binding to/by an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 mM, for example, ≤1 µM; e.g., ≤100 nM, for example, ≤10 nM and for example, ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to an antigen, when the equilibrium binding constant ($K_d$) is ≤1 µM, for example, ≤100 nM, for example, ≤10 nM, and for example, ≤100 pM to about 1 pM, as measured by assays such as radioligand binding assays, surface plasmon resonance (SPR), flow cytometry binding assay, or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide," as referred to herein, refers to a polymeric boron of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and for example, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the disclosure selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the disclosure and a nucleic acid sequence of interest will be at least 80%, and more typically with increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, for example, at least 90 percent sequence identity, for example, at least 95 percent sequence identity, and for example, at least 99 percent sequence identity.

In some embodiments, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Suitable conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, for example, at least 80%, 90%, 95%, and for example, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, for example, at least 14 amino acids long, for example, at least 20 amino acids long, usually at least 50 amino acids long, and for example, at least 70 amino acids long. The term "analog" as used herein refers to polypeptides which are comprised of a segment of at least 25 amino acids that has substantial identity to a portion of a deduced amino acid sequence and which has specific binding to CD47, under suitable binding conditions. Typically, polypeptide analogs comprise a conservative amino acid substitution (or addition or deletion) with respect to the naturally-occurring sequence. Analogs typically are at least 20 amino acids long, for example, at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, and/or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, the terms "treat," treating," "treatment," and the like refer to reducing and/or ameliorating a disorder and/or symptoms associated therewith. By "alleviate" and/or "alleviating" is meant decrease, suppress, attenuate, diminish, arrest, and/or stabilize the development or progression of a disease such as, for example, a cancer. It will be appreciated that, although not precluded, treating a disorder or condition does not require that the disorder, condition or symptoms associated therewith be completely eliminated.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present.

Generally, a substantially pure composition will comprise more than about 80 percent of all macromolecular species present in the composition, for example, more than about 85%, 90%, 95%, and 99%. In some embodiments, the object species is purified to essential homogeneity (contaminant species cannot be detected in the composition by conventional detection methods) wherein the composition consists essentially of a single macromolecular species.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

By "effective amount" is meant the amount required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "subject" is meant a mammal, including, but not limited to, a human or non-human mammal, such as a bovine, equine, canine, rodent, ovine, primate, camelid, or feline.

The term "administering," as used herein, refers to any mode of transferring, delivering, introducing, or transporting a therapeutic agent to a subject in need of treatment with such an agent. Such modes include, but are not limited to, oral, topical, intravenous, intraperitoneal, intramuscular, intradermal, intranasal, and subcutaneous administration.

By "fragment" is meant a portion of a polypeptide or nucleic acid molecule. This portion contains, for example, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

41BB (CD137, TNFRSF9) Targeting

41BB is a member of the TNF receptor superfamily that is predominately expressed on activated T-cells and NK cells and serves as a co-stimulatory molecule. Agonizing 41BB enhances T cell proliferation and survival, cytolytic activity and cytokine secretion (e.g., IL-2, TNFα and INFγ). In mice, 41BB engagement has been shown to enhance anti-tumor immunity. (Croft, 2009, Nat Rev Immunol 9:271-285; Lynch, 2008, Immunol Rev. 22: 277-286). Importantly, tumor infiltrating cytotoxic T-cells (CTLs), have been shown to be express 41BB and it is these 41BB positive CTLs that have the highest anti-tumor cytotoxic activity (Ye et al Clin Cancer Res; 20(1): 44-55). The ligand for 41BB, 41BBL, naturally forms a homotrimer any thereby suggests that signaling is mediated by higher order clustering of 41BB. This is activation mechanism is shared with many members of the TNFRSF. Interest in exploiting 41BB signaling for anti-tumor immunotherapy has prompted the development of therapeutic 41BB antibodies. However, the capacity of bivalent 41BB antibodies to induce signaling is weak in absence of an exogenous clustering event. This can be achieved to some degree through the interaction with Fcγ-receptors (FcγRs), yet this can also lead to depletion of the 41BB-expressing cell through effector mechanisms (e.g. ADCC and ADCP). Furthermore, competition with the high concentration of IgG in serum attenuates efficient FcγR interactions. Therefore, current bivalent antibodies targeting 41BB are either ineffective agonists or have the liability of depleting the vary cells wherein 41BB signaling is desired. It has previously been shown that the therapeutic 41BB antibody, PF-05082566 is only capable of mediated 41BB signaling with cross-linked with anti-human secondary antibody (Fisher et al Cancer Immunol Immunother (2012) 61:1721-1733). Therefore, there exists a need for optimized 41BB agonist capable of mediating signaling in the absence of an exogenous crosslinking agent or FcγR interaction. The fusion proteins of the present disclosure are capable of mediating potent 41BB signaling 1) without any additional interactions when formatted as a multivalent fusion protein or 2) conditionally when engaged with at least a second antigen interaction when formatted as a multispecific fusion protein. The fusion proteins of the present disclosure are capable of standalone (multivalent) or conditional (multispecific) co-stimulatory activity on T-cell and NK cells.

Exemplary amino acid sequences of 41BB binding single domain antibodies are shown below:

4H04:

(SEQ ID NO: 16)

QVQLQESGGGLVQAGDSLRLSCAAS[GWAFDNYG]MAWFRQAPGKEREFIGR[LAWNGGST]DYADS

VKGRFTISRDNPKNTLYLQMNNLKPEDTAVYYC[ARQRSYSGYGIRTPQTYDY]WGQGTQVT

-continued

CDR1:
(SEQ ID NO: 17)
GWAFDNYG

CDR2:
(SEQ ID NO: 18)
LAWNGGST

CDR3:
(SEQ ID NO: 19)
ARQRSYSGYGIRTPQTYDY

4E1:
(SEQ ID NO: 20)
QVQLQQSGGGLVQAGDSLRLSCAAS GWAFGNYG MAWFRRAPGKEREFIGR LAWNGGST DYVDS

VKGRFTISRDNPKNTLYLQMNNLKPDDTAVYYC ARQRSYSRYDIRTPQTYDY WGQGTQVT

CDR1:
(SEQ ID NO: 21)
GWAFGNYG

CDR2:
(SEQ ID NO: 18)
LAWNGGST

CDR3:
(SEQ ID NO: 22)
ARQRSYSRYDIRTPQTYDY

4F5:
(SEQ ID NO: 23)
QVQLVQSGGGLVQPGGSLRLSCAAS GWAFDNYG MAWFRQAPGKEREFIGR LAWNGGST DYADS

VKGRFTISRDNPKNTLYLQMNSLKPEDTAVYYC ARQRSYSRYGIRAPQTYDY WGQGTQVT

CDR1:
(SEQ ID NO: 17)
GWAFDNYG

CDR2:
(SEQ ID NO: 18)
LAWNGGST

CDR3:
(SEQ ID NO: 24)
ARQRSYSRYGIRAPQTYDY

RH3:
(SEQ ID NO: 25)
QVQLQESGGGLVQPGGSLRLSCAVS GFSFSINA MGWYRQAPGKRREFLAA IDSGRNTV YAVSV

KGRFTISRDNAKNTVYLQMNSLKPEDTAIYYC GLLKGNRVVSPSVAY WGQGTQVT

CDR1:
(SEQ ID NO: 26)
GFSFSINA

CDR2:
(SEQ ID NO: 27)
IDSGRNT

CDR3:
(SEQ ID NO: 28)
GLLKGNRVVSPSVAY

D1:
(SEQ ID NO: 29)
EVQPVQSGGGLVQAGESLRLSCAAS ATIFSNNA MGWYRQAPGKQRELVAT ITTGGFT NYRDSV

KGRFDISRDNAKNTVYLQMNNLKPEDTAVYYC NVVLRYSRDYSYTTVKEY WGQGTQV

CDR1:

```
                                             (SEQ ID NO: 30)
ATIFSNNA

CDR2:
                                             (SEQ ID NO: 31)
ITTGGFT

CDR3:
                                             (SEQ ID NO: 32)
NVVLRYSRDYSYTTVKEY

1G3:
                                            (SEQ ID NO: 432)
QVQLVQSGGGLVQPGGSLRLSCAASGFTFSSYAMSWVRQAPGKGLEWVSAIPAGDGSTKYADS

VKGRFTISRDNAKNTVYLQMDSLKPEDTAVYFCAKSRGWSTVDDMDYWGKGTQV

CDR1:
                                            (SEQ ID NO: 433)
GFTFSSYA

CDR2:
                                            (SEQ ID NO: 434)
IPAGDGST

CDR3:
                                            (SEQ ID NO: 435)
AKSRGWSTVDDMDY

1H4:
                                            (SEQ ID NO: 436)
QVQLVQSGGGLVQPGGSLRLSCVVSGFTFRSYAMSWVRQAPGKGLEWVSTINSGESSTKYADS

VKGRFTISRDDAKNTLYLQMSDLKPEDTAVYFCAKHRGWSTVDDINYWGKGTQV

CDR1:
                                            (SEQ ID NO: 437)
GFTFRSYA

CDR2:
                                            (SEQ ID NO: 438)
INSGESST

CDR3:
                                            (SEQ ID NO: 439)
AKHRGWSTVDDINY

1H1:
                                            (SEQ ID NO: 440)
QVQLVQSGGGLVQPGGSLRLSCAASGFTFDDHAMSWVRQAPGKGLEWVSAISWNGHYTYYAES

MKGRFAISRDNAKNTLYLQMNSLKSEDTAVYYCVKGWRGSYTRDRPFASWGQGTQV

CDR1:
                                            (SEQ ID NO: 441)
GFTFDDHA

CDR2:
                                            (SEQ ID NO: 442)
ISWNGHYT

CDR3:
                                            (SEQ ID NO: 443)
VKGWRGSYTRDRPFAS

1H8:
                                            (SEQ ID NO: 444)
EVQLVQSGGGLVQPGGSLRLSCAASGFTFSSYYMSWVRQAPGKGLEWVSTISTNTGGGSTYYA

YADSVKGRFTISRDNAKNTLYLEMNSLKPEDTAQYYCVRTRWEGVYDYWGLGTQV

CDR1:
                                            (SEQ ID NO: 445)
GFTFSSYY
```

-continued

CDR2:
(SEQ ID NO: 446)
ISTNTGGGST

CDR3:
(SEQ ID NO: 447)
VRTRWEGVYDY

Hz4E1-v1:
(SEQ ID NO: 33)
EVQLLESGGGEVQPGGSLRLSCAAS GWAFGNYG MAWFRQAPGKGLEWVAR LAWNGGST DYAES

VKGRFTISRDNAKNTLYLQMSSLRAEDTAVYYC ARQRSYSRYDIRTPQTYDY WGQGTLVTVKP

CDR1:
(SEQ ID NO: 21)
GWAFGNYG

CDR2:
(SEQ ID NO: 18)
LAWNGGST

CDR3:
(SEQ ID NO: 22)
ARQRSYSRYDIRTPQTYDY

Hz4E1-v3:
(SEQ ID NO: 34)
EVQLLESGGGEVQPGGSLRLSCAAS GWAFGNYG MAWFRQAPGKGREFVAR LAWNGGST DYAES

VKGRFTISRDNAKNTLYLQMSSLRAEDTAVYYC ARQRSYSRYDIRTPQTYDY WGQGTLVTVKP

CDR1:
(SEQ ID NO: 21)
GWAFGNYG

CDR2:
(SEQ ID NO: 18)
LAWNGGST

CDR3:
(SEQ ID NO: 22)
ARQRSYSRYDIRTPQTYDY hz4E01v7-1:
(SEQ ID NO: 35)
EVQLLESGGGEVQPGGSLRLSCAAS GWAFGNYG MAWFRQAPGKEREFVSR LAWNGGST DYVAE

SVKGRFTISRDNAKNTLYLQMSSLRAEDTAVYYC ARQRSYSRYDIRTPQTYDY WGQGTLVTVK

CDR1:
(SEQ ID NO: 21)
GWAFGNYG

CDR2:
(SEQ ID NO: 18)
LAWNGGST

CDR3:
(SEQ ID NO: 22)
ARQRSYSRYDIRTPQTYDY hz4E01v8:
(SEQ ID NO: 36)
EVQLLESGGGEVQPGGSLRLSCAAS GWAFGNYG MAWFRQAPGKEREFIGR LAWNGGST DYVES

VKGRFTISRDNPKNTLYLQMSSLRAEDTAVYYC ARQRSYSRYDIRTPQTY DYWGQGTLVTVKP

CDR1:
(SEQ ID NO: 21)
GWAFGNYG

CDR2:

```
                                                            (SEQ ID NO: 18)
LAWNGGST

CDR3:
                                                            (SEQ ID NO: 22)
ARQRSYSRYDIRTPQTYDY hz4E01v9:
                                                            (SEQ ID NO: 37)
EVQLLESGGGEVQPGGSLRLSCAAS[GWAFGNYG]MAWFRQAPGKEREFVSR[LAWNGGST]DYVES

VKGRFTISRDNAKNTLYLQMSSLRAEDTAVYYC[ARQRSYSRYDIRTPQTYDY]WGQGTLVTVKP

CDR1:
                                                            (SEQ ID NO: 21)
GWAFGNYG

CDR2:
                                                            (SEQ ID NO: 18)
LAWNGGST

CDR3:
                                                            (SEQ ID NO: 22)
ARQRSYSRYDIRTPQTYDY hz4E01v10:
                                                            (SEQ ID NO: 38)
EVQLLESGGGEVQPGGSLRLSCAAS[GWAFGNYG]MAWFRQAPGKEREFVSR[LAWNGGST]DYVES

VKGRFTISRDNPKNTLYLQMSSLRAEDTAVYYC[ARQRSYSRYDIRTPQTYDY]WGQGTLVTVKP

CDR1:
                                                            (SEQ ID NO: 21)
GWAFGNYG

CDR2:
                                                            (SEQ ID NO: 18)
LAWNGGST

CDR3:
                                                            (SEQ ID NO: 22)
ARQRSYSRYDIRTPQTYDY hz4E01v11:
                                                            (SEQ ID NO: 39)
EVQLLESGGGEVQPGGSLRLSCAAS[GWAFGNYG]MAWFRQAPGKEREFIGR[LAWNGGST]DYVES

VKGRFTISRDNAKNTLYLQMSSLRAEDTAVYYC[ARQRSYSRYDIRTPQTYDY]WGQGTLVTVKP

CDR1:
                                                            (SEQ ID NO: 21)
GWAFGNYG

CDR2:
                                                            (SEQ ID NO: 18)
LAWNGGST

CDR3:
                                                            (SEQ ID NO: 22)
ARQRSYSRYDIRTPQTYDY hz4E01v12:
                                                            (SEQ ID NO: 40)
EVQLLESGGGEVQPGGSLRLSCAAS[GWAFGNYG]MAWFRQAPGKEREFIGR[LAWNGGST]DYVES

VKGRFTISRDNPKNTLYLQMSSLRAEDTAVYYC[ARQRSYSRYDIRTPQTYDY]WGQGTLVTVKP

CDR1:
                                                            (SEQ ID NO: 21)
GWAFGNYG

CDR2:
                                                            (SEQ ID NO: 18)
LAWNGGST
```

-continued

```
CDR3:
                                                     (SEQ ID NO: 22)
ARQRSYSRYDIRTPQTYDY hz4E01v13:
                                                     (SEQ ID NO: 41)
EVQLLESGGGEVQPGGSLRLSCAASGWAFGNYGMAWFRQAPGKEREFIGRLAWQGGSTDYVES

VKGRFTISRDNPKNTLYLQMSSLRAEDTAVYYCARQRSYSRYDIRTPQTYDYWGQGTLVTVKP

CDR1:
                                                     (SEQ ID NO: 21)
GWAFGNYG

CDR2:
                                                     (SEQ ID NO: 42)
LAWQGGST

CDR3:
                                                     (SEQ ID NO: 22)
ARQRSYSRYDIRTPQTYDY hz4E01v14:
                                                     (SEQ ID NO: 43)
EVQLLESGGGEVQPGGSLRLSCAASGWAFGNYGMAWFRQAPGKEREFIGRLAWNAGSTDYVES

VKGRFTISRDNPKNTLYLQMSSLRAEDTAVYYCARQRSYSRYDIRTPQTYDYWGQGTLVTVKP

CDR1:
                                                     (SEQ ID NO: 21)
GWAFGNYG

CDR2:
                                                     (SEQ ID NO: 44)
LAWNAGST

CDR3:
                                                     (SEQ ID NO: 22)
ARQRSYSRYDIRTPQTYDY hz4E01v16:
                                                     (SEQ ID NO: 45)
EVQLLESGGGEVQPGGSLRLSCAASGWAFGNYGMAWFRQAPGKEREFVSRLAWQGGSTDYVES

VKGRFTISRDNAKNTLYLQMSSLRAEDTAVYYCARQRSYSRYDIRTPQTYDYWGQGTLVTVKP

CDR1:
                                                     (SEQ ID NO: 21)
GWAFGNYG

CDR2:
                                                     (SEQ ID NO: 42)
LAWQGGST

CDR3:
                                                     (SEQ ID NO: 22)
ARQRSYSRYDIRTPQTYDY hz4E01v17:
                                                     (SEQ ID NO: 46)
EVQLLESGGGEVQPGGSLRLSCAASGWAFGNYGMAWFRQAPGKEREFVSRLAWNAGSTDYVES

VKGRFTISRDNAKNTLYLQMSSLRAEDTAVYYCARQRSYSRYDIRTPQTYDYWGQGTLVTVKP

CDR1:
                                                     (SEQ ID NO: 21)
GWAFGNYG

CDR2:
                                                     (SEQ ID NO: 44)
LAWNAGST

CDR3:
```

-continued

ARQRSYSRYDIRTPQTYDY                                    (SEQ ID NO: 22)

hz4E01v18:
                                                       (SEQ ID NO: 47)
EVQLLESGGGEVQPGGSLRLSCAASGWAFGNYGMAWFRQAPGKEREFVSRLAWGGGSTDYVES

VKGRFTISRDNAKNTLYLQMSSLRAEDTAVYYCARQRSYSRYDIRTPQTYDYWGQGTLVTVKP

CDR1:                                                  (SEQ ID NO: 21)
GWAFGNYG

CDR2:                                                  (SEQ ID NO: 48)
LAWGGGST

CDR3:                                                  (SEQ ID NO: 22)
ARQRSYSRYDIRTPQTYDY hz4E01v21:
                                                       (SEQ ID NO: 49)
EVQLLESGGGEVQPGGSLRLSCAASGWAFSNYGMAWFRQAPGKEREFVSRLAWGGGSTDYVES

VKGRFTISRDNAKNTLYLQMSSLRAEDTAVYYCARQRSYSRYDIRTPQTYDYWGQGTLVTVKP

CDR1:                                                  (SEQ ID NO: 50)
GWAFSNYG

CDR2:                                                  (SEQ ID NO: 48)
LAWGGGST

CDR3:                                                  (SEQ ID NO: 22)
ARQRSYSRYDIRTPQTYDY hz4E01v22:
                                                       (SEQ ID NO: 51)
EVQLLESGGGEVQPGGSLRLSCAASGWAFGNYGMAWFRQAPGKEREFVSRLAWSGGSTDYVES

VKGRFTISRDNAKNTLYLQMSSLRAEDTAVYYCARQRSYSRYDIRTPQTYDYWGQGTLVTVKP

CDR1:                                                  (SEQ ID NO: 21)
GWAFGNYG

CDR2:                                                  (SEQ ID NO: 52)
LAWSGGST

CDR3:                                                  (SEQ ID NO: 22)
ARQRSYSRYDIRTPQTYDY hz4E01v23:
                                                       (SEQ ID NO: 53)
EVQLLESGGGEVQPGGSLRLSCAASGWAFSNYGMAWFRQAPGKEREFVSRLAWSGGSTDYVES

VKGRFTISRDNAKNTLYLQMSSLRAEDTAVYYCARQRSYSRYDIRTPQTYDYWGQGTLVTVKP

CDR1:                                                  (SEQ ID NO: 50)
GWAFSNYG

CDR2:                                                  (SEQ ID NO: 52)
LAWSGGST

CDR3:                                                  (SEQ ID NO: 22)
ARQRSYSRYDIRTPQTYDY hz4E01v24:
(SEQ ID NO: 54)
EVQLLESGGGEVQPGGSLRLSCAAS GWAFGNYG MAWFRQAPGKEREFVSR LAWGGGST DYVES

VKGRFTISRDNAKNTLYLQMSSLRAEDTAVYYC ARQRSYSGYDIRTPQTYDY WGQGTLVTVKP

CDR1:
(SEQ ID NO: 21)
GWAFGNYG

CDR2:
(SEQ ID NO: 48)
LAWGGGST

CDR3:
(SEQ ID NO: 55)
ARQRSYSGYDIRTPQTYDY hz4E01v25:
(SEQ ID NO: 56)
EVQLLESGGGEVQPGGSLRLSCAAS GWAFGNYG MAWFRQAPGKEREFVSR LAWGGGST DYVES

VKGRFTISRDNAKNTLYLQMSSLRAEDTAVYYC ARQRSYSRYGIRTPQTYDY WGQGTLVTVKP

CDR1:
(SEQ ID NO: 21)
GWAFGNYG

CDR2:
(SEQ ID NO: 48)
LAWGGGST

CDR3:
(SEQ ID NO: 57)
ARQRSYSRYGIRTPQTYDY hz4E01v26:
(SEQ ID NO: 58)
EVQLLESGGGEVQPGGSLRLSCAAS GWAFGNYG MAWFRQAPGKEREFVSR LAWGGGST DYVES

VKGRFTISRDNAKNTLYLQMSSLRAEDTAVYYC ARQRSYSGYGIRTPQTYDY WGQGTLVTVKP

CDR1:
(SEQ ID NO: 21)
GWAFGNYG

CDR2:
(SEQ ID NO: 48)
LAWGGGST

CDR3:
(SEQ ID NO: 19)
ARQRSYSGYGIRTPQTYDY hzRH3-v1:
(SEQ ID NO: 59)
EVQLLESGGGEVQPGGSLRLSCAAS GFSFSINA MGWYRQAPGKGLEWVAA IDSGRNTV YAESV

KGRFTISRDNAKNTLYLQMSSLRAEDTAVYYC GLLKGNRVVSPSVAY WGQGTLVTVKP

CDR1:
(SEQ ID NO: 26)
GFSFSINA

CDR2:
(SEQ ID NO: 27)
IDSGRNT

CDR3:
(SEQ ID NO: 28)
GLLKGNRVVSPSVAY hzRH3v5-1:

-continued

```
                                                       (SEQ ID NO: 60)
EVQLLESGGGEVQPGGSLRLSCAAS GFSFSINA MGWYRQAPGKRREFVAA IESGRNTV YAESV

KGRFTISRDNAKNTVYLQMSSLRAEDTAVYYC GLLKGNRVVSPSVAY WGQGTLVTVKP

CDR1:
                                                       (SEQ ID NO: 26)
GFSFSINA

CDR2:
                                                       (SEQ ID NO: 61)
IESGRNT

CDR3:
                                                       (SEQ ID NO: 28)
GLLKGNRVVSPSVAY hzRH3v5-2:
                                                       (SEQ ID NO: 62)
EVQLLESGGGEVQPGGSLRLSCAAS GFSFSINA MGWYRQAPGKRREFVAA IYSGRNT VYAESV

KGRFTISRDNAKNTVYLQMSSLRAEDTAVYYC GLLKGNRVVSPSVAY WGQGTLVTVKP

CDR1:
                                                       (SEQ ID NO: 26)
GFSFSINA

CDR2:
                                                       (SEQ ID NO: 63)
IYSGRNT

CDR3:
                                                       (SEQ ID NO: 28)
GLLKGNRVVSPSVAY hzRH3v5-3
                                                       (SEQ ID NO: 64)
EVQLLESGGGEVQPGGSLRLSCAAS GFTFSINA MGWYRQAPGKRREFVAA IESGRNT VYAESV

KGRFTISRDNAKNTVYLQMSSLRAEDTAVYYC GLLKGNRVVSPSVAY WGQGTLVTVKP

CDR1:
                                                       (SEQ ID NO: 65)
GFTFSINA

CDR2:
                                                       (SEQ ID NO: 61)
IESGRNT

CDR3:
                                                       (SEQ ID NO: 28)
GLLKGNRVVSPSVAY hzRH3v5-6
                                                       (SEQ ID NO: 66)
EVQLLESGGGEVQPGGSLRLSCAAS GFSFSINA MSWYRQAPGKRREFVAA IESGRNT VYAESV

KGRFTISRDNAKNTVYLQMSSLRAEDTAVYYC GLLKGNRVVSPSVAY WGQGTLVTVKP

CDR1:
                                                       (SEQ ID NO: 67)
GFSFSINA

CDR2:
                                                       (SEQ ID NO: 61)
IESGRNT

CDR3:
                                                       (SEQ ID NO: 28)
GLLKGNRVVSPSVAY hzRH3v5-8
```

-continued

```
                                            (SEQ ID NO: 68)
EVQLLESGGGEVQPGGSLRLSCAAS GFTFSSNA MGWYRQAPGKRREFVAA IESGRNT VYAESV

KGRFTISRDNAKNTVYLQMSSLRAEDTAVYYC GLLKGNRVVSPSVAY WGQGTLVTVKP

CDR1:
                                            (SEQ ID NO: 69)
GFTFSSNA

CDR2:
                                            (SEQ ID NO: 61)
IESGRNT

CDR3:
                                            (SEQ ID NO: 28)
GLLKGNRVVSPSVAY hzRH3v5-10
                                            (SEQ ID NO: 70)
EVQLLESGGGEVQPGGSLRLSCAAS GFSFSINA MGWYRQAPGKRREFVAA IESSRNT VYAESV

KGRFTISRDNAKNTVYLQMSSLRAEDTAVYYC GLLKGNRVVSPSVAY WGQGTLVTVKP

CDR1:
                                            (SEQ ID NO: 26)
GFSFSINA

CDR2:
                                            (SEQ ID NO: 71)
IESSRNT

CDR3:
                                            (SEQ ID NO: 28)
GLLKGNRVVSPSVAY hzRH3v5-12
                                            (SEQ ID NO: 72)
EVQLLESGGGEVQPGGSLRLSCAAS GFSFSINA MGWYRQAPGKRREFVAA IESGSNT VYAESV

KGRFTISRDNAKNTVYLQMSSLRAEDTAVYYC GLLKGNRVVSPSVAY WGQGTLVTVKP

CDR1:
                                            (SEQ ID NO: 26)
GFSFSINA

CDR2:
                                            (SEQ ID NO: 73)
IESGSNT

CDR3:
                                            (SEQ ID NO: 28)
GLLKGNRVVSPSVAY hzRH3v5-14
                                            (SEQ ID NO: 74)
EVQLLESGGGEVQPGGSLRLSCAAS GFSFSINA MGWYRQAPGKRREFVAA IESGRST VYAESV

KGRFTISRDNAKNTVYLQMSSLRAEDTAVYYC GLLKGNRVVSPSVAY WGQGTLVTVKP

CDR1:
                                            (SEQ ID NO: 26)
GFSFSINA

CDR2:
                                            (SEQ ID NO: 75)
IESGRST

CDR3:
                                            (SEQ ID NO: 28)
GLLKGNRVVSPSVAY hzRH3v5-15
```

```
                                                        (SEQ ID NO: 76)
EVQLLESGGGEVQPGGSLRLSCAASGFSFSINAMGWYRQAPGKRREFVAAIESGRNTYYAESV

KGRFTISRDNAKNTVYLQMSSLRAEDTAVYYCGLLKGNRVVSPSVAYWGQGTLVTVKP

CDR1:
                                                        (SEQ ID NO: 26)
GFSFSINA

CDR2:
                                                        (SEQ ID NO: 77)
IESGRNT

CDR3:
                                                        (SEQ ID NO: 28)
GLLKGNRVVSPSVAY hzRH3v5-16
                                                        (SEQ ID NO: 78)
EVQLLESGGGEVQPGGSLRLSCAASGFSFSINAMGWYRQAPGKRREFVAAIYSGSSTVYAESV

KGRFTISRDNAKNTVYLQMSSLRAEDTAVYYCGLLKGNRVVSPSVAYWGQGTLVTVKP

CDR1:
                                                        (SEQ ID NO: 26)
GFSFSINA

CDR2:
                                                        (SEQ ID NO: 79)
IYSGSST

CDR3:
                                                        (SEQ ID NO: 28)
GLLKGNRVVSPSVAY hzRH3v7
                                                        (SEQ ID NO: 80)
EVQLLESGGGEVQPGGSLRLSCAVSGFSFSINAMGWYRQAPGKRREFVAAIESGRNTVYAESV

KGRFTISRDNAKNTVYLQMSSLRAEDTAVYYCGLLKGNRVVSPSVAYWGQGTLVTVKP

CDR1:
                                                        (SEQ ID NO: 26)
GFSFSINA

CDR2:
                                                        (SEQ ID NO: 61)
IESGRNT

CDR3:
                                                        (SEQ ID NO: 28)
GLLKGNRVVSPSVAY hzRH3v8
                                                        (SEQ ID NO: 81)
EVQLLESGGGEVQPGGSLRLSCAASGFSFSINAMGWYRQAPGKRREFVAAIESGRNTVYAVSV

KGRFTISRDNAKNTVYLQMSSLRAEDTAVYYCGLLKGNRVVSPSVAYWGQGTLVTVKP

CDR1:
                                                        (SEQ ID NO: 26)
GFSFSINA

CDR2:
                                                        (SEQ ID NO: 61)
IESGRNT

CDR3:
                                                        (SEQ ID NO: 28)
GLLKGNRVVSPSVAY hzRH3v9
```

-continued

```
                                               (SEQ ID NO: 82)
EVQLLESGGGEVQPGGSLRLSCAASGFSFSINAMGWYRQAPGKGREFVAAIESGRNTVYAESV

KGRFTISRDNAKNTVYLQMSSLRAEDTAVYYCGLLKGNRVVSPSVAYWGQGTLVTVKP

CDR1:
                                               (SEQ ID NO: 26)
GFSFSINA

CDR2:
                                               (SEQ ID NO: 61)
IESGRNT

CDR3:
                                               (SEQ ID NO: 28)
GLLKGNRVVSPSVAY hzRH3v13
                                               (SEQ ID NO: 83)
EVQLLESGGGEVQPGGSLRLSCAASGFSFSINAMGWYRQAPGKRREFLAAIESGRNTVYAESV

KGRFTISRDNAKNTVYLQMSSLRAEDTAVYYCGLLKGNRVVSPSVAYWGQGTLVTVKP

CDR1:
                                               (SEQ ID NO: 26)
GFSFSINA

CDR2:
                                               (SEQ ID NO: 61)
IESGRNT

CDR3:
                                               (SEQ ID NO: 28)
GLLKGNRVVSPSVAY
```

In some embodiments, the 41BB binding domain comprises or is derived from an antibody sequence or antigen-binding fragment thereof that includes a combination of a variable heavy chain (VH) sequence and a variable light chain (VL) sequence selected from the group consisting of:

```
VH Sequences:
                                               (SEQ ID NO: 84)
QVQLVQSGAEVKKPGSSVKVSCKASGGTFNSYAISWVRQAPGQGLEWMG
GIIPGFGTANYAQKFQGRVTITADESTSTAYMELSSLRSEDTAVYYCAR
KNEEDGGFDHWGQGTLVTVSS (SEQ ID NO: 85)
QVQLVESGGGLVQPGGSLRLSCAASGFTFSDYYMHWVRQAPGKGLEWVS
VISGSGSNTYYADSVKGRFTISRDNSKNTLYLQMNSLRAEDTAVYYCAR
LYAQFEGDFWGQGTLVTVSS (SEQ ID NO: 86)
QVQLVQSGAEVKKPGESLKISCKGSGYSFSTYWISWVRQMPGKGLEWMG
KIYPGDSYTNYSPSFQGQVTISADKSISTAYLQWSSLKASDTAMYYCAR
GYGIFDYWGQGTLVTVSS (SEQ ID NO: 87)
EVQLVQSGAEVKKPGESLRISCKGSGYSFSTYWISWVRQMPGKGLEWMG
KIYPGDSYTNYSPSFQGQVTISADKSISTAYLQWSSLKASDTAMYYCAR
GYGIFDYWGQGTLVTVSS VL Sequences:
                                               (SEQ ID NO: 88)
DIELTQPPSVSVAPGQTARISCSGDNLGDYYASWYQQKPGQAPVLVIYD
DSNRPSGIPERFSGSNSGNTATLTISGTQAEDEADYYCQTWDGTLHFVF
GGGTKLTVL (SEQ ID NO: 89)
DIELTQPPSVSVAPGQTARISCSGDNIGSKYVSWYQQKPGQAPVLVIYS
DSERPSGIPERFSGSNSGNTATLTISGTQAEDEADYYCQSWDGSISRVF
GGGTKLTVL (SEQ ID NO: 90)
DIELTQPPSVSVAPGQTARISCSGDNIGDQYAHWYQQKPGQAPVVVIYQ
DKNRPSGIPERFSGSNSGNTATLTISGTQAEDEADYYCATYTGFGSLAV
FGGGTKLTVL (SEQ ID NO: 91)
SYELTQPPSVSVSPGQTASITCSGDNIGDQYAHWYQQKPGQSPVLVIYQ
DKNRPSGIPERFSGSNSGNTATLTISGTQAMDEADYYCATYTGFGSLAV
FGGGTKLTVL (SEQ ID NO: 92)
SYELTQPPSVSVSPGQTASITCSGDNIGDQYAHWYQQKPGQSPVVVIYQ
DKNRPSGIPERFSGSNSGNTATLTISGTQAMDEADYYCATYTGFGSLAV
FGGGTKLTVL (SEQ ID NO: 93)
DIELTQPPSVSVAPGQTARISCSGDNIGDQYAHWYQQKPGQAPVVVIYQ
DKNRPSGIPERFSGSNSGNTATLTISGTQAEDEADYYCSTYTFVGFTTV
FGGGTKLTVL (SEQ ID NO: 94)
SYELTQPPSVSVSPGQTASITCSGDNIGDQYAHWYQQKPGQSPVLVIYQ
DKNRPSGIPERFSGSNSGNTATLTISGTQAMDEADYYCSTYTFVGFTTV
FGGGTKLTVL (SEQ ID NO: 95)
SYELTQPPSVSVSPGQTASITCSGDNIGDQYAHWYQQKPGQSPVVVIYQ
DKNRPSGIPERFSGSNSGNTATLTISGTQAMDEADYYCSTYTFVGFTTV
FGGGTKLTVL
```

In some embodiments, the 41BB binding domain comprises or is derived from an antibody sequence or antigen-binding fragment thereof that includes a combination of a heavy chain (HC) sequence and a light chain (LC) sequence selected from the group consisting of:

HC Sequences:

(SEQ ID NO: 96)
QVQLQQWGAGLLKPSETLSLTCAVYGGSFSGYYWSWIRQSPEKGLEWIGE

INHGGYVTYNPSLESRVTISVDTSKNQFSLKLSSVTAADTAVYYCARDYG

PGNYDWYFDLWGRGTLVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK (SEQ ID NO: 97)
QVQLQQWGAGLLKPSETLSLTCAVYGGSFSGYYWSWIRQSPEKGLEWIGE

INHGGYVTYNPSLESRVTISVDTSKNQFSLKLSSVTAADTAVYYCARDYG

PGNYDWYFDLWGRGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

LC Sequences:

(SEQ ID NO: 98)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPALTF

GGGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTH

QGLSSPVTKSFNRGEC

In some embodiments, the 41BB binding domain comprises or is derived from an antibody sequence or antigen-binding fragment thereof selected from the antibody sequences described in US Patent Application Publication No. 20160244528, the contents of which are hereby incorporated by reference in their entirety.

In some embodiments, the 41BB binding domain comprises or is derived from an antibody sequence or antigen-binding fragment thereof selected from the antibody sequences described in U.S. Pat. No. 8,337,850, the contents of which are hereby incorporated by reference in their entirety.

In some embodiments, the 41BB binding domain comprises or is derived from an antibody sequence or antigen-binding fragment thereof selected from the antibody sequences described in PCT Publication No. WO 2005/035584, the contents of which are hereby incorporated by reference in their entirety.

In some embodiments, the 41BB binding domain comprises or is derived from an antibody sequence or antigen-binding fragment thereof selected from the antibody sequences described in EP Patent No. EP 1670828 B1, the contents of which are hereby incorporated by reference in their entirety.

In some embodiments, the 41BB binding domain comprises or is derived from an antibody sequence or antigen-binding fragment thereof selected from the antibody sequences described in PCT Publication No. WO 2006/088447, the contents of which are hereby incorporated by reference in their entirety.

In some embodiments, the 41BB binding domain comprises or is derived from an antibody sequence or antigen-binding fragment thereof selected from the antibody sequences described in US Patent Application Publication No. 20080166336, the contents of which are hereby incorporated by reference in their entirety.

In some embodiments, the 41BB binding domain comprises or is derived from an anti-cancer fusion protein sequence or antigen-binding fragment thereof selected from the sequences described in PCT Publication No. WO 2016/177802, the contents of which are hereby incorporated by reference in their entirety. In some embodiments, the 41BB binding domain comprises or is derived from an amino acid sequence comprising:

(SEQ ID NO: 99)
QDSTSDLIPAPPLSKVPLQQNFQDNQFHGKWYVVGQAGNIRLREDKDPIK

MMATIYELKEDKSYDVTMVKFDDKKCMYDIWTFVPGSQPGEFTLGKIKSF

PGHTSSLVRVVSTNYNQHAMVFFKFVFQNREEFYITLYGRTKELTSELKE

NFIRFSKSLGLPENHIVFPVPIDQCIDG

In some embodiments, the 41BB binding domain comprises or is derived from an 41BB-targeting polypeptide sequence or antigen-binding fragment thereof selected from the sequences described in PCT Publication No. WO 2016/177762, the contents of which are hereby incorporated by reference in their entirety. In some embodiments, the 41BB binding domain comprises or is derived from an amino acid sequence comprising:

PDL1 Targeting

In some embodiments, the fusion proteins are multispecific containing at least a first binding domain, e.g., a TBD, and a second binding domain directed toward Program Death Ligand 1 (PD-L1). In these, embodiments, the binding to PD-L1 is capable of providing the additional cross-linking function and TNFRSF activation is achieved with only one or two TBDs. In these embodiments, the TNFRSF signaling is enhanced and focused by the presence of a PD-L1 expressing cell.

PDL1 is a 40 kDa type I transmembrane protein that forms a complex with its receptor programmed cell death protein 1 (PD1), also known as CD279. Engagement of PDL1 with its receptor PD1 on T cells delivers a signal that inhibits TCR-mediated activation of IL-2 production and T cell proliferation. Aberrant expression and/or activity of PDL1 and PDL1-related signaling has been implicated in the pathogenesis of many diseases and disorders, such as cancer, inflammation, and autoimmunity.

In some embodiments, the PD-L1 binding portion is single domain antibody. In some embodiments, the PDL1 binding portion of the fusion blocks or dampens the interaction of PDL1 and PD-1. Exemplary PDL1-targeting single domain sequences are shown below:

28A10:
(SEQ ID NO: 100)
QVQLQESGGGLVQAGGSLRLACTTSGGIFNIRPISWYRQPPGMQREWVATIAFGGATNYANSI

KGRFTASRDNAKNTVYLQMNGLKPEDTAVYYCNAFEIWGQGTQVTV

CDR1:
(SEQ ID NO: 101)
GGIFNIRP

CDR2:
(SEQ ID NO: 102)
IAFGGAT

CDR3:
(SEQ ID NO: 103)
NAFEI

28A2:
(SEQ ID NO: 104)
QLQLQESGGGLVRAGGSLRLACTTSGGIFAIKPISWYRQPPGQEREWVTITTSSGATNYANSI

KGRFTVARDNAKNTVYLQMNDLKLEDTAVYYCNVFEYWGQGTQVTV

CDR1:
(SEQ ID NO: 105)
GGIFAIKP

CDR2:
(SEQ ID NO: 106)
TTSSGAT

CDR3:
(SEQ ID NO: 107)
NVFEY

B03:
(SEQ ID NO: 108)
QVQLQESGGDLVQAGSSLRLACATSGGVFNIRPISWYRQPPGKQREWVATIASGGATNYANSI

KGRFTASRDNAKNTVYLQMNGLKPEDTAVYYCNAFEVWGQGTQVTV

CDR1:
(SEQ ID NO: 109)
GGVFNIRP

CDR2:
(SEQ ID NO: 110)
IASGGAT

CDR3:
(SEQ ID NO: 111)
NAFEV

B10:
(SEQ ID NO: 112)
QVQLQQSGGGLVQAGGSLRLACTTSGGIFNIRPISWYRQPPGMQREWVATIASGGATNYANSI

KGRFTASRDNAKNTVYLQMNGLKPEDTAVYYCNTLNFWGRGTQVTV

CDR1:
(SEQ ID NO: 101)
GGIFNIRP

CDR2:
(SEQ ID NO: 110)
IASGGAT

CDR3:
(SEQ ID NO: 113)
NTLNF

D02:
(SEQ ID NO: 114)

QVQLQESGGGLVQAGGSLRLACTTS[GGIFNIRP]ISWYRQPPGMQREWVAT[IASGGAT]NYANSI

KGRFTASRDNAKNTVYLQMNGLKPEDTAVYYC[NVFEI]WGQGTQVTV

CDR1:
(SEQ ID NO: 101)
GGIFNIRP

CDR2:
(SEQ ID NO: 110)
IASGGAT

CDR3:
(SEQ ID NO: 115)
NVFEI

A03:
(SEQ ID NO: 116)
QVQLQQSGGGLVQAGGSLRLACITS[GGIFNIRP]ISWYRQPPGKQREWVAT[IASGGAA]NYANSI

KGRFTASRDNAKNTVYLQMNGLKPEDTAVYYC[NAFEN]WGQGTQVTV

CDR1:
(SEQ ID NO: 101)
GGIFNIRP

CDR2:
(SEQ ID NO: 117)
IASGGAA

CDR3:
(SEQ ID NO: 118)
NAFEN hz28A2v1
(SEQ ID NO: 119)
QVQLQESGGGEVQPGGSLRLSCAAS[GGIFAIKP]ISWYRQAPGKQREWVST[TTSSGAT]NYAESV

KGRFTISRDNAKNTLYLQMSSLRAEDTAVYYC[NVFEY]WGQGTLVTVKP

CDR1:
(SEQ ID NO: 105)
GGIFAIKP

CDR2:
(SEQ ID NO: 106)
TTSSGAT

CDR3:
(SEQ ID NO: 107)
NVFEY hz28A2v1-1
(SEQ ID NO: 120)
EVQLQESGGGEVQPGGSLRLSCAAS[GGIFAIKP]ISWYRQAPGKQREWVST[TTSSGAT]NYAESV

KGRFTISRDNAKNTLYLQMSSLRAEDTAVYYC[NVFEY]WGQGTLVTVKP

CDR1:
(SEQ ID NO: 105)
GGIFAIKP

CDR2:
(SEQ ID NO: 106)
TTSSGAT

CDR3:
(SEQ ID NO: 107)
NVFEY hz28A2v2
(SEQ ID NO: 121)
EVQLLESGGGEVQPGGSLRLSCAAS[GGIFAIKP]ISWYRQAPGKQREWVST[TTSSGAT]NYAESV

KGRFTISRDNAKNTLYLQMSSLRAEDTAVYYC NVFEY WGQGTLVTVKP

CDR1:
(SEQ ID NO: 105)
GGIFAIKP

CDR2:
(SEQ ID NO: 106)
TTSSGAT

CDR3:
(SEQ ID NO: 107)
NVFEY hz28A2v3
(SEQ ID NO: 122)
EVQLLESGGGEVQPGGSLRLSCAAS GGIFAIKP ISWYRQAPGKQREWVST TTSSGAT NYAESV

KGRFTISRDNAKNTLYLQMSSLRAEDTAVYYC NVFEY WGQGTLVTVKP

CDR1:
(SEQ ID NO: 105)
GGIFAIKP

CDR2:
(SEQ ID NO: 106)
TTSSGAT

CDR3:
(SEQ ID NO: 107)
NVFEY hz28A2v4:
(SEQ ID NO: 123)
EVQLLESGGGEVQPGGSLRLSCAAS GGIFAIKP ISWYRQAPGKQREWVTT TTSSGAT NYAESV

KGRFTISRDNAKNTVYLQMSSLRAEDTAVYYC NVFEY WGQGTLVTVKP

CDR1:
(SEQ ID NO: 105)
GGIFAIKP

CDR2:
(SEQ ID NO: 106)
TTSSGAT

CDR3:
(SEQ ID NO: 107)
NVFEY hz28A2v5:
(SEQ ID NO: 124)
EVQLLESGGGEVQPGGSLRLSCAAS GGIFAIKP ISWYRQAPGKQREWVST TTSSGAT NYAESV

KGRFTISRDNAKNTLYLQMSSLRAEDTAVYYC NVFEY WGQGTLVTVKP

CDR1:
(SEQ ID NO: 105)
GGIFAIKP

CDR2:
(SEQ ID NO: 106)
TTSSGAT

CDR3:
(SEQ ID NO: 107)
NVFEY

In other embodiments, the PD-L1 binding portion is derived from the extracellular domain of PD-1 containing at least the IgV domain as shown below:

```
                                           (SEQ ID NO: 125)
PTFSPALLVVTEGDNATFTCSFSNTSESFVLNWYRMSPSNQTDKLAAFP

EDRSQPGQDCRFRVTQLPNGRDFHMSVVRARRNDSGTYLCGAISLAPKA

QIKESLRAELRVT
```

In some embodiments, the PDL1 binding domain comprises or is derived from a known anti-PDL1 antibody sequence or antigen-binding fragment thereof. In some embodiments, the PDL1 binding domain comprises or is derived from an antibody sequence disclosed in PCT Publication No. WO 2016/149201, the contents of which are hereby incorporated by reference in their entirety.

In some embodiments, the PDL1 binding domain comprises or is derived from an antibody sequence or antigen-binding fragment thereof that includes a combination of a variable heavy chain (VH) sequence and a variable light chain (VL) sequence selected from the group consisting of:

```
VH Sequences:
                                           (SEQ ID NO: 126)
QVQLVQSGAEVKKPGASVKVSCKASGYTFTDYGFSWVRQAPGQGLEWMGWITAYNGNTNYAQK

LQGRVTMTTDTSTSTVYMELRSLRSDDTAVYYCARDYFYGMDVWGQGTTVTVSS (SEQ ID NO: 127)
QVQLVQSGAEVKKPGSSVKVSCKTSGDTFSTYAISWVRQAPGQGLEWMGGIIPIFGKAHYAQK

FQGRVTITADESTSTAYMELSSLRSEDTAVYFCARKFHFVSGSPFGMDVWGQGTTVTVSS (SEQ ID NO: 128)
QVQLVQSGAEVKKPGASVKVSCKASGYTFTSYDVHWVRQAPGQRLEWMGWLHADTGITKFSQK

FQGRVTITRDTSASTAYMELSSLRSEDTAVYYCARERIQLWFDYWGQGT (SEQ ID NO: 129)
QVQLVQSGAEVKKPGSSVKVSCKVSGGIFSTYAINWVRQAPGQGLEWMGGIIPIFGTANHAQK

FQGRVTITADESTSTAYMELSSLRSEDTAVYYCARDQGIAAALFDYWGQGTLVTVSS (SEQ ID NO: 130)
EVQLVESGGGLVQPGRSLRLSCAVSGFTFDDYVVHWVRQAPGKGLEWVSGNSGNIGYADSVKG

RFTISRDNAKNSLYLQMNSLRAEDTALYYCAVPFDYWGQGTLVTVSS (SEQ ID NO: 131)
QVQLVQSGAEVKKPGSSVKVSCKTSGDTFSSYAISWVRQAPGQGLEWMGGIIPIFGRAHYAQK

FQGRVTITADESTSTAYMELSSLRSEDTAVYFCARKFHFVSGSPFGMDVWGQGTTVTVSS (SEQ ID NO: 132)
QVQLVQSGAEVKKPGSSVKVSCKTSGGTFSSYAISWVRQAPGQGLEWMGGIIPIFGKAHYAQK

FQGRVTITADESTTTAYMELSSLRSEDTAVYYCARKYDYVSGSPFGMDVWGQGTTVTVSS (SEQ ID NO: 133)
QVQLVQSGAEVKKPGSSVKVSCKASGGTFSSYAINWVRQAPGQGLEWMGGIIPIFGSANYAQK

FQDRVTITADESTSAAYMELSSLRSEDTAVYYCARDSSGWSRYYMDVWGQGTTVTVSS (SEQ ID NO: 134)
QVQLVQSGAEVKEPGSSVKVSCKASGGTFNSYAISWVRQAPGQGLEWMGGIIPLFGIAHYAQK

FQGRVTITADESTNTAYMDLSSLRSEDTAVYYCARKYSYVSGSPFGMDVWGQGTTVTVSS (SEQ ID NO: 135)
EVQLVESGGGLVQPGRSLRLSCAASGITFDDYGMHWVRQAPGKGLEWVSGISWNRGRIEYADS

VKGRFTISRDNAKNSLYLQMNSLRAEDTALYYCAKGRFRYFDWFLDYWGQGTLVTVSS (SEQ ID NO: 136)
QMQLVQSGGGLVQPGGSLRLSCAASGFTFSSYWMSWVRQAPGKGLEWVANIKQDGSEKYYVDS

VKGRFTISRDNAKNSLYLQMNSLRAEDTAVYYCARDYFWSGFSAFDIWGKGTLVTVS

VL Sequences:
                                           (SEQ ID NO: 137)
EIVLTQSPATLSLSPGERATLSCRASQSVSSYLVWYQQKPGQAPRLLIYDASNRATGIPARFS

GSGSGTDFTLTISSLEPEDFAVYYCQQRSNWPRTFGQGTKVEIK (SEQ ID NO: 138)
EIVLTQSPATLSLSPGERATLSCRASQSVSSYLAWYQQKPGQAPRLLIYDASNRATGIPARFS

GSGSGTDFTLTISSLEPEDFAVYYCQQRSNWPTFGQGTKVEIK
```

```
                                    (SEQ ID NO: 139)
DIQMTQSPSSLSASVGDRVTITCRASQGISSWLAWYQQKPEKAPKSLIYAASSLQSGVPSRFS

GSGSGTDFTLTISSLQPEDFATYYCQQYNSYPYTFGQGTKLEIK (SEQ ID NO: 140)
EIVLTQSPGTLSLSPGERATLSCRASQSVSSSYLAWYQQKPGQAPRLLIYGASSRATGIPDRF

SGSGSGTDFTLTISRLEPEDFAVYYCQQYGSSPWTFGQGTKVEIK (SEQ ID NO: 141)
EIVLTQSPGTLSLSPGERATLSCRASQSVSSSYLAWYQQKPGQAPRLLIYGASSRATGIPDRF

SGSGSGTDFTLTISRLEPEDFAVYYCQQYGSSPFGGGTKVEIK (SEQ ID NO: 142)
EIVLTQSPATLSLSPGERATLSCRASQSVSSYLAWYQQKPGQAPRLLIYDASNRATGIPARFS

GSGSGTDFTLTISSLEPEDFAVYYCQQRSNWPTFGQGTRLEIK (SEQ ID NO: 143)
AIQLTQSPSSLSASVGDRVTITCRASQGISSALAWYQQKPGKAPKLLIYDASSLESGVPSRFS

GSGSGTDFTLTISSLQPEDFATYYCQQFNSYPFTFGPGTKVDIK (SEQ ID NO: 144)
DIVMTQSPSTLSASVGDRVTITCRASQGISSWLAWYQQKPGRAPKVLIYKASTLESGVPSRFS

GSGSGTDFTLTISSLQPEDFATYYCQQSYSTPWTFGQGTKLEIK
```

In some embodiments, the PDL1 binding domain comprises or is derived from an antibody sequence or antigen-binding fragment thereof that includes a combination of a VH sequence and a VL sequence selected from the group consisting of:

```
VH Sequence:
                                    (SEQ ID NO: 145)
EVQLVESGGGLVQPGGSLRLSCAASGFTFSRYWMSWVRQAPGKGLEWVAN

IKQDGSEKYYVDSVKGRFTISRDNAKNSLYLQMNSLRAEDTAVYYCAREG

GWFGELAFDYWGQGTLVTVSS

VL Sequence:
                                    (SEQ ID NO: 146)
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIK
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                    (SEQ ID NO: 147)
EVQLVESGGGLVQPGGSLRLSCAASGFTFSDSWIHWVRQAPGKGLEWVAWISPYGGSTYYADS

VKGRFTISADTSKNTAYLQMNSLRAEDTAVYYCARRHWPGGFDYWGQGTLVTVSA (SEQ ID NO: 148)
EVQLVESGGGLVQPGGSLRLSCAASGFTFSGSWIHWVRQAPGKGLEWVAWILPYGGSSYYADS

VKGRFTISADTSKNTAYLQMNSLRAEDTAVYYCARRHWPGGFDYWGQGTLVTVSA

VL Sequences:
                                    (SEQ ID NO: 149)
DIQMTQSPSSLSASVGDRVTITCRASQDVSTAVAWYQQKPGKAPKLLIYSASFLYSGVPSRFS

GSGSGTDFTLTISSLQPEDFATYYCQQYLYHPATFGQGTKVEIKR (SEQ ID NO: 150)
DIQMTQSPSSLSASVGDRVTITCRASQDVSTAVAWYQQKPGKAPKLLIYSASFLYSGVPSRFS

GSGSGTDFTLTISSLQPEDFATYYCQQYYNVPWTFGQGTKVEIKR (SEQ ID NO: 151)
DIQMTQSPSSLSASVGDRVTITCRASQDVSTAVAWYQQKPGKAPKLLIYSASFLYSGVPSRFS

GSGSGTDFTLTISSLQPEDFATYYCQQYYAPPWTFGQGTKVEIKR
```

```
                                                      (SEQ ID NO: 152)
DIQMTQSPSSLSASVGDRVTITCRASQDVSTAVAWYQQKPGKAPKLLIYSASFLYSGVPSRFS

GSGSGTDFTLTISSLQPEDFATYYCQQYYTVPWTFGQGTKVEIKR (SEQ ID NO: 153)
DIQMTQSPSSLSASVGDRVTITCRASQVINTFLAWYQQKPGKAPKLLIYSASTLASGVPSRFS

GSGSGTDFTLTISSLQPEDFATYYCQQYYTVPRTFGQGTKVEIKR (SEQ ID NO: 154)
DIQMTQSPSSLSASVGDRVTITCRASQDVSTAVAWYQQKPGKAPKLLIYSASFLYSGVPSRFS

GSGSGTDFTLTISSLQPEDFATYYCQQGYGVPRTFGQGTKVEIKR (SEQ ID NO: 155)
DIQMTQSPSSLSASVGDRVTITCRASQDVSTAVAWYQQKPGKAPKLLIYSASFLYSGVPSRFS

GSGSGTDFTLTISSLQPEDFATYYCQQYLFTPPTFGQGTKVEIKR (SEQ ID NO: 156)
DIQMTQSPSSLSASVGDRVTITCRASQDVSTAVAWYQQKPGKAPKLLIYSASFLYSGVPSRFS

GSGSGTDFTLTISSLQPEDFATYYCQQYFITPTTFGQGTKVEIKR (SEQ ID NO: 157)
DIQMTQSPSSLSASVGDRVTITCRASQDVSTAVAWYQQKPGKAPKLLIYSASFLYSGVPSRFS

GSGSGTDFTLTISSLQPEDFATYYCQQYYYTPPTFGQGTKVEIKR (SEQ ID NO: 158)
DIQMTQSPSSLSASVGDRVTITCRASQDVSTAVAWYQQKPGKAPKLLIYSASFLYSGVPSRFS

GSGSGTDFTLTISSLQPEDFATYYCQQFFYTPPTFGQGTKVEIKR (SEQ ID NO: 159)
DIQMTQSPSSLSASVGDRVTITCRASQDVSTAVAWYQQKPGKAPKLLIYSASFLYSGVPSRFS

GSGSGTDFTLTISSLQPEDFATYYCQQSLFTPPTFGQGTKVEIKR (SEQ ID NO: 160)
DIQMTQSPSSLSASVGDRVTITCRASQDVSTAVAWYQQKPGKAPKLLIYSASFLYSGVPSRFS

GSGSGTDFTLTISSLQPEDFATYYCQQSLYTPPTFGQGTKVEIKR (SEQ ID NO: 161)
DIQMTQSPSSLSASVGDRVTITCRASQDVSTAVAWYQQKPGKAPKLLIYSASFLYSGVPSRFS

GSGSGTDFTLTISSLQPEDFATYYCQQSWYHPPTFGQGTKVEIKR (SEQ ID NO: 162)
DIQMTQSPSSLSASVGDRVTITCRASQDVSTAVAWYQQKPGKAPKLLIYSASFLYSGVPSRFS

GSGSGTDFTLTISSLQPEDFATYYCQQYFIPPTFGQGTKVEIKR (SEQ ID NO: 163)
DIQMTQSPSSLSASVGDRVTITCRASQDVSTAVAWYQQKPGKAPKLLIYSASFLYSGVPSRFS

GSGSGTDFTLTISSLQPEDFATYYCQQYWYTPTTFGQGTKVEIKR (SEQ ID NO: 164)
DIQMTQSPSSLSASVGDRVTITCRASQDVSTAVAWYQQKPGKAPKLLIYSASFLYSGVPSRFS

GSGSGTDFTLTISSLQPEDFATYYCQQSYFIPPTFGQGTKVEIKR
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                                (SEQ ID NO: 165)
METGLRWLLLVAVLKGVQCLSVEESGGRLVTPGTPLTLTCTASGFTITNYHMFWVRQAPGKGL

EWIGVITSSGIGSSSTTYYATWAKGRFTISKTSTTVNLRITSPTTEDTATYFCARDYFTNTYY

ALDIWGPGTLVTVSS (SEQ ID NO: 166)
QVQLVQSGAEVKKPGSSVKVSCKTSGDTFSTYAISWVRQAPGQGLEWMGGIIPIFGKAHYAQK

FQGRVTITADESTSTAYMELSSLRSEDTAVYFCARKFHFVSGSPFGMDVWGQGTTVTVSS (SEQ ID NO: 167)
QVQLVQSGAEVKKPGASVKVSCKASGYTFTSYDVHWVRQAPGQRLEWMGWLHADTGITKFSQK

FQGRVTITRDTSASTAYMELSSLRSEDTAVYYCARERIQLWFDYWGQGTLVTVSS (SEQ ID NO: 168)
QVQLVQSGAEVKKPGSSVKVSCKVSGGIFSTYAINWVRQAPGQGLEWMGGIIPIFGTANHAQK

FQGRVTITADESTSTAYMELSSLRSEDTAVYYCARDQGIAAALFDYWGQGTLVTVSS (SEQ ID NO: 169)
EVQLVESGGGLVQPGRSLRLSCAVSGFTFDDYVVHWVRQAPGKGLEWVSGISGNSGNIGYADS

VKGRFTISRDNAKNSLYLQMNSLRAEDTALYYCAVPFDYWGQGTLVTVSS (SEQ ID NO: 170)
QVQLVQSGAEVKKPGSSVKVSCKTSGDTFSSYAISWVRQAPGQGLEWMGGIIPIFGRAHYAQK

FQGRVTITADESTSTAYMELSSLRSEDTAVYFCARKFHFVSGSPFGMDVWGQGTTVTVSS (SEQ ID NO: 171)
QVQLVQSGAEVKKPGSSVKVSCKTSGGTFSSYAISWVRQAPGQGLEWMGGIIPIFGKAHYAQK

FQGRVTITADESTTTAYMELSSLRSEDTAVYYCARKYDYVSGSPFGMDVWGQGTTVTVSS (SEQ ID NO: 172)
QVQLVQSGAEVKKPGSSVKVSCKASGGTFSSYAINWVRQAPGQGLEWMGGIIPIFGSANYAQK

FQDRVTITADESTSAAYMELSSLRSEDTAVYYCARDSSGWSRYYMDVWGQGTTVTVSS (SEQ ID NO: 173)
QVQLVQSGAEVKEPGSSVKVSCKASGGTFNSYAISWVRQAPGQGLEWMGGIIPLFGIAHYAQK

FQGRVTITADESTNTAYMDLSSLRSEDTAVYYCARKYSYVSGSPFGMDVWGQGTTVTVSS (SEQ ID NO: 174)
EVQLVESGGGLVQPGRSLRLSCAASGITFDDYGMHWVRQAPGKGLEWVSGISWNRGRIEYADS

VKGRFTISRDNAKNSLYLQMNSLRAEDTALYYCAKGRFRYFDWFLDYWGQGTLVTVSS

VL Sequences:
                                                (SEQ ID NO: 175)
MDTRAPTQLLGLLLLWLPGARCALVMTQTPSSTSTAVGGTVTIKCQASQSISVYLAWYQQKPG

QPPKLLIYSASTLASGVPSRFKGSRSGTEYTLTISGVQREDAATYYCLGSAGS (SEQ ID NO: 176)
EIVLTQSPATLSLSPGERATLSCRASQSVSSYLVWYQQKPGQAPRLLIYDASNRATGIPARFS

GSGSGTDFTLTISSLEPEDFAVYYCQQRSNWPRTFGQGTKVEIK (SEQ ID NO: 177)
EIVLTQSPATLSLSPGERATLSCRASQSVSSYLAWYQQKPGQAPRLLIYDASNRATGIPARFS

GSGSGTDFTLTISSLEPEDFAVYYCQQRSNWPTFGQGTKVEIK (SEQ ID NO: 178)
DIQMTQSPSSLSASVGDRVTITCRASQGISSWLAWYQQKPEKAPKSLIYAASSLQSGVPSRFS

GSGSGTDFTLTISSLQPEDFATYYCQQYNSYPYTFGQGTKLEIK
```

```
                                                (SEQ ID NO: 179)
EIVLTQSPGTLSLSPGERATLSCRASQSVSSSYLAWYQQKPGQAPRLLIYGASSRATGIPDRF

SGSGSGTDFTLTISRLEPEDFAVYYCQQYGSSPWTFGQGTKVEIK (SEQ ID NO: 180)
EIVLTQSPGTLSLSPGERATLSCRASQSVSSSYLAWYQQKPGQAPRLLIYGASSRATGIPDRF

SGSGSGTDFTLTISRLEPEDFAVYYCQQYGSSPFGGGTKVEIK (SEQ ID NO: 181)
EIVLTQSPATLSLSPGERATLSCRASQSVSSYLAWYQQKPGQAPRLLIYDASNRATGIPARFS

GSGSGTDFTLTISSLEPEDFAVYYCQQRSNWPTFGQGTRLEIK (SEQ ID NO: 182)
AIQLTQSPSSLSASVGDRVTITCRASQGISSALAWYQQKPGKAPKLLIYDASSLESGVPSRFS

GSGSGTDFTLTISSLQPEDFATYYCQQFNSYPFTFGPGTKVDIK
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                                (SEQ ID NO: 183)
EVQLLESGGGLVQPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGQGTLVTVSS

VL Sequences:
                                                (SEQ ID NO: 184)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                                (SEQ ID NO: 185)
EVKLQESGPSLVKPSQTLSLTCSVTGYSITSDYWNWIRKFPGNKLEYVGYISYTGSTYYNPSL

KSRISITRDTSKNQYYLQLNSVTSEDTATYYCARYGGWLSPFDYWGQGTTLTVSS (SEQ ID NO: 186)
EVQLQESGPGLVAPSQSLSITCTVSGFSLTTYSINWIRQPPGKGLEWLGVMWAGGGTNSNSVL

KSRLIISKDNSKSQVFLKMNSLQTDDTARYYCARYYGNSPYYAIDYWGQGTSVTVSS (SEQ ID NO: 187)
EVKLQESGPSLVKPSQTLSLTCSVTGYSIISDYWNWIRKFPGNKLEYLGYISYTGSTYYNPSL

KSRISITRDTSKNQYYLQLNSVTTEDTATYYCARRGGWLLPFDYWGQGTTLTVSS (SEQ ID NO: 188)
EVKLQESGPSLVKPGASVKLSCKASGYTFTSYDINWVKQRPGQGLEWIGWIFPRDNNTKYNEN

FKGKATLTVDTSSTTAYMELHSLTSEDSAVYFCTKENWVGDFDYWGQGTTLTLSS (SEQ ID NO: 189)
EVQLQQSGPDLVTPGASVRISCQASGYTFPDYYMNWVKQSHGKSLEWIGDIDPNYGGTTYNQK

FKGKAILTVDRSSSTAYMELRSLTSEDSAVYYCARGALTDWGQGTSLTVSS (SEQ ID NO: 190)
EIVLTQSPATLSLSPGERATLSCRASSSVSYIYWFQQKPGQSPRPLIYAAFNRATGIPARFSG

SGSGTDYTLTISSLEPEDFAVYYCQQWSNNPLTFGQGTKVEIK (SEQ ID NO: 191)
QVQLVQSGAEVKKPGASVKVSCKASGYTFPDYYMNWVRQAPGQGLEWMGDIDPNYGGTNYAQK

FQGRVTMTRDTSISTAYMELSRLRSDDTAVYYCARGALTDWGQGTMVTVSS (SEQ ID NO: 192)
QVQLVQSGAEVKKPGASVKVSCKASGYTFPDYYMNWVRQAPGQSLEWMGDIDPNYGGTNYNQK

FQGRVTMTRDTSISTAYMELSRLRSDDTAVYYCARGALTDWGQGTMVTVSS
```

```
                                                    (SEQ ID NO: 193)
EVQLVQSGAEVKKPGASVKVSCKASGYTFPDYYMNWVRQAPGQSLEWMGDIDPNYGGTNYNQK

FQGRVTMTVDRSSSTAYMELSRLRSDDTAVYYCARGALTDWGQGTMVTVSS (SEQ ID NO: 194)
EVQLVESGGGLVQPGRSLRLSCTASGYTFPDYYMNWVRQAPGKGLEWVGDIDPNYGGTTYAAS

VKGRFTISVDRSKSIAYLQMSSLKTEDTAVYYCTRGALTDWGQGTMVTVSS (SEQ ID NO: 195)
EVQLVESGGGLVQPGRSLRLSCTASGYTFPDYYMNWVRQAPGKGLEWVGDIDPNYGGTTYNAS

VKGRFTISVDRSKSIAYLQMSSLKTEDTAVYYCARGALTDWGQGTMVTVSS

VL Sequences:
                                                    (SEQ ID NO: 196)
DIVMTQSHKLMSTSVGDRVSITCKASQDVGTAVAWYQQKPGQSPKLLIYWASTRHTGVPDRFT

GSGSGTDFTLTISNVQSEDLADYFCQQDSSYPLTFGAGTKVELK (SEQ ID NO: 197)
DIVTTQSHKLMSTSVGDRVSITCKASQDVGTAVAWYQQKPGQSPKLLIYWASTRHTGVPDRFT

GSGSGTDFTLTISNVQSEDLADYFCQQDSSYPLTFGAGTKVELK (SEQ ID NO: 198)
DIVMTQSPSSLAVSVGEKVSMGCKSSQSLLYSSNQKNSLAWYQQKPGQSPKLLIDWASTRESG

VPDRFTGSGSGTDFTLTISSVKAEDLAVYYCQQYYGYPLTFGAGTKLELK (SEQ ID NO: 199)
DIVMTQSPAIMSASPGEKVTMTCSASSSIRYMHWYQQKPGTSPKRWISDTSKLTSGVPARFSG

SGSGTSYALTISSMEAEDAATYYCHQRSSYPWTFGGGTKLEIK (SEQ ID NO: 200)
QIVLSQSPAILSASPGEKVTMTCRASSSVSYIYWFQQKPGSSPKPWIYATFNLASGVPARFSG

SGSGTSYSLTISRVETEDAATYYCQQWSNNPLTFGAGTKLELK (SEQ ID NO: 201)
EIVLTQSPATLSLSPGERATLSCRASSSVSYIYWFQQKPGQAPRLLIYAAFNRATGIPARFSG

SGSGTDYTLTISSLEPEDFAVYYCQQWSNNPLTFGQGTKVEIK (SEQ ID NO: 202)
QIVLTQSPATLSLSPGERATLSCRASSSVSYIYWFQQKPGQSPRPLIYATFNLASGIPARFSG

SGSGTSYTLTISRLEPEDFAVYYCQQWSNNPLTFGQGTKVEIK (SEQ ID NO: 203)
DIQLTQSPSSLSASVGDRVTITCRASSGVSYIYWFQQKPGKAPKLLIYAAFNLASGVPSRFSG

SGSGTEYTLTISSLQPEDFATYYCQQWSNNPLTFGQGTKVEIK (SEQ ID NO: 204)
DIQLTQSPSSLSASVGDRVTITCRASSGVSYIYWFQQKPGKAPKPLIYAAFNLASGVPSRFSG

SGSGTEYTLTISSLQPEDFATYYCQQWSNNPLTFGQGTKVEIK (SEQ ID NO: 205)
DIQLTQSPSILSASVGDRVTITCRASSSVSYIYWFQQKPGKAPKPLIYATFNLASGVPSRFSG

SGSGTSYTLTISSLQPEDFATYYCQQWSNNPLTFGQGTKVEIK
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                              (SEQ ID NO: 206)
QVQLVQSGAEVKKPGASVKVSCKASGYTFTSYGISWVRQAPGQGLEWMGWISAYNGNTNYAQK LQGRVTMTTDTSTSTAYMELRSLRSDDTAVYYCARALPSGTILVGGWFDPWGQGTLVTVSS
                                              (SEQ ID NO: 207)
EVQLVQSGGGVVQPGRSLRLSCAASGFTFSSYALSWVRQAPGKGLEWVSAISGGGGSTYYADS VKGRFTISRDNSKNTLYLQMNSLRAEDTAVYYCAKDVFPETFSMNYGMDVWGQGTLVTVSS
                                              (SEQ ID NO: 208)
QVQLVQSGGGVVQPGGSLRLSCAASGFTFDDYAMHWVRQAPGKGLEWVSLISGDGGSTYYADS

VKGRFTISRDNSKNSLYLQMNSLRTEDTALYYCAKVLLPCSSTSCYGSVGAFDIWGQGTTVTV

SS
                                              (SEQ ID NO: 209)
QVQLVQSGGSVVRPGESLRLSCVASGFIFDNYDMSWVRQVPGKGLEWVSRVNWNGGSTTYADA

VKGRFTISRDNTKNSLYLQMNNLRAEDTAVYYCVREFVGAYDLWGQGTTVTVSS
                                              (SEQ ID NO: 210)
QVQLVQSGAEVKKPGATVKVSCKVFGDTFRGLYIHWVRQAPGQGLEWMGGIIPIFGTANYAQK

FQGRVTITTDESTSTAYMELSSLRSEDTAVYYCASGLRWGIWGWFDPWGQGTLVTVSS
                                              (SEQ ID NO: 211)
EVQLVQSGAELKKPGSSVKVSCKAFGGTFSDNAISWVRQAPGQGPEWMGGIIPIFGKPNYAQK

FQGRVTITADESTSTAYMVLSSLRSEDTAVYYCARTMVRGFLGVMDVWGQGTTVTVSS
                                              (SEQ ID NO: 212)
QVQLVQSGGGLVQPGGSLRLSCAASGFTFSSYAMSWVRQAPGKGLEWVSAISGSGGSTYYADS

VKGRFTISRDNSKNTLYLQMNSLRAEDTAVYYCAKDQFVTIFGVPRYGMDVWGQGTTVTVSS
                                              (SEQ ID NO: 213)
QVQLVQSGAEVKKPGSSVKVSCKASGGTFSSYAISWVRQAPGQGLEWMGGIIPIFGTANYAQK

FQGRVTITADKSTSTAYMELSSLRSEDTAVYYCARGRQMFGAGIDFWGPGTLVTVSS
                                              (SEQ ID NO: 214)
EVQLVESGAEVKKPGSSVKVSCKVSGGTFGTYALNWVRQAPGQGLEWMGRIVPLIGLVNYAHN

FEGRISITADKSTGTAYMELSNLRSDDTAVYYCAREVYGGNSDYWGQGTLVTVSS
                                              (SEQ ID NO: 215)
QVQLVQSGGEVKKPGASVKVSCKASGYTLSSHGITWVRQAPGQGLEWMGWISAHNGHASNAQK

VEDRVTMTTDTSTNTAYMELRSLTADDTAVYYCARVHAALYYGMDVWGQGTLVTVSS
                                              (SEQ ID NO: 216)
QVQLQESGGGVVQPGRSLRLSCSASGFTFSRHGMHWVRQAPGKGLEWVAVISHDGSVKYYADS

MKGRFSISRDNSNNTLYLQMDSLRADDTAVYYCARGLSYQVSGWFDPWGQGTLVTVSS
                                              (SEQ ID NO: 217)
NFMLTQPHSVSESPGKTVTISCTRSSGSIASNYVQWYQQRPGSSPTTVIYEDNQRPSGVPDRF

SGSIDTSSNSASLTISGLKTKDEADYYCQSYDGITVIFGGGTKLTVL
                                              (SEQ ID NO: 218)
NFMLTQPHSVSGSPGKTVTLPCTRSSGSIASHYVQWYQQRPGSAPTTVIYEDNKRPSGVPDRF

SGSIDSSSNSASLSISGLKTEDEADYYCQSYDSSNRWVFGGGTKLTVL
                                              (SEQ ID NO: 219)
LPVLTQPASLSASPGASASLTCTLRSGLNVGSYRIYWYQQKPGSRPQYLLNYKSDSNKQQASG

VPSRFSGSKDASANAGILLISGLQSEDEADYYCMIWYSSAVVFGGGTKLTVL
```

-continued

VL Sequences:

(SEQ ID NO: 220)
NFMLTQPHSVSESPGKTVTISCTRSSGNIASNYVQWYQQRPGSAPTTVIYEDNQRPSGVPDRF
SGSIDSSSNSASLTISGLKTEDEADYYCQSYDSSNLWVFGGGTKLTVL (SEQ ID NO: 221)
SSELTQDPAVSVALGQTVRITCQGDSLRSYYASWYQQKPGQAPVLVIYGKNNRPSGIPDRFSG
SSSGNTASLTITGAQAEDEADYYCNSRDSSGNHYVFGTGTKVTVL (SEQ ID NO: 222)
LPVLTQAPSVSVAPGKTARITCGGSDIGRKSVHWYQQKPGQAPALVIYSDRDRPSGISERFSG
SNSGNTATLTISRVEAGDEADYYCQVWDNNSDHYVFGAGTELIVL (SEQ ID NO: 223)
QSALTQPASVSGSPGQSITISCTGTSSDVGGYNYVSWYQQHPGKAPKLMIYDVSNRPSGVSNR
FSGSKSGNTASLTISGLQAEDEADYYCSSYTSSTLPFGGGTKLTVL (SEQ ID NO: 224)
EIVLTQSPATLSLSPGERATLSCRASQSIGNSLAWYQQKPGQAPRLLMYGASSRATGIPDRFS
GSGAGTDFTLTISSLEPEDFATYYCQQHTIPTFSFGPGTKVEVK (SEQ ID NO: 225)
DIVMTQTPSFLSASIGDRVTITCRASQGIGSYLAWYQQRPGEAPKLLIYAASTLQSGVPSRFS
GSGSGTDFTLTISNLQPEDFATYYCQQLNNYPITFGQGTRLEIK (SEQ ID NO: 226)
QSALTQPPSVSVSPGQTANIPCSGDKLGNKYAYWYQQKPGQSPVLLIYQDIKRPSRIPERFSG
SNSADTATLTISGTQAMDEADYYCQTWDNSVVFGGGTKLTVL (SEQ ID NO: 227)
NFMLTQPHSVSESPGKTVTISCTRSSGSIDSNYVQWYQQRPGSAPTTVIYEDNQRPSGVPDRF
SGSIDSSSNSASLTISGLKTEDEADYYCQSYDSNNRHVIFGGGTKLTVL (SEQ ID NO: 228)
NFMLTQPHSVSESPGKTVTISCTRSSGNIGTNYVQWYQQRPGSAPVALIYEDYRRPSGVPDRF
SGSIDSSSNSASLIISGLKPEDEADYYCQSYHSSGWEFGGGTKLTVL (SEQ ID NO: 229)
QSVLTQPPSVSVAPGQTARITCGGNNIGSKGVHWYQQKPGQAPVLVVYDDSDRPSGIPERFSG
SNSGNTATLTISRVEAGDEADYYCQVWDSSSDHWVFGGGTKLTVL (SEQ ID NO: 230)
NFMLTQPHSVSESPGKTVTISCTRSSGSIASNYVQWYQQRPGSAPTTVIYEDNQRPSGVPDRF
SGSIDSSSNSASLTISGLKTEDEADYYCQSYDSTTPSVFGGGTKLTVL (SEQ ID NO: 231)
QVQLVQSGAEVKKPGASVKVSCKASGYTFTSYGISWVRQAPGQGLEWMGWTSPHNGLTAFAQI
LEGRVTMTTDTSTNTAYMELRNLTFDDTAVYFCAKVHPVFSYALDVWGQGTLVTVSS (SEQ ID NO: 232)
EVQLVESGAEVMNPGSSVRVSCRGSGGDFSTYAFSWVRQAPGQGLEWMGRIIPILGIANYAQK
FQGRVTITADKSTSTAYMELSSLRSDDTAVYYCARDGYGSDPVLWGQGTLVTVSS (SEQ ID NO: 233)
EVQLVQSGAEVKKPGASVKVSCKASGYTFTNYGISWVRQAPGQGLEWMGWISAYNGNTNYAQK
VQGRVTMTTDTSTSTGYMELRSLRSDDTAVYYCARGDFRKPFDYWGQGTLVTVSS

In some embodiments, the PDL1 binding domain comprises or is derived from an antibody sequence or antigen-binding fragment thereof that includes a combination of a VH sequence and a VL sequence selected from the group consisting of:

VH Sequences:

(SEQ ID NO: 234)
EVQLVQSGPELKKPGASVKMSCKASGYTFTSYVMHWVKQAPGQRLEWIGYVNPFNDGTKYNEM

FKGRATLTSDKSTSTAYMELSSLRSEDSAVYYCARQAWGYPWGQGTLVTVSS (SEQ ID NO: 235)
EVQLVQSGAEVKKPGASVKMSCKASGYTFTSYVMHWVKQAPGQRLEWIGYVNPFNDGTKYNEM

FKGRATLTSDKSTSTAYMELSSLRSEDTAVYYCARQAWGYPWGQGTLVTVSS (SEQ ID NO: 236)
EVQLVQSGAEVKKPGASVKMSCKASGYTFTSYVMHWVRQAPGQRLEWIGYVNPFNDGTKYNEM

FKGRATLTSDKSTSTAYMELSSLRSEDTAVYYCARQAWGYPWGQGTLVTVSS (SEQ ID NO: 237)
EVQLVQSGAEVKKPGASVKVSCKASGYTFTSYVMHWVRQAPGQRLEWIGYVNPFNDGTKYNEM

FKGRATLTSDKSTSTAYMELSSLRSEDTAVYYCARQAWGYPWGQGTLVTVSS (SEQ ID NO: 238)
EVQLVQSGAEVKKPGASVKVSCKASGYTFTSYVMHWVRQAPGQRLEWIGYVNPFNDGTKYNEM

FKGRATITSDKSTSTAYMELSSLRSEDTAVYYCARQAWGYPWGQGTLVTVSS

VL Sequences:

(SEQ ID NO: 239)
DIVLTQSPASLALSPGERATLSCRATESVEYYGTSLVQWYQQKPGQPPKLLIYAASSVDSGVP

SRFSGSGSGTDFTLTINSLEEEDAAMYFCQQSRRVPYTFGQGTKLEIK (SEQ ID NO: 240)
DIVLTQSPATLSLSPGERATLSCRATESVEYYGTSLVQWYQQKPGQPPKLLIYAASSVDSGVP

SRFSGSGSGTDFTLTINSLEAEDAAMYFCQQSRRVPYTFGQGTKLEIK (SEQ ID NO: 241)
EIVLTQSPATLSLSPGERATLSCRATESVEYYGTSLVQWYQQKPGQPPKLLIYAASSVDSGVP

SRFSGSGSGTDFTLTINSLEAEDAAMYFCQQSRRVPYTFGQGTKLEIK (SEQ ID NO: 242)
DIVLTQSPATLSLSPGERATLSCRATESVEYYGTSLVQWYQQKPGQPPKLLIYAASSVDSGVP

SRFSGSGSGTDFTLTINSLEAEDAATYFCQQSRRVPYTFGQGTKLEIK

In some embodiments, the PDL1 binding domain comprises or is derived from an antibody sequence or antigen-binding fragment thereof that includes a combination of a VH sequence and a VL sequence selected from the group consisting of:

VH Sequences:

(SEQ ID NO: 243)
EVQLVQSGAEVKKPGSSVKVSCKASGGTFSSYAISWVRQAPGQGLEWMGGIIPIFGTANYAQK

FQGRVTITADKSTSTAYMELSSLRSEDTAVYYCAREGTIYDSSGYSFDYWGQGTLVTVSS (SEQ ID NO: 244)
EVQLVQSGAEVKKPGSSVKVSCKASGGTFSSYAISWVRQAPGQGLEWMGIINPSGGSTSYAQK

FQGRVSMTRDTSTSTVYMELSSLTSEDTAVYYCARDLFPHIYGNYYGMDIWGQGTTVTVSS (SEQ ID NO: 245)
QVQLVQSGAEVKKPGSSVKVSCKASGGTFSSYAISWVRQAPGQGLEWMGGIIPIFGTANYAQK

FQGRVTITADKSTSTAYMELSSLRSEDTAVYYCARLAVPGAFDIWGQGTMVTVSS

-continued (SEQ ID NO: 246)
EVQLVESGGGVVQPGRSLRLSCAASGFTFSSYAMHWVRQAPGKGLAVISYDGSNKYYADSVKG
RFTISRDNSKNTLYLQMNSLRAEDTAVYYCARGQWLVTELDYWGQGTLVTVSS (SEQ ID NO: 247)
EVQLVESGSEVEKPGSSVKVSCKASGGTFSDSGISWVRQAPGQGLEWMGGIIPMFATPYYAQK
FQDRVTITADESTSTVYMELSGLRSDDTAVFYCARDRGRGHLPWYFDLWGRGTLVTVSS (SEQ ID NO: 248)
EVQLVESGAEVKKPGSSVKVSCKASGGTFSSYAISWVRQAPGQGLEWMGGIIPIFGTANYAQK
FQGRVTITADESTSTAYMELSSLRSEDTAVYYCARAPYYYYYMDVWGQGTTVTVSS (SEQ ID NO: 249)
EVQLLESGAEVKKPGSSVKVSCKASGGTLSRYALSWVRQAPGQGPEWVGAIIPIFGTPHYSKK
FQDRVIITVDTSTNTAFMELSSLRFEDTALYFCARGHDEYDISGYHRLDYWGQGTLVTVSS (SEQ ID NO: 250)
QVQLVQSGSELKKPGSSVKVSCKASGYSFSGYYIHWVRQAPGQGLEWMGWIDPNSGVTNYVRR
FQGRVTMTRDTSLSTAYMELSGLTADDTAVYYCARDENLWQFGYLDYWGQGTLVTVSS (SEQ ID NO: 251)
QVQLVQSGAEVKKPGSSVKVSCKASGGTFSRYGVHWVRQAPGQGLEWMGRLIPIVSMTNYAQK
FQDRVSITTDKSTGTAYMELRSLTSEDTALYYCASVGQQLPWVFFAWGQGTLVTVSS (SEQ ID NO: 252)
QVQLVESGGGVVQPGRSLRLSCAASGFTFSSYAMHWVRQAPGKGLEWVAVISFDGSNKYYADS
VRGRFTISRDNSKNTLYLQMNSLRTEDTAVYYCARGWLDRDIDYWGQGTLVTVSS (SEQ ID NO: 253)
EVQLVESGGGVVQPGRSLRLSCAASGFTFSSYAMHWVRQAPGKGLEWVAVISFDGSNKYYADS
VRGRFTISRDNSKNTLYLQMNSLRTEDTAVYYCARGWLDRDIDYWGQGTLVTVSS (SEQ ID NO: 254)
EVQLVQSGGGLVQPGGSLRLSCAASGFTFSDYGMHWVRQPPGKGLEWLAVISYDGSYKIHADS
VQGRFTISRDNAKNSVFLQMNSLKTEDTAVYYCTTDRKWLAWHGMDVWGQGTTVTVSS (SEQ ID NO: 255)
EVQLVQSGAEVKKPGSSVKVSCKASGGTFSSYAISWVRQAPGQGLEWMGGIIPIFGTANYAQK
FQGRVTITADESTSTAYMELSSLRSEDTAVYYCARDGIVADFQHWGQGTLVTVSS (SEQ ID NO: 256)
EVQLVESGAEVKKPGASVKVSCKASGDTFSRYGITWVRQAPGRGLEWMGNIVPFFGATNYAQK
FQGRLTITADKSSYTSYMDLSSLRSDDTAVYYCARDHFYGSGGYFDYWGQGTLVTVSS (SEQ ID NO: 257)
EVQLLESGAEVKKPGASVKVSCKASGYTFNSYDINWVRQAPGQGLEWMGGIIPVFGTANYAES
FQGRVTMTADHSTSTAYMELNNLRSEDTAVYYCARDRWHYESRPMDVWGQGTTVTVSS (SEQ ID NO: 258)
EVQLVESGGGLVRPGGSLRLACAASGFSFSDYYMTWIRQAPGRGLEWIAYISDSGQTVHYADS
VKGRFTISRDNTKNSLFLQVNTLRAEDTAVYYCAREDLLGYYLQSWGQGTLVTVSS (SEQ ID NO: 259)
QVQLQQSGPGLVKPSQTLSLTCAISGDSVSSNSAAWNWIRQSPSRGLEWLGRTYYRSKWYNDY
AVSVKSRITINPDTSKNQFSLQLNSVTPEDTAVYYCARDEPRAVAGSQAYYYYGMDVWGQGTT
VTVSS (SEQ ID NO: 260)
EVQLVQSGAEVKKPGASVKVSCKASGYTFTSYYMHWVRQAPGQGLEWMGIINPSDGSTSYAQK
FQGRVTMTRDTSTSTVHMELSSLRSEDTAVYYCARDLFPHIYGNYYGMDIWGQGTTVTVSS -continued

```
                                                 (SEQ ID NO: 261)
QMQLVQSGGGVVQPGRSLRLSCAASGFTFSSYAMHWVRQAPGKGLEWVAVISFDGSNKYYADS

VRGRFTISRDNSKNTLYLQMNSLRTEDTAVYYCARGWLDRDIDYWGQGTLVTVSS (SEQ ID NO: 262)
QVQLVQSGGGVVQPGRSLRLSCAASGFTFSSYAMHWVRQAPGKGLEWVAVISFDGSNKYYADS

VRGRFTISRDNSKNTLYLQMNSLRTEDTAVYYCARGWLDRDIDYWGQGTLVTVSS

VL Sequences:
                                                 (SEQ ID NO: 263)
QSVLTQPPSVSAAPGQKVTISCSGNNSNIANNYVSWYQQLPGTAPKLLIYDNNYRPSGIPDRF

SGSKSGTSATLDITGLQTGDEADYYCGVWDGSLTTGVFGGGTKLTVL (SEQ ID NO: 264)
AIQMTQSPSSLSASVGDRVTITCRASQGISNYLAWYQQKPGKVPKLLIYAASTLESGVPSRFS

GSGSGTDFTLTISSLQPEDLATYYCQQLHTFPLTFGGGTKVEIK (SEQ ID NO: 265)
QPVLTQPPSASGSPGQSVTISCTGTSSDVGAYNFVSWYRQHPGKAPKLMIYEVNKRPSGVPDR

FSGSKSGNTASLTVSGLQAEDEADYYCSSYAGTNSLGIFGTGTKLTVL (SEQ ID NO: 266)
QSVVTQPPSVSAAPGQKVTISCSGSSSDIGNHYVSWYQQLPGTAPKLLIYDNNQRPSGIPDRF

SGSKSGTSATLAITGLQTGDEADYYCGTWDNSLSPHLLFGGGTKLTVL (SEQ ID NO: 267)
QSVLTQPPSVSAAPGQKVTISCSGSSSNMGNNYVSWYKQVPGTAPKLLIYENDKRPSGIPDRF

SGSKSGTSATLGITGLQTGDEADYYCGTWDNSLSGFVFASGTKVTVL (SEQ ID NO: 268)
QSALTQPASVSGSLGQSVTISCTGSSSDVGSYNLVSWYQQHPGKAPNLMIYDVSKRSGVSNRF

SGSKSGNTASLTISGLQAEDEADYYCSSYTGISTVVFGGGTKLTVL (SEQ ID NO: 269)
QSVLTQPASVSGSPGQSITISCTGTSSDVGSYNLVSWYQQHPGKAPKLMIYEVSKRPSGVSNR

FSGSKSGNTASLTISGLQAEDEADYYCSSYGGFNNLLFGGGTKLTVL (SEQ ID NO: 270)
DIVMTQSPSSLSASIGDRVTITCRASQRISAYVNWYQQKPGKAPKVLIYAASSLRSGVPSRFS

GSGSGTDFTLTISSLQPEDFATYYCQQTYSSPWTFGQGTKVEIK (SEQ ID NO: 271)
QSVLTQPPSASGSPGQSVTISCTGTSSDIGGYDSVSWYQQHPGKAPKLMIYDVSKRPSGVSNR

FSGSKSGNTASLTISGLQAEDEADYYCSSYTSSSIFFYVFGTGTKVTVL (SEQ ID NO: 272)
LPVLTQPASVSGSPGQSITISCTGTTSDIGGYDYVSWYQQHPGKAPKLMIYDVSKRPSGVSNR

FSGSKSGNTASLTISGLQAEDEADYYCSSYTSSSTHVFGTGTKLTVL (SEQ ID NO: 273)
QSALTQPASVSGSPGQSITISCTGTSSDVGGYNYVSWYQQHPGKAPKLMIYDVSNRPSGVSNR

FSGSKSGNTASLTISGLQAEDEADYYCSSYRSSTLGPVFGGGTKLTVL (SEQ ID NO: 274)
QAGLTQPPSVSEAPRQRVTISCSGSSSNIGNNAVNWYQQLPGKAPKLLIYYDDLLPSGVSDRF

SGSKSGTSASLAISGLQSEDEADYYCAAWDDSLNGYVFGTGTKLTVL (SEQ ID NO: 275)
QSALTQPRSVSGSPGQSVTISCTGTSSDVGGYNYVSWYQQHPGKAPKLMIYDVSKRPSGVPDR

FSGSKSGNTASLTISGLQAEDEADYYCSSYTSSTTHVFGTGTKVTVL (SEQ ID NO: 276)
QSVVTQPPSVSAAPGQKVTISCSGSSSNIGNNYVSWYQQLPGTAPKLLIYDNNKRPSGIPDRF

SGSKSGTSATLGITGLQTGDEADYYCGTWDSSLSVWVFGGGTQLTVL
```

```
                                                    (SEQ ID NO: 277)
QSVLTQPASVSGSPGQSITISCTGTSSDVGGYNYVSWYQQHPGRAPRLMIYDVSNRPSGVSNR

FSGSKSGNTASLTISGLQAEDEGDYYCSSYTSGGTLGPVFGGGTKLTVL (SEQ ID NO: 278)
QAGLTQPPSASGTPGQRVTISCSGSSSNIGSNTVNWYQQLPGTAPKLLIYSNNQRPSGVPDRF

SGSKSGTSASLAISGLQSEDEADYYCAAWDDSLNGWVFGGGTKLTVL (SEQ ID NO: 279)
AIRMTQSPSSLSASVGDRVTITCRASQSISNYLNWYQQRPGKAPNLLIYAASSLQSGVPSRFS

GSGSGTDFTLTISSLQPEDFATYYCQQTYSTPYTFGQGTKLEIK (SEQ ID NO: 280)
QSVLTQPASVSGSPGQSITISCTGTSSDVGGYNYVSWYRQHPGKAPKLMIYDVSYRPSGVSNR

FSGSKSGNTASLTISGLQAEDEADYYCSSYTDSSTRYVFGTGTKLTVL (SEQ ID NO: 281)
QPVLTQPPSASGTPGQRVAISCSGSRSNIEINSVNWYQQLPGTAPKLLIYDNNKRPSGIPDRF

SGSKSGTSATLGITGLQTGDEADYYCGSWDSSLSADVFGTGTKLTVL (SEQ ID NO: 282)
QSVLTQPPSVSAAPGKKVTISCSGSSSNIGNNYVSWYQQLPGTAPKLLIYRNNQRPSGVPDRF

SGSKSGTSASLAISGLQSEDEADYYCATWDDSLNGWVFGGGTKLTVL (SEQ ID NO: 283)
QSVVTQPPSVSGAPGQRVTISCTGSSSNIGAGYDVHWYQQLPGTAPKLLIYGNNNRHSGVPDR

FSGSKSGTSASLAITGLQAEDEAEFFCGTWDSRLTTYVFGSGTKLTVL (SEQ ID NO: 284)
QSVVTQPPSVSAAPGQKVTISCSGSSSNIGNNYVSWYQQLPGTAPKLLIYDNNKRPSGIPDRF

SGSKSGTSATLGITGLQTGDEADYYCGTWDSSLSAVVFGGGTKLTVL (SEQ ID NO: 285)
VIWMTQSPSSLSASVGDRVTITCAASSLQSWYQQKPGKAPKLLIYEASTLESGVPSRFSGSGS

GTEFTLTISSLQPEDFATYYCQQSYSTPYTFGQGTKLEIK (SEQ ID NO: 286)
QSVVTQPPSVSAAPGQKVTISCSGSSSNIGNNYVSWYQQVPGTAPKLLIYDNNKRPSGIPDRF

SGSNSDTSATLGITGLQTGDEADYYCGTWDSSLSAWVFGGGTKLTVL (SEQ ID NO: 287)
QSVVTQPPSVSAAPGQKVTISCSGSSSNIGNNYVSWYQQLPGTAPKLLIYDNNKRPSGIPDRF

SGSKSGTSATLGITGLQTGDEADYYCGTWDSSLSAGSVVFGGGTKLTVL (SEQ ID NO: 288)
SYELMQPPSVSVAPGKTATIACGGENIGRKTVHWYQQKPGQAPVLVIYYDSDRPSGIPERFSG

SNSGNTATLTISRVEAGDEADYYCLVWDSSSDHRIFGGGTKLTVL (SEQ ID NO: 289)
SYELMQPPSVSVAPGKTATIACGGENIGRKTVHWYQQKPGQAPVLVIYYDSDRPSGIPERFSG

SNSGNTATLTISRVEAGDEADYYCQVWDSSSDHRIFGGGTKLTVL (SEQ ID NO: 290)

SNSGNTATLTISRVEAGDEADYYCQVWDSSSDHRIFGGGTKLTVL (SEQ ID NO: 291)
SYELMQPPSVSVAPGKTATIACGGENIGRKTVHWYQQKPGQAPVLVIYYDSDRPSGIPERFSG

SNSGNTATLTISRVEAGDEADYYCQVWDSSSDHRIFGGGTKLTVL
```

In some embodiments, the PDL1 binding domain comprises or is derived from an antibody sequence or antigen-binding fragment thereof that includes a combination of a heavy chain (HC) and a light chain sequence (LC) selected from the group consisting of:

HC Sequences:

(SEQ ID NO: 292)
QVQLVQSGVEVKKPGASVKVSCKASGYTFTNYYMYWVRQAPGQGLEWM
GGINPSNGGTNFNEKFKNRVTLTTDSSTTTAYMELKSLQFDDTAVYYC
ARRDYRFDMGFDYWGQGTTVTVSSASTKGPSVFPLAPCSRSTSESTAA
LGCLVKDYFPEPVTVSWNSGALTSGVHTFPAVLQSSGLYSLSSVVTVP
SSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTI
SKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEAL
HNHYTQKSLSLSLGK (SEQ ID NO: 293)
QVQLVESGGGVVQPGRSLRLDCKASGITFSNSGMHWVRQAPGKGLEWV
AVIWYDGSKRYYADSVKGRFTISRDNSKNTLFLQMNSLRAEDTAVYYC
ATNDDYWGQGTLVTVSSASTKGPSVFPLAPCSRSTSESTAALGCLVKD
YFPEPVTVSWNSGALTSGVHTFPAVLQSSGLYSLSSVVTVPSSSLGTK
TYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQK
SLSLSLGK

LC Sequences:

(SEQ ID NO: 294)
EIVLTQSPATLSLSPGERATLSCRASKGVSTSGYSYLHWYQQKPGQAP
RLLIYLASYLESGVPARFSGSGSGTDFTLTISSLEPEDFAVYYCQHSR
DLPLTFGGGTKVEIKRTVAAPSVFIFPPSDEQLKSGTASVVCLLNNFY
PREAKVQWKVDNALQSGNSQESVTEQDSKDSTYSLSSTLTLSKADYEK
HKVYACEVTHQGLSSPVTKSFNRGEC (SEQ ID NO: 295)
EIVLTQSPATLSLSPGERATLSCRASQSVSSYLAWYQQKPGQAPRLLI
YDASNRATGIPARFSGSGSGTDFTLTISSLEPEDFAVYYCQQSSNWPR
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC

In some embodiments, the PDL1 binding domain comprises or is derived from an antibody sequence or antigen-binding fragment thereof that includes a combination of a VH sequence and a VL sequence selected from the group consisting of:

VH Sequences:

(SEQ ID NO: 296)
EVQLVESGGGLVQPGGSLRLSCAASGFTFSDSWIHWVRQAPGKGLEWV
AWISPYGGSTYYADSVKGRFTISADTSKNTAYLQMNSLRAEDTAVYYC
ARRHWPGGFDYWGQGTLVTVSSASTK (SEQ ID NO: 297)
EVQLVESGGGLVQPGGSLRLSCAASGFTFSDSWIHWVRQAPGKGLEWV
AWISPYGGSTYYADSVKGRFTISADTSKNTAYLQMNSLRAEDTAVYYC
ARRHWPGGFDYWGQGTLVTVSS

HC Sequences:

(SEQ ID NO: 298)
EVQLVESGGGLVQPGGSLRLSCAASGFTFSDSWIHWVRQAPGKGLEWV
AWISPYGGSTYYADSVKGRFTISADTSKNTAYLQMNSLRAEDTAVYYC
ARRHWPGGFDYWGQGTLVTVSSASTKGPSVFPLAPSSKSTSGGTAALG
CLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNA
KTKPREEQYASTYRVVSVLTVLHQDWLNGKEYKCKVSNKALPAPIEKT
ISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEA
LHNHYTQKSLSLSPG

VL Sequences:

(SEQ ID NO: 299)
DIQMTQSPSSLSASVGDRVTITCRASQDVSTAVAWYQQKPGKAPKLLI
YSASFLYSGVPSRFSGSGSGTDFTLTISSLQPEDFATYYCQQYLYHPA
TFGQGTKVEIKR

LC Sequences:

(SEQ ID NO: 300)
DIQMTQSPSSLSASVGDRVTITCRASQDVSTAVAWYQQKPGKAPKLLI
YSASFLYSGVPSRFSGSGSGTDFTLTISSLQPEDFATYYCQQYLYHPA
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC

In some embodiments, the PDL1 binding domain comprises or is derived from an antibody sequence or antigen-binding fragment thereof that includes a combination of a VH sequence and a VL sequence selected from the group consisting of:

VH Sequences:

(SEQ ID NO: 301)
EVQLVESGGGLVQPGGSLRLSCAASGFTFSRFWMSWVRQAPGKGLEWV
ANINQDGTEKYYVDSVKGRFTISRDNAKNSLYLQMNSLRAGDTAVYYC
ANTYYDFWSGHFDYWGQGTLVTVSS (SEQ ID NO: 302)
QEHLVESGGGVVQPGRSLRLSCEASGFTFSNFGMHWVRQAPGKGLEWV
AALWSDGSNKYYADSVKGRVTISRDNSKNTLYLQMNSLRAEDTAVYYC
ARGRGAPGIPIFGYWGQGTLVTVSS

-continued (SEQ ID NO: 303)
EVQLVESGGGLVKPGGSLRLSCAASGFTFSNAWMSWVRQAPGKGLEWV
GRIKRKTDGGTTDYAAPVKGRFTISRDDSKNTLHLQMNSLKTEDTAVY
YCTTDDIVVVPAVMREYYFGMDVWGQGTTVTVSS (SEQ ID NO: 304)
QVQLVQSGAEVKKPGASVQVSCKASGYSFTGYYIHWVRQAPGQGLEWM
GWINPNSGTKKYAHKFQGRVTMTRDTSIDTAYMILSSLISDDTAVYYC
ARDEDWNFGSWFDSWGQGTLVTVSS (SEQ ID NO: 305)
QVHLVQSGAEVKKPGASVKVSCKASGYTFTGYYIHWVRQAPGHGLEWM
GWLNPNTGTTKYIQNFQGRVTMTRDTSSSTAYMELTRLRSDDTAVYYC
ARDEDWNYGSWFDTWGQGTLVTVSS (SEQ ID NO: 306)
EVQLVESGGGVVRPGGSLRLSCAASGFTFDDYGMTWVRQAPGRGLEWV
SGIHWHGKRTGYADSVKGRFTISRDNAKKSLYLQMNSLKGEDTALYHC
VRGGMSTGDWFDPWGQGTLVIVSS (SEQ ID NO: 307)
EVQLVESGGGVVRPGGSLRLSCAASGFTFDDYGMTWVRQVPGKGLEWV
SGIHWSGRSTGYADSVKGRFTISRDNAKNSLYLQMNSLRAEDTALYYC
ARGGMSTGDWFDPWGQGTLVTVSS (SEQ ID NO: 308)
EVQLVESGGGLVQPGGSLRLSCAASGFTVGSNYMNWVRQAPGKGLEWV
SVIYSGGSTYYADSVKGRFTISRLTSKNTLYLQMSSLRPEDTAVYYCA
RGIRGLDVWGQGTTVTVSS (SEQ ID NO: 309)
EERLVESGGDLVQPGGSLRLSCAASGITVGTNYMNWVRQAPGKGLEWV
SVISSGGNTHYADSVKGRFIMSRQTSKNTLYLQMNSLETEDTAVYYCA
RGIRGLDVWGQGTMVTVSS (SEQ ID NO: 310)
QVQLVQSGAEVKMPGSSVRVSCKASGGIFSSSTISWVRQAPGQGLEWM
GEIIPVFGTVNYAQKFQDRVIFTADESTTTAYMELSSLKSGDTAVYFC
ARNWGLGSFYIWGQGTMVTVSS (SEQ ID NO: 311)
EVQLVESGGDLVHPGRSLRLSCAASGFPFDEYAMHWVRQVPGKGLEWV
SGISWSNNNIGYADSVKGRFTISRDNAKNSLYLQMNSLRPEDTAFYYC
AKSGIFDSWGQGTLVTVSS (SEQ ID NO: 312)
EVQLVESGGGVVQPGRSLRLSCAASGFTFSSYGMHWVRQAPGKGLEWV
TLISYEGRNKYYADSVKGRFTISRDNSKNTLYLQMNSLRAEDTAVYYC
AKDRTLYGMDVWGQGTTVTVSS (SEQ ID NO: 313)
QVTLRESGPALVKTTQTLTLTCTFSGFSLSTNRMCVTWIRQPPGKALE
WLARIDWDGVKYYNTSLKTRLTISKDTSKNQVVLTMTNMDPVDTATFY
CARSTSLTFYYFDWGQGTLVTVSS (SEQ ID NO: 314)
EVQLVESGGGLVQPGGSLRLSCAASEFTVGTNHMNWVRQAPGKGLEWV
SVIYSGGNTFYADSVKGRFTISRHTSKNTLYLQMNSLTAEDTAVYYCA
RGLGGMDVWGQGTTVTVSS (SEQ ID NO: 315)
EVQLVESGGGLVQRGESLRLYCAASGFTFSKYWMNWVRQAPGKGLEWV
ANIKGDGSEKYYVDSVKGRFTISRDNAKNSLYLQMNSLRAEDTAVYYC
ARDYWGSGYYFDFWGQGTLVTVSS (SEQ ID NO: 316)
EVQLVESGGGLVQSGGSLRLSCAASGFTFSSYWMSWVRQAPGKGLEWV
ANIKQDGSEKYYVDSVKGRFTISRDNAKNSLYLQMNSLRADDTAVYYC
ARDDIVVVPAPMGYYYYYFGMDVWGQGTTVTVSS (SEQ ID NO: 317)
EVQLVESGGGLVQPGRSLRLSCAASGFTFDDFAMHWVRQAPGKGLEWV
SGISWTGGNMDYANSVKGRFTISREDAKNSLYLQMNSLRAADTALYYC
VKDIRGIVATGGAFDIWGRGTMVTVSS (SEQ ID NO: 318)
EVQLVESGGGLVQPGGSLRLSCAASGFTVGTNYMNWVRQAPGKGLEWI
SVIYSGGSTFYADSVKGRFTISRQTSQNTLYLQMNSLRPEDTAVYYCA
RGIRGFDIWGQGTMVTVSS (SEQ ID NO: 319)
EVQLVESGGGLVQPGGSLRLSCAASGFTISTNYMNWVRQAPGKGLEWV
AVIYSSGSTYYIDSVKGRFTISRLTSKNTVYLQMSSLNSEDTAVYYCA
RGIRGFDIWGQGTMVTVSS (SEQ ID NO: 320)
EVQLVESGGGLVQPGRSLRLSCAASGFTIDDSAMHWVRQTPGKGLEWV
SGISWKSGSIGYADSVRGRFTISRDNAKNSLYLQMNSLRVEDTALYYC
VKDIRGNWNYGGNWFDPWGQGTLVTVSS (SEQ ID NO: 321)
EVQLVESGGGLVQPGGSLRLSCEASGFTVGVNHMNWVRQAPGKGLEWV
SVIFSSGRTFYGDYVKGRLTIFRQTSQNTVYLQMNSLRSEDTAIYYCA
RGIGGLDIWGRGTMVTVSS (SEQ ID NO: 322)
EVQLVESGGGLVQPGRSLRLSCAASGFTFDDYALHWVRQAPGKGLEWV
SGISWTGGTIDYADSVKGRFTISRDNAKNSLYLQMSSLRTEDTAIYYC
TRDIRGNWKYGGWFDPWGQGTLVTVSS (SEQ ID NO: 323)
QVQLVQSGTEVKKPGASVKVSCKASGYTFTAYYMHWVRQAPGQGLDWM
GWISPNSGFTNYAQKFQGRVTMTRDTSINTFYMELSGLRSDDTAVYYC
AREGSTHHNSFDPWGQGTLVTVSS (SEQ ID NO: 324)
EVQLVESGGGLVQPGGSLRLSCAASGFTVGTNFMNWVRQAPGKGLEWV
SAIYSGGTANYADSVKGRFTISRDTSRNTLYLQMNSLRTEDTAVYYCA
RGGGMDVWGQGTTVTVSS (SEQ ID NO: 325)
QVQLVQSGAEVKKPGSSVKVSCKASGGTFNTYVLSWVRQAPGQGLEWM

GEIIPILGAANYAQNFQGRVTFTTDESTNTAYMDLSSLRSEDTAVYYC

ARDRTSGGFDPWGQGTLVTVSS (SEQ ID NO: 326)
QVQLVQSGAEVEKPGASVKVSCKASGYIFTHYGISWVRQAPGQGLEWV

GWISPYNGYTDYAQKLQGRVTLTTDTSTTTAYMELRNLRSDDTAMYYC

SRGRGPYWSFDLWGRGTLVTVSS

VL Sequences:
(SEQ ID NO: 327)
DIQMTQSPSTLSASVGDRVTITCRASQSISNWLAWYQQKPGKAPKLLI

YKASSLESGVPSRFSGSGSGTEFTLTISSLQPDDFATYYCQQYHSYSY

TFGQGTKEIK (SEQ ID NO: 328)
DIQMTQSPSSLSASVGDRVTITCRASQGIRNDLGWYQQKPGKAPKRLI

YTASSLQSGVPSRFSGSGSGTEFTLTISSLQPEDFATYYCLQHNSYPL

TFGGGTKVAIK (SEQ ID NO: 329)
DIQMTQSPSSLSASVGDRVTITCRTSQGIRNDLGWYQQKPGKAPKRLI

YAASSLQSGVPSRFSGSGSGTEFTLTISSLQPEDFATYYCLQHNNYPY

TFGQGTKLEIK (SEQ ID NO: 330)
DIVMTQTPLSSPVTLGQPASISCRSSQTLVHGDGNTYLSWIQQRPGQP

PRLLIYKVSNQFSGVPDRFSGSGAGTDFTLKISRVEAEDVGLYFCMQA

THFPITFGQGTRLEIK (SEQ ID NO: 331)
DIVMTQTPLSSPVTLGQPASISCRSSPSLVHSDGNTYLSWLQQRPGQP

PRLLIYKISNRFSGVPDRFSGSGAGTDFTLKISRVEAEDVGVYYCMQA

THFPITFGQGTRLEIR (SEQ ID NO: 332)
DIQMTQSPSSLSASLGDRVTITCRASQSINSYLNWYQQKPGKAPKLLI

YVASSLQSGVPSRFSGSGSGTEFTLTISNLQPEDFATYYCQQSYSTPP

ITFGQGTRLEIK (SEQ ID NO: 333)
DIQMTQSPSSLSASVGDRVTITCRASQSISSYLNWYQQKPGKAPKLLI

YVASSLQSGVPSRFSGSGSGTDFTLTISSLQPEDFATYYCQQSYSTPP

ITFGQGTRLEIK (SEQ ID NO: 334)
DIQMTQSPSSLSASVGDRVTITCRASQTINIYLNWYQQKPGRAPRLLI

YAASSLQSGVPSRFSGSGSGTDFTLTISSLQPEDFATYYCHQSYSTPP

ITFGQGTRLEIK (SEQ ID NO: 335)
DIQMTQSPSSLSASVGDRVTITCRASQSMSSYLNWYQQKPGRAPKLLI

FAASSLQSGVPSRFSGSGSGTDFTLTISSLQPEDFATYYCQQSYSTPP

ITFGQGTRLEIK (SEQ ID NO: 336)
EIVLTQSPGTLSLSPGERATLSCRASQSFNFNYLAWYQQKPGQAPRLL

IYGASSRATGIPDRFSGSGSGTDFTLTINRLEPEDFGVFYCQQYESAP

WTFGQGTKVEIK (SEQ ID NO: 337)
DIQMTQSPSSLSASVGDRVTITCRASQSISSYLNWYQQKPGKLLIYAA

SSLQSGVPSRFSGGGSGTDFTLTISSLRPEDFATYYCQQSYCTPPITF

GQGTRLEIK (SEQ ID NO: 338)
DIQMTQSPSSLSASVGDRVTITCRASQSISSYLNWYQQKPGKAPKLLI

YAASSLQSGVPSRFSGSGSGTDFTLTISSLQPEDFATYYCQQSYSTPP

ITFGQGTRLEIK (SEQ ID NO: 339)
DRVTITCRASQVISNYLAWYQQKPGKVPRLLIYAASTLQSGVPSRFSG

SGSGTDFTLTISSLQPEDVATYYCQKYNSAPRTFGQGTKVEIK (SEQ ID NO: 340)
DIQMTQSPSSLSASVGDRVTITCRASQNINNYLNWYQQKPGKAPKLLI

YAASSFQNAVPSRFSGSGSGTDFTLTISSLQPEDFATYYCQQSYNTPL

TFGGGTKVEIK (SEQ ID NO: 341)
DIQMTQSPSSLSASVGDRVTITCRASQGIRNDLGWYQQKPGKAPKRLI

YAASSLQSGVPSRFSGSGSGTEFTLTISSLQPEDFATYYCLQHNSYPY

TFGQGTKLEIK (SEQ ID NO: 342)
DIQMTQSPSSLSASVGDRVTITCRASQSISSYLNWYQQKPGKAPKLLI

YAASSLQSGVPSRFSGSGSGTDFTLTISSLQPEDFATYYCQQSYSTPP

ITFGQGTRLEIK

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 343)
QSLEESGGRLVKPDETLTITCTVSGIDLSSNGLTWVRQAPGEGLEWIG

TINKDASAYYASWAKGRLTISKPSSTKVDLKITSPTTEDTATYFCGRI

AFKTGTSIWGPGTLVTVSS

VL Sequences:
(SEQ ID NO: 344)
AIVMTQTPSPVSAAVGGTVTINCQASESVYSNNYLSWFQQKPGQPPKL

LIYLASTLASGVPSRFKGSGSGTQFTLTISGVQCDDAATYYCIGGKSS

STDGNAFGGGTEVVVR

In some embodiments, the PDL1 binding domain comprises or is derived from an antibody sequence or antigen-binding fragment thereof that includes a combination of a VH sequence and a VL sequence selected from the group consisting of:

VH Sequences:

(SEQ ID NO: 345)
QMQLVQSGAEVKKPGSSVKVSCKASGGTFSSYAISWVRQAPGQGLEWM
GGIIPIFGTANYAQKFQGRVTITADESTSTAYMELSSLRSEDTAVYYC
ARGNIVATITPLDYWGQGTLVTVSS (SEQ ID NO: 346)
QPVLTQPPSVSAAPGQKVTISCSGSSSNIANNYVSWYQQLPGTAPKLL
IFANNKRPSGIPDRFSGSKSGTSAALDITGLQTGDEADYYCGTWDSDL
RAGVFGGGTKLTVL (SEQ ID NO: 347)
EVQLVQSGAEVKKPGSSVKVSCKASGGTFSSYAISWVRQAPGQGLEWM
GGIIPIFGTANYAQKFQGRVTITADKSTSTAYMELSSLRSEDTAVYYC
AREGTIYDSSGYSFDYWGQGTLVTVSS (SEQ ID NO: 348)
QVQLVESGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 349)
EVQLVESGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 350)
QVQLVESGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 351)
EVQLVESGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 352)
EVQLVESGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 353)
QVQLVESGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 354)
QVQLVQSGAEVKKPGSSVKVSCKASGGTFSRYGVHWVRQAPGQGLEWM
GRLIPIVSMTNYAQKFQDRVSITTDKSTGTAYMELRSLTSEDTALYYC
ASVGQQLPWVFFAWGQGTLVTVSS (SEQ ID NO: 355)
QMQLVQSGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 356)
QVQLVQSGGGVVQPGRSLRLSCAASGFTFSSYAMHWVRQAPGKGLEWV
AVISFDGSNKYYADSVRGRFTISRDNSKNTLYLQMNSLRTEDTAVYYC
ARGWLDRDIDYWGQGTLVTVSS (SEQ ID NO: 357)
QMQLVQSGAEVKKPGSSVKVSCKASGGTFSSYAYSWVRQAPGQGLEWM
GGIIPSFGTANYAQKFQGRVTITADESTSTAYMELSSLRSEDTAVYYC
ARGPIVATITPLDYWGQGTLVTVSS (SEQ ID NO: 358)
QMQLVQSGAEVKKPGSSVKVSCKASGGTFSSYAYSWVRQAPGQGLEWM
GGIIPIFGTANYAQKFQGRVTITADESTSTAYMELSSLRSEDTAVYYC
ARGPIVATITPLDYWGQGTLVTVSS (SEQ ID NO: 359)
QMQLVQSGAEVKKPGSSVKVSCKASGGTFSSYAYSWVRQAPGQGLEWM
GGIIPSFGTANYAQKFQGRVTITADESTSTAYMELSSLRSEDTAVYYC
ARGPIVATITPLDYWGQGTLVTVSS (SEQ ID NO: 360)
QMQLVQSGAEVKKPGSSVKVSCKASGGTFSSYAISWVRQAPGQGLEWM
GGIIPAFGTANYAQKFQGRVTITADESTSTAYMELSSLRSEDTAVYYC
ARGPIVATITPLDYWGQGTLVTVSS

VL Sequences:

(SEQ ID NO: 361)
SYELMQPPSVSVAPGKTATIACGGENIGRKTVHWYQQKPGQAPVLIY
YDSDRPSGIPERFSGSNSGNTATLTISRVEAGDEADYYCQVWDSSSDH
RIFGGGTKLTVL (SEQ ID NO: 362)
AIRMTQSPSSLSASVGDRVTITCRASQSISSYLNWYQQKPGKAPKLLI
YTTSSLKSGVPSRFSGSGSGTDFTLTISRLQPEDFATYYCQQSYSSTW
TFGRGTKVEIK (SEQ ID NO: 363)
QSVLTQPPSVSAAPGQKVTISCSGNNSNIANNYVSWYQQLPGTAPKLL
IYDNNYRPSGIPDRFSGSKSGTSATLDITGLQTGDEADYYCGVWDGSL
TTGVFGGGTKLTVL (SEQ ID NO: 364)
LPVLTQPASVSGSPGQSITISCTGTTSDIGGYDYVSWYQQHPGKAPKL
MIYDVSKRPSGVSNRFSGSKSGNTASLTISGLQAEDEADYYCSSYTSS
STHVFGTGTKLTVL (SEQ ID NO: 365)
QSALTQPASVSGSPGQSITISCTGTSSDVGGYNYVSWYQQHPGKAPKL
MIYDVSNRPSGVSNRFSGSKSGNTASLTISGLQAEDEADYYCSSYRSS
TLGPVFGGGTKLTVL (SEQ ID NO: 366)
QAGLTQPPSVSEAPRQRVTISCSGSSSNIGNNAVNWYQQLPGKAPKLL
IYYDDLLPSGVSDRFSGSKSGTSASLAISGLQSEDEADYYCAAWDDSL
NGYVFGTGTKLTVL

-continued (SEQ ID NO: 367)
QSALTQPRSVSGSPGQSVTISCTGTSSDVGGYNYVSWYQQHPGKAPKL

MIYDVSKRPSGVPDRFSGSKSGNTASLTISGLQAEDEADYYCSSYTSS

TTHVFGTGTKVTVL (SEQ ID NO: 368)
QSVVTQPPSVSAAPGQKVTISCSGSSSNIGNNYVSWYQQLPGTAPKLL

IYDNNKRPSGIPDRFSGSKSGTSATLGITGLQTGDEADYYCGTWDSSL

SVWVFGGGTQLTVL (SEQ ID NO: 369)
QSVLTQPASVSGSPGQSITISCTGTSSDVGGYNYVSWYQQHPGRAPRL

MIYDVSNRPSGVSNRFSGSKSGNTASLTISGLQAEDEGDYYCSSYTSG

GTLGPVFGGGTKLTVL (SEQ ID NO: 370)
QSVVTQPPSVSAAPGQKVTISCSGSSSNIGNNYVSWYQQLPGTAPKLL

IYDNNKRPSGIPDRFSGSKSGTSATLGITGLQTGDEADYYCGTWDSSL

SAVVFGGGTKLTVL (SEQ ID NO: 371)
QSVVTQPPSVSAAPGQKVTISCSGSSSNIGNNYVSWYQQVPGTAPKLL

IYDNNKRPSGIPDRFSGSNSDTSATLGITGLQTGDEADYYCGTWDSSL

SAWVFGGGTKLTVL (SEQ ID NO: 372)
QSVVTQPPSVSAAPGQKVTISCSGSSSNIGNNYVSWYQQLPGTAPKLL

IYDNNKRPSGIPDRFSGSKSGTSATLGITGLQTGDEADYYCGTWDSSL

SAGSVVFGGGTKLTVL (SEQ ID NO: 373)
SYELMQPPSVSVAPGKTATIACGGENIGRKTVHWYQQKPGQAPVLVIY

YDSDRPSGIPERFSGSNSGNTATLTISRVEAGDEADYYCLVWDSSSDH

RIFGGGTKLTVL (SEQ ID NO: 374)
SYELMQPPSVSVAPGKTATIACGGENIGRKTVHWYQQKPGQAPVLVIY

YDSDRPSGIPERFSGSNSGNTATLTISRVEAGDEADYYCQVWDSSSDH

RIFGGGTKLTVL (SEQ ID NO: 375)
SYELMQPPSVSVAPGKTATIACGGENIGRKTVHWYQQKPGQAPVLVIY

YDSDRPSGIPERFSGSNSGNTATLTISRVEAGDEADYYCQVWDSSSDH

RIFGGGTKLTVL (SEQ ID NO: 376)
SYELMQPPSVSVAPGKTATIACGGENIGRKTVHWYQQKPGQAPVLVIY

YDSDRPSGIPERFSGSNSGNTATLTISRVEAGDEADYYCQVWDSSSDH

RIFGGGTKLTVL

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 377)
QVQLVQSGSEVKKSGSSVKVSCKTSGGTFSITNYAINWVRQAPGQGLE

WMGGILPIFGAAKYAQKFQDRVTITADESTNTAYLELSSLTSEDTAMY

YCARGKRWLQSDLQYWGQGTLVTVSS

VL Sequences:
(SEQ ID NO: 378)
QPVLTQPASVSGSPGQSITISCTGSSSDVGSYDLVSWYQQSPGKVPKL

LIYEGVKRPSGVSNRFSGSKSGNTASLTISGLQAEDEADYYCSSYAGT

RNFVFGGGTQLTVL

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 379)
EVQLLESGGGLVQPGGSLRLSCAASGFTFSSYAMSWVRQAPGKGLEWV

SSIYSTGGATAYADSVKGRFTISRDNSKNTLYLQMNSLRAEDTAVYYC

AKSSAGQSRPGFDYWGQGTLVTVSS (SEQ ID NO: 380)
EVQLLESGGGLVQPGGSLRLSCAASGFTFSSYAMSWVRQAPGKGLEWV

SSIYSTGGATAYADSVKGRFTISRDNSKNTLYLQMNSLRAEDTAVYYC

AKSSAGQSWPGFDYWGQGTLVTVSS (SEQ ID NO: 381)
EVQLLESGGGLVQPGGSLRLSCAASGFTFSSYAMSWVRQAPGKGLEWV

SSIYSTGGATAYADSVKGRFTISRDNSKNTLYLQMNSLRAEDTAVYYC

AKSSAGQSFPGFDYWGQGTLVTVSS (SEQ ID NO: 382)
EVQLLESGGGLVQPGGSLRLSCAASGFTFSSYAMSWVRQAPGKGLEWV

SSIYSTGGATAYADSVKGRFTISRDNSKNTLYLQMNSLRAEDTAVYYC

AKWSAAFDYWGQGTLVTVSS (SEQ ID NO: 383)
EVQLLESGGGLVQPGGSLRLSCAASGFTFSSYAMSWVRQAPGKGLEWV

SSIYSTGGATAYADSVKGRFTISRDNSKNTLYLQMNSLRAEDTAVYYC

AKWSAGYDYWGQGTLVTVSS (SEQ ID NO: 384)
EVQLLESGGGLVQPGGSLRLSCAASGFTFSSYAMSWVRQAPGKGLEWV

SSIYSTGGATAYADSVKGRFTISRDNSKNTLYLQMNSLRAEDTAVYYC

AKWSKGFDYWGQGTLVTVSS (SEQ ID NO: 385)
EVQLLESGGGLVQPGGSLRLSCAASGFTFSSYAMSWVRQAPGKGLEWV

SSIWKQGIVTVYDSVKGRFTISRDNSKNTLYLQMNSLRAEDTAVYYCA

KSSAGFDYWGQGTLVTV (SEQ ID NO: 386)
EVQLLESGGGLVQPGGSLRLSCAASGFTFSSYAMSWVRQAPGKGLEWV

SSIWRNGIVTVYDSVKGRFTISRDNSKNTLYLQMNSLRAEDTAVYYCA

KSSAGFDYWGQGTLVTVSS (SEQ ID NO: 387)
EVQLLESGGGLVQPGGSLRLSCAASGFTFSSYAMSWVRQAPGKGLEWV
SDIWKQGMVTVYDSVKGRFTISRDNSKNTLYLQMNSLRAEDTAVYYCA
KSSAGFDYWGQGTLVTVSS (SEQ ID NO: 388)
EVQLLESGGGLVQPGGSLRLSCAASGFTFSSYAMSWVRQAPGKGLEWV
SSIWRQGLATAYDSVKGRFTISRDNSKNTLYLQMNSLRAEDTAVYYCA
KSSAGFDYWGQGTLVTVSS (SEQ ID NO: 389)
EVQLLESGGGLVQPGGSLRLSCAASGFTFSSYAMSWVRQAPGKGLEWV
SEIVATGILTSYDSVKGRFTISRDNSKNTLYLQMNSLRAEDTAVYYCA
KSSAGFDYWGQGTLVTVSS (SEQ ID NO: 390)
EVQLLESGGGLVQPGGSLRLSCAASGFTFSSYAMSWVRQAPGKGLEWV
SSIGRQGLITVYDSVKGRFTISRDNSKNTLYLQMNSLRAEDTAVYYCA
KSSAGFDYWGQGTLVTVSS (SEQ ID NO: 391)
EVQLLESGGGLVQPGGSLRLSCAASGFTFSSYAMSWVRQAPGKGLEWV
SSIWYQGLVTVYDSVKGRFTISRDNSKNTLYLQMNSLRAEDTAVYYCA
KSSAGFDYWGQGTLVTVSS (SEQ ID NO: 392)
EVQLLESGGGLVQPGGSLRLSCAASGFTFSSYAMSWVRQAPGKGLEWV
SDIWKQGFATADSVKGRFTISRDNSKNTLYLQMNSLRAEDTAVYYCAK
SSAGFDYWGQGTLVTVSS (SEQ ID NO: 393)
EVQLLESGGGLVQPGGSLRLSCAASGFTFSSYAMSWVRQAPGKGLEWV
SSIWKQGIVTVYDSVKGRFTISRDNSKNTLYLQMNSLRAEDTAVYYCA
KSSAGFDYWGQGTLVTVSS (SEQ ID NO: 394)
EVQLLESGGGLVQPGGSLRLSCAASGFTFSSYAMSWVRQAPGKGLEWV
SSIWRQGLATAYDSVKGRFTISRDNSKNTLYLQMNSLRAEDTAVYYCA
KSSAGFDYWGQGTLVTVSS (SEQ ID NO: 395)
EVQLLESGGGLVQPGGSLRLSCAASGFTFSSYAMSWVRQAPGKGLEWV
SSIWRNGIVTVYADSVKGRFTISRDNSKNTLYLQMNSLRAEDTAVYYC
AKWSAAFDYWGQGTLVTVSS (SEQ ID NO: 396)
EVQLLESGGGLVQPGGSLRLSCAASGFTFSSYAMSWVRQAPGKGLEWV
SSIWRNGIVTVYADSVKGRFTISRDNSKNTLYLQMNSLRAEDTAVYYC
AKWSAGYDYWGQGTLVTVSS (SEQ ID NO: 397)
EVQLLESGGGLVQPGGSLRLSCAASGFTFSSYAMSWVRQAPGKGLEWV
SSIWRNGIVTVYADSVKGRFTISRDNSKNTLYLQMNSLRAEDTAVYYC
AKWSKGFDYWGQGTLVTVSS (SEQ ID NO: 398)
EVQLLESGGGLVQPGGSLRLSCAASGFTFSSYAMetSWVRQAPGKGLE
WVSSIWYQGLVTVYADSVKGRFTISRDNSKNTLYLQMetNSLRAEDTA
VYYCAKWSAAFDYWGQGTLVTVSS (SEQ ID NO: 399)
EVQLLESGGGLVQPGGSLRLSCAASGFTFSSYAMSWVRQAPGKGLEWV
SSIWYQGLVTVYADSVKGRFTISRDNSKNTLYLQMNSLRAEDTAVYYC
AKWSAGYDYWGQGTLVTVSS (SEQ ID NO: 400)
EVQLLESGGGLVQPGGSLRLSCAASGFTFSSYAMSWVRQAPGKGLEWV
SSIWYQGLVTVYADSVKGRFTISRDNSKNTLYLQMNSLRAEDTAVYYC
AKWSKGFDYWGQGTLVTVSS

VL Sequences:

(SEQ ID NO: 401)
DIQMTQSPSSLSASVGDRVTITCRASQSISSYLNWYQQKPGKAPKLLI
YYASTLQSGVPSRFSGSGSGTDFTLTISSLQPEDFATYYCQQDNGYPS
TFGQGTKVEIKR (SEQ ID NO: 402)
DIQMTQSPSSLSASVGDRVTITCRASQSISSYLNWYQQKPGKAPKLLI
YYASTLQSGVPSRFSGSGSGTDFTLTISSLQPEDFATYYCQQDNGYPS
TFGQGTKVEIKR (SEQ ID NO: 403)
DIQMTQSPSSLSASVGDRVTITCRASQSISSYLNWYQQKPGKAPKLLI
YAASSLQSGVPSRFSGSGSGTDFTLTISSLQPEDFATYYCQQDNGYPS
TFGGGTKVEIKR

In some embodiments, the PDL1 binding domain comprises or is derived from an antibody sequence or antigen-binding fragment thereof that includes a single chain Fv (scFv) sequence selected from the group consisting of:

(SEQ ID NO: 404)
EVQLLESGGGLVQPGGSLRLSCAASGFTFSSYAMSWVRQAPGKGLEWV
SDITASGQRTTYADSVKGRFTISRDNSKNTLYLQMNSLRAEDTAVYYC
ARSKIAFDYWGQGTLVTVSSGGGGSGGGGSGGGGSTDIQMTQSPSSLS
ASVGDRVTITCRASQSISSYLNWYQQKPGKAPKLLIYKASRLQSGVPS
RFSGSGSGTDFTLTISSLQPEDFATYYCQQRALKPVTFGQGTKVEIKR (SEQ ID NO: 405)
EVQLLESGGGLVQPGGSLRLSCAASGFTFSSYAMSWVRQAPGKGLEWV
SSINKDGHYTSYADSVKGRFTISRDNSKNTLYLQMNSLRAEDTAVYYC
AKNLDEFDYWGQGTLVTVSSGGGGSGGGGSGGGGSTDIQMTQSPSSLS
ASVGDRVTITCRASQSISSYLNWYQQKPGKAPKLLIYAASSLQSGVPS
RFSGSGSGTDFTLTISSLQPEDFATYYCQQSYSTPNTFGQGTKVEIKR (SEQ ID NO: 406)
EVQLLESGGGLVQPGGSLRLSCAASGFTFSSYAMSWVRQAPGKGLEWV
SSIMATGAGTLYADSVKGRFTISRDNSKNTLYLQMNSLRAEDTAVYYC
AKDGAGFDYWGQGTLVTVSSGGGGSGGGGSGGGGSTDIQMTQSPSSLS
ASVGDRVTITCRASQSISSYLNWYQQKPGKAPKLLIYSASQLQSGVPS
RFSGSGSGTDFTLTISSLQPEDFATYYCQQANSRPSTFGQGTKVEIKR (SEQ ID NO: 407)
EVQLLESGGGLVQPGGSLRLSCAASGFTFSSYAMSWVRQAPGKGLQWV
STITSSGAATYYADSVKGRFTISRDNSKNTLYLQMNSLRAEDTAVYYC
AKNYTGFDYWGQGTLVTVSSGGGGSGGGGSGGGGSTDIQMTQSPSSLS
ASVGDRVTITCRASQSISSYLNWYQQKPGKAPKLLIYNASSLQSGVPS
RFSGSGSGTDFTLTISSLQPEDFATYYCQQYTYGPGTFGQGTKVEIKR (SEQ ID NO: 408)
EVQLLESGGGLVQPGGSLRLSCAASGFTFSSYAMSWVRQAPGKGLEWV
SSIYSTGGATAYADSVKGRFTISRDNSKNTLYLQMNSLRAEDTAVYYC
AKSSAGFDYWGQGTLVTVSSGGGGSGGGGSGGGGSTDIQMTQSPSSLS
ASVGDRVTITCRASQSISSYLNWYQQKPGKAPKLLIYYASTLQSGVPS
RFSGSGSGTDFTLTISSLQPEDFATYYCQQDNGYPSTFGQGTKVEIKR

PDL1x41BB Dual Targeting

In some embodiments, the fusion proteins are bispecific molecules that include a TBD that binds 41BB and a binding domain directed toward PDL1. In these, embodiments, the binding to PDL1 is capable of providing the additional crosslinking function and TNFRSF activation can be achieved with only one or two anti-41BB TBDs. In these embodiments, the TNFRSF signaling is enhanced and focused by the presence of a PDL1 expressing cell.

Tetravalent 41BB agonist: hzRH3v5-1
(SEQ ID NO: 448)
EVQLLESGGGEVQPGGSLRLSCAASGFSFSINAMGWYRQAPGKRREFV
AAIESGRNTVYAESVKGRFTISRDNAKNTVYLQMSSLRAEDTAVYYCG
LLKGNRVVSPSVAYWGQGTLVTVKPGGGGDKTHTCPPCPAPGGPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHN
HYTQKSLSLSPGSGGGGSGGGGSEVQLLESGGGEVQPGGSLRLSCAAS
GFSFSINAMGWYRQAPGKRREFVAAIESGRNTVYAESVKGRFTISRDN
AKNTVYLQMSSLRAEDTAVYYCGLLKGNRVVSPSVAYWGQGTLVTVKP
GG

Bispecific PDL1 x 41BB: hz28A2v5 x hzRH3v5-1
(SEQ ID NO: 449)
EVQLLESGGGEVQPGGSLRLSCAASGGIFAIKPISWYRQAPGKQREWV
STTTSSGATNYAESVKGRFTISRDNAKNTLYLQMSSLRAEDTAVYYCN
VFEYWGQGTLVTVKPGGSGGSEVQLLESGGGEVQPGGSLRLSCAASGF
SFSINAMGWYRQAPGKRREFVAAIESGRNTVYAESVKGRFTISRDNAK
NTVYLQMSSLRAEDTAVYYCGLLKGNRVVSPSVAYWGQGTLVTVKPGG
GGDKTHTCPPCPAPGGPSVFLFPPKPKDTLMISRTPEVTCVVVDVSHE
DPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTVD
KSRWQQGNVFSCSVMHEALHNHYTQKSLSLSPGK Bispecific PDL1 x 41BB: hz28A2v5 x hzRH3v5-2
(SEQ ID NO: 450)
EVQLLESGGGEVQPGGSLRLSCAASGGIFAIKPISWYRQAPGKQREWV
STTTSSGATNYAESVKGRFTISRDNAKNTLYLQMSSLRAEDTAVYYCN
VFEYWGQGTLVTVKPGGSGGSEVQLLESGGGEVQPGGSLRLSCAASGF
SFSINAMGWYRQAPGKRREFVAAIYSGRNTVYAESVKGRFTISRDNAK
NTVYLQMSSLRAEDTAVYYCGLLKGNRVVSPSVAYWGQGTLVTVKPGG
GGDKTHTCPPCPAPGGPSVFLFPPKPKDTLMISRTPEVTCVVVDVSHE
DPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTVD
KSRWQQGNVFSCSVMHEALHNHYTQKSLSLSPGK Bispecific PDL1 x 41BB: hz28A2v5 x hzRH3v5-16
(SEQ ID NO: 451)
EVQLLESGGGEVQPGGSLRLSCAASGGIFAIKPISWYRQAPGKQREWV
STTTSSGATNYAESVKGRFTISRDNAKNTLYLQMSSLRAEDTAVYYCN
VFEYWGQGTLVTVKPGGSGGSEVQLLESGGGEVQPGGSLRLSCAASGF
SFSINAMGWYRQAPGKRREFVAAIYSGSSTVYAESVKGRFTISRDNAK
NTVYLQMSSLRAEDTAVYYCGLLKGNRVVSPSVAYWGQGTLVTVKPGG
GGDKTHTCPPCPAPGGPSVFLFPPKPKDTLMISRTPEVTCVVVDVSHE
DPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTVD
KSRWQQGNVFSCSVMHEALHNHYTQKSLSLSPGK Bispecific PDL1 x 41BB: hz28A2v5 x hz4E01v16
(SEQ ID NO: 452)
EVQLLESGGGEVQPGGSLRLSCAASGGIFAIKPISWYRQAPGKQREWV
STTTSSGATNYAESVKGRFTISRDNAKNTLYLQMSSLRAEDTAVYYCN
VFEYWGQGTLVTVKPGGSGGSEVQLLESGGGEVQLLESGGGEVQPGGS
LRLSCAASGWAFGNYGMAWFRQAPGKEREFVSRLAWQGGSTDYVESVK
GRFTISRDNAKNTLYLQMSSLRAEDTAVYYCARQRSYSRYDIRTPQTY
DYWGQGTLVTVKPGGGGDKTHTCPPCPAPGGPSVFLFPPKPKDTLMIS
RTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYT
LPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG
K Bispecific PDL1 x 41BB: hz28A2v5 x hz4E01v18
(SEQ ID NO: 453)
EVQLLESGGGEVQPGGSLRLSCAASGGIFAIKPISWYRQAPGKQREWV
STTTSSGATNYAESVKGRFTISRDNAKNTLYLQMSSLRAEDTAVYYCN
VFEYWGQGTLVTVKPGGSGGSEVQLLESGGGEVQLLESGGGEVQPGGS
LRLSCAASGWAFGNYGMAWFRQAPGKEREFVSRLAWGGGSTDYVESVK
GRFTISRDNAKNTLYLQMSSLRAEDTAVYYCARQRSYSRYDIRTPQTY

```
DYWGQGTLVTVKPGGGGDKTHTCPPCPAPGGPSVFLFPPKPKDTLMIS

RTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYT

LPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

K

Bispecific PDL1 x 41BB: hz28A2v5 x hz4E01v21
                                        (SEQ ID NO: 454)
EVQLLESGGGEVQPGGSLRLSCAASGGIFAIKPISWYRQAPGKQREWV

STTTSSGATNYAESVKGRFTISRDNAKNTLYLQMSSLRAEDTAVYYCN

VFEYWGQGTLVTVKPGGSGGSEVQLLESGGGEVQLLESGGGEVQPGGS

LRLSCAASGWAFSNYGMAWFRQAPGKEREFVSRLAWGGGSTDYVESVK

GRFTISRDNAKNTLYLQMSSLRAEDTAVYYCARQRSYSRYDIRTPQTY

DYWGQGTLVTVKPGGGGDKTHTCPPCPAPGGPSVFLFPPKPKDTLMIS

RTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYT

LPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

K

Bispecific PDL1 x 41BB: hz28A2v5 x hz4E01v22
                                        (SEQ ID NO: 455)
EVQLLESGGGEVQPGGSLRLSCAASGGIFAIKPISWYRQAPGKQREWV

STTTSSGATNYAESVKGRFTISRDNAKNTLYLQMSSLRAEDTAVYYCN

VFEYWGQGTLVTVKPGGSGGSEVQLLESGGGEVQLLESGGGEVQPGGS

LRLSCAASGWAFGNYGMAWFRQAPGKEREFVSRLAWSGGSTDYVESVK

GRFTISRDNAKNTLYLQMSSLRAEDTAVYYCARQRSYSRYDIRTPQTY

DYWGQGTLVTVKPGGGGDKTHTCPPCPAPGGPSVFLFPPKPKDTLMIS

RTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYT

LPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

K

Bispecific PDL1 x 41BB: hz28A2v5 x hz4E01v23
                                        (SEQ ID NO: 456)
EVQLLESGGGEVQPGGSLRLSCAASGGIFAIKPISWYRQAPGKQREWV

STTTSSGATNYAESVKGRFTISRDNAKNTLYLQMSSLRAEDTAVYYCN

VFEYWGQGTLVTVKPGGSGGSEVQLLESGGGEVQLLESGGGEVQPGGS

LRLSCAASGWAFSNYGMAWFRQAPGKEREFVSRLAWSGGSTDYVESVK

GRFTISRDNAKNTLYLQMSSLRAEDTAVYYCARQRSYSRYDIRTPQTY

DYWGQGTLVTVKPGGGGDKTHTCPPCPAPGGPSVFLFPPKPKDTLMIS

RTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYT

LPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

K
```

Folate Receptor Alpha (FRα) Targeting

In some embodiments, the fusion proteins are multispecific containing a TBD and a binding domain directed toward Folate Receptor Alpha (FRα). In these, embodiments, the binding to FRα is capable of providing the additional crosslinking function and TNFRSF activation can be achieved with only one or two TBDs. In these embodiments, the TNFRSF signaling is enhanced and focused by the presence of a FRα expressing cell.

Exemplary FRα-targeting single domain sequences are shown below:

```
Fra-5:
                                                (SEQ ID NO: 409)
QLQLQESGGGLVQAGGSLRLSCAAS GIMFYISD MGWYRQAPGKQREFVAT ITSGGTT NYADSV

EGRFSISRDNAKNTVYLQMNSLEPEDTAVYYC TAHGPTYGSTWDDL WGQGTQVTVKPGG

CDR1:
                                                (SEQ ID NO: 410)
GIMFYISD

CDR2:
                                                (SEQ ID NO: 411)
TITSGGTTNY

CDR3:
                                                (SEQ ID NO: 412)
TAHGPTYGSTWDDL

Fra-6:
                                                (SEQ ID NO: 413)
QVQLQESGGGLVQAGGSLRLSCAAS ETFGVVFT LGWYRQTPGKQREFVAR VTGTDTV DYADSV

KGRFTISSDFARNTVYLQMNNLKPEDTAVYYC NTGAY WGQGTQVTVKPGG

CDR1:
```

-continued

```
                                              (SEQ ID NO: 414)
TFGVVFT

CDR2:
                                              (SEQ ID NO: 415)
VTGTDTV

CDR3:
                                              (SEQ ID NO: 416)
NTGAY

Fra-57:
                                              (SEQ ID NO: 417)
QVQLVQSGGGLVQTGGSLRLSCAASGRTASTYSMGWFRQAPGKERQFVARIIWSTGSTYYTNS

VEGRFTISRDIAKNTLYLQMNSLEPEDTAVYYCTAREPTGYDYWGQGTQVTVKPGG

CDR1:
                                              (SEQ ID NO: 418)
GRTASTYS

CDR2:
                                              (SEQ ID NO: 419)
IWSTGST

CDR3:
                                              (SEQ ID NO: 420)
TAREPTGYDY

1A3:
                                              (SEQ ID NO: 421)
QLQLQESGGGLVQAGGSLGLSCAASGSIFRFGARGWYRQAPGKQRELVAIITSGGSTNYADSV

QGRFTISRDNAKNMVYLQMNGLKSGDTAVYYCAADRSDAVGVGWDYWGQGTQVTVKPGG

CDR1:
                                              (SEQ ID NO: 422)
GSIFRFGA

CDR2:
                                              (SEQ ID NO: 423)
ITSGGST

CDR3:
                                              (SEQ ID NO: 424)
AADRSDAVGVGWDY

1F3:
                                              (SEQ ID NO: 425)
QVQLQQSGGGLVQTGGSLRLSCAASGRTASTYSMGWFRQAPGKERQFVARIIWSTGSTYYTNS

VEGRFTISRDIAKNTLYLQMNSLEPEDTAVYYCTARDPTGYDYWGQGTQVTVKPGG

CDR1:
                                              (SEQ ID NO: 418)
GRTASTYS

CDR2:
                                              (SEQ ID NO: 426)
IIWSTGST

CDR3:
                                              (SEQ ID NO: 427)
TARDPTGYDY

1G10:
                                              (SEQ ID NO: 428)
QLQLQESGGGLVQAGGSLRLSCAASGSIFSIDATAWYRQAPGKQRELVAIITSSGSTNYPDSV

KGRFTISRDNAKNTVYLQMNSLNPEDTALYSCNAITRMGGSTYDFWGQGTQVTVKPGG

CDR1:
```

-continued

GSIFSIDA (SEQ ID NO: 429)

CDR2:

ITSSGST (SEQ ID NO: 430)

CDR3:

NAITRMGGSTYDF (SEQ ID NO: 431)

The disclosure will be further described in the following examples, which do not limit the scope of the disclosure described in the claims.

EXAMPLES

Example 1

41BB-Targeting Single Domain Antibodies Bind 41BB

Figure 2B:
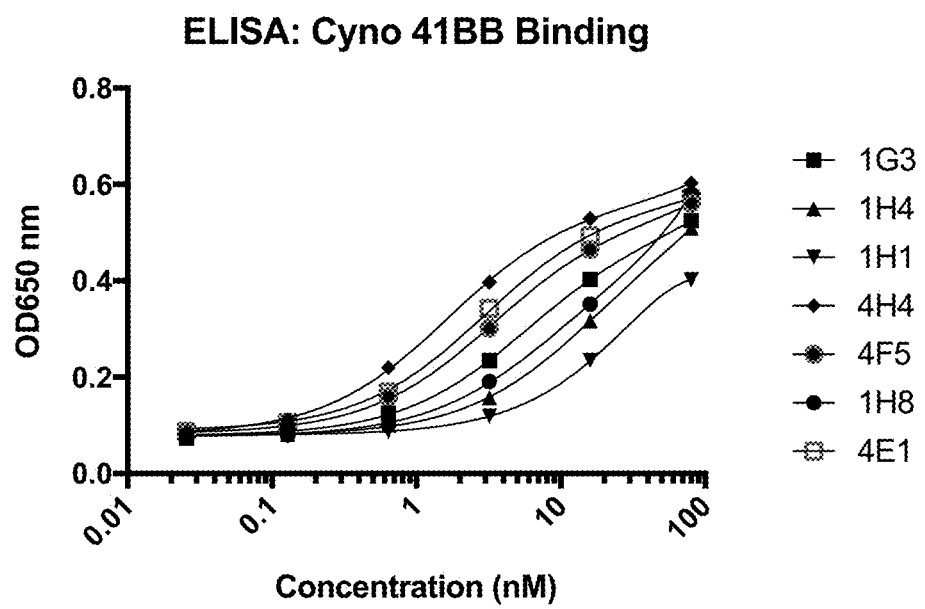
Figure 3:
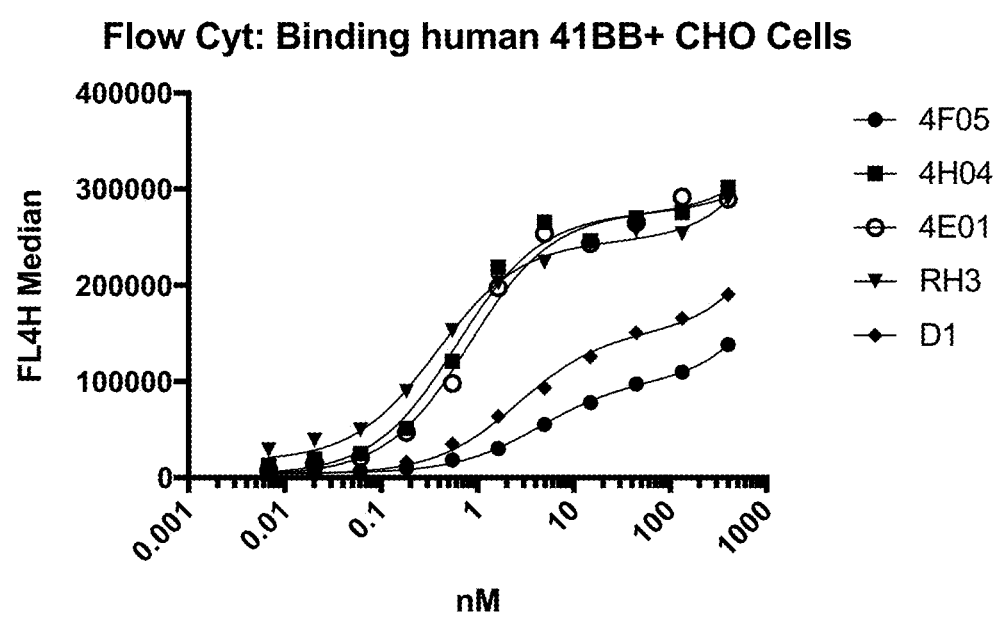
FIG. 3 is a graph demonstrating the ability of 41BB single domain antibodies (sdAbs) to bind cell surface 41BB. Binding was assessed by flow cytometry using 41BB expressing CHO cells and data is presented as median fluorescence intensity.
Figure 4:
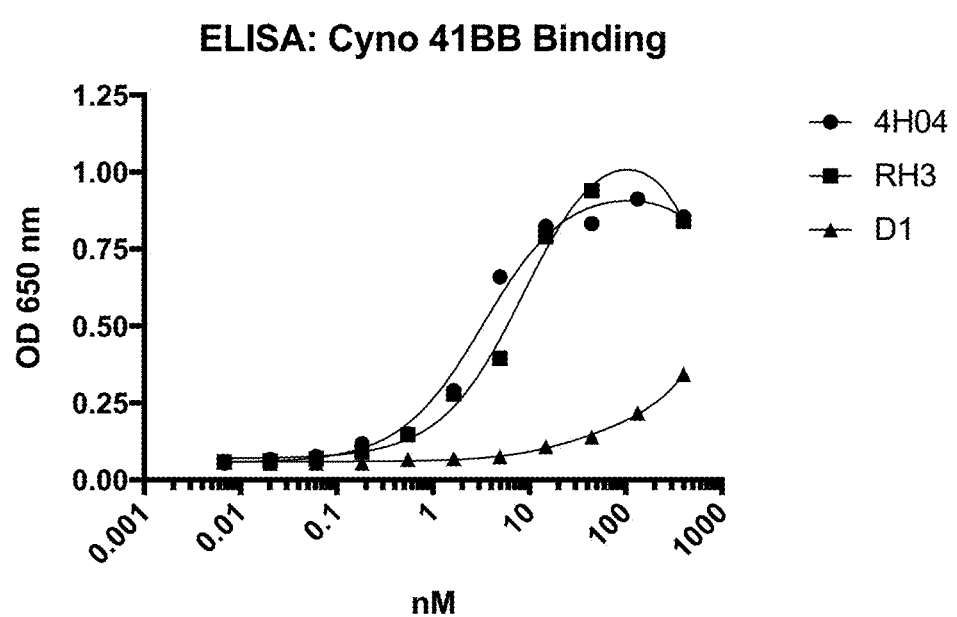
FIG. 4 is a graph demonstrating the ability of 41BB single domain antibodies, RH3 and 4H04 to bind cynomolgus monkey 41BB. Binding was assessed by ELISA wherein recombinant 41BB-mFc protein was immobilized on a Medisorp 96 well plate.
Figure 5:
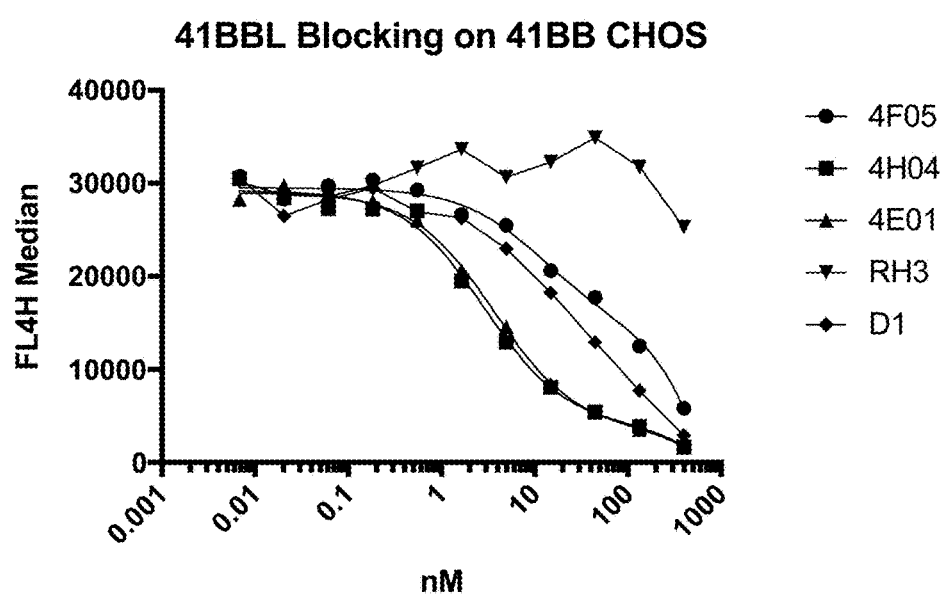
FIG. 5 is a graph demonstrating the capacity of 41BB single domain antibodies (VHHs) to block the interaction between 41BB and 41BBL. All single domain antibodies tested, with the exception of RH3 blocks the interaction between 41BB and 41BBL. Blocking was assessed by flow cytometry using a recombinant 41BB fusion protein and 41BB expressing CHO cells, data is presented as median fluorescence intensity.

The 41BB-targeting single domain antibodies (sdAbs) referred to herein as 1G3 (SEQ ID NO: 432), 1H4 (SEQ ID NO: 436), 1H1 (SEQ ID NO: 440), 4H4 (SEQ ID NO: 16), 1H8 (SEQ ID NO: 444), 4F5 (SEQ ID NO: 23), and 4E1 (SEQ ID NO: 20) bind recombinant human 41BB (FIG. 2A), cynomolgus 41BB (FIG. 2B). The 41BB-targeting single domain antibodies (sdAbs) referred to herein as 4F5 (SEQ ID NO: 23), 4H04 (SEQ ID NO: 16), 4E01 (SEQ ID NO: 20), RH03 (SEQ ID NO: 25), and D1 (SEQ ID NO: 29) bind human 41BB expressed on the cell surface of CHO cells (FIG. 3). The 41BB-targeting sdAbs referred to herein as 4H04, RH03, and bind cynomolgus 41BB. For FIG. 2A, FIG. 2B, and FIG. 4, binding was assessed by ELISA wherein recombinant 41BB-mFc fusion protein (a fusion protein containing 41BB operably linked to a mouse Fc region) was immobilized on a Medisorp 96 well plate. For FIG. 3, binding was assessed by flow cytometry using 41BB expressing CHO cells, and the data is presented as median fluorescence intensity.

Example 2

41BB-Targeting Single Domain Antibodies Block 41BB

The 41BB-targeting single domain antibodies (sdAbs) referred to herein as 4F05 (SEQ ID NO: 23), 4H04 (SEQ ID NO: 16), 4E01 (SEQ ID NO: 20), RH03 (SEQ ID NO: 25), and D1 (SEQ ID NO: 29) block the interaction between 41BB and its ligand 41BBL. All single domain antibodies tested, with the exception of RH3 blocks the interaction between 41BB and 41BBL. Blocking was assessed by flow cytometry using a recombinant 41BB fusion protein and 41BB expressing CHO cells, data is presented as median fluorescence intensity.

Figure 6:
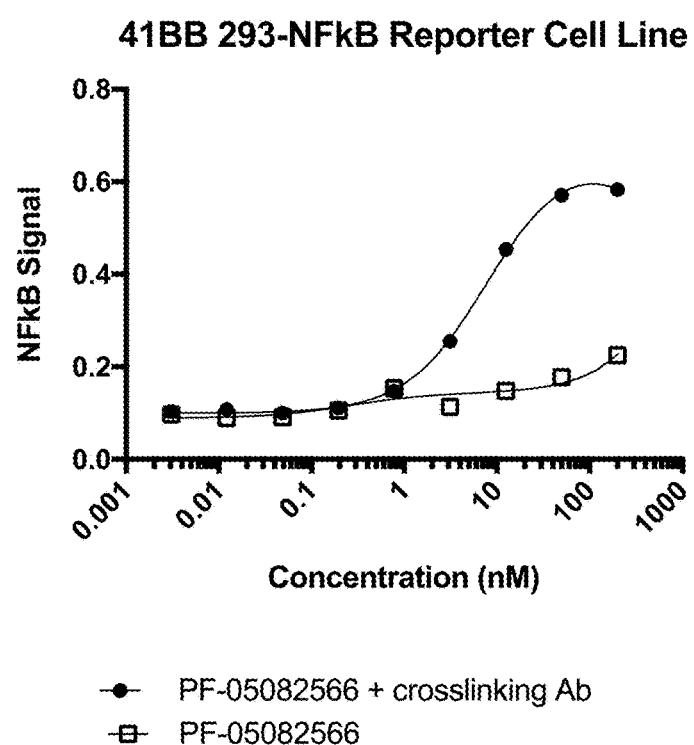
FIG. 6 is a graph demonstrating the inability of a conventional bivalent anti-41BB antibody PF-05082566 to induce 41BB signaling unless further clustered with an exogenous crosslinking anti-human IgG antibody. 41BB signaling was monitored using a NF-kB reporter 293 cell line expressing 41BB.

In contrast to the 41BB sdAbs of the disclosure, conventional bivalent anti-41BB antibodies do not induce 41BB signaling unless further clustered with an exogenous cross-linking anti-human IgG antibody. FIG. 6 demonstrates the inability of a conventional bivalent anti-41BB antibody PF-05082566, which is disclosed in U.S. Pat. No. 8,337,850, to induce 41BB signaling unless further clustered with an exogenous crosslinking anti-human IgG antibody. In FIG. 6, 41BB signaling was monitored using a NF-kB reporter 293 cell line expressing 41BB.

Example 3

PDL1-Targeting Single Domain Antibodies Bind PDL1 and Block the Interaction Between PLD1 and PD1

Figure 7A:
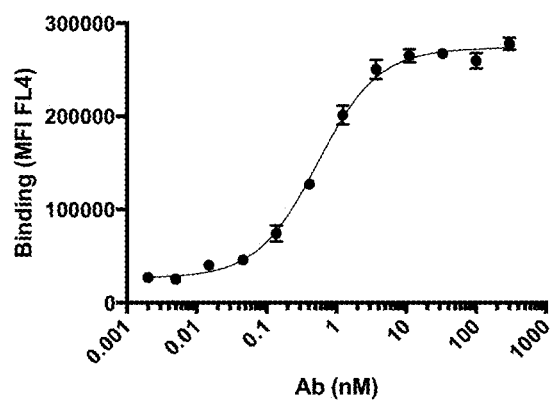
FIGS. 7A and 7B are a pair of graphs demonstrating the capacity of an exemplary PDL1 single domain antibody (28A10) to bind cell surface PDL1 and to block the interaction with PD1. Binding (FIG. 7A) was assessed by flow cytometry on PDL1 expressing CHO cells. Blocking (FIG. 7B) was assessed by flow cytometry using a recombinant PD1 fusion protein and PDL1 expressing CHO cells, data is presented as median fluorescence intensity.
Figure 7B:
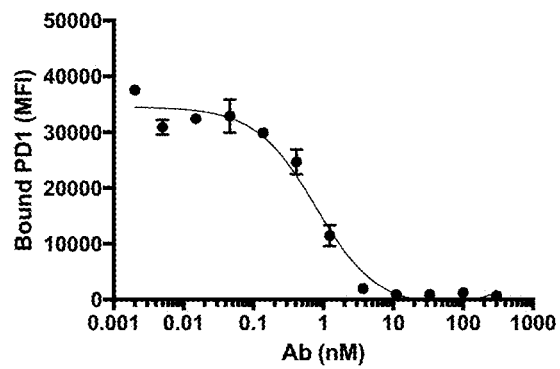

The studies presented herein use an exemplary PDL1 single domain antibody (sdAb), referred to herein as 28A10 (SEQ ID NO: 100) to demonstrate that the PDL1-targeting sdAbs of the disclosure bind cell surface PDL1 (FIG. 7A) and block the interaction of PDL1 with PD1 (FIG. 7B). Binding was assessed by flow cytometry on PDL1 expressing CHO cells, and blocking was assessed by flow cytometry using a recombinant PD1 fusion protein and PDL1 expressing CHO cells. The data presented in FIGS. 7A and 7B are presented as median fluorescence intensity.

Example 4

PDL1-41BB Targeting Fusion Proteins

The disclosure provides fusion proteins that target at least PDL1 and 41BB. These bispecific PDL1-41BB targeting fusion proteins are agonists of PDL1-dependent 41BB mediated signaling. FIGS. 8A and 8B are conceptual schematics wherein the bispecific fusion proteins have minimal 41BB agonistic properties (FIG. 8A) unless bound by a PD-L1 expressing cell (FIG. 8B). FIG. 8C demonstrates the ability of a PDL1-positive cell, in this case, a population of PDL1 transfected CHO cells, to mediate 41BB signaling and the inability of PDL1-negative cell, in this case, a population of untransfected CHO cells, to mediate 41BB signaling. Two distinct bispecific fusion proteins are shown in this figure, each containing a distinct 41BB binding VHH (e.g., 4E01 or RH3) and the same PD-L1 VHH, 28A10. 41BB signaling was monitored using a NF-kB reporter 293 cell line expressing 41BB. This reporter cell line implements an NF-kB driven secreted alkaline phosphatase, to monitor NF-kB signaling.

Figure 9A:
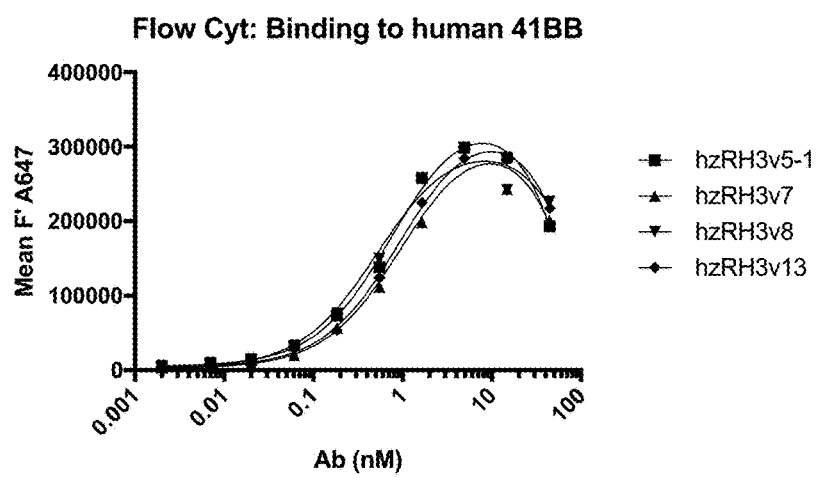
FIGS. 9A, 9B, 9C, 9D, and 9E are a series of graphs demonstrating the binding to human (FIG. 9A and FIG. 9C) or cynomolgus monkey (FIG. 9B and FIG. 9D) 41BB of humanized RH3 variants. Binding was assessed by flow cytometry on 41BB expressing 293freestyle cells.
Figure 9B:
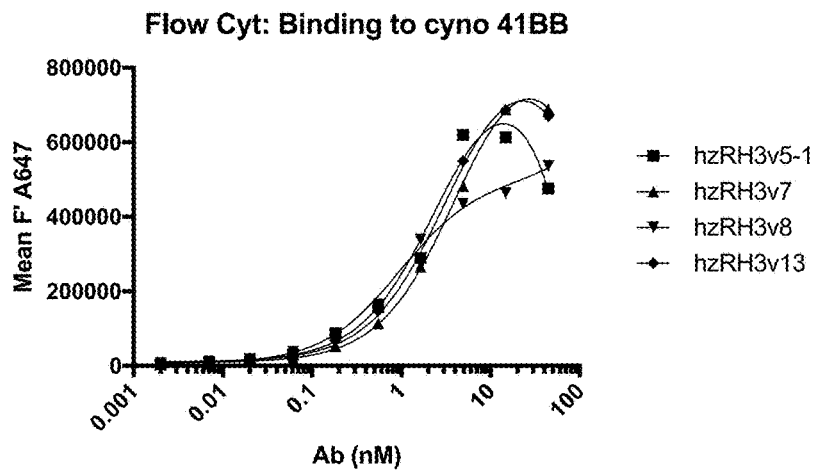
Figure 9C:
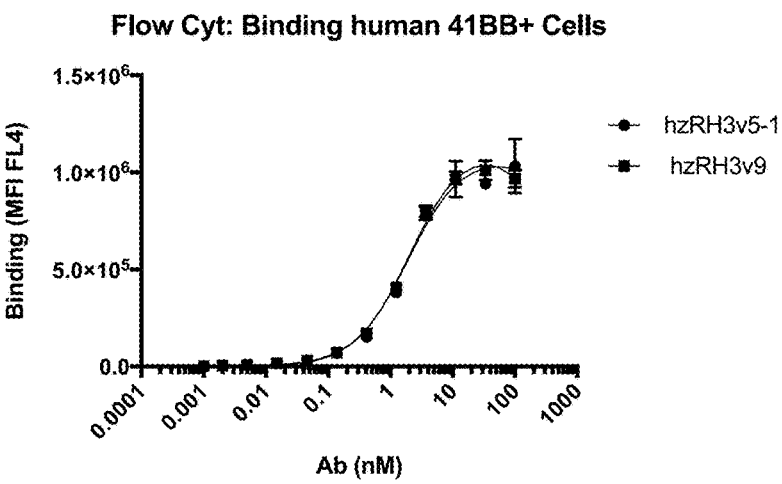
Figure 9D:
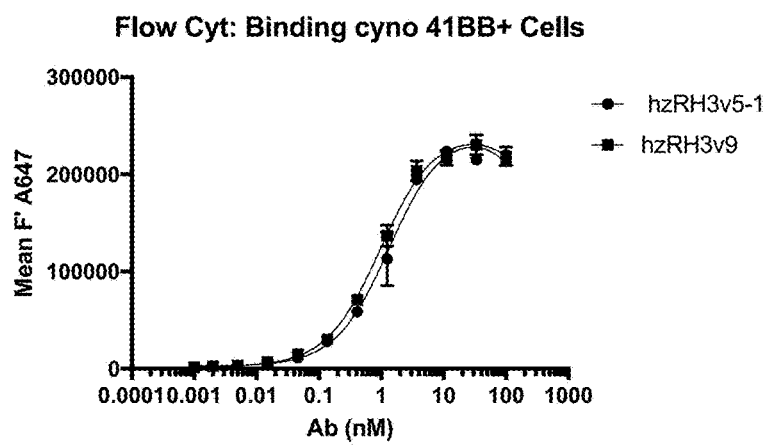

The PDL1-41BB targeting fusion proteins of the disclosure include a humanized anti-41BB sequence. In the studies presented herein, the PDL1-41BB targeting fusion proteins of the disclosure include a humanized anti-41BB sequence such as hzRH3v5-1 (SEQ ID NO: 30) and/or hzRH3v9 (SEQ ID NO: 82) bind both human and cynomolgus 41BB (FIGS. 9A, 9B), including human 41BB and cynomolgus 41BB expressed on the surface of CHO cells (FIGS. 9C, 9D). Binding was assessed by flow cytometry on 41BB expressing 293freestyle cells.

Figure 9E:
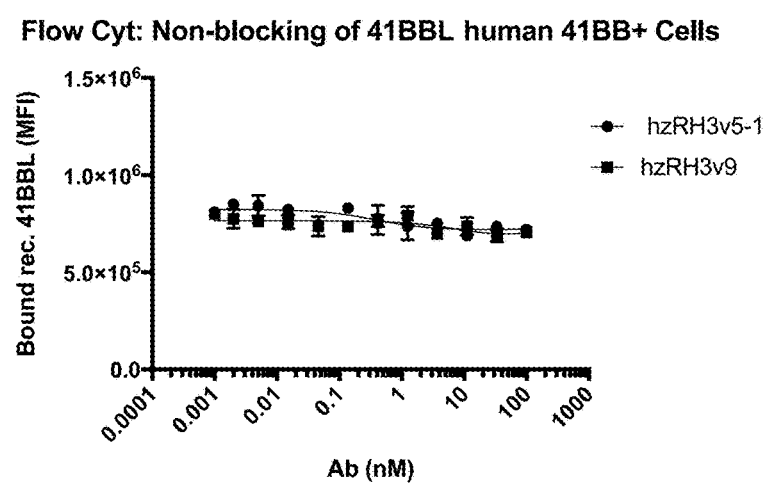

The humanized variants hzRH3v5-1 and hzRH3v9 do not block binding of 41BBL to cell surface 41BB as shown in FIG. 9E. In these studies, a recombinant fusion protein 41BBL-mFc, containing a mouse Fc region, was used, and bound 41BBL was detected using an anti-mouse IgG-Fc specific secondary antibody.

Figure 10:
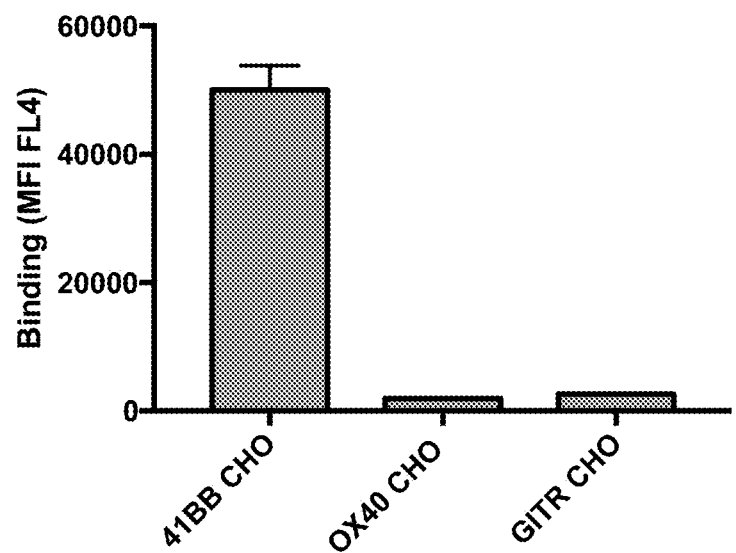
FIG. 10 is a graph demonstrating the specific binding of hzRH3v5-1 (40 nM) to 41BB compared to other TNFRSF members OX40 and GITR. Binding was assessed by flow cytometry using CHO cells expressing the given TNFRSF member.

The humanized variant hzRH3v5-1 specifically binds 41BB as compared to the other TNFRSF members OX40 and GITR (FIG. 10). Binding was assessed by flow cytometry using CHO cells expressing the given TNFRSF member.

Figure 11A:
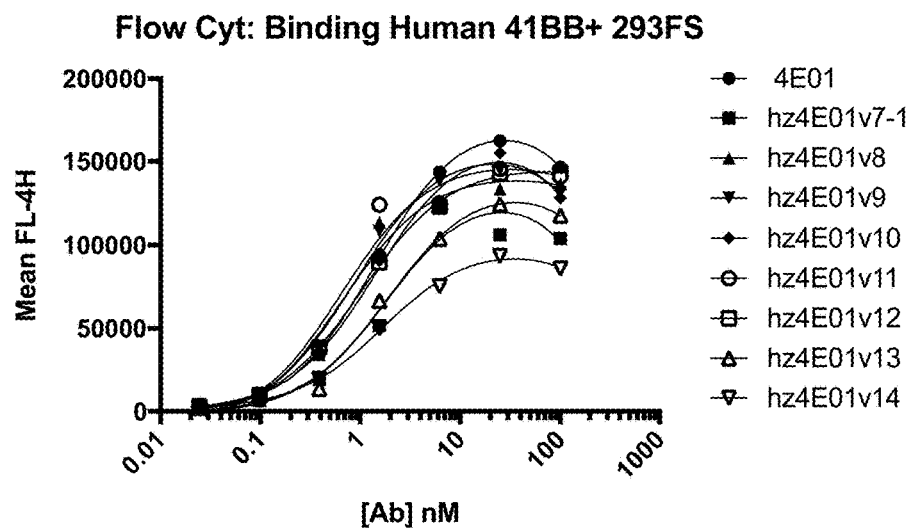
FIGS. 11A, 11B, 11C, and 11D are a series of graphs demonstrating the binding to human (FIG. 11A and FIG. 11C) or cynomolgus monkey (FIG. 11B) 41BB of humanized 4E01 variants. Binding was assessed by flow cytometry on 41BB expressing 293freestyle cells.
Figure 11B:
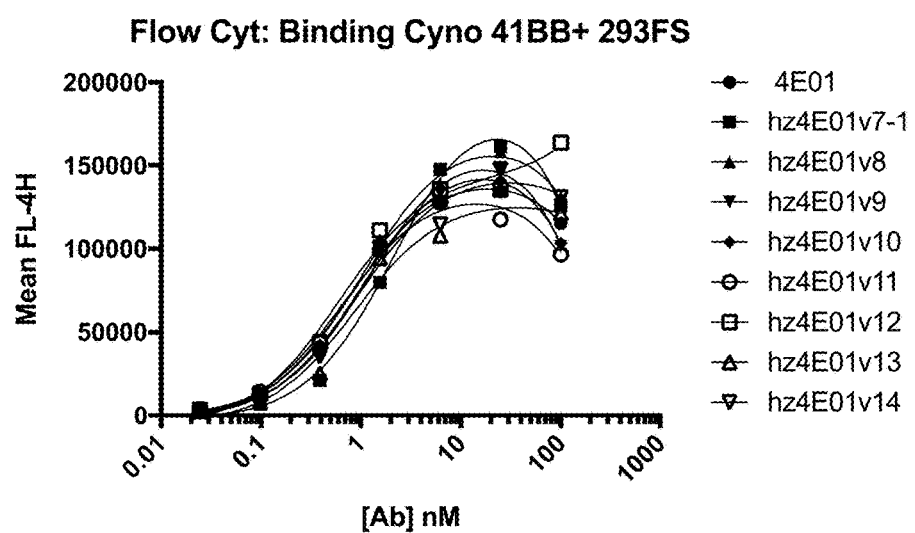
Figure 11C:
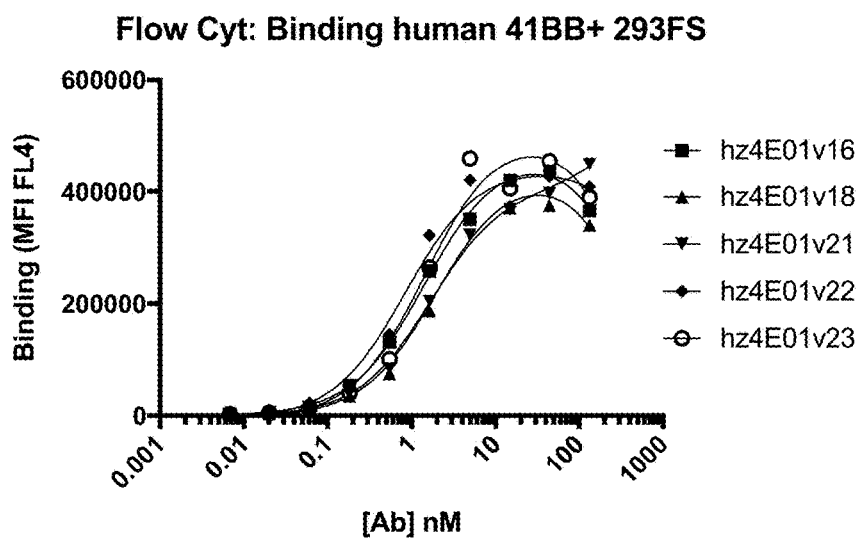
Figure 11D:
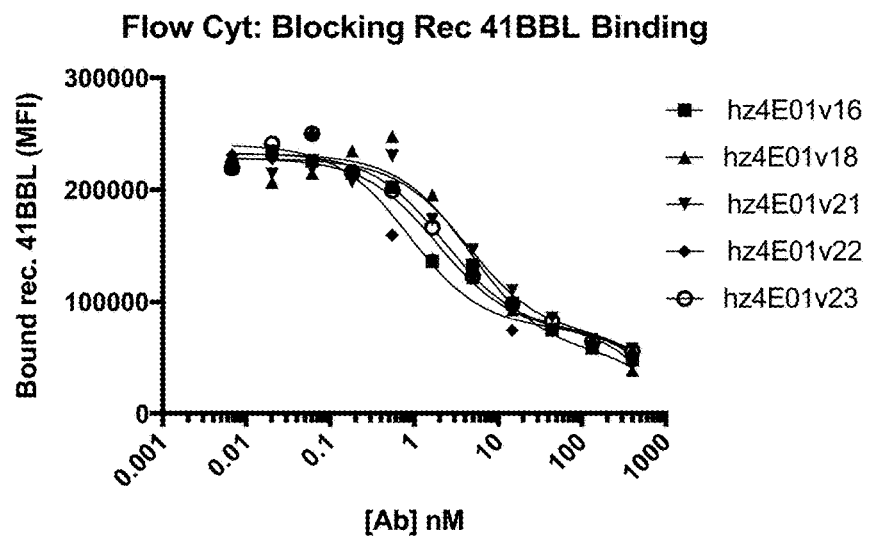

Additional humanized 41BB variants were analyzed. FIGS. 11A, 11B, 11C, and 11D demonstrate the binding to human (FIG. 11A and FIG. 11C) or cynomolgus monkey (FIG. 11B) 41BB of the humanized 4E01 variants. Binding was assessed by flow cytometry on 41BB expressing 293freestyle cells. FIG. 11D demonstrates that the humanized variants hz4E01v16, hz4E01v18, hz4E01v21, hz4E01v22 and hz4E01v23 block binding of 41BBL to cell surface 41BB. In these studies, a recombinant fusion protein 41BBL-mFc, containing a mouse Fc region was used and bound 41BBL was detected using an anti-mouse IgG-Fc specific secondary antibody.

Figure 12:
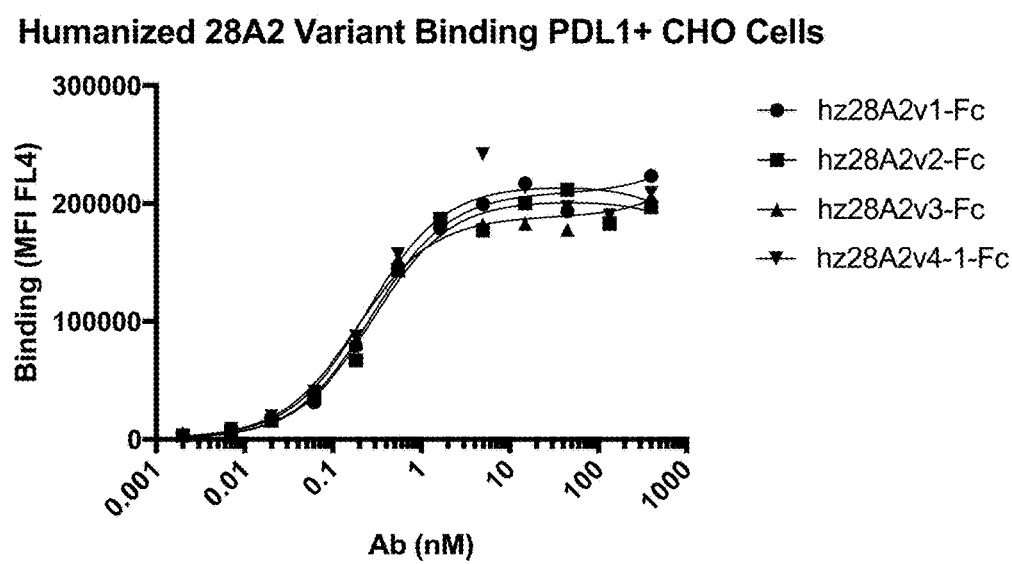
FIG. 12 is a graph demonstrating binding of humanized single domain antibodies targeting PDL1. Binding was assessed by flow cytometry on PDL1-expressing CHO cells.

The PDL1-41BB targeting fusion proteins of the disclosure also include a humanized anti-PDL1 sequence. In the studies presented herein, the PDL1-41BB targeting fusion proteins of the disclosure include a humanized anti-PDL1 sequence such as hz28A2v1 (SEQ ID NO: 120), hz28A2v2 (SEQ ID NO: 121), hz28A2v3 (SEQ ID NO: 122), and hz28A2v4-1 (SEQ ID NO: 123). FIG. 12 demonstrates binding of humanized single domain antibodies targeting PDL1. Binding was assessed by flow cytometry on PDL1-expressing CHO cells.

Figure 13:
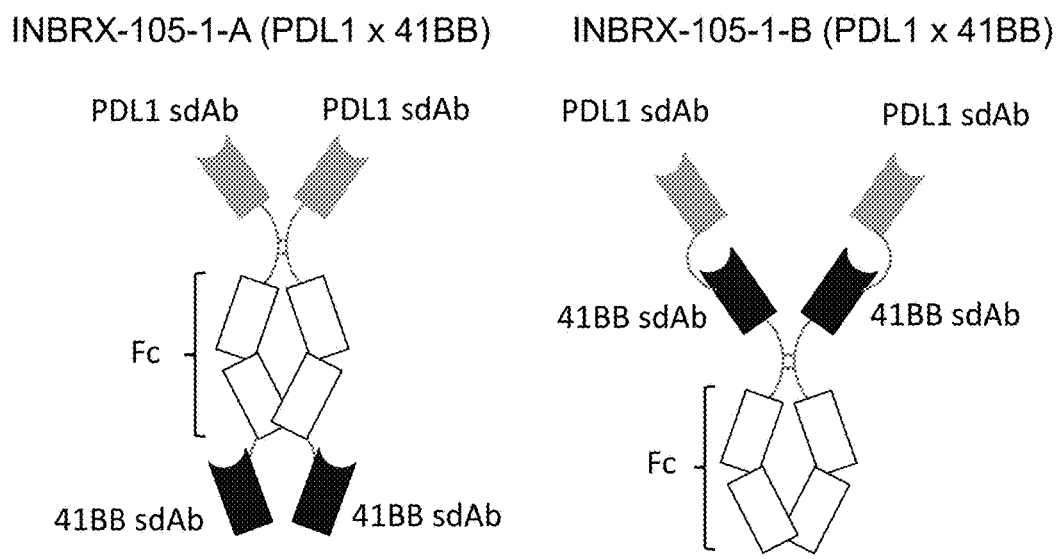
FIG. 13 is a schematic of two exemplary formats of a PDL1x41BB bispecific, INBRX-105-1. INBRX-105-1-A (left) has the PDL1 and 41BB binding domains, located at opposing terminal positions with a central Fc region, whereas INBRX-105-1-B (right) has the PDL1 and 41BB binding domains positioned in tandem, N-terminal to an Fc region.

FIG. 13 is a schematic of two exemplary formats of a PDL1x41BB bispecific fusion protein of the disclosure, referred to herein as INBRX-105-1. INBRX-105-1-A (left) has the PDL1 and 41BB binding domains located at opposing terminal positions with a central Fc region, whereas INBRX-105-1-B (right) has the PDL1 and 41BB binding domains positioned in tandem, N-terminal to an Fc region.

These two formats were further evaluated for their ability to bind human or cynomolgus monkey 41BB, to block the interaction between 41BB and 41BBL, to bind PDL1, and to block the interaction between PDL1 and PD1.

Figure 14A:
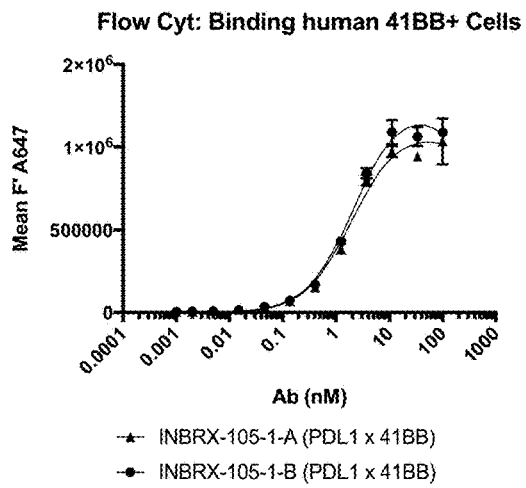
FIGS. 14A, 14B, and 14C are a series of graphs demonstrating the equivalent binding to human (FIG. 14A) or cynomolgus monkey (FIG. 14B) 41BB by the two distinct formats of a bispecific fusion protein targeting PDL1 and 41BB referred to herein as INBRX-105-1-A and INBRX-105-1-B. Binding was assessed by flow cytometry on 41BB expressing 293freestyle cells.
Figure 14B:
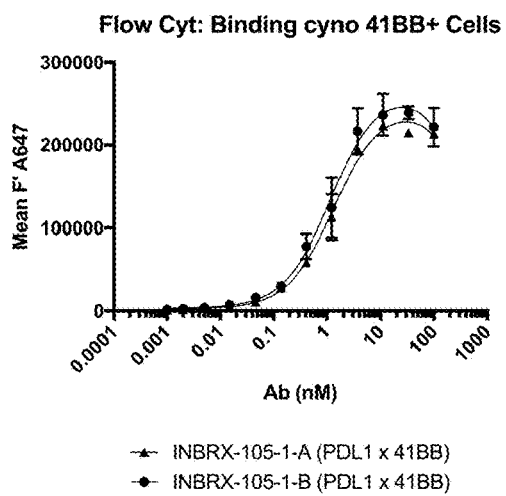
Figure 14C:
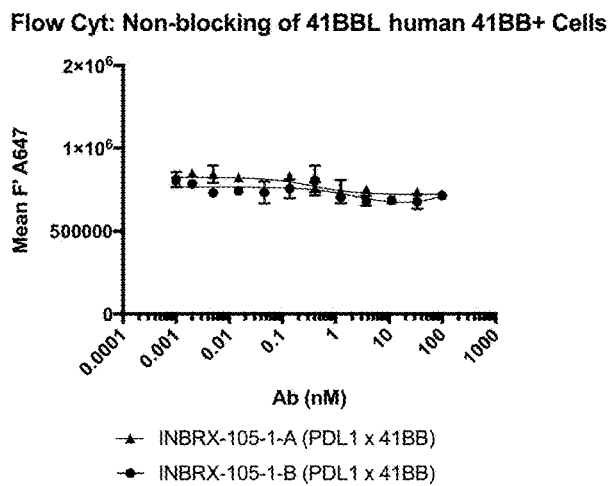
Figure 15A:
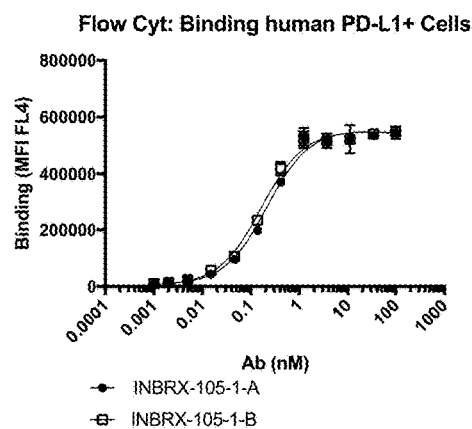
FIGS. 15A, 15B, 15C, and 15D are a series of graphs demonstrating the equivalent binding (FIG. 15A and FIG. 15C). and PD1 blocking (FIG. 15B and FIG. 15D) by the two distinct formats of a bispecific fusion protein targeting PDL1 and 41BB referred to herein as INBRX-105-1-A and INBRX-105-1-B. Binding was assessed by flow cytometry on human (FIG. 15A) or cynomolgus monkey (FIG. 15C) PDL1 expressing 293freestyle cells. Blocking was assessed by flow cytometry using on human (FIG. 15B) or cynomolgus monkey (FIG. 15D) PDL1 expressing 293freestyle cells with either recombinant human (FIG. 15B) or cynomolgus monkey (FIG. 15D) PD1-mFc fusion protein. Bound PD1 was detected using an anti-mouse IgG-Fc specific secondary antibody.
Figure 15B:
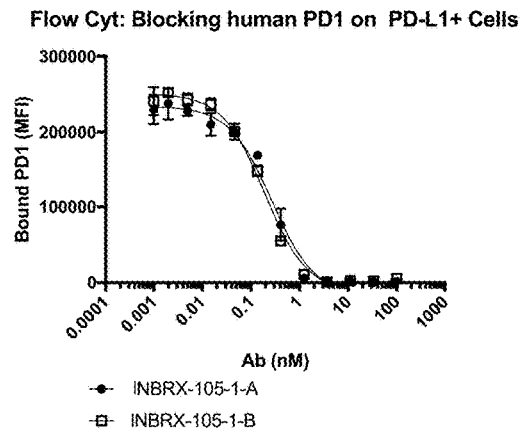
Figure 15C:
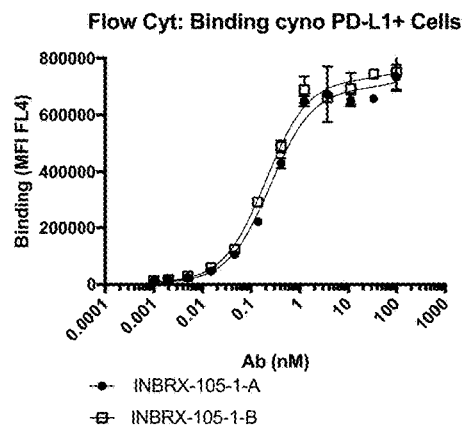
Figure 15D:
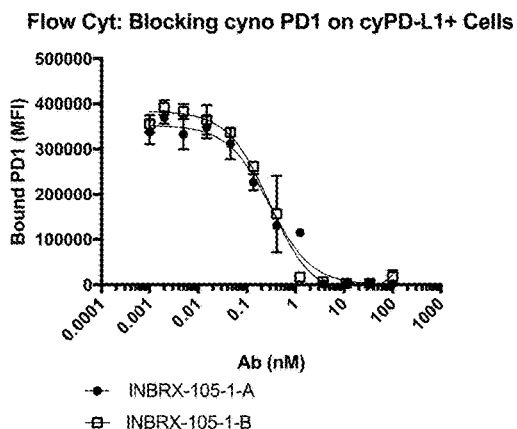

In particular, FIGS. 14A, 14B, and 14C demonstrate the equivalent binding to human (FIG. 14A) or cynomolgus monkey (FIG. 14B) 41BB by the two distinct formats of a bispecific fusion protein targeting PDL1 and 41BB referred to herein as INBRX-105-1-A and INBRX-105-1-B and illustrated in FIG. 13. Binding was assessed by flow cytometry on 41BB expressing 293freestyle cells. In the studies presented herein, hzRH3v5-1 (SEQ ID NO: 124) is the 41BB binding domain used in both formats. As shown in FIG. 14C, the bispecific fusion protein containing hzRh3v5-1 does not block 41BBL binding to cell surface 41BB. In these studies, a recombinant fusion protein of 41BBL and a mouse Fc region was used, and bound 41BBL was detected using an anti-mouse IgG-Fc specific secondary antibody.

Furthermore, FIGS. 15A, 15B, 15C, and 15D demonstrate the equivalent binding (FIG. 15A and FIG. 15C) and PD1 blocking (FIG. 15B and FIG. 15D) by the two distinct formats of a bispecific fusion protein targeting PDL1 and 41BB referred to herein as INBRX-105-1-A and INBRX-105-1-B. Binding was assessed by flow cytometry on human (FIG. 15A) or cynomolgus monkey (FIG. 15C) PDL1 expressing 293freestyle cells. Blocking was assessed by flow cytometry using on human (FIG. 15B) or cynomolgus monkey (FIG. 15D) PDL1 expressing 293freestyle cells with either recombinant human (FIG. 15B) or cynomolgus monkey (FIG. 15D) PD1-mFc fusion protein. Bound PD1 was detected using an anti-mouse IgG-Fc specific secondary antibody. In the studies presented herein, hz28A2v5 is the PDL1-binding domain used in both formats.

Figure 16:
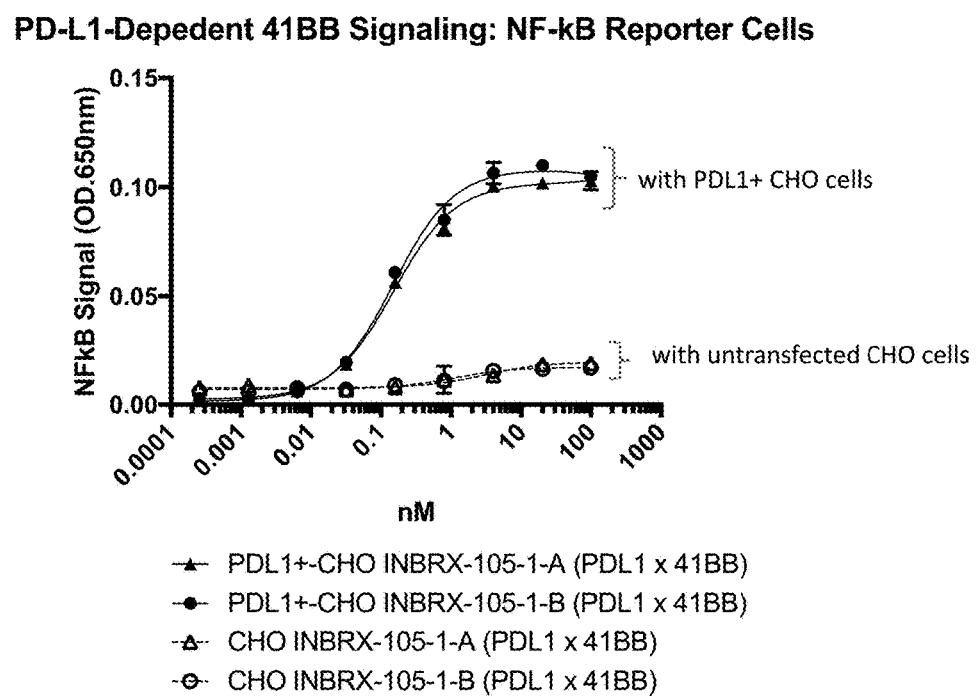
FIG. 16 is a graph demonstrating the ability of humanized versions of a PDL1x41BB bispecific fusion protein (INBRX-105-1) to induce PDL1-dependent 41BB agonism. A 41BB-expressing HEK293 NF-kB reporter cell line was used to assess 41BB signaling and a PDL1-expressing CHO cell line was used as the source of PDL1.

The PDL1x41BB bispecific fusion proteins were evaluated for their ability to induce PDL1-dependent 41BB agonism. FIG. 16 demonstrates the ability of humanized versions of a PDL1x41BB bispecific fusion protein (INBRX-105-1) to induce PDL1-dependent 41BB agonism. Compared herein are two distinct formats, INBRX-105-1-A vs INBRX-105-1-B, having the PDL1 and 41BB binding domains positioned at opposite termini or in tandem within the fusion protein, respectively. Notably, INBRX-105-1-A vs INBRX-105-1-B demonstrate equivalent PDL1-dependent agonistic activities. A 41BB-expressing HEK293 NF-kB reporter cell line was used to assess 41BB signaling and a PDL1-expressing CHO cell line was used as the source of PDL1. This reporter cell line implements an NF-kB driven secreted alkaline phosphatase, to monitor NF-kB signaling.

Figure 17A:
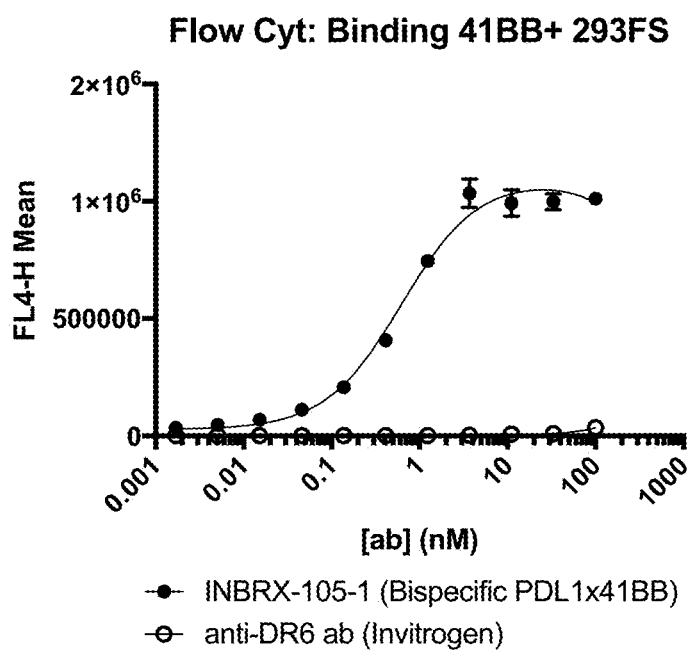
FIGS. 17A and 17B are a pair of graphs demonstrating the 41BB-specific binding by the 41BB-binding portion of a PDL1x41BB bispecific fusion protein (INBRX-105-1) of the present disclosure. Binding was assessed on 41BB (FIG. 17A) or the closest homolog, TNFRSF21/DR6 (FIG. 17B), expressing 293freestyle cells by flow cytometry. An anti-DR6 antibody (Invitrogen) was used to as positive control for DR6 expression.
Figure 17B:
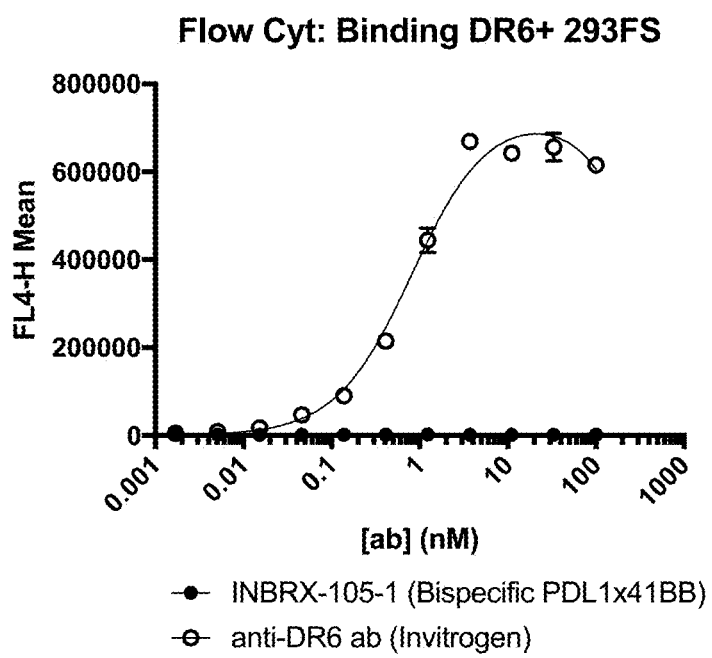
Figure 18A:
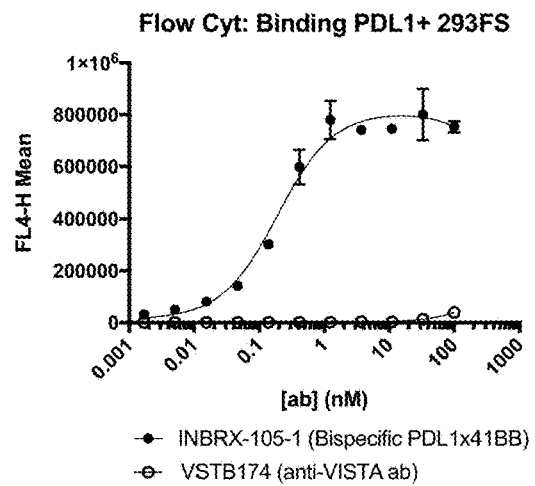
FIGS. 18A, 18B, and 18C are a series of graphs demonstrating the PDL1-specific binding by the PDL1-binding portion of a PDL1x41BB bispecific fusion protein (INBRX-105-1) of the present disclosure. Binding was assessed on PDL1 (FIG. 18A), and its closest homologs PDL2 (FIG. 18B) or VISTA/PDL3 (FIG. 18C), expressing 293freestyle cells by flow cytometry. Anti-PDL2 and anti-VISTA antibodies were used to as positive controls for PDL2 and PDL3 expression respectively.
Figure 18B:
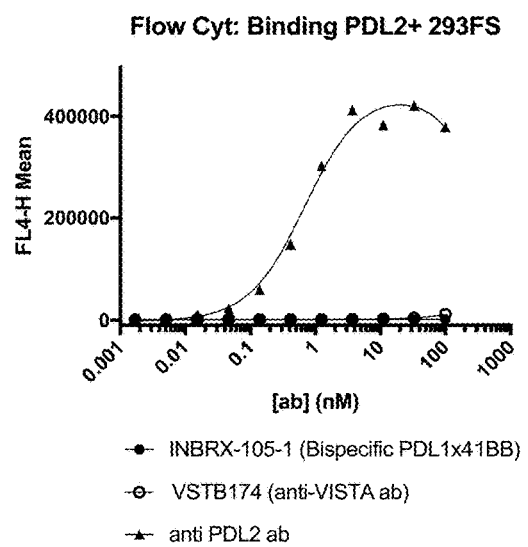
Figure 18C:
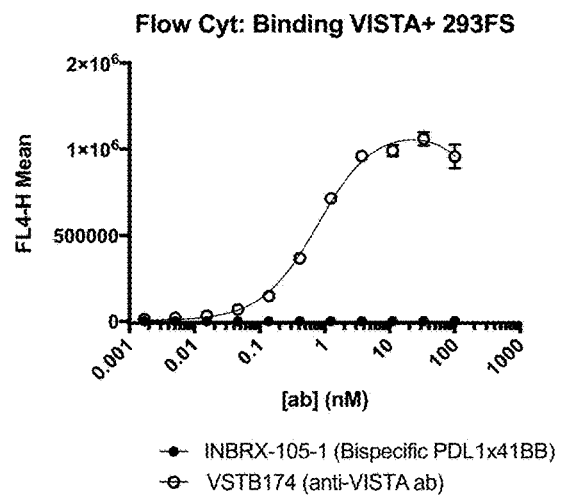

The ability of the 41BB-specific binding and the PDL1-specific binding by the binding domains in the PDL1x41BB bispecific fusion proteins was evaluated. FIGS. 17A and 17B demonstrate the 41BB-specific binding by the 41BB-binding portion of a PDL1x41BB bispecific fusion protein (INBRX-105-1) of the present disclosure. Binding was assessed on 41BB (FIG. 17A) or the closest homolog, TNFRSF21/DR6 (FIG. 17B), expressing 293freestyle cells by flow cytometry. An anti-DR6 antibody (Invitrogen) was used to as positive control for DR6 expression. In addition, FIGS. 18A, 18B, and 18C demonstrate the PDL1-specific binding by the PDL1-binding portion of a PDL1x41BB bispecific fusion protein (INBRX-105-1) of the present disclosure. Binding was assessed on PDL1 (FIG. 18A), the closest homologs PDL2 (FIG. 18B) or VISTA/PDL3 (FIG. 18C), expressing 293freestyle cells by flow cytometry. An anti-PDL2 antibody and an anti-VISTA antibody known as VSTB174, which is disclosed in PCT Publication No. WO 2015/097536, were used to as positive controls for PDL2 and PDL3 expression respectively.

Figure 19A:
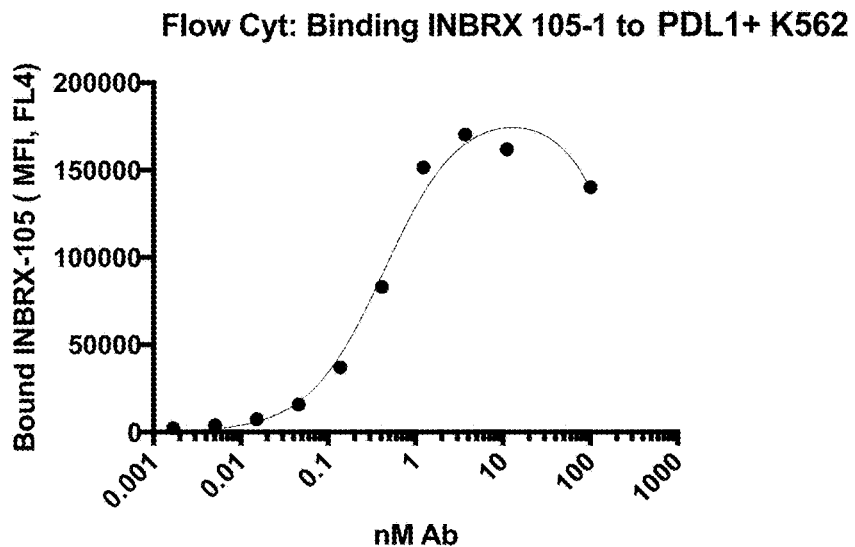
FIGS. 19A and 19B are a pair of graphs demonstrating the ability of a PDL1x41BB bispecific fusion protein to simultaneously bind PDL1 and 41BB. Bound 41BB was detected using an anti-mouse IgG-Fc specific secondary antibody.
Figure 19B:
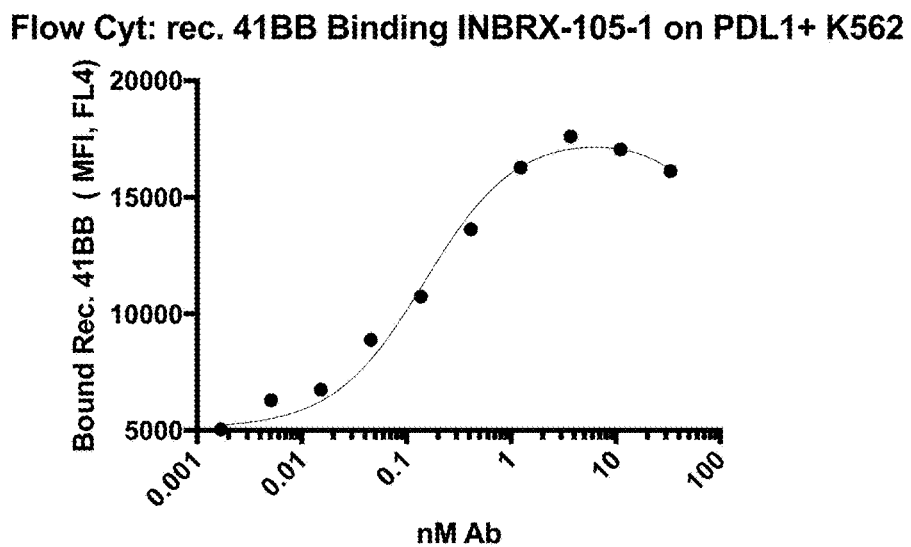

The ability of the PDL1x41BB bispecific fusion proteins to simultaneously bind both 41BB and PDL1 was evaluated. FIGS. 19A and 19B demonstrate the ability of a PDL1x41BB bispecific fusion protein to simultaneously bind PDL1 and 41BB. INBRX-105-1 was titrated onto PDL1 expressing K562 cells and 25 nM recombinant 41BB-mFc proteins was added. Bound 41BB was detected using an anti-mouse IgG-Fc specific secondary antibody. FIG. 19A. is a graph showing the binding of INBRX-105-1 to the PDL1 expressing K562 cells. FIG. 19B is a graph showing the binding of recombinant 41BB to INBRX-105-1 on the PDL1 expressing cells.

Figure 20:
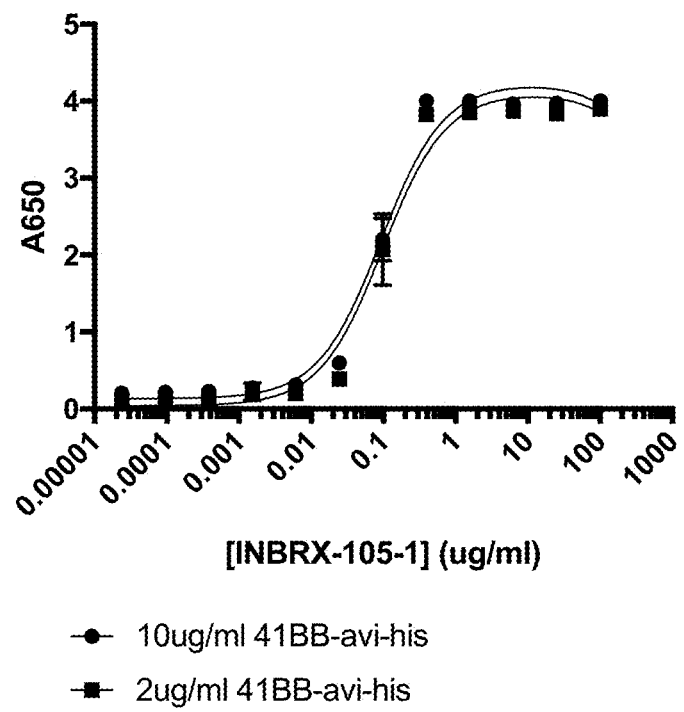
FIG. 20 is a graph demonstrating the ability of a PDL1x41BB bispecific fusion protein to simultaneously bind recombinant PDL1 and recombinant 41BB in an ELISA. Bound recombinant 41BB was detected via streptavidin-HRP.

FIG. 20 demonstrates the ability of a PDL1x41BB bispecific fusion protein to simultaneously bind recombinant PDL1 and recombinant 41BB in an ELISA. INBRX-105-1 was titrated on to immobilized (Medisorp plate) recombinant PDL1, subsequently either 2 or 10 µg/ml biotinylated-recombinant 41BB (His-tagged) was added. Bound recombinant 41BB was detected via streptavidin-HRP.

Figure 21A:
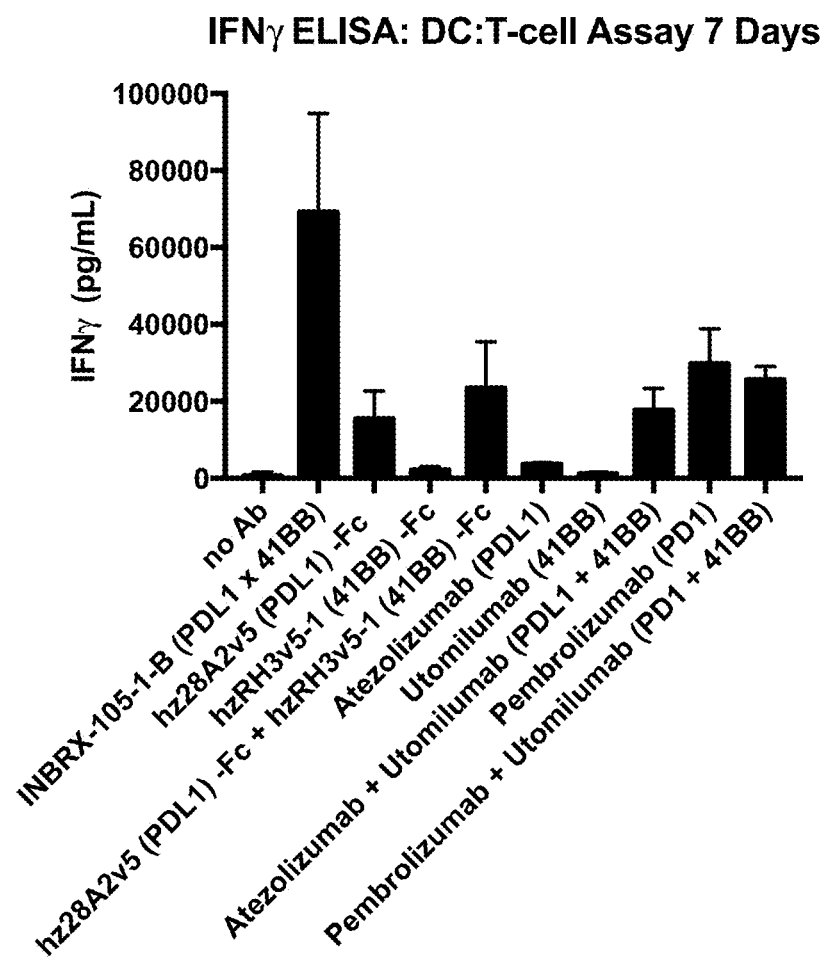
FIGS. 21A, 21B, and 21C are a series of graphs demonstrating the effect of a PDL1x41BB bispecific fusion protein (INBRX-105-1) of the present disclosure on T-cell activation and proliferation. INFγ production in the cell supernatant was monitored using an ELISA and normalized to the standard curve. T-cell proliferation was monitored by flow cytometry using CTV labeling of T-cells. T-cell activation was assessed by the presence of the activation marker CD25 monitored by flow cytometry. Antibodies were used at 10 nM.
Figure 21B:
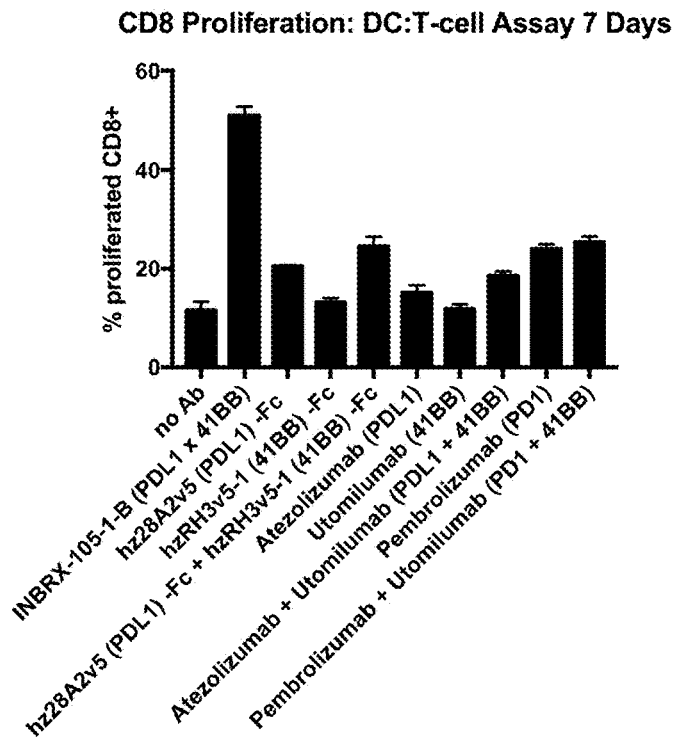
Figure 21C:
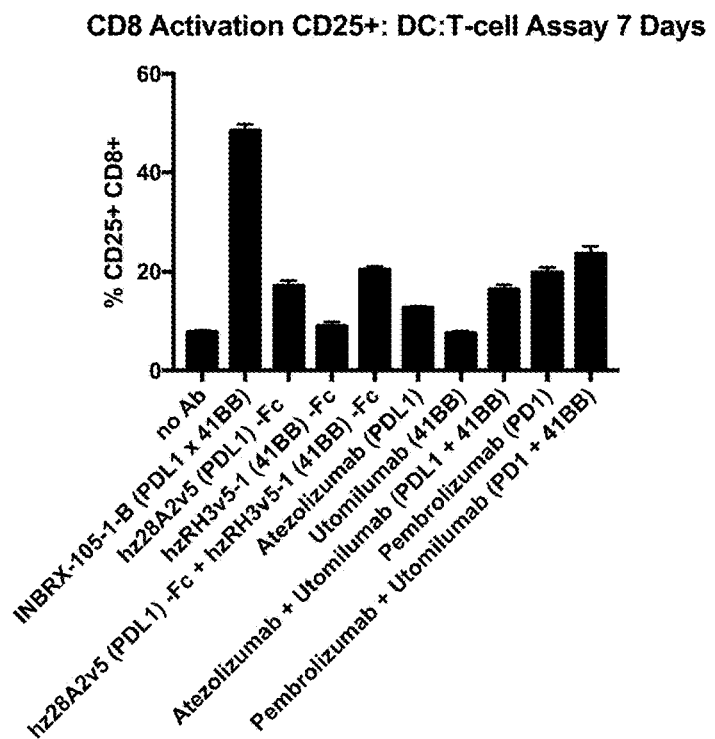

The effect of the PDL1x41BB bispecific fusion proteins to on T-cell activation and proliferation was evaluated. FIGS. 21A, 21B, and 21C demonstrate the effect of a PDL1x41BB bispecific fusion protein (INBRX-105-1) of the present disclosure on T-cell activation and proliferation. Herein an autologous in vitro co-culture system implementing immature DC (iDC) and donor matched T-cells was conducted for 7 days. PDL1$^+$ iDC were derived by enriching the monocyte population (EasySep™ Human Monocyte Enrichment Kit, STEMCELL Technologies Inc.) from human donor PBMCs and culturing them in 500 U/ml GM-CSF and 250 U/ml IL-4 for 7 days. Autologous T-cells were enriched at the same time (EasySep™ Human T-cell Enrichment Kit, STEM-CELL Technologies Inc.) and cryopreserved until iDC derivation was complete. Enriched T-cells were added to iDC at approximately 20:1 (T-cell:iDC) and co-cultured for at least 7 days in the presence of IL-7. The PDL1x41BB bispecific, INBRX-105-1, is superior to the monospecific PDL1 sdAb-Fc fusion protein (hz28A2v5-Fc), the 41BB sdAb-Fc fusion protein (hzRH3v5-1-Fc), the combination of the hz28A2v5-Fc and hzRH3v5-1-Fc, the anti-PDL1 antibody Atezolizumab, the anti-41BB antibody, Utomilumab (PF-05082566, disclosed in U.S. Pat. No. 8,337,850), or the anti-PD1 antibody Prembrolizumab, and combinations thereof, at inducing INFγ (FIG. 21A) or mediating CD8+ T-cell proliferation (FIG. 21B) and activation (FIG. 21C). INFγ production in the cell supernatant was monitored using an ELISA and normalized to the standard curve. T-cell proliferation was monitored by flow cytometry using CTV labeling of T-cells. T-cell activation was assessed by the presence of the activation marker CD25 monitored by flow cytometry. Antibodies were used at 10 nM. INBRX-105-1 seemingly augments low level and/or tonic T-cell activation/signaling events that is dampened by the PDL1:PD1 interaction.

Figure 22A:
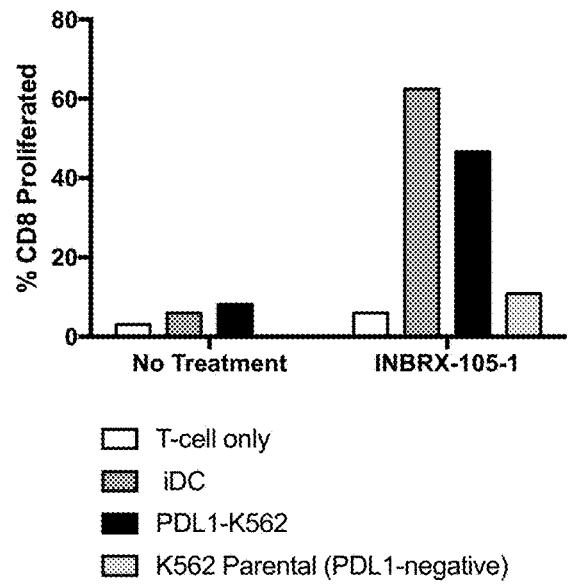
FIGS. 22A and 22B are a pair of graphs demonstrating PDL1-dependent 41BB agonism mediated by a PDL1x41BB bispecific fusion protein (INBRX-105-1) of the present disclosure. CD8⁻ T-cell proliferation (FIG. 22A) was monitored using CTV labeling and INFγ production (FIG. 22B) in the cell supernatant was monitored using an ELISA and normalized to the standard curve.
Figure 22B:
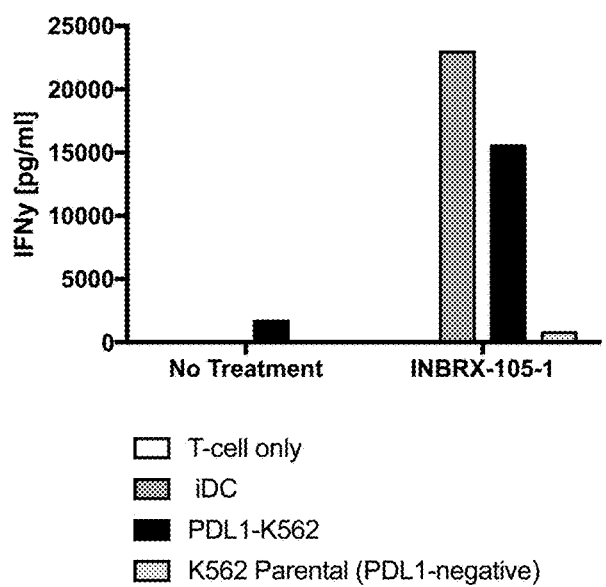

FIGS. 22A and 22B demonstrate PDL1-dependent 41BB agonism mediated by a PDL1x41BB bispecific fusion protein (INBRX-105-1) of the present disclosure. In these studies, T-cells were cultured alone or with autologous immature DCs (iDC, PDL1-expressing), a PDL1-expressing K562 cell line or the parental K562 cell line (PDL1-negative) in the presence or absence of 10 nM INBRX-105-1 for 7 days. CD8+ T-cell proliferation (FIG. 22A) was monitored using CTV labeling and INFγ production (FIG. 22B) in the cell supernatant was monitored using an ELISA and normalized to the standard curve.

Figure 23:
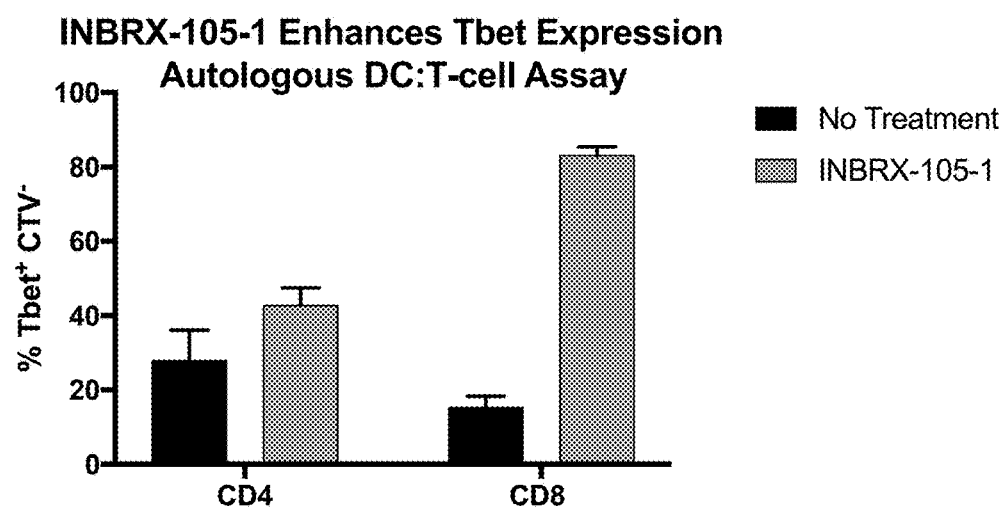
FIG. 23 is a graph demonstrating the capacity of a PDL1x41BB bispecific fusion protein (INBRX-105-1) of the present disclosure to enhance the Th1 lineage defining transcription factor, T-bet, expression in T-cell populations. T-bet expression was assessed on CD4$^+$ and CD8$^-$ T-cell population by flow cytometry via intracellular staining following fixation and permeabilization.

FIG. 23 demonstrates the capacity of a PDL1x41BB bispecific fusion protein (INBRX-105-1) of the present disclosure to enhance the Th1 lineage defining transcription factor, T-bet, expression in T-cell populations. Herein T-cells were co-cultured with autologous immature DCs for 7 days in the presence or absence of INBRX-105-1. T-bet expression was assessed on CD4+ and CD8+ T-cell population by flow cytometry via intracellular staining following fixation and permeabilization. INBRX-105-1 has a more dramatic effect on T-bet expression in CD8+ T-cells.

Figure 24A:
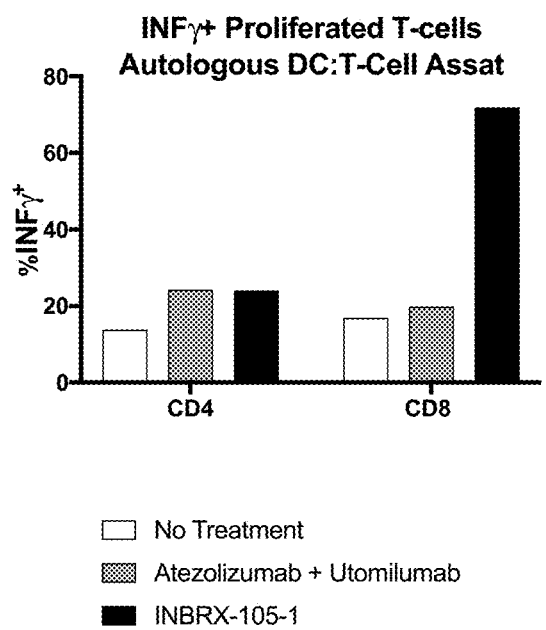
FIGS. 24A and 24B are a pair graphs contrasting the capacity of a PDL1x41BB bispecific fusion protein (INBRX-105-1) of the present disclosure and the combination of monospecific antibodies Atezolizumab (anti-PDL1) and Utomilumab (anti-41BB) to induce INFγ (FIG. 24A) or TNFα (FIG. 24B) production from CD4$^+$ or CD8$^+$ T-cells. Cytokine expression was assessed on CD4$^+$ and CD8$^+$ T-cell population by flow cytometry via intracellular staining following fixation and permeabilization.
Figure 24B:
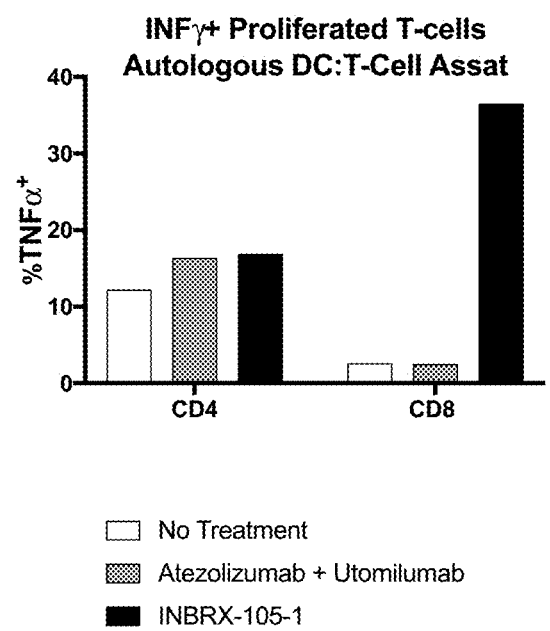

The PDL1x41BB bispecific fusion proteins of the disclosure were compared to various known monospecific antibodies. FIGS. 24A and 24B contrast the capacity of a PDL1x41BB bispecific fusion protein (INBRX-105-1) of the present disclosure and the combination of monospecific antibodies Atezolizumab (anti-PDL1) and Utomilumab (anti-41BB) to induce INFγ (FIG. 24A) or TNFα (FIG. 24B) production from CD4+ or CD8+ T-cells. Herein T-cells were co-cultured with autologous immature DCs for 7 days in the presence or absence of INBRX-105-1 or the combination of the monospecific antibodies. INBRX-105-1 is far superior at T-cell co-stimulation compared to monospecific antibodies targeting the same antigens. Cytokine expression was assessed on CD4+ and CD8+ T-cell population by flow cytometry via intracellular staining following fixation and permeabilization.

Figure 25A:
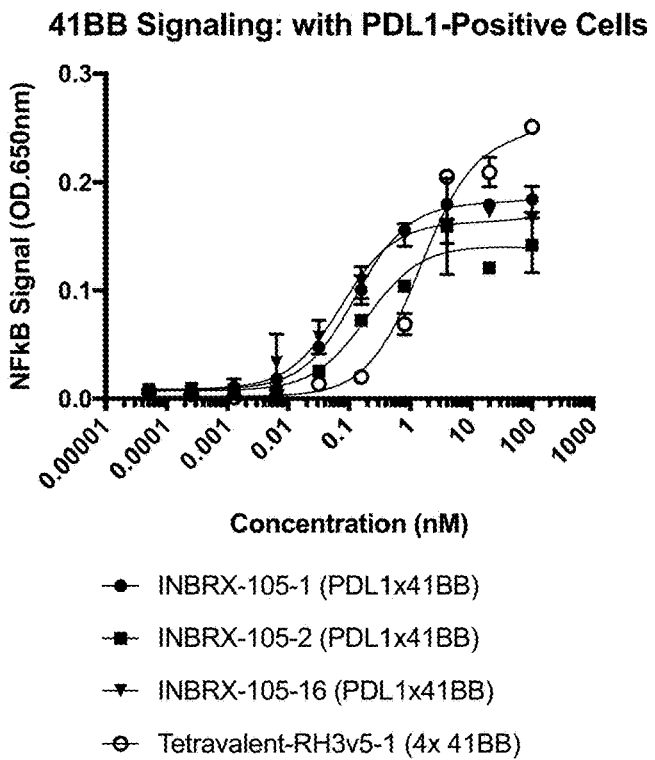
FIGS. 25A and 25B are a pair of graphs demonstrating the agonistic capacity of a tetravalent 41BB-binding fusion protein and PDL1x41BB bispecific fusion proteins of the present disclosure in the presence of an additional PDL1 positive (FIG. 25A) or negative (FIG. 25B) cell line. Herein a 41BB-expressing HEK293 NF-kB reporter cell was used and co-incubated with either the PDL1-negative K562 cell line (FIG. 25B) or a stably transfected, PDL1-expressing K562 cell line (FIG. 25A).
Figure 25B:
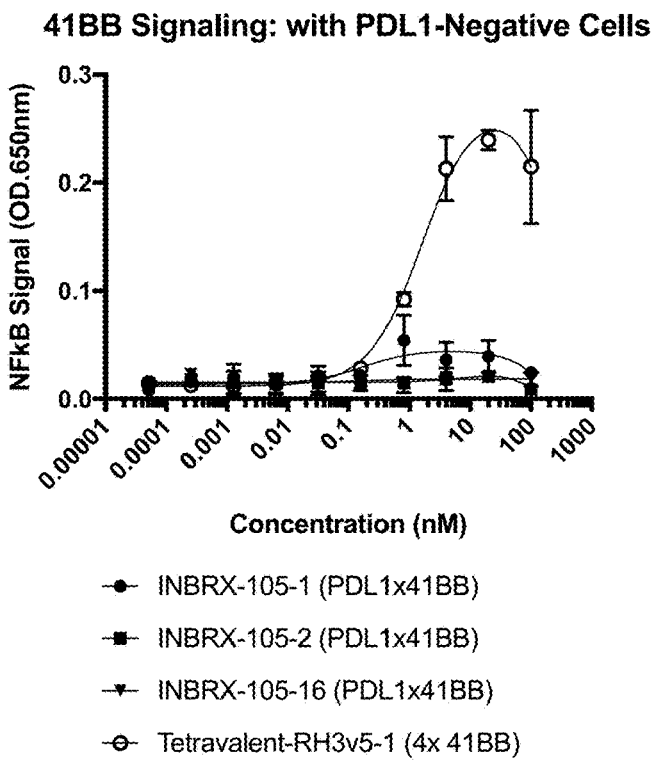

FIGS. 25A and 25B demonstrate the agonistic capacity of a tetravalent 41BB-binding fusion protein and PDL1x41BB bispecific fusion proteins of the present disclosure in the presence of an additional PDL1 positive (FIG. 25A) or negative (FIG. 25B) cell line. Notably only the tetravalent 41BB binding fusion protein is capable of inducing 41BB signaling in the absence of a PDL1 expressing cell line. The bispecific PDL1x41BB fusion proteins (INBRX-105-1, INBRX-105-2 and INBRX-105-16) only induced 41BB signaling when bound to cell surface PDL1 as shown in FIG. 25A. This demonstrates that bivalent engagement of 41BB, as is the case of INBRX-105, is insufficient to effectively cluster and mediate productive 41BB signaling. Engagement of a second cell surface antigen, PDL1 as in the present example, enables further clustering of 41BB and productive signaling. Herein a 41BB-expressing HEK293 NF-kB reporter cell was used and co-incubated with either the PDL1-negative K562 cell line (FIG. 25B) or a stably transfected, PDL1-expressing K562 cell line (FIG. 25A). INBRX-105-1 incorporates the 41BB-targeting sdAb: hzRH3v5-1, INBRX-105-2 incorporates the 41BB-targeting sdAb: hzRH3v5-2 and INBRX-105-16 incorporates the 41BB-targeting sdAb: hzRH3v5-16 and all incorporate the hz28A2v5 PDL1-targeting sdAb. The tetravalent 41BB-targeting fusion protein used herein has the following format comprising hzRH3v5-1-Fc-hzRH3v5-1.

What is claimed is:

1. An isolated polypeptide comprising at least one VHH domain that binds PDL1 and at least one VHH domain that binds 41BB, wherein each VHH domain that binds PDL1 comprises a CDR1 comprising the amino acid sequence of SEQ ID NO: 105, a CDR2 comprising the amino acid sequence of SEQ ID NO: 106, and a CDR3 comprising the amino acid sequence of SEQ ID NO: 107; and wherein each VHH domain that binds 41BB comprises a CDR1, a CDR2, and a CDR3, respectively, comprising the amino acid sequences of SEQ ID NOs: 26, 27 and 28; or SEQ ID NOs: 26, 61, and 28; or SEQ ID NOs: 26, 63, and 28; or SEQ ID NOs: 26, 71, and 28; or SEQ ID NOs: 26, 73, and 28; or SEQ ID NOs: 26, 75, and 28; or SEQ ID NOs: 26, 77, and 28; or SEQ ID NOs: 26, 79, and 28; or SEQ ID NOs: 65, 61, and 28; or SEQ ID NOs: 67, 61, and 28; or SEQ ID NOs: 69, 61, and 28.

2. The isolated polypeptide of claim 1, wherein at least one VHH domain that binds PDL1 is humanized.

3. The isolated polypeptide of claim 1, wherein at least one VHH domain that binds PDL1 comprises an amino acid sequence that is at least 95% identical to an amino acid sequence selected from SEQ ID NOs: 104 and 119-124.

4. The isolated polypeptide of claim 1, wherein at least one VHH domain that binds PDL1 comprises an amino acid sequence selected from SEQ ID NOs: 104 and 119-124.

5. The isolated polypeptide of claim 1, wherein at least one VHH domain that binds PDL1 comprises the amino acid sequence of SEQ ID NO: 124.

6. The isolated polypeptide of claim 1, wherein at least one VHH domain that binds 41BB is humanized.

7. The isolated polypeptide of claim 1, wherein at least one VHH domain that binds 41BB comprises an amino acid sequence that is at least 95% identical to an amino acid sequence selected from SEQ ID NOs: 25, 59, 60, 62, 64, 66, 68, 70, 72, 74, 76, 78, 80, 81, 82, and 83.

8. The isolated polypeptide of claim 1, wherein at least one VHH domain that binds 41BB comprises an amino acid sequence selected from SEQ ID NOs: 25, 59, 60, 62, 64, 66, 68, 70, 72, 74, 76, 78, 80, 81, 82, and 83.

9. The isolated polypeptide of claim 1, wherein at least one VHH domain that binds 41BB comprises the amino acid sequence of SEQ ID NO: 60.

10. The isolated polypeptide of claim 1, wherein at least one VHH domain that binds 41BB comprises a CDR1 comprising the amino acid sequence of SEQ ID NO: 26, a CDR2 comprising the amino acid sequence of SEQ ID NO: 61, and a CDR3 comprising the amino acid sequence of SEQ ID NO: 28.

11. The isolated polypeptide of claim 1, wherein each VHH domain that binds 41BB comprises the amino acid sequence of SEQ ID NO: 60.

12. The isolated polypeptide of claim 1, wherein the polypeptide comprises one VHH domain that binds 41BB, wherein the VHH domain that binds 41BB comprises a CDR1 comprising the amino acid sequence of SEQ ID NO: 26, a CDR2 comprising the amino acid sequence of SEQ ID NO: 61, and a CDR3 comprising the amino acid sequence of SEQ ID NO: 28.

13. The isolated polypeptide of claim 12, wherein the VHH domain that binds 41BB is humanized.

14. The isolated polypeptide of claim 12, wherein the VHH domain that binds 41BB comprises the amino acid sequence of SEQ ID NO: 60.

15. The isolated polypeptide of claim 1, wherein the isolated polypeptide comprises an Fc region.

16. The isolated polypeptide of claim 15, wherein the Fc region comprises an amino acid sequence that is at least 97% identical to an amino acid sequence selected from SEQ ID NOs: 1-6.

17. The isolated polypeptide of claim 15, wherein the Fc region comprises an amino acid sequence selected from SEQ ID NOs: 1-6.

18. The isolated polypeptide of claim 15, which forms a homodimer under physiological conditions.

19. The isolated polypeptide of claim 15, wherein the polypeptide has the structure VHH-Linker-VHH-Linker-Hinge-Fc.

20. The isolated polypeptide of claim 19, wherein each linker is, independently, 5-20 amino acids in length.

21. The isolated polypeptide of claim 19, wherein the hinge comprises a sequence selected from SEQ ID NOs: 7-9.

22. The isolated polypeptide of claim 1, wherein each VHH domain that binds 41BB comprises a CDR1 comprising the amino acid sequence of SEQ ID NO: 26, a CDR2 comprising the amino acid sequence of SEQ ID NO: 61, and a CDR3 comprising the amino acid sequence of SEQ ID NO: 28.

23. The isolated polypeptide of claim 22, wherein the isolated polypeptide comprises two VHH domains that bind PDL1.

24. The isolated polypeptide of claim 23, wherein the isolated polypeptide comprises two VHH domains that bind 41BB.

25. The isolated polypeptide of claim 22, wherein the isolated polypeptide comprises two VHH domains that bind 41BB.

26. The isolated polypeptide of claim 1, wherein the isolated polypeptide comprises two VHH domains that bind PDL1.

27. The isolated polypeptide of claim 26, wherein the isolated polypeptide comprises two VHH domains that bind 41BB.

28. The isolated polypeptide of claim 1, wherein the isolated polypeptide comprises two VHH domains that bind 41BB.

29. The isolated polypeptide of claim 1, wherein each VI-11-1 domain of the isolated polypeptide is humanized.

30. The isolated polypeptide of claim 1, wherein the PDL1 is human PDL1, and wherein the 41BB is human 41BB.

31. The isolated polypeptide of claim 1, wherein the polypeptide comprises one VHH domain that binds PDL1.

32. The isolated polypeptide of claim 31, wherein the VHH domain that binds PDL1 is humanized.

33. The isolated polypeptide of claim 31, wherein the VHH domain that binds PDL1 comprises the amino acid sequence of SEQ ID NO: 124.

34. The isolated polypeptide of claim 33, wherein the polypeptide comprises one VHH domain that binds 41BB, wherein the VHH domain that binds 41BB comprises the amino acid sequence of SEQ ID NO: 60.

35. The isolated polypeptide of claim 34, wherein the isolated polypeptide comprises an Fc region.

36. The isolated polypeptide of claim 35, wherein the Fc region comprises an amino acid sequence that is at least 97% identical to an amino acid sequence selected from SEQ ID NOs: 1-6.

37. The isolated polypeptide of claim 35, wherein the Fc region comprises an amino acid sequence selected from SEQ ID NOs: 1-6.

38. The isolated polypeptide of claim 35, wherein the polypeptide has the structure VHH-Linker-VHH-Linker-Hinge-Fc.

39. The isolated polypeptide of claim 38, wherein each linker is, independently, 5-20 amino acids in length.

40. The isolated polypeptide of claim 38, wherein the hinge comprises a sequence selected from SEQ ID NOs: 7-9.

41. The isolated polypeptide of claim 38, which forms a homodimer under physiological conditions.

42. The isolated polypeptide of claim 35, which forms a homodimer under physiological conditions.

43. The isolated polypeptide of claim 31, wherein the polypeptide comprises one VHH domain that binds 41BB, wherein the VHH domain that binds 41BB comprises a CDR1 comprising the amino acid sequence of SEQ ID NO: 26, a CDR2 comprising the amino acid sequence of SEQ ID NO: 61, and a CDR3 comprising the amino acid sequence of SEQ ID NO: 28.

44. The isolated polypeptide of claim 43, wherein the PDL1 is human PDL1, and wherein the 41BB is human 41BB.

45. A method of treating cancer comprising administering to a subject with cancer a polypeptide of claim 43.

46. The method of claim 45, wherein the cancer is selected from carcinoma, sarcoma, lymphoma, and leukemia.

47. A method of increasing T cell activation and/or proliferation comprising contacting T cells with a polypeptide of claim 43.

48. The method of claim 47, wherein the T cells are CD4+ T cells and/or CD8+ T cells.

49. A method of treating cancer comprising administering to a subject with cancer a polypeptide of claim 1.

50. The method of claim 49, wherein the cancer is selected from carcinoma, sarcoma, lymphoma, and leukemia.

51. A method of increasing T cell activation and/or proliferation comprising contacting T cells with a polypeptide of claim 1.

52. The method of claim 51, wherein the T cells are CD4+ T cells and/or CD8+ T cells.

53. An isolated polypeptide comprising a first VHH domain ($VHH_1$) that binds PDL1 and a second VHH domain ($VHH_2$) that binds 41BB, wherein $VHH_1$ comprises a CDR1 comprising the amino acid sequence of SEQ ID NO: 105, a CDR2 comprising the amino acid sequence of SEQ ID NO: 106, and a CDR3 comprising the amino acid sequence of SEQ ID NO: 107; and $VHH_2$ comprises a CDR1 comprising the amino acid sequence of SEQ ID NO: 26, a CDR2 comprising the amino acid sequence of SEQ ID NO: 61, and a CDR3 comprising the amino acid sequence of SEQ ID NO: 28; and wherein the polypeptide has the structure $VHH_1$-Linker-$VHH_2$-Linker-Hinge-Fc.

54. The isolated polypeptide of claim 53, wherein the first VHH domain comprises the amino acid sequence of SEQ ID NO: 124 and the second VHH domain comprises the amino acid sequence of SEQ ID NO: 60, and wherein the Fc region comprises an amino acid sequence that is at least 97% identical to an amino acid sequence selected from SEQ ID NOs: 1-6.

55. The isolated polypeptide of claim 54, wherein the Fc region comprises an amino acid sequence that is at least 97% identical to the sequence of SEQ ID NO: 2.

56. The isolated polypeptide of claim 54, wherein the Fc region comprises the amino acid sequence of SEQ ID NO: 2.

57. The isolated polypeptide of claim 53, wherein the polypeptide comprises an amino acid sequence that is at least 97% identical to the sequence of SEQ ID NO: 449.

58. The isolated polypeptide of claim 53, wherein the polypeptide comprises the amino acid sequence of SEQ ID NO: 449.

59. The isolated polypeptide of claim 58, which forms a dimer at physiological conditions.

60. The isolated polypeptide of claim 53, wherein the PDL1 is human PDL1, and wherein the 41BB is human 41BB.

61. A method of treating cancer comprising administering to a subject with cancer a polypeptide of claim 53.

62. The method of claim 61, wherein the cancer is selected from carcinoma, sarcoma, lymphoma, and leukemia.

63. A method of increasing T cell activation and/or proliferation comprising contacting T cells with a polypeptide of claim 53.

64. The method of claim 63, wherein the T cells are CD4+ T cells and/or CD8+ T cells.

\* \* \* \* \*

UNITED STATES PATENT AND TRADEMARK OFFICE
CERTIFICATE OF CORRECTION

PATENT NO. : 10,501,551 B2
APPLICATION NO. : 15/404016
DATED : December 10, 2019
INVENTOR(S) : Brendan P. Eckelman et al.

Page 1 of 1

It is certified that error appears in the above-identified patent and that said Letters Patent is hereby corrected as shown below:

In the Claims

Claim 29 Column 481, Line 29, "VI-11-1" should read --VHH--.

Signed and Sealed this
Fourth Day of February, 2020

Andrei Iancu
*Director of the United States Patent and Trademark Office*

SEQUENCE LISTING

```
<160> NUMBER OF SEQ ID NOS: 456

<210> SEQ ID NO 1
<211> LENGTH: 218
<212> TYPE: PRT
<213> ORGANISM: Artificial Sequence
<220> FEATURE:
<223> OTHER INFORMATION: chemically synthesized

<400> SEQUENCE: 1

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60
```

```
Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 2
<211> LENGTH: 215
<212> TYPE: PRT
<213> ORGANISM: Artificial Sequence
<220> FEATURE:
<223> OTHER INFORMATION: chemically synthesized

<400> SEQUENCE: 2

Pro Ala Pro Gly Gly Pro Ser Val Phe Leu Phe Pro Pro Lys Pro Lys
  1               5                  10                  15

Asp Thr Leu Met Ile Ser Arg Thr Pro Glu Val Thr Cys Val Val Val
             20                  25                  30

Asp Val Ser His Glu Asp Pro Glu Val Lys Phe Asn Trp Tyr Val Asp
         35                  40                  45

Gly Val Glu Val His Asn Ala Lys Thr Lys Pro Arg Glu Glu Gln Tyr
 50                  55                  60

Asn Ser Thr Tyr Arg Val Val Ser Val Leu Thr Val Leu His Gln Asp
 65                  70                  75                  80

Trp Leu Asn Gly Lys Glu Tyr Lys Cys Lys Val Ser Asn Lys Ala Leu
                 85                  90                  95

Pro Ala Pro Ile Glu Lys Thr Ile Ser Lys Ala Lys Gly Gln Pro Arg
            100                 105                 110

Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205
```

Leu Ser Leu Ser Pro Gly Lys
    210             215

<210> SEQ ID NO 3
<211> LENGTH: 217
<212> TYPE: PRT
<213> ORGANISM: Artificial Sequence
<220> FEATURE:
<223> OTHER INFORMATION: chemically synthesized

<400> SEQUENCE: 3

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210             215

<210> SEQ ID NO 4
<211> LENGTH: 218
<212> TYPE: PRT
<213> ORGANISM: Artificial Sequence
<220> FEATURE:
<223> OTHER INFORMATION: chemically synthesized

<400> SEQUENCE: 4

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
            85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
            115                 120                 125

Met Thr Lys Asn Gln Val Ser Leu Thr Cys Leu Val Lys Gly Phe Tyr
            130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
            165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
            195                 200                 205

Gln Lys Ser Leu Ser Leu Ser Pro Gly Lys
            210                 215

<210> SEQ ID NO 5
<211> LENGTH: 218
<212> TYPE: PRT
<213> ORGANISM: Artificial Sequence
<220> FEATURE:
<223> OTHER INFORMATION: chemically synthesized

<400> SEQUENCE: 5

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
            35                  40                  45

Tyr Val Asp Gly Val Glu Val His Asn Ala Lys Thr Lys Pro Arg Glu
        50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
            85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
            115                 120                 125

Met Thr Lys Asn Gln Val Ser Leu Thr Cys Leu Val Lys Gly Phe Tyr
            130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
            165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
            195                 200                 205

Gln Lys Ser Leu Ser Leu Ser Leu Gly Lys
            210                 215

<210> SEQ ID NO 6
<211> LENGTH: 218
<212> TYPE: PRT
<213> ORGANISM: Artificial Sequence
<220> FEATURE:
<223> OTHER INFORMATION: chemically synthesized

<400> SEQUENCE: 6

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215
```

<210> SEQ ID NO 7
<211> LENGTH: 14
<212> TYPE: PRT
<213> ORGANISM: Artificial Sequence
<220> FEATURE:
<223> OTHER INFORMATION: chemically synthesized

<400> SEQUENCE: 7

```
Glu Pro Lys Ser Ser Asp Lys Thr His Thr Cys Pro Pro Cys
1               5                   10
```

<210> SEQ ID NO 8
<211> LENGTH: 9
<212> TYPE: PRT
<213> ORGANISM: Artificial Sequence
<220> FEATURE:
<223> OTHER INFORMATION: chemically synthesized

<400> SEQUENCE: 8

```
Asp Lys Thr His Thr Cys Pro Pro Cys
1               5
```

<210> SEQ ID NO 9
<211> LENGTH: 11
<212> TYPE: PRT
<213> ORGANISM: Artificial Sequence
<220> FEATURE:
<223> OTHER INFORMATION: chemically synthesized

<400> SEQUENCE: 9

Glu Ser Lys Tyr Gly Pro Pro Cys Pro Pro Cys
1               5                   10

<210> SEQ ID NO 10
<211> LENGTH: 6
<212> TYPE: PRT
<213> ORGANISM: Artificial Sequence
<220> FEATURE:
<223> OTHER INFORMATION: chemically synthesized

<400> SEQUENCE: 10

Gly Gly Ser Gly Gly Ser
1               5

<210> SEQ ID NO 11
<211> LENGTH: 9
<212> TYPE: PRT
<213> ORGANISM: Artificial Sequence
<220> FEATURE:
<223> OTHER INFORMATION: chemically synthesized

<400> SEQUENCE: 11

Gly Gly Ser Gly Gly Ser Gly Gly Ser
1               5

<210> SEQ ID NO 12
<211> LENGTH: 12
<212> TYPE: PRT
<213> ORGANISM: Artificial Sequence
<220> FEATURE:
<223> OTHER INFORMATION: chemically synthesized

<400> SEQUENCE: 12

Gly Gly Ser Gly Gly Ser Gly Gly Ser Gly Gly Ser
1               5                   10

<210> SEQ ID NO 13
<211> LENGTH: 15
<212> TYPE: PRT
<213> ORGANISM: Artificial Sequence
<220> FEATURE:
<223> OTHER INFORMATION: chemically synthesized

<400> SEQUENCE: 13

Gly Gly Ser Gly Gly Ser Gly Gly Ser Gly Gly Ser Gly Gly Ser
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: chemically synthesized

<400> SEQUENCE: 14

Gly Gln Gly Thr Leu Val Thr Val Lys Pro Gly Gly
1               5                   10

```
<210> SEQ ID NO 15
<211> LENGTH: 12
<212> TYPE: PRT
<213> ORGANISM: Artificial Sequence
<220> FEATURE:
<223> OTHER INFORMATION: chemically synthesized

<400> SEQUENCE: 15

Gly Gln Gly Thr Leu Val Thr Val Glu Pro Gly Gly
1               5                   10

<210> SEQ ID NO 16
<211> LENGTH: 123
<212> TYPE: PRT
<213> ORGANISM: Artificial Sequence
<220> FEATURE:
<223> OTHER INFORMATION: chemically synthesized

<400> SEQUENCE: 16

Gln Val Gln Leu Gln Glu Ser Gly Gly Leu Val Gln Ala Gly Asp
1               5                   10                  15

Ser Leu Arg Leu Ser Cys Ala Ala Ser Gly Trp Ala Phe Asp Asn Tyr
                20                  25                  30

Gly Met Ala Trp Phe Arg Gln Ala Pro Gly Lys Glu Arg Glu Phe Ile
            35                  40                  45

Gly Arg Leu Ala Trp Asn Gly Gly Ser Thr Asp Tyr Ala Asp Ser Val
        50                  55                  60

Lys Gly Arg Phe Thr Ile Ser Arg Asp Asn Pro Lys Asn Thr Leu Tyr
65                  70                  75                  80

Leu Gln Met Asn Asn Leu Lys Pro Glu Asp Thr Ala Val Tyr Tyr Cys
                85                  90                  95

Ala Arg Gln Arg Ser Tyr Ser Gly Tyr Gly Ile Arg Thr Pro Gln Thr
            100                 105                 110

Tyr Asp Tyr Trp Gly Gln Gly Thr Gln Val Thr
        115                 120

<210> SEQ ID NO 17
<211> LENGTH: 8
<212> TYPE: PRT
<213> ORGANISM: Artificial Sequence
<220> FEATURE:
<223> OTHER INFORMATION: chemically synthesized

<400> SEQUENCE: 17

Gly Trp Ala Phe Asp Asn Tyr Gly
1               5

<210> SEQ ID NO 18
<211> LENGTH: 8
<212> TYPE: PRT
<213> ORGANISM: Artificial Sequence
<220> FEATURE:
<223> OTHER INFORMATION: chemically synthesized

<400> SEQUENCE: 18

Leu Ala Trp Asn Gly Gly Ser Thr
1               5

<210> SEQ ID NO 19
<211> LENGTH: 19
<212> TYPE: PRT
<213> ORGANISM: Artificial Sequence
<220> FEATURE:
<223> OTHER INFORMATION: chemically synthesized
```

<400> SEQUENCE: 19

Ala Arg Gln Arg Ser Tyr Ser Gly Tyr Gly Ile Arg Thr Pro Gln Thr
1               5                   10                  15

Tyr Asp Tyr

<210> SEQ ID NO 20
<211> LENGTH: 123
<212> TYPE: PRT
<213> ORGANISM: Artificial Sequence
<220> FEATURE:
<223> OTHER INFORMATION: chemically synthesized

<400> SEQUENCE: 20

Gln Val Gln Leu Gln Gln Ser Gly Gly Leu Val Gln Ala Gly Asp
1               5                   10                  15

Ser Leu Arg Leu Ser Cys Ala Ala Ser Gly Trp Ala Phe Gly Asn Tyr
                20                  25                  30

Gly Met Ala Trp Phe Arg Arg Ala Pro Gly Lys Glu Arg Glu Phe Ile
            35                  40                  45

Gly Arg Leu Ala Trp Asn Gly Gly Ser Thr Asp Tyr Val Asp Ser Val
        50                  55                  60

Lys Gly Arg Phe Thr Ile Ser Arg Asp Asn Pro Lys Asn Thr Leu Tyr
65                  70                  75                  80

Leu Gln Met Asn Asn Leu Lys Pro Asp Asp Thr Ala Val Tyr Tyr Cys
                85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Gln Val Thr
        115                 120

<210> SEQ ID NO 21
<211> LENGTH: 8
<212> TYPE: PRT
<213> ORGANISM: Artificial Sequence
<220> FEATURE:
<223> OTHER INFORMATION: chemically synthesized

<400> SEQUENCE: 21

Gly Trp Ala Phe Gly Asn Tyr Gly
1               5

<210> SEQ ID NO 22
<211> LENGTH: 19
<212> TYPE: PRT
<213> ORGANISM: Artificial Sequence
<220> FEATURE:
<223> OTHER INFORMATION: chemically synthesized

<400> SEQUENCE: 22

Ala Arg Gln Arg Ser Tyr Ser Arg Tyr Asp Ile Arg Thr Pro Gln Thr
1               5                   10                  15

Tyr Asp Tyr

<210> SEQ ID NO 23
<211> LENGTH: 123
<212> TYPE: PRT
<213> ORGANISM: Artificial Sequence
<220> FEATURE:
<223> OTHER INFORMATION: chemically synthesized

<400> SEQUENCE: 23

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Trp Ala Phe Asp Asn Tyr
            20                  25                  30

Gly Met Ala Trp Phe Arg Gln Ala Pro Gly Lys Glu Arg Glu Phe Ile
        35                  40                  45

Gly Arg Leu Ala Trp Asn Gly Gly Ser Thr Asp Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Gln Arg Ser Tyr Ser Arg Tyr Gly Ile Arg Ala Pro Gln Thr
            100                 105                 110

Tyr Asp Tyr Trp Gly Gln Gly Thr Gln Val Thr
        115                 120
```

```
<210> SEQ ID NO 24
<211> LENGTH: 19
<212> TYPE: PRT
<213> ORGANISM: Artificial Sequence
<220> FEATURE:
<223> OTHER INFORMATION: chemically synthesized

<400> SEQUENCE: 24

Ala Arg Gln Arg Ser Tyr Ser Arg Tyr Gly Ile Arg Ala Pro Gln Thr
1               5                   10                  15

Tyr Asp Tyr
```

```
<210> SEQ ID NO 25
<211> LENGTH: 118
<212> TYPE: PRT
<213> ORGANISM: Artificial Sequence
<220> FEATURE:
<223> OTHER INFORMATION: chemically synthesized

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Val Ser Gly Phe Ser Phe Ser Ile Asn
            20                  25                  30

Ala Met Gly Trp Tyr Arg Gln Ala Pro Gly Lys Arg Arg Glu Phe Leu
        35                  40                  45

Ala Ala Ile Asp Ser Gly Arg Asn Thr Val Tyr Ala Val Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ile Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Gln Val Thr
        115
```

```
<210> SEQ ID NO 26
<211> LENGTH: 8
<212> TYPE: PRT
<213> ORGANISM: Artificial Sequence
```

```
<220> FEATURE:
<223> OTHER INFORMATION: chemically synthesized

<400> SEQUENCE: 26

Gly Phe Ser Phe Ser Ile Asn Ala
1               5

<210> SEQ ID NO 27
<211> LENGTH: 7
<212> TYPE: PRT
<213> ORGANISM: Artificial Sequence
<220> FEATURE:
<223> OTHER INFORMATION: chemically synthesized

<400> SEQUENCE: 27

Ile Asp Ser Gly Arg Asn Thr
1               5

<210> SEQ ID NO 28
<211> LENGTH: 15
<212> TYPE: PRT
<213> ORGANISM: Artificial Sequence
<220> FEATURE:
<223> OTHER INFORMATION: chemically synthesized

<400> SEQUENCE: 28

Gly Leu Leu Lys Gly Asn Arg Val Val Ser Pro Ser Val Ala Tyr
1               5                   10                  15

<210> SEQ ID NO 29
<211> LENGTH: 120
<212> TYPE: PRT
<213> ORGANISM: Artificial Sequence
<220> FEATURE:
<223> OTHER INFORMATION: chemically synthesized

<400> SEQUENCE: 29

Glu Val Gln Pro Val Gln Ser Gly Gly Leu Val Gln Ala Gly Glu
1               5                   10                  15

Ser Leu Arg Leu Ser Cys Ala Ala Ser Ala Thr Ile Phe Ser Asn
                20                  25                  30

Ala Met Gly Trp Tyr Arg Gln Ala Pro Gly Lys Gln Arg Glu Leu Val
            35                  40                  45

Ala Thr Ile Thr Thr Gly Gly Phe Thr Asn Tyr Arg Asp Ser Val Lys
        50                  55                  60

Gly Arg Phe Asp Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Val Val Leu Arg Tyr Ser Arg Asp Tyr Ser Tyr Thr Thr Val Lys Glu
            100                 105                 110

Tyr Trp Gly Gln Gly Thr Gln Val
        115                 120

<210> SEQ ID NO 30
<211> LENGTH: 8
<212> TYPE: PRT
<213> ORGANISM: Artificial Sequence
<220> FEATURE:
<223> OTHER INFORMATION: chemically synthesized

<400> SEQUENCE: 30

Ala Thr Ile Phe Ser Asn Asn Ala
```

<210> SEQ ID NO 31
<211> LENGTH: 7
<212> TYPE: PRT
<213> ORGANISM: Artificial Sequence
<220> FEATURE:
<223> OTHER INFORMATION: chemically synthesized

<400> SEQUENCE: 31

Ile Thr Thr Gly Gly Phe Thr
1               5

<210> SEQ ID NO 32
<211> LENGTH: 18
<212> TYPE: PRT
<213> ORGANISM: Artificial Sequence
<220> FEATURE:
<223> OTHER INFORMATION: chemically synthesized

<400> SEQUENCE: 32

Asn Val Val Leu Arg Tyr Ser Arg Asp Tyr Ser Tyr Thr Thr Val Lys
1               5                   10                  15

Glu Tyr

<210> SEQ ID NO 33
<211> LENGTH: 126
<212> TYPE: PRT
<213> ORGANISM: Artificial Sequence
<220> FEATURE:
<223> OTHER INFORMATION: chemically synthesized

<400> SEQUENCE: 33

Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Gly Leu Glu Trp Val
        35                  40                  45

Ala Arg Leu Ala Trp Asn Gly Gly Ser Thr Asp Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 34
<211> LENGTH: 126
<212> TYPE: PRT
<213> ORGANISM: Artificial Sequence
<220> FEATURE:
<223> OTHER INFORMATION: chemically synthesized

<400> SEQUENCE: 34

Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Gly Arg Glu Phe Val
            35                  40                  45

Ala Arg Leu Ala Trp Asn Gly Gly Ser Thr Asp Tyr Ala Glu Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
                    100                 105                 110

Tyr Asp Tyr Trp Gly Gln Gly Thr Leu Val Thr Val Lys Pro
            115                 120                 125

<210> SEQ ID NO 35
<211> LENGTH: 126
<212> TYPE: PRT
<213> ORGANISM: Artificial Sequence
<220> FEATURE:
<223> OTHER INFORMATION: chemically synthesized

<400> SEQUENCE: 35

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
            35                  40                  45

Ser Arg Leu Ala Trp Asn Gly Gly Ser Thr Asp Tyr Val Ala Glu Ser
        50                  55                  60

Val Lys Gly Arg Phe Thr Ile Ser Arg Asp Asn Ala Lys Asn Thr Leu
65                  70                  75                  80

Tyr Leu Gln Met Ser Ser Leu Arg Ala Glu Asp Thr Ala Val Tyr Tyr
                85                  90                  95

Cys Ala Arg Gln Arg Ser Tyr Ser Arg Tyr Asp Ile Arg Thr Pro Gln
                    100                 105                 110

Thr Tyr Asp Tyr Trp Gly Gln Gly Thr Leu Val Thr Val Lys
            115                 120                 125

<210> SEQ ID NO 36
<211> LENGTH: 126
<212> TYPE: PRT
<213> ORGANISM: Artificial Sequence
<220> FEATURE:
<223> OTHER INFORMATION: chemically synthesized

<400> SEQUENCE: 36

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Ile
            35                  40                  45

Gly Arg Leu Ala Trp Asn Gly Gly Ser Thr Asp Tyr Val Glu Ser Val
        50                  55                  60

Lys Gly Arg Phe Thr Ile Ser Arg Asp Asn Pro Lys Asn Thr Leu Tyr
65                  70                  75                  80

Leu Gln Met Ser Ser Leu Arg Ala Glu Asp Thr Ala Val Tyr Tyr Cys 85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 37
<211> LENGTH: 126
<212> TYPE: PRT
<213> ORGANISM: Artificial Sequence
<220> FEATURE:
<223> OTHER INFORMATION: chemically synthesized

<400> SEQUENCE: 37

Glu Val Gln Leu Leu Glu Ser Gly Gly Glu Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Asn Gly Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
            85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 38
<211> LENGTH: 126
<212> TYPE: PRT
<213> ORGANISM: Artificial Sequence
<220> FEATURE:
<223> OTHER INFORMATION: chemically synthesized

<400> SEQUENCE: 38

Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Asn Gly Gly Ser Thr Asp Tyr Val Glu Ser Val
    50                  55                  60

Lys Gly Arg Phe Thr Ile Ser Arg Asp Asn Pro Lys Asn Thr Leu Tyr
65                  70                  75                  80

Leu Gln Met Ser Ser Leu Arg Ala Glu Asp Thr Ala Val Tyr Tyr Cys
            85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 39
<211> LENGTH: 126

```
<212> TYPE: PRT
<213> ORGANISM: Artificial Sequence
<220> FEATURE:
<223> OTHER INFORMATION: chemically synthesized

<400> SEQUENCE: 39

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Ile
        35                  40                  45

Gly Arg Leu Ala Trp Asn Gly Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 40
<211> LENGTH: 126
<212> TYPE: PRT
<213> ORGANISM: Artificial Sequence
<220> FEATURE:
<223> OTHER INFORMATION: chemically synthesized

<400> SEQUENCE: 40

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Ile
        35                  40                  45

Gly Arg Leu Ala Trp Asn Gly Gly Ser Thr Asp Tyr Val Glu Ser Val
    50                  55                  60

Lys Gly Arg Phe Thr Ile Ser Arg Asp Asn Pro Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 41
<211> LENGTH: 126
<212> TYPE: PRT
<213> ORGANISM: Artificial Sequence
<220> FEATURE:
<223> OTHER INFORMATION: chemically synthesized

<400> SEQUENCE: 41

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
```

```
                    20                  25                  30

Gly Met Ala Trp Phe Arg Gln Ala Pro Gly Lys Glu Arg Glu Phe Ile
                35                  40                  45

Gly Arg Leu Ala Trp Gln Gly Gly Ser Thr Asp Tyr Val Glu Ser Val
            50                  55                  60

Lys Gly Arg Phe Thr Ile Ser Arg Asp Asn Pro Lys Asn Thr Leu Tyr
65                  70                  75                  80

Leu Gln Met Ser Ser Leu Arg Ala Glu Asp Thr Ala Val Tyr Tyr Cys
                    85                  90                  95

Ala Arg Gln Arg Ser Tyr Ser Arg Tyr Asp Ile Arg Thr Pro Gln Thr
                100                 105                 110

Tyr Asp Tyr Trp Gly Gln Gly Thr Leu Val Thr Val Lys Pro
            115                 120                 125

<210> SEQ ID NO 42
<211> LENGTH: 8
<212> TYPE: PRT
<213> ORGANISM: Artificial Sequence
<220> FEATURE:
<223> OTHER INFORMATION: chemically synthesized

<400> SEQUENCE: 42

Leu Ala Trp Gln Gly Gly Ser Thr
1               5

<210> SEQ ID NO 43
<211> LENGTH: 126
<212> TYPE: PRT
<213> ORGANISM: Artificial Sequence
<220> FEATURE:
<223> OTHER INFORMATION: chemically synthesized

<400> SEQUENCE: 43

Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
                20                  25                  30

Gly Met Ala Trp Phe Arg Gln Ala Pro Gly Lys Glu Arg Glu Phe Ile
                35                  40                  45

Gly Arg Leu Ala Trp Asn Ala Gly Ser Thr Asp Tyr Val Glu Ser Val
            50                  55                  60

Lys Gly Arg Phe Thr Ile Ser Arg Asp Asn Pro Lys Asn Thr Leu Tyr
65                  70                  75                  80

Leu Gln Met Ser Ser Leu Arg Ala Glu Asp Thr Ala Val Tyr Tyr Cys
                    85                  90                  95

Ala Arg Gln Arg Ser Tyr Ser Arg Tyr Asp Ile Arg Thr Pro Gln Thr
                100                 105                 110

Tyr Asp Tyr Trp Gly Gln Gly Thr Leu Val Thr Val Lys Pro
            115                 120                 125

<210> SEQ ID NO 44
<211> LENGTH: 8
<212> TYPE: PRT
<213> ORGANISM: Artificial Sequence
<220> FEATURE:
<223> OTHER INFORMATION: chemically synthesized

<400> SEQUENCE: 44

Leu Ala Trp Asn Ala Gly Ser Thr
1               5
```

<210> SEQ ID NO 45
<211> LENGTH: 126
<212> TYPE: PRT
<213> ORGANISM: Artificial Sequence
<220> FEATURE:
<223> OTHER INFORMATION: chemically synthesized

<400> SEQUENCE: 45

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Gln Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 46
<211> LENGTH: 126
<212> TYPE: PRT
<213> ORGANISM: Artificial Sequence
<220> FEATURE:
<223> OTHER INFORMATION: chemically synthesized

<400> SEQUENCE: 46

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Asn Ala Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 47
<211> LENGTH: 126
<212> TYPE: PRT
<213> ORGANISM: Artificial Sequence
<220> FEATURE:
<223> OTHER INFORMATION: chemically synthesized

<400> SEQUENCE: 47

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
                20                  25                  30

Gly Met Ala Trp Phe Arg Gln Ala Pro Gly Lys Glu Arg Glu Phe Val
            35                  40                  45

Ser Arg Leu Ala Trp Gly Gly Ser Thr Asp Tyr Val Glu Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
                100                 105                 110

Tyr Asp Tyr Trp Gly Gln Gly Thr Leu Val Thr Val Lys Pro
            115                 120                 125
```

<210> SEQ ID NO 48
<211> LENGTH: 8
<212> TYPE: PRT
<213> ORGANISM: Artificial Sequence
<220> FEATURE:
<223> OTHER INFORMATION: chemically synthesized

<400> SEQUENCE: 48

```
Leu Ala Trp Gly Gly Gly Ser Thr
1               5
```

<210> SEQ ID NO 49
<211> LENGTH: 126
<212> TYPE: PRT
<213> ORGANISM: Artificial Sequence
<220> FEATURE:
<223> OTHER INFORMATION: chemically synthesized

<400> SEQUENCE: 49

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Ser Asn Tyr
                20                  25                  30

Gly Met Ala Trp Phe Arg Gln Ala Pro Gly Lys Glu Arg Glu Phe Val
            35                  40                  45

Ser Arg Leu Ala Trp Gly Gly Ser Thr Asp Tyr Val Glu Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
                100                 105                 110

Tyr Asp Tyr Trp Gly Gln Gly Thr Leu Val Thr Val Lys Pro
            115                 120                 125
```

<210> SEQ ID NO 50
<211> LENGTH: 8
<212> TYPE: PRT
<213> ORGANISM: Artificial Sequence
<220> FEATURE:
<223> OTHER INFORMATION: chemically synthesized

```
<400> SEQUENCE: 50

Gly Trp Ala Phe Ser Asn Tyr Gly
1               5

<210> SEQ ID NO 51
<211> LENGTH: 126
<212> TYPE: PRT
<213> ORGANISM: Artificial Sequence
<220> FEATURE:
<223> OTHER INFORMATION: chemically synthesized

<400> SEQUENCE: 51

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Ser Gly Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 52
<211> LENGTH: 8
<212> TYPE: PRT
<213> ORGANISM: Artificial Sequence
<220> FEATURE:
<223> OTHER INFORMATION: chemically synthesized

<400> SEQUENCE: 52

Leu Ala Trp Ser Gly Gly Ser Thr
1               5

<210> SEQ ID NO 53
<211> LENGTH: 126
<212> TYPE: PRT
<213> ORGANISM: Artificial Sequence
<220> FEATURE:
<223> OTHER INFORMATION: chemically synthesized

<400> SEQUENCE: 53

Glu Val Gln Leu Leu Glu Ser Gly Gly Gly Val Gln Pro Gly Gly
1               5                   10                  15

Ser Leu Arg Leu Ser Cys Ala Ala Ser Gly Trp Ala Phe Ser Asn Tyr
            20                  25                  30

Gly Met Ala Trp Phe Arg Gln Ala Pro Gly Lys Glu Arg Glu Phe Val
        35                  40                  45

Ser Arg Leu Ala Trp Ser Gly Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95
```

```
Ala Arg Gln Arg Ser Tyr Ser Arg Tyr Asp Ile Arg Thr Pro Gln Thr
            100                 105                 110

Tyr Asp Tyr Trp Gly Gln Gly Thr Leu Val Thr Val Lys Pro
            115                 120                 125

<210> SEQ ID NO 54
<211> LENGTH: 126
<212> TYPE: PRT
<213> ORGANISM: Artificial Sequence
<220> FEATURE:
<223> OTHER INFORMATION: chemically synthesized

<400> SEQUENCE: 54

Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Gly Gly Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Gly Tyr Asp Ile Arg Thr Pro Gln Thr
            100                 105                 110

Tyr Asp Tyr Trp Gly Gln Gly Thr Leu Val Thr Val Lys Pro
            115                 120                 125

<210> SEQ ID NO 55
<211> LENGTH: 19
<212> TYPE: PRT
<213> ORGANISM: Artificial Sequence
<220> FEATURE:
<223> OTHER INFORMATION: chemically synthesized

<400> SEQUENCE: 55

Ala Arg Gln Arg Ser Tyr Ser Gly Tyr Asp Ile Arg Thr Pro Gln Thr
1               5                   10                  15

Tyr Asp Tyr

<210> SEQ ID NO 56
<211> LENGTH: 126
<212> TYPE: PRT
<213> ORGANISM: Artificial Sequence
<220> FEATURE:
<223> OTHER INFORMATION: chemically synthesized

<400> SEQUENCE: 56

Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Gly Gly Gly Ser Thr Asp Tyr Val Glu Ser Val
    50                  55                  60

Lys Gly Arg Phe Thr Ile Ser Arg Asp Asn Ala Lys Asn Thr Leu Tyr
```

```
                65                  70                  75                  80
Leu Gln Met Ser Ser Leu Arg Ala Glu Asp Thr Ala Val Tyr Tyr Cys
                85                  90                  95

Ala Arg Gln Arg Ser Tyr Ser Arg Tyr Gly Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 57
<211> LENGTH: 19
<212> TYPE: PRT
<213> ORGANISM: Artificial Sequence
<220> FEATURE:
<223> OTHER INFORMATION: chemically synthesized

<400> SEQUENCE: 57

Ala Arg Gln Arg Ser Tyr Ser Arg Tyr Gly Ile Arg Thr Pro Gln Thr
1               5                   10                  15

Tyr Asp Tyr

<210> SEQ ID NO 58
<211> LENGTH: 126
<212> TYPE: PRT
<213> ORGANISM: Artificial Sequence
<220> FEATURE:
<223> OTHER INFORMATION: chemically synthesized

<400> SEQUENCE: 58

Glu Val Gln Leu Leu Glu Ser Gly Gly Gly Glu Val Gln Pro Gly Gly
1               5                   10                  15

Ser Leu Arg Leu Ser Cys Ala Ala Ser Gly Trp Ala Phe Gly Asn Tyr
            20                  25                  30

Gly Met Ala Trp Phe Arg Gln Ala Pro Gly Lys Glu Arg Glu Phe Val
        35                  40                  45

Ser Arg Leu Ala Trp Gly Gly Gly Ser Thr Asp Tyr Val Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Arg Ser Tyr Ser Gly Tyr Gly Ile Arg Thr Pro Gln Thr
            100                 105                 110

Tyr Asp Tyr Trp Gly Gln Gly Thr Leu Val Thr Val Lys Pro
        115                 120                 125

<210> SEQ ID NO 59
<211> LENGTH: 121
<212> TYPE: PRT
<213> ORGANISM: Artificial Sequence
<220> FEATURE:
<223> OTHER INFORMATION: chemically synthesized

<400> SEQUENCE: 59

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Gly Leu Glu Trp Val
        35                  40                  45
```

```
Ala Ala Ile Asp Ser Gly Arg Asn Thr Val Tyr Ala Glu Ser Val Lys
        50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120
```

<210> SEQ ID NO 60
<211> LENGTH: 121
<212> TYPE: PRT
<213> ORGANISM: Artificial Sequence
<220> FEATURE:
<223> OTHER INFORMATION: chemically synthesized

<400> SEQUENCE: 60

```
Glu Val Gln Leu Leu Glu Ser Gly Gly Gly Val Gln Pro Gly Gly
 1               5                  10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
        50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120
```

<210> SEQ ID NO 61
<211> LENGTH: 7
<212> TYPE: PRT
<213> ORGANISM: Artificial Sequence
<220> FEATURE:
<223> OTHER INFORMATION: chemically synthesized

<400> SEQUENCE: 61

```
Ile Glu Ser Gly Arg Asn Thr
 1               5
```

<210> SEQ ID NO 62
<211> LENGTH: 121
<212> TYPE: PRT
<213> ORGANISM: Artificial Sequence
<220> FEATURE:
<223> OTHER INFORMATION: chemically synthesized

<400> SEQUENCE: 62

```
Glu Val Gln Leu Leu Glu Ser Gly Gly Gly Val Gln Pro Gly Gly
 1               5                  10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
```

```
            35                  40                  45
Ala Ala Ile Tyr Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 63
<211> LENGTH: 7
<212> TYPE: PRT
<213> ORGANISM: Artificial Sequence
<220> FEATURE:
<223> OTHER INFORMATION: chemically synthesized

<400> SEQUENCE: 63

Ile Tyr Ser Gly Arg Asn Thr
 1               5

<210> SEQ ID NO 64
<211> LENGTH: 121
<212> TYPE: PRT
<213> ORGANISM: Artificial Sequence
<220> FEATURE:
<223> OTHER INFORMATION: chemically synthesized

<400> SEQUENCE: 64

Glu Val Gln Leu Leu Glu Ser Gly Gly Glu Val Gln Pro Gly Gly
 1               5                  10                  15

Ser Leu Arg Leu Ser Cys Ala Ala Ser Gly Phe Thr Phe Ser Ile Asn
             20                  25                  30

Ala Met Gly Trp Tyr Arg Gln Ala Pro Gly Lys Arg Arg Glu Phe Val
         35                  40                  45

Ala Ala Ile Glu Ser Gly Arg Asn Thr Val Tyr Ala Glu Ser Val Lys
     50                 55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 65
<211> LENGTH: 8
<212> TYPE: PRT
<213> ORGANISM: Artificial Sequence
<220> FEATURE:
<223> OTHER INFORMATION: chemically synthesized

<400> SEQUENCE: 65

Gly Phe Thr Phe Ser Ile Asn Ala
 1               5

<210> SEQ ID NO 66
```

<211> LENGTH: 121
<212> TYPE: PRT
<213> ORGANISM: Artificial Sequence
<220> FEATURE:
<223> OTHER INFORMATION: chemically synthesized

<400> SEQUENCE: 66

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Ser Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 67
<211> LENGTH: 8
<212> TYPE: PRT
<213> ORGANISM: Artificial Sequence
<220> FEATURE:
<223> OTHER INFORMATION: chemically synthesized

<400> SEQUENCE: 67

Gly Phe Ser Phe Ser Ile Asn Ala
1               5

<210> SEQ ID NO 68
<211> LENGTH: 121
<212> TYPE: PRT
<213> ORGANISM: Artificial Sequence
<220> FEATURE:
<223> OTHER INFORMATION: chemically synthesized

<400> SEQUENCE: 68

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Ser Asn
            20                  25                  30

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 69
<211> LENGTH: 8
<212> TYPE: PRT
<213> ORGANISM: Artificial Sequence
<220> FEATURE:
<223> OTHER INFORMATION: chemically synthesized

<400> SEQUENCE: 69

Gly Phe Thr Phe Ser Ser Asn Ala
1               5

<210> SEQ ID NO 70
<211> LENGTH: 121
<212> TYPE: PRT
<213> ORGANISM: Artificial Sequence
<220> FEATURE:
<223> OTHER INFORMATION: chemically synthesized

<400> SEQUENCE: 70

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

Ala Ala Ile Glu Ser Ser Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 71
<211> LENGTH: 7
<212> TYPE: PRT
<213> ORGANISM: Artificial Sequence
<220> FEATURE:
<223> OTHER INFORMATION: chemically synthesized

<400> SEQUENCE: 71

Ile Glu Ser Ser Arg Asn Thr
1               5

<210> SEQ ID NO 72
<211> LENGTH: 121
<212> TYPE: PRT
<213> ORGANISM: Artificial Sequence
<220> FEATURE:
<223> OTHER INFORMATION: chemically synthesized

<400> SEQUENCE: 72

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

```
Ala Ala Ile Glu Ser Gly Ser Asn Thr Val Tyr Ala Glu Ser Val Lys
         50                  55                  60

Gly Arg Phe Thr Ile Ser Arg Asp Asn Ala Lys Asn Thr Val Tyr Leu
 65              70                  75                      80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
            115                 120
```

<210> SEQ ID NO 73
<211> LENGTH: 7
<212> TYPE: PRT
<213> ORGANISM: Artificial Sequence
<220> FEATURE:
<223> OTHER INFORMATION: chemically synthesized

<400> SEQUENCE: 73

```
Ile Glu Ser Gly Ser Asn Thr
 1               5
```

<210> SEQ ID NO 74
<211> LENGTH: 121
<212> TYPE: PRT
<213> ORGANISM: Artificial Sequence
<220> FEATURE:
<223> OTHER INFORMATION: chemically synthesized

<400> SEQUENCE: 74

```
Glu Val Gln Leu Leu Glu Ser Gly Gly Gly Val Gln Pro Gly Gly
 1               5                  10                  15

Ser Leu Arg Leu Ser Cys Ala Ala Ser Gly Phe Ser Phe Ser Ile Asn
             20                  25                  30

Ala Met Gly Trp Tyr Arg Gln Ala Pro Gly Lys Arg Arg Glu Phe Val
             35                  40                  45

Ala Ala Ile Glu Ser Gly Arg Ser Thr Val Tyr Ala Glu Ser Val Lys
         50                  55                  60

Gly Arg Phe Thr Ile Ser Arg Asp Asn Ala Lys Asn Thr Val Tyr Leu
 65              70                  75                      80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
            115                 120
```

<210> SEQ ID NO 75
<211> LENGTH: 7
<212> TYPE: PRT
<213> ORGANISM: Artificial Sequence
<220> FEATURE:
<223> OTHER INFORMATION: chemically synthesized

<400> SEQUENCE: 75

```
Ile Glu Ser Gly Arg Ser Thr
 1               5
```

<210> SEQ ID NO 76
<211> LENGTH: 121
<212> TYPE: PRT

<213> ORGANISM: Artificial Sequence
<220> FEATURE:
<223> OTHER INFORMATION: chemically synthesized

<400> SEQUENCE: 76

```
Glu Val Gln Leu Leu Glu Ser Gly Gly Glu Val Gln Pro Gly Gly
1               5                  10                  15
Ser Leu Arg Leu Ser Cys Ala Ala Ser Gly Phe Ser Phe Ser Ile Asn
            20                  25                  30
Ala Met Gly Trp Tyr Arg Gln Ala Pro Gly Lys Arg Arg Glu Phe Val
        35                  40                  45
Ala Ala Ile Glu Ser Gly Arg Asn Thr Tyr Tyr Ala Glu Ser Val Lys
    50                  55                  60
Gly Arg Phe Thr Ile Ser Arg Asp Asn Ala Lys Asn Thr Val Tyr Leu
65                  70                  75                  80
Gln Met Ser Ser Leu Arg Ala Glu Asp Thr Ala Val Tyr Tyr Cys Gly
                85                  90                  95
Leu Leu Lys Gly Asn Arg Val Val Ser Pro Ser Val Ala Tyr Trp Gly
            100                 105                 110
Gln Gly Thr Leu Val Thr Val Lys Pro
        115                 120
```

<210> SEQ ID NO 77
<211> LENGTH: 7
<212> TYPE: PRT
<213> ORGANISM: Artificial Sequence
<220> FEATURE:
<223> OTHER INFORMATION: chemically synthesized

<400> SEQUENCE: 77

```
Ile Glu Ser Gly Arg Asn Thr
1               5
```

<210> SEQ ID NO 78
<211> LENGTH: 121
<212> TYPE: PRT
<213> ORGANISM: Artificial Sequence
<220> FEATURE:
<223> OTHER INFORMATION: chemically synthesized

<400> SEQUENCE: 78

```
Glu Val Gln Leu Leu Glu Ser Gly Gly Gly Val Gln Pro Gly Gly
1               5                  10                  15
Ser Leu Arg Leu Ser Cys Ala Ala Ser Gly Phe Ser Phe Ser Ile Asn
            20                  25                  30
Ala Met Gly Trp Tyr Arg Gln Ala Pro Gly Lys Arg Arg Glu Phe Val
        35                  40                  45
Ala Ala Ile Tyr Ser Gly Ser Ser Thr Val Tyr Ala Glu Ser Val Lys
    50                  55                  60
Gly Arg Phe Thr Ile Ser Arg Asp Asn Ala Lys Asn Thr Val Tyr Leu
65                  70                  75                  80
Gln Met Ser Ser Leu Arg Ala Glu Asp Thr Ala Val Tyr Tyr Cys Gly
                85                  90                  95
Leu Leu Lys Gly Asn Arg Val Val Ser Pro Ser Val Ala Tyr Trp Gly
            100                 105                 110
Gln Gly Thr Leu Val Thr Val Lys Pro
        115                 120
```

<210> SEQ ID NO 79

```
<211> LENGTH: 7
<212> TYPE: PRT
<213> ORGANISM: Artificial Sequence
<220> FEATURE:
<223> OTHER INFORMATION: chemically synthesized

<400> SEQUENCE: 79

Ile Tyr Ser Gly Ser Ser Thr
1               5

<210> SEQ ID NO 80
<211> LENGTH: 121
<212> TYPE: PRT
<213> ORGANISM: Artificial Sequence
<220> FEATURE:
<223> OTHER INFORMATION: chemically synthesized

<400> SEQUENCE: 80

Glu Val Gln Leu Leu Glu Ser Gly Gly Gly Glu Val Gln Pro Gly Gly
1               5                   10                  15

Ser Leu Arg Leu Ser Cys Ala Val Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 81
<211> LENGTH: 121
<212> TYPE: PRT
<213> ORGANISM: Artificial Sequence
<220> FEATURE:
<223> OTHER INFORMATION: chemically synthesized

<400> SEQUENCE: 81

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Val Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120
```

-continued

```
<210> SEQ ID NO 82
<211> LENGTH: 121
<212> TYPE: PRT
<213> ORGANISM: Artificial Sequence
<220> FEATURE:
<223> OTHER INFORMATION: chemically synthesized

<400> SEQUENCE: 82

Glu Val Gln Leu Leu Glu Ser Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Gly Arg Glu Phe Val
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 83
<211> LENGTH: 121
<212> TYPE: PRT
<213> ORGANISM: Artificial Sequence
<220> FEATURE:
<223> OTHER INFORMATION: chemically synthesized

<400> SEQUENCE: 83

Glu Val Gln Leu Leu Glu Ser Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Leu
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 84
<211> LENGTH: 119
<212> TYPE: PRT
<213> ORGANISM: Artificial Sequence
<220> FEATURE:
<223> OTHER INFORMATION: chemically synthesized

<400> SEQUENCE: 84

Gln Val Gln Leu Val Gln Ser Gly Ala Glu Val Lys Lys Pro Gly Ser
```

```
1               5                   10                  15
Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
            35                  40                  45

Gly Gly Ile Ile Pro Gly Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
                    85                  90                  95

Ala Arg Lys Asn Glu Glu Asp Gly Gly Phe Asp His Trp Gly Gln Gly
                100                 105                 110

Thr Leu Val Thr Val Ser Ser
            115
```

<210> SEQ ID NO 85
<211> LENGTH: 118
<212> TYPE: PRT
<213> ORGANISM: Artificial Sequence
<220> FEATURE:
<223> OTHER INFORMATION: chemically synthesized

<400> SEQUENCE: 85

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Val Arg Gln Ala Pro Gly Lys Gly Leu Glu Trp Val
            35                  40                  45

Ser Val Ile Ser Gly Ser Gly Ser Asn Thr Tyr Tyr Ala Asp Ser Val
            50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Arg Leu Tyr Ala Gln Phe Glu Gly Asp Phe Trp Gly Gln Gly Thr
                100                 105                 110

Leu Val Thr Val Ser Ser
            115
```

<210> SEQ ID NO 86
<211> LENGTH: 116
<212> TYPE: PRT
<213> ORGANISM: Artificial Sequence
<220> FEATURE:
<223> OTHER INFORMATION: chemically synthesized

<400> SEQUENCE: 86

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
            35                  40                  45

Gly Lys Ile Tyr Pro Gly Asp Ser Tyr Thr Asn Tyr Ser Pro Ser Phe
            50                  55                  60
```

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 87
<211> LENGTH: 116
<212> TYPE: PRT
<213> ORGANISM: Artificial Sequence
<220> FEATURE:
<223> OTHER INFORMATION: chemically synthesized

<400> SEQUENCE: 87

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 88
<211> LENGTH: 107
<212> TYPE: PRT
<213> ORGANISM: Artificial Sequence
<220> FEATURE:
<223> OTHER INFORMATION: chemically synthesized

<400> SEQUENCE: 88

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Asp Tyr Tyr Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Gly Thr Leu His Phe
                85                  90                  95

Val Phe Gly Gly Gly Thr Lys Leu Thr Val Leu
            100                 105

<210> SEQ ID NO 89
```

<211> LENGTH: 107
<212> TYPE: PRT
<213> ORGANISM: Artificial Sequence
<220> FEATURE:
<223> OTHER INFORMATION: chemically synthesized

<400> SEQUENCE: 89

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Lys Tyr Val
            20                  25                  30

Ser Trp Tyr Gln Gln Lys Pro Gly Gln Ala Pro Val Leu Val Ile Tyr
        35                  40                  45

Ser Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Ser Ile Ser Arg
                85                  90                  95

Val Phe Gly Gly Gly Thr Lys Leu Thr Val Leu
            100                 105

<210> SEQ ID NO 90
<211> LENGTH: 108
<212> TYPE: PRT
<213> ORGANISM: Artificial Sequence
<220> FEATURE:
<223> OTHER INFORMATION: chemically synthesized

<400> SEQUENCE: 90

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asp Gln Tyr Ala
            20                  25                  30

His Trp Tyr Gln Gln Lys Pro Gly Gln Ala Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 91
<211> LENGTH: 108
<212> TYPE: PRT
<213> ORGANISM: Artificial Sequence
<220> FEATURE:
<223> OTHER INFORMATION: chemically synthesized

<400> SEQUENCE: 91

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                 85                  90                  95

Ala Val Phe Gly Gly Gly Thr Lys Leu Thr Val Leu
            100                 105

<210> SEQ ID NO 92
<211> LENGTH: 108
<212> TYPE: PRT
<213> ORGANISM: Artificial Sequence
<220> FEATURE:
<223> OTHER INFORMATION: chemically synthesized

<400> SEQUENCE: 92

Ser Tyr Glu Leu Thr Gln Pro Pro Ser Val Ser Val Ser Pro Gly Gln
 1               5                   10                  15

Thr Ala Ser Ile Thr Cys Ser Gly Asp Asn Ile Gly Asp Gln Tyr Ala
                20                  25                  30

His Trp Tyr Gln Gln Lys Pro Gly Gln Ser Pro Val Val Val Ile Tyr
            35                  40                  45

Gln Asp Lys Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                 85                  90                  95

Ala Val Phe Gly Gly Gly Thr Lys Leu Thr Val Leu
            100                 105

<210> SEQ ID NO 93
<211> LENGTH: 108
<212> TYPE: PRT
<213> ORGANISM: Artificial Sequence
<220> FEATURE:
<223> OTHER INFORMATION: chemically synthesized

<400> SEQUENCE: 93

Asp Ile Glu Leu Thr Gln Pro Pro Ser Val Ser Val Ala Pro Gly Gln
 1               5                   10                  15

Thr Ala Arg Ile Ser Cys Ser Gly Asp Asn Ile Gly Asp Gln Tyr Ala
                20                  25                  30

His Trp Tyr Gln Gln Lys Pro Gly Gln Ala Pro Val Val Val Ile Tyr
            35                  40                  45

Gln Asp Lys Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Thr Tyr Thr Phe Val Gly Phe Thr
                 85                  90                  95

Thr Val Phe Gly Gly Gly Thr Lys Leu Thr Val Leu
            100                 105

<210> SEQ ID NO 94
<211> LENGTH: 108
<212> TYPE: PRT
<213> ORGANISM: Artificial Sequence

```
<220> FEATURE:
<223> OTHER INFORMATION: chemically synthesized

<400> SEQUENCE: 94

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Thr Tyr Thr Phe Val Gly Phe Thr
                85                  90                  95

Thr Val Phe Gly Gly Gly Thr Lys Leu Thr Val Leu
            100                 105

<210> SEQ ID NO 95
<211> LENGTH: 108
<212> TYPE: PRT
<213> ORGANISM: Artificial Sequence
<220> FEATURE:
<223> OTHER INFORMATION: chemically synthesized

<400> SEQUENCE: 95

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Thr Tyr Thr Phe Val Gly Phe Thr
                85                  90                  95

Thr Val Phe Gly Gly Gly Thr Lys Leu Thr Val Leu
            100                 105

<210> SEQ ID NO 96
<211> LENGTH: 448
<212> TYPE: PRT
<213> ORGANISM: Artificial Sequence
<220> FEATURE:
<223> OTHER INFORMATION: chemically synthesized

<400> SEQUENCE: 96

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60
```

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 97
<211> LENGTH: 451
<212> TYPE: PRT
<213> ORGANISM: Artificial Sequence
<220> FEATURE:
<223> OTHER INFORMATION: chemically synthesized

<400> SEQUENCE: 97

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 98
<211> LENGTH: 216
<212> TYPE: PRT
<213> ORGANISM: Artificial Sequence
<220> FEATURE:
<223> OTHER INFORMATION: chemically synthesized

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 99
<211> LENGTH: 178
<212> TYPE: PRT
<213> ORGANISM: Artificial Sequence
<220> FEATURE:
<223> OTHER INFORMATION: chemically synthesized

<400> SEQUENCE: 99

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
            35                  40                  45

Ile Lys Met Met Ala Thr Ile Tyr Glu Leu Lys Glu Asp Lys Ser Tyr
 50                  55                  60

Asp Val Thr Met Val Lys Phe Asp Asp Lys Lys Cys Met Tyr Asp Ile
 65                  70                  75                  80

Trp Thr Phe Val Pro Gly Ser Gln Pro Gly Glu Phe Thr Leu Gly Lys
                 85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 100
<211> LENGTH: 109
<212> TYPE: PRT
<213> ORGANISM: Artificial Sequence
<220> FEATURE:
<223> OTHER INFORMATION: chemically synthesized

<400> SEQUENCE: 100

Gln Val Gln Leu Gln Glu Ser Gly Gly Gly Leu Val Gln Ala Gly Gly
 1               5                  10                  15

Ser Leu Arg Leu Ala Cys Thr Thr Ser Gly Gly Ile Phe Asn Ile Arg
             20                  25                  30

Pro Ile Ser Trp Tyr Arg Gln Pro Pro Gly Met Gln Arg Glu Trp Val
         35                  40                  45

Ala Thr Ile Ala Phe Gly Gly Ala Thr Asn Tyr Ala Asn Ser Ile Lys
 50                  55                  60

Gly Arg Phe Thr Ala Ser Arg Asp Asn Ala Lys Asn Thr Val Tyr Leu
 65                  70                  75                  80

Gln Met Asn Gly Leu Lys Pro Glu Asp Thr Ala Val Tyr Tyr Cys Asn
                 85                  90                  95

Ala Phe Glu Ile Trp Gly Gln Gly Thr Gln Val Thr Val
                100                 105

<210> SEQ ID NO 101
<211> LENGTH: 8
<212> TYPE: PRT
<213> ORGANISM: Artificial Sequence
<220> FEATURE:
<223> OTHER INFORMATION: chemically synthesized

<400> SEQUENCE: 101

Gly Gly Ile Phe Asn Ile Arg Pro
 1               5

<210> SEQ ID NO 102
<211> LENGTH: 7
<212> TYPE: PRT
<213> ORGANISM: Artificial Sequence
<220> FEATURE:

<223> OTHER INFORMATION: chemically synthesized

<400> SEQUENCE: 102

Ile Ala Phe Gly Gly Ala Thr
1               5

<210> SEQ ID NO 103
<211> LENGTH: 5
<212> TYPE: PRT
<213> ORGANISM: Artificial Sequence
<220> FEATURE:
<223> OTHER INFORMATION: chemically synthesized

<400> SEQUENCE: 103

Asn Ala Phe Glu Ile
1               5

<210> SEQ ID NO 104
<211> LENGTH: 109
<212> TYPE: PRT
<213> ORGANISM: Artificial Sequence
<220> FEATURE:
<223> OTHER INFORMATION: chemically synthesized

<400> SEQUENCE: 104

Gln Leu Gln Leu Gln Glu Ser Gly Gly Leu Val Arg Ala Gly Gly
1               5                   10                  15

Ser Leu Arg Leu Ala Cys Thr Thr Ser Gly Gly Ile Phe Ala Ile Lys
            20                  25                  30

Pro Ile Ser Trp Tyr Arg Gln Pro Pro Gly Gln Glu Arg Glu Trp Val
        35                  40                  45

Thr Thr Thr Thr Ser Ser Gly Ala Thr Asn Tyr Ala Asn Ser Ile Lys
    50                  55                  60

Gly Arg Phe Thr Val Ala Arg Asp Asn Ala Lys Asn Thr Val Tyr Leu
65                  70                  75                  80

Gln Met Asn Asp Leu Lys Leu Glu Asp Thr Ala Val Tyr Tyr Cys Asn
                85                  90                  95

Val Phe Glu Tyr Trp Gly Gln Gly Thr Gln Val Thr Val
            100                 105

<210> SEQ ID NO 105
<211> LENGTH: 8
<212> TYPE: PRT
<213> ORGANISM: Artificial Sequence
<220> FEATURE:
<223> OTHER INFORMATION: chemically synthesized

<400> SEQUENCE: 105

Gly Gly Ile Phe Ala Ile Lys Pro
1               5

<210> SEQ ID NO 106
<211> LENGTH: 7
<212> TYPE: PRT
<213> ORGANISM: Artificial Sequence
<220> FEATURE:
<223> OTHER INFORMATION: chemically synthesized

<400> SEQUENCE: 106

Thr Thr Ser Ser Gly Ala Thr
1               5

<210> SEQ ID NO 107

```
<211> LENGTH: 5
<212> TYPE: PRT
<213> ORGANISM: Artificial Sequence
<220> FEATURE:
<223> OTHER INFORMATION: chemically synthesized

<400> SEQUENCE: 107

Asn Val Phe Glu Tyr
1               5

<210> SEQ ID NO 108
<211> LENGTH: 109
<212> TYPE: PRT
<213> ORGANISM: Artificial Sequence
<220> FEATURE:
<223> OTHER INFORMATION: chemically synthesized

<400> SEQUENCE: 108

Gln Val Gln Leu Gln Glu Ser Gly Gly Asp Leu Val Gln Ala Gly Ser
1               5                   10                  15

Ser Leu Arg Leu Ala Cys Ala Thr Ser Gly Gly Val Phe Asn Ile Arg
            20                  25                  30

Pro Ile Ser Trp Tyr Arg Gln Pro Pro Gly Lys Gln Arg Glu Trp Val
        35                  40                  45

Ala Thr Ile Ala Ser Gly Gly Ala Thr Asn Tyr Ala Asn Ser Ile Lys
    50                  55                  60

Gly Arg Phe Thr Ala Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Asn
                85                  90                  95

Ala Phe Glu Val Trp Gly Gln Gly Thr Gln Val Thr Val
            100                 105

<210> SEQ ID NO 109
<211> LENGTH: 8
<212> TYPE: PRT
<213> ORGANISM: Artificial Sequence
<220> FEATURE:
<223> OTHER INFORMATION: chemically synthesized

<400> SEQUENCE: 109

Gly Gly Val Phe Asn Ile Arg Pro
1               5

<210> SEQ ID NO 110
<211> LENGTH: 7
<212> TYPE: PRT
<213> ORGANISM: Artificial Sequence
<220> FEATURE:
<223> OTHER INFORMATION: chemically synthesized

<400> SEQUENCE: 110

Ile Ala Ser Gly Gly Ala Thr
1               5

<210> SEQ ID NO 111
<211> LENGTH: 5
<212> TYPE: PRT
<213> ORGANISM: Artificial Sequence
<220> FEATURE:
<223> OTHER INFORMATION: chemically synthesized

<400> SEQUENCE: 111

Asn Ala Phe Glu Val
```

```
<210> SEQ ID NO 112
<211> LENGTH: 109
<212> TYPE: PRT
<213> ORGANISM: Artificial Sequence
<220> FEATURE:
<223> OTHER INFORMATION: chemically synthesized

<400> SEQUENCE: 112

Gln Val Gln Leu Gln Gln Ser Gly Gly Gly Leu Val Gln Ala Gly Gly
1               5                   10                  15

Ser Leu Arg Leu Ala Cys Thr Thr Ser Gly Gly Ile Phe Asn Ile Arg
            20                  25                  30

Pro Ile Ser Trp Tyr Arg Gln Pro Pro Gly Met Gln Arg Glu Trp Val
        35                  40                  45

Ala Thr Ile Ala Ser Gly Gly Ala Thr Asn Tyr Ala Asn Ser Ile Lys
    50                  55                  60

Gly Arg Phe Thr Ala Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Asn
                85                  90                  95

Thr Leu Asn Phe Trp Gly Arg Gly Thr Gln Val Thr Val
            100                 105

<210> SEQ ID NO 113
<211> LENGTH: 5
<212> TYPE: PRT
<213> ORGANISM: Artificial Sequence
<220> FEATURE:
<223> OTHER INFORMATION: chemically synthesized

<400> SEQUENCE: 113

Asn Thr Leu Asn Phe
1               5

<210> SEQ ID NO 114
<211> LENGTH: 109
<212> TYPE: PRT
<213> ORGANISM: Artificial Sequence
<220> FEATURE:
<223> OTHER INFORMATION: chemically synthesized

<400> SEQUENCE: 114

Gln Val Gln Leu Gln Glu Ser Gly Gly Gly Leu Val Gln Ala Gly Gly
1               5                   10                  15

Ser Leu Arg Leu Ala Cys Thr Thr Ser Gly Gly Ile Phe Asn Ile Arg
            20                  25                  30

Pro Ile Ser Trp Tyr Arg Gln Pro Pro Gly Met Gln Arg Glu Trp Val
        35                  40                  45

Ala Thr Ile Ala Ser Gly Gly Ala Thr Asn Tyr Ala Asn Ser Ile Lys
    50                  55                  60

Gly Arg Phe Thr Ala Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Asn
                85                  90                  95

Val Phe Glu Ile Trp Gly Gln Gly Thr Gln Val Thr Val
            100                 105

<210> SEQ ID NO 115
```

```
<211> LENGTH: 5
<212> TYPE: PRT
<213> ORGANISM: Artificial Sequence
<220> FEATURE:
<223> OTHER INFORMATION: chemically synthesized

<400> SEQUENCE: 115

Asn Val Phe Glu Ile
1               5

<210> SEQ ID NO 116
<211> LENGTH: 109
<212> TYPE: PRT
<213> ORGANISM: Artificial Sequence
<220> FEATURE:
<223> OTHER INFORMATION: chemically synthesized

<400> SEQUENCE: 116

Gln Val Gln Leu Gln Gln Ser Gly Gly Gly Leu Val Gln Ala Gly Gly
1               5                   10                  15

Ser Leu Arg Leu Ala Cys Ile Thr Ser Gly Gly Ile Phe Asn Ile Arg
            20                  25                  30

Pro Ile Ser Trp Tyr Arg Gln Pro Pro Gly Lys Gln Arg Glu Trp Val
        35                  40                  45

Ala Thr Ile Ala Ser Gly Gly Ala Ala Asn Tyr Ala Asn Ser Ile Lys
    50                  55                  60

Gly Arg Phe Thr Ala Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Asn
                85                  90                  95

Ala Phe Glu Asn Trp Gly Gln Gly Thr Gln Val Thr Val
            100                 105

<210> SEQ ID NO 117
<211> LENGTH: 7
<212> TYPE: PRT
<213> ORGANISM: Artificial Sequence
<220> FEATURE:
<223> OTHER INFORMATION: chemically synthesized

<400> SEQUENCE: 117

Ile Ala Ser Gly Gly Ala Ala
1               5

<210> SEQ ID NO 118
<211> LENGTH: 5
<212> TYPE: PRT
<213> ORGANISM: Artificial Sequence
<220> FEATURE:
<223> OTHER INFORMATION: chemically synthesized

<400> SEQUENCE: 118

Asn Ala Phe Glu Asn
1               5

<210> SEQ ID NO 119
<211> LENGTH: 111
<212> TYPE: PRT
<213> ORGANISM: Artificial Sequence
<220> FEATURE:
<223> OTHER INFORMATION: chemically synthesized

<400> SEQUENCE: 119

Gln Val Gln Leu Gln Glu Ser Gly Gly Gly Glu Val Gln Pro Gly Gly
```

```
  1               5                  10                  15
Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
            35                  40                  45

Ser Thr Thr Thr Ser Ser Gly Ala Thr Asn Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro
            100                 105                 110
```

<210> SEQ ID NO 120
<211> LENGTH: 111
<212> TYPE: PRT
<213> ORGANISM: Artificial Sequence
<220> FEATURE:
<223> OTHER INFORMATION: chemically synthesized

<400> SEQUENCE: 120

```
Glu Val Gln Leu Gln Glu Ser Gly Gly Gly Val Gln Pro Gly Gly
1               5                  10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
            35                  40                  45

Ser Thr Thr Thr Ser Ser Gly Ala Thr Asn Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro
            100                 105                 110
```

<210> SEQ ID NO 121
<211> LENGTH: 111
<212> TYPE: PRT
<213> ORGANISM: Artificial Sequence
<220> FEATURE:
<223> OTHER INFORMATION: chemically synthesized

<400> SEQUENCE: 121

```
Glu Val Gln Leu Leu Glu Ser Gly Gly Gly Glu Val Gln Pro Gly Gly
1               5                  10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
            35                  40                  45

Ser Thr Thr Thr Ser Ser Gly Ala Thr Asn Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95
```

```
Val Phe Glu Tyr Trp Gly Gln Gly Thr Leu Val Thr Val Lys Pro
            100                 105                 110

<210> SEQ ID NO 122
<211> LENGTH: 111
<212> TYPE: PRT
<213> ORGANISM: Artificial Sequence
<220> FEATURE:
<223> OTHER INFORMATION: chemically synthesized

<400> SEQUENCE: 122

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
            35                  40                  45

Ser Thr Thr Thr Ser Ser Gly Ala Thr Asn Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro
            100                 105                 110

<210> SEQ ID NO 123
<211> LENGTH: 111
<212> TYPE: PRT
<213> ORGANISM: Artificial Sequence
<220> FEATURE:
<223> OTHER INFORMATION: chemically synthesized

<400> SEQUENCE: 123

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
            35                  40                  45

Thr Thr Thr Thr Ser Ser Gly Ala Thr Asn Tyr Ala Glu Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro
            100                 105                 110

<210> SEQ ID NO 124
<211> LENGTH: 111
<212> TYPE: PRT
<213> ORGANISM: Artificial Sequence
<220> FEATURE:
<223> OTHER INFORMATION: chemically synthesized

<400> SEQUENCE: 124

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
```

```
                20                  25                  30

Pro Ile Ser Trp Tyr Arg Gln Ala Pro Gly Lys Gln Arg Glu Trp Val
            35                  40                  45

Ser Thr Thr Thr Ser Ser Gly Ala Thr Asn Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro
            100                 105                 110

<210> SEQ ID NO 125
<211> LENGTH: 111
<212> TYPE: PRT
<213> ORGANISM: Artificial Sequence
<220> FEATURE:
<223> OTHER INFORMATION: chemically synthesized

<400> SEQUENCE: 125

Pro Thr Phe Ser Pro Ala Leu Leu Val Val Thr Glu Gly Asp Asn Ala
 1               5                  10                  15

Thr Phe Thr Cys Ser Phe Ser Asn Thr Ser Glu Ser Phe Val Leu Asn
                20                  25                  30

Trp Tyr Arg Met Ser Pro Ser Asn Gln Thr Asp Lys Leu Ala Ala Phe
            35                  40                  45

Pro Glu Asp Arg Ser Gln Pro Gly Gln Asp Cys Arg Phe Arg Val Thr
 50                  55                  60

Gln Leu Pro Asn Gly Arg Asp Phe His Met Ser Val Val Arg Ala Arg
 65                  70                  75                  80

Arg Asn Asp Ser Gly Thr Tyr Leu Cys Gly Ala Ile Ser Leu Ala Pro
                85                  90                  95

Lys Ala Gln Ile Lys Glu Ser Leu Arg Ala Glu Leu Arg Val Thr
            100                 105                 110

<210> SEQ ID NO 126
<211> LENGTH: 117
<212> TYPE: PRT
<213> ORGANISM: Artificial Sequence
<220> FEATURE:
<223> OTHER INFORMATION: chemically synthesized

<400> SEQUENCE: 126

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Gly Phe Ser Trp Val Arg Gln Ala Pro Gly Gln Gly Leu Glu Trp Met
            35                  40                  45

Gly Trp Ile Thr Ala Tyr Asn Gly Asn Thr Asn Tyr Ala Gln Lys Leu
            50                  55                  60

Gln Gly Arg Val Thr Met Thr Thr Asp Thr Ser Thr Ser Thr Val Tyr
 65                  70                  75                  80

Met Glu Leu Arg Ser Leu Arg Ser Asp Thr Ala Val Tyr Tyr Cys
                85                  90                  95

Ala Arg Asp Tyr Phe Tyr Gly Met Asp Val Trp Gly Gln Gly Thr Thr
            100                 105                 110
```

Val Thr Val Ser Ser
        115

<210> SEQ ID NO 127
<211> LENGTH: 123
<212> TYPE: PRT
<213> ORGANISM: Artificial Sequence
<220> FEATURE:
<223> OTHER INFORMATION: chemically synthesized

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 128
<211> LENGTH: 112
<212> TYPE: PRT
<213> ORGANISM: Artificial Sequence
<220> FEATURE:
<223> OTHER INFORMATION: chemically synthesized

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
            100                 105                 110

<210> SEQ ID NO 129
<211> LENGTH: 120
<212> TYPE: PRT
<213> ORGANISM: Artificial Sequence
<220> FEATURE:
<223> OTHER INFORMATION: chemically synthesized

<400> SEQUENCE: 129

Gln Val Gln Leu Val Gln Ser Gly Ala Glu Val Lys Lys Pro Gly Ser

```
                1               5                    10                   15
Ser Val Lys Val Ser Cys Lys Val Ser Gly Gly Ile Phe Ser Thr Tyr
                20                   25                   30

Ala Ile Asn Trp Val Arg Gln Ala Pro Gly Gln Gly Leu Glu Trp Met
                35                   40                   45

Gly Gly Ile Ile Pro Ile Phe Gly Thr Ala Asn His Ala Gln Lys Phe
            50                   55                   60

Gln Gly Arg Val Thr Ile Thr Ala Asp Glu Ser Thr Ser Thr Ala Tyr
65                  70                   75                   80

Met Glu Leu Ser Ser Leu Arg Ser Glu Asp Thr Ala Val Tyr Tyr Cys
                85                   90                   95

Ala Arg Asp Gln Gly Ile Ala Ala Ala Leu Phe Asp Tyr Trp Gly Gln
                100                  105                  110

Gly Thr Leu Val Thr Val Ser Ser
            115                  120

<210> SEQ ID NO 130
<211> LENGTH: 110
<212> TYPE: PRT
<213> ORGANISM: Artificial Sequence
<220> FEATURE:
<223> OTHER INFORMATION: chemically synthesized

<400> SEQUENCE: 130

Glu Val Gln Leu Val Glu Ser Gly Gly Gly Leu Val Gln Pro Gly Arg
1               5                    10                   15

Ser Leu Arg Leu Ser Cys Ala Val Ser Gly Phe Thr Phe Asp Asp Tyr
                20                   25                   30

Val Val His Trp Val Arg Gln Ala Pro Gly Lys Gly Leu Glu Trp Val
                35                   40                   45

Ser Gly Asn Ser Gly Asn Ile Gly Tyr Ala Asp Ser Val Lys Gly Arg
            50                   55                   60

Phe Thr Ile Ser Arg Asp Asn Ala Lys Asn Ser Leu Tyr Leu Gln Met
65                  70                   75                   80

Asn Ser Leu Arg Ala Glu Asp Thr Ala Leu Tyr Tyr Cys Ala Val Pro
                85                   90                   95

Phe Asp Tyr Trp Gly Gln Gly Thr Leu Val Thr Val Ser Ser
                100                  105                  110

<210> SEQ ID NO 131
<211> LENGTH: 123
<212> TYPE: PRT
<213> ORGANISM: Artificial Sequence
<220> FEATURE:
<223> OTHER INFORMATION: chemically synthesized

<400> SEQUENCE: 131

Gln Val Gln Leu Val Gln Ser Gly Ala Glu Val Lys Lys Pro Gly Ser
1               5                    10                   15

Ser Val Lys Val Ser Cys Lys Thr Ser Gly Asp Thr Phe Ser Ser Tyr
                20                   25                   30

Ala Ile Ser Trp Val Arg Gln Ala Pro Gly Gln Gly Leu Glu Trp Met
                35                   40                   45

Gly Gly Ile Ile Pro Ile Phe Gly Arg Ala His Tyr Ala Gln Lys Phe
            50                   55                   60

Gln Gly Arg Val Thr Ile Thr Ala Asp Glu Ser Thr Ser Thr Ala Tyr
65                  70                   75                   80
```

```
Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
            115                 120
```

<210> SEQ ID NO 132
<211> LENGTH: 123
<212> TYPE: PRT
<213> ORGANISM: Artificial Sequence
<220> FEATURE:
<223> OTHER INFORMATION: chemically synthesized

<400> SEQUENCE: 132

```
Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Tyr Asp Tyr Val Ser Gly Ser Pro Phe Gly Met Asp Val
            100                 105                 110

Trp Gly Gln Gly Thr Thr Val Thr Val Ser Ser
            115                 120
```

<210> SEQ ID NO 133
<211> LENGTH: 121
<212> TYPE: PRT
<213> ORGANISM: Artificial Sequence
<220> FEATURE:
<223> OTHER INFORMATION: chemically synthesized

<400> SEQUENCE: 133

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Ser Ala Asn Tyr Ala Gln Lys Phe
    50                  55                  60

Gln Asp Arg Val Thr Ile Thr Ala Asp Glu Ser Thr Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Ser Arg Tyr Tyr Met Asp Val Trp Gly
            100                 105                 110

Gln Gly Thr Thr Val Thr Val Ser Ser
        115                 120
```

<210> SEQ ID NO 134

<211> LENGTH: 123
<212> TYPE: PRT
<213> ORGANISM: Artificial Sequence
<220> FEATURE:
<223> OTHER INFORMATION: chemically synthesized

<400> SEQUENCE: 134

Gln Val Gln Leu Val Gln Ser Gly Ala Glu Val Lys Glu Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Ile Ala His Tyr Ala Gln Lys Phe
    50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Lys Tyr Ser Tyr Val Ser Gly Ser Pro Phe Gly Met Asp Val
            100                 105                 110

Trp Gly Gln Gly Thr Thr Val Thr Val Ser Ser
        115                 120

<210> SEQ ID NO 135
<211> LENGTH: 121
<212> TYPE: PRT
<213> ORGANISM: Artificial Sequence
<220> FEATURE:
<223> OTHER INFORMATION: chemically synthesized

<400> SEQUENCE: 135

Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Asp Tyr
            20                  25                  30

Gly Met His Trp Val Arg Gln Ala Pro Gly Lys Gly Leu Glu Trp Val
        35                  40                  45

Ser Gly Ile Ser Trp Asn Arg Gly Arg Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Phe Arg Tyr Phe Asp Trp Phe Leu Asp Tyr Trp Gly
            100                 105                 110

Gln Gly Thr Leu Val Thr Val Ser Ser
        115                 120

<210> SEQ ID NO 136
<211> LENGTH: 120
<212> TYPE: PRT
<213> ORGANISM: Artificial Sequence
<220> FEATURE:
<223> OTHER INFORMATION: chemically synthesized

<400> SEQUENCE: 136

Gln Met Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Phe Trp Ser Gly Phe Ser Ala Phe Asp Ile Trp Gly
            100                 105                 110

Lys Gly Thr Leu Val Thr Val Ser
        115                 120

<210> SEQ ID NO 137
<211> LENGTH: 107
<212> TYPE: PRT
<213> ORGANISM: Artificial Sequence
<220> FEATURE:
<223> OTHER INFORMATION: chemically synthesized

<400> SEQUENCE: 137

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 138
<211> LENGTH: 106
<212> TYPE: PRT
<213> ORGANISM: Artificial Sequence
<220> FEATURE:
<223> OTHER INFORMATION: chemically synthesized

<400> SEQUENCE: 138

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

```
Phe Gly Gln Gly Thr Lys Val Glu Ile Lys
            100                 105

<210> SEQ ID NO 139
<211> LENGTH: 107
<212> TYPE: PRT
<213> ORGANISM: Artificial Sequence
<220> FEATURE:
<223> OTHER INFORMATION: chemically synthesized

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 140
<211> LENGTH: 108
<212> TYPE: PRT
<213> ORGANISM: Artificial Sequence
<220> FEATURE:
<223> OTHER INFORMATION: chemically synthesized

<400> SEQUENCE: 140

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 141
<211> LENGTH: 106
<212> TYPE: PRT
<213> ORGANISM: Artificial Sequence
<220> FEATURE:
<223> OTHER INFORMATION: chemically synthesized

<400> SEQUENCE: 141

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Gly Gly Gly Thr Lys Val Glu Ile Lys
            100                 105

<210> SEQ ID NO 142
<211> LENGTH: 106
<212> TYPE: PRT
<213> ORGANISM: Artificial Sequence
<220> FEATURE:
<223> OTHER INFORMATION: chemically synthesized

<400> SEQUENCE: 142

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Arg Leu Glu Ile Lys
            100                 105

<210> SEQ ID NO 143
<211> LENGTH: 107
<212> TYPE: PRT
<213> ORGANISM: Artificial Sequence
<220> FEATURE:
<223> OTHER INFORMATION: chemically synthesized

<400> SEQUENCE: 143

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 144
<211> LENGTH: 107
<212> TYPE: PRT
<213> ORGANISM: Artificial Sequence
<220> FEATURE:
<223> OTHER INFORMATION: chemically synthesized

<400> SEQUENCE: 144

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105

<210> SEQ ID NO 145
<211> LENGTH: 121
<212> TYPE: PRT
<213> ORGANISM: Artificial Sequence
<220> FEATURE:
<223> OTHER INFORMATION: chemically synthesized

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 146
<211> LENGTH: 108
<212> TYPE: PRT
<213> ORGANISM: Artificial Sequence
<220> FEATURE:
<223> OTHER INFORMATION: chemically synthesized

<400> SEQUENCE: 146

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Val Ser Ser
            20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

<210> SEQ ID NO 147
<211> LENGTH: 118
<212> TYPE: PRT
<213> ORGANISM: Artificial Sequence
<220> FEATURE:
<223> OTHER INFORMATION: chemically synthesized

<400> SEQUENCE: 147

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115
```

<210> SEQ ID NO 148
<211> LENGTH: 118
<212> TYPE: PRT
<213> ORGANISM: Artificial Sequence
<220> FEATURE:
<223> OTHER INFORMATION: chemically synthesized

<400> SEQUENCE: 148

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Trp Ile His Trp Val Arg Gln Ala Pro Gly Lys Gly Leu Glu Trp Val
        35                  40                  45

Ala Trp Ile Leu Pro Tyr Gly Ser Ser Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 149
<211> LENGTH: 108
<212> TYPE: PRT
<213> ORGANISM: Artificial Sequence
<220> FEATURE:
<223> OTHER INFORMATION: chemically synthesized

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 150
<211> LENGTH: 108
<212> TYPE: PRT
<213> ORGANISM: Artificial Sequence
<220> FEATURE:
<223> OTHER INFORMATION: chemically synthesized

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Val Pro Trp
                85                  90                  95

Thr Phe Gly Gln Gly Thr Lys Val Glu Ile Lys Arg
            100                 105

<210> SEQ ID NO 151
<211> LENGTH: 108
<212> TYPE: PRT
<213> ORGANISM: Artificial Sequence
<220> FEATURE:
<223> OTHER INFORMATION: chemically synthesized

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ala Pro Pro Trp
                85                  90                  95

Thr Phe Gly Gln Gly Thr Lys Val Glu Ile Lys Arg
            100                 105

<210> SEQ ID NO 152
<211> LENGTH: 108
<212> TYPE: PRT
<213> ORGANISM: Artificial Sequence
<220> FEATURE:
<223> OTHER INFORMATION: chemically synthesized

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Val Pro Trp
                85                  90                  95

Thr Phe Gly Gln Gly Thr Lys Val Glu Ile Lys Arg
            100                 105

<210> SEQ ID NO 153
<211> LENGTH: 108
<212> TYPE: PRT
<213> ORGANISM: Artificial Sequence
<220> FEATURE:
<223> OTHER INFORMATION: chemically synthesized

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asn Thr Phe
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Val Pro Arg
                85                  90                  95

```
Thr Phe Gly Gln Gly Thr Lys Val Glu Ile Lys Arg
            100                 105
```

```
<210> SEQ ID NO 154
<211> LENGTH: 108
<212> TYPE: PRT
<213> ORGANISM: Artificial Sequence
<220> FEATURE:
<223> OTHER INFORMATION: chemically synthesized

<400> SEQUENCE: 154
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Val Pro Arg
                85                  90                  95

Thr Phe Gly Gln Gly Thr Lys Val Glu Ile Lys Arg
            100                 105
```

```
<210> SEQ ID NO 155
<211> LENGTH: 108
<212> TYPE: PRT
<213> ORGANISM: Artificial Sequence
<220> FEATURE:
<223> OTHER INFORMATION: chemically synthesized

<400> SEQUENCE: 155
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg
            100                 105
```

```
<210> SEQ ID NO 156
<211> LENGTH: 108
<212> TYPE: PRT
<213> ORGANISM: Artificial Sequence
<220> FEATURE:
<223> OTHER INFORMATION: chemically synthesized

<400> SEQUENCE: 156
```

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ile Thr Pro Thr
                85                  90                  95

Thr Phe Gly Gln Gly Thr Lys Val Glu Ile Lys Arg
            100                 105

<210> SEQ ID NO 157
<211> LENGTH: 108
<212> TYPE: PRT
<213> ORGANISM: Artificial Sequence
<220> FEATURE:
<223> OTHER INFORMATION: chemically synthesized

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Thr Pro Pro
                85                  90                  95

Thr Phe Gly Gln Gly Thr Lys Val Glu Ile Lys Arg
            100                 105

<210> SEQ ID NO 158
<211> LENGTH: 108
<212> TYPE: PRT
<213> ORGANISM: Artificial Sequence
<220> FEATURE:
<223> OTHER INFORMATION: chemically synthesized

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Phe Tyr Thr Pro Pro
                85                  90                  95

Thr Phe Gly Gln Gly Thr Lys Val Glu Ile Lys Arg
            100                 105

```
<210> SEQ ID NO 159
<211> LENGTH: 108
<212> TYPE: PRT
<213> ORGANISM: Artificial Sequence
<220> FEATURE:
<223> OTHER INFORMATION: chemically synthesized

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Phe Thr Pro Pro
                85                  90                  95

Thr Phe Gly Gln Gly Thr Lys Val Glu Ile Lys Arg
            100                 105

<210> SEQ ID NO 160
<211> LENGTH: 108
<212> TYPE: PRT
<213> ORGANISM: Artificial Sequence
<220> FEATURE:
<223> OTHER INFORMATION: chemically synthesized

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Thr Pro Pro
                85                  90                  95

Thr Phe Gly Gln Gly Thr Lys Val Glu Ile Lys Arg
            100                 105

<210> SEQ ID NO 161
<211> LENGTH: 108
<212> TYPE: PRT
<213> ORGANISM: Artificial Sequence
<220> FEATURE:
<223> OTHER INFORMATION: chemically synthesized

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Trp Tyr His Pro Pro
                 85                  90                  95

Thr Phe Gly Gln Gly Thr Lys Val Glu Ile Lys Arg
                100                 105
```

<210> SEQ ID NO 162
<211> LENGTH: 108
<212> TYPE: PRT
<213> ORGANISM: Artificial Sequence
<220> FEATURE:
<223> OTHER INFORMATION: chemically synthesized

<400> SEQUENCE: 162

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Phe Tyr Ile Pro Pro
                 85                  90                  95

Thr Phe Gly Gln Gly Thr Lys Val Glu Ile Lys Arg
                100                 105
```

<210> SEQ ID NO 163
<211> LENGTH: 108
<212> TYPE: PRT
<213> ORGANISM: Artificial Sequence
<220> FEATURE:
<223> OTHER INFORMATION: chemically synthesized

<400> SEQUENCE: 163

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Tyr Thr Pro Thr
                 85                  90                  95

Thr Phe Gly Gln Gly Thr Lys Val Glu Ile Lys Arg
                100                 105
```

<210> SEQ ID NO 164

```
<211> LENGTH: 108
<212> TYPE: PRT
<213> ORGANISM: Artificial Sequence
<220> FEATURE:
<223> OTHER INFORMATION: chemically synthesized

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Phe Ile Pro Pro
                85                  90                  95

Thr Phe Gly Gln Gly Thr Lys Val Glu Ile Lys Arg
            100                 105

<210> SEQ ID NO 165
<211> LENGTH: 141
<212> TYPE: PRT
<213> ORGANISM: Artificial Sequence
<220> FEATURE:
<223> OTHER INFORMATION: chemically synthesized

<400> SEQUENCE: 165

Met Glu Thr Gly Leu Arg Trp Leu Leu Leu Val Ala Val Leu Lys Gly
1               5                   10                  15

Val Gln Cys Leu Ser Val Glu Glu Ser Gly Gly Arg Leu Val Thr Pro
            20                  25                  30

Gly Thr Pro Leu Thr Leu Thr Cys Thr Ala Ser Gly Phe Thr Ile Thr
        35                  40                  45

Asn Tyr His Met Phe Trp Val Arg Gln Ala Pro Gly Lys Gly Leu Glu
    50                  55                  60

Trp Ile Gly Val Ile Thr Ser Ser Gly Ile Gly Ser Ser Thr Thr
65                  70                  75                  80

Tyr Tyr Ala Thr Trp Ala Lys Gly Arg Phe Thr Ile Ser Lys Thr Ser
                85                  90                  95

Thr Thr Val Asn Leu Arg Ile Thr Ser Pro Thr Thr Glu Asp Thr Ala
            100                 105                 110

Thr Tyr Phe Cys Ala Arg Asp Tyr Phe Thr Asn Thr Tyr Tyr Ala Leu
        115                 120                 125

Asp Ile Trp Gly Pro Gly Thr Leu Val Thr Val Ser Ser
    130                 135                 140

<210> SEQ ID NO 166
<211> LENGTH: 123
<212> TYPE: PRT
<213> ORGANISM: Artificial Sequence
<220> FEATURE:
<223> OTHER INFORMATION: chemically synthesized

<400> SEQUENCE: 166

Gln Val Gln Leu Val Gln Ser Gly Ala Glu Val Lys Lys Pro Gly Ser
1               5                   10                  15
```

```
Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
                100                 105                 110

Trp Gly Gln Gly Thr Thr Val Thr Val Ser Ser
            115                 120
```

<210> SEQ ID NO 167
<211> LENGTH: 118
<212> TYPE: PRT
<213> ORGANISM: Artificial Sequence
<220> FEATURE:
<223> OTHER INFORMATION: chemically synthesized

<400> SEQUENCE: 167

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
                100                 105                 110

Leu Val Thr Val Ser Ser
            115
```

<210> SEQ ID NO 168
<211> LENGTH: 120
<212> TYPE: PRT
<213> ORGANISM: Artificial Sequence
<220> FEATURE:
<223> OTHER INFORMATION: chemically synthesized

<400> SEQUENCE: 168

```
Gln Val Gln Leu Val Gln Ser Gly Ala Glu Val Lys Lys Pro Gly Ser
1               5                   10                  15

Ser Val Lys Val Ser Cys Lys Val Ser Gly Gly Ile Phe Ser Thr Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Ala Asn His Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp Gln Gly Ile Ala Ala Leu Phe Asp Tyr Trp Gly Gln
            100                 105                 110

Gly Thr Leu Val Thr Val Ser Ser
        115                 120

<210> SEQ ID NO 169
<211> LENGTH: 113
<212> TYPE: PRT
<213> ORGANISM: Artificial Sequence
<220> FEATURE:
<223> OTHER INFORMATION: chemically synthesized

<400> SEQUENCE: 169

Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
            20                  25                  30

Val Val His Trp Val Arg Gln Ala Pro Gly Lys Gly Leu Glu Trp Val
        35                  40                  45

Ser Gly Ile Ser Gly Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Val Pro Phe Asp Tyr Trp Gly Gln Gly Thr Leu Val Thr Val Ser
            100                 105                 110

Ser

<210> SEQ ID NO 170
<211> LENGTH: 123
<212> TYPE: PRT
<213> ORGANISM: Artificial Sequence
<220> FEATURE:
<223> OTHER INFORMATION: chemically synthesized

<400> SEQUENCE: 170

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 171
```

```
<211> LENGTH: 123
<212> TYPE: PRT
<213> ORGANISM: Artificial Sequence
<220> FEATURE:
<223> OTHER INFORMATION: chemically synthesized

<400> SEQUENCE: 171

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Tyr Asp Tyr Val Ser Gly Ser Pro Phe Gly Met Asp Val
            100                 105                 110

Trp Gly Gln Gly Thr Thr Val Thr Val Ser Ser
        115                 120

<210> SEQ ID NO 172
<211> LENGTH: 121
<212> TYPE: PRT
<213> ORGANISM: Artificial Sequence
<220> FEATURE:
<223> OTHER INFORMATION: chemically synthesized

<400> SEQUENCE: 172

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Ser Ala Asn Tyr Ala Gln Lys Phe
    50                  55                  60

Gln Asp Arg Val Thr Ile Thr Ala Asp Glu Ser Thr Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Ser Arg Tyr Tyr Met Asp Val Trp Gly
            100                 105                 110

Gln Gly Thr Thr Val Thr Val Ser Ser
        115                 120

<210> SEQ ID NO 173
<211> LENGTH: 123
<212> TYPE: PRT
<213> ORGANISM: Artificial Sequence
<220> FEATURE:
<223> OTHER INFORMATION: chemically synthesized

<400> SEQUENCE: 173

Gln Val Gln Leu Val Gln Ser Gly Ala Glu Val Lys Glu Pro Gly Ser
1               5                   10                  15
```

```
Ser Val Lys Val Ser Cys Lys Ala Ser Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Ile Ala His Tyr Ala Gln Lys Phe
    50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Lys Tyr Ser Tyr Val Ser Gly Ser Pro Phe Gly Met Asp Val
            100                 105                 110

Trp Gly Gln Gly Thr Thr Val Thr Val Ser Ser
        115                 120
```

<210> SEQ ID NO 174
<211> LENGTH: 121
<212> TYPE: PRT
<213> ORGANISM: Artificial Sequence
<220> FEATURE:
<223> OTHER INFORMATION: chemically synthesized

<400> SEQUENCE: 174

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Asp Tyr
            20                  25                  30

Gly Met His Trp Val Arg Gln Ala Pro Gly Lys Gly Leu Glu Trp Val
        35                  40                  45

Ser Gly Ile Ser Trp Asn Arg Gly Arg Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Phe Arg Tyr Phe Asp Trp Phe Leu Asp Tyr Trp Gly
            100                 105                 110

Gln Gly Thr Leu Val Thr Val Ser Ser
        115                 120
```

<210> SEQ ID NO 175
<211> LENGTH: 116
<212> TYPE: PRT
<213> ORGANISM: Artificial Sequence
<220> FEATURE:
<223> OTHER INFORMATION: chemically synthesized

<400> SEQUENCE: 175

```
Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ser Ser
            20                  25                  30

Thr Ser Thr Ala Val Gly Gly Thr Val Thr Ile Lys Cys Gln Ala Ser
        35                  40                  45

Gln Ser Ile Ser Val Tyr Leu Ala Trp Tyr Gln Gln Lys Pro Gly Gln
    50                  55                  60

Pro Pro Lys Leu Leu Ile Tyr Ser Ala Ser Thr Leu Ala Ser Gly Val
65                  70                  75                  80
```

Pro Ser Arg Phe Lys Gly Ser Arg Ser Gly Thr Glu Tyr Thr Leu Thr
            85                  90                  95

Ile Ser Gly Val Gln Arg Glu Asp Ala Ala Thr Tyr Tyr Cys Leu Gly
        100                 105                 110

Ser Ala Gly Ser
        115

<210> SEQ ID NO 176
<211> LENGTH: 107
<212> TYPE: PRT
<213> ORGANISM: Artificial Sequence
<220> FEATURE:
<223> OTHER INFORMATION: chemically synthesized

<400> SEQUENCE: 176

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 177
<211> LENGTH: 106
<212> TYPE: PRT
<213> ORGANISM: Artificial Sequence
<220> FEATURE:
<223> OTHER INFORMATION: chemically synthesized

<400> SEQUENCE: 177

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 178
<211> LENGTH: 107
<212> TYPE: PRT
<213> ORGANISM: Artificial Sequence
<220> FEATURE:
<223> OTHER INFORMATION: chemically synthesized

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 179
<211> LENGTH: 108
<212> TYPE: PRT
<213> ORGANISM: Artificial Sequence
<220> FEATURE:
<223> OTHER INFORMATION: chemically synthesized

<400> SEQUENCE: 179

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 180
<211> LENGTH: 106
<212> TYPE: PRT
<213> ORGANISM: Artificial Sequence
<220> FEATURE:
<223> OTHER INFORMATION: chemically synthesized

<400> SEQUENCE: 180

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Ser Pro
                85                  90                  95

Phe Gly Gly Gly Thr Lys Val Glu Ile Lys
            100                 105

<210> SEQ ID NO 181
<211> LENGTH: 106
<212> TYPE: PRT
<213> ORGANISM: Artificial Sequence
<220> FEATURE:
<223> OTHER INFORMATION: chemically synthesized

<400> SEQUENCE: 181

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Arg Leu Glu Ile Lys
            100                 105

<210> SEQ ID NO 182
<211> LENGTH: 107
<212> TYPE: PRT
<213> ORGANISM: Artificial Sequence
<220> FEATURE:
<223> OTHER INFORMATION: chemically synthesized

<400> SEQUENCE: 182

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 183
<211> LENGTH: 120
<212> TYPE: PRT
<213> ORGANISM: Artificial Sequence
<220> FEATURE:
<223> OTHER INFORMATION: chemically synthesized

<400> SEQUENCE: 183
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
            115                 120
```

<210> SEQ ID NO 184
<211> LENGTH: 110
<212> TYPE: PRT
<213> ORGANISM: Artificial Sequence
<220> FEATURE:
<223> OTHER INFORMATION: chemically synthesized

<400> SEQUENCE: 184

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 185
<211> LENGTH: 118
<212> TYPE: PRT
<213> ORGANISM: Artificial Sequence
<220> FEATURE:
<223> OTHER INFORMATION: chemically synthesized

<400> SEQUENCE: 185

```
Glu Val Lys Leu Gln Glu Ser Gly Pro Ser Leu Val Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Val
        35                  40                  45

Gly Tyr Ile Ser Tyr Thr Gly Ser Thr Tyr Tyr Asn Pro Ser Leu Lys
50                  55                  60

Ser Arg Ile Ser Ile Thr Arg Asp Thr Ser Lys Asn Gln Tyr Tyr Leu
65                  70                  75                  80
```

```
Gln Leu Asn Ser Val Thr Ser Glu Asp Thr Ala Thr Tyr Tyr Cys Ala
                85                  90                  95

Arg Tyr Gly Gly Trp Leu Ser Pro Phe Asp Tyr Trp Gly Gln Gly Thr
            100                 105                 110

Thr Leu Thr Val Ser Ser
        115

<210> SEQ ID NO 186
<211> LENGTH: 120
<212> TYPE: PRT
<213> ORGANISM: Artificial Sequence
<220> FEATURE:
<223> OTHER INFORMATION: chemically synthesized

<400> SEQUENCE: 186

Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Ser Ile Asn Trp Ile Arg Gln Pro Pro Gly Lys Gly Leu Glu Trp Leu
        35                  40                  45

Gly Val Met Trp Ala Gly Gly Thr Asn Ser Asn Ser Val Leu Lys
    50                  55                  60

Ser Arg Leu Ile Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Tyr Tyr Gly Asn Ser Pro Tyr Tyr Ala Ile Asp Tyr Trp Gly Gln
            100                 105                 110

Gly Thr Ser Val Thr Val Ser Ser
        115                 120

<210> SEQ ID NO 187
<211> LENGTH: 118
<212> TYPE: PRT
<213> ORGANISM: Artificial Sequence
<220> FEATURE:
<223> OTHER INFORMATION: chemically synthesized

<400> SEQUENCE: 187

Glu Val Lys Leu Gln Glu Ser Gly Pro Ser Leu Val Lys Pro Ser Gln
1               5                   10                  15

Thr Leu Ser Leu Thr Cys Ser Val Thr Gly Tyr Ser Ile Ile Ser Asp
            20                  25                  30

Tyr Trp Asn Trp Ile Arg Lys Phe Pro Gly Asn Lys Leu Glu Tyr Leu
        35                  40                  45

Gly Tyr Ile Ser Tyr Thr Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Arg Gly Gly Trp Leu Leu Pro Phe Asp Tyr Trp Gly Gln Gly Thr
            100                 105                 110

Thr Leu Thr Val Ser Ser
        115
```

```
<210> SEQ ID NO 188
<211> LENGTH: 118
<212> TYPE: PRT
<213> ORGANISM: Artificial Sequence
<220> FEATURE:
<223> OTHER INFORMATION: chemically synthesized

<400> SEQUENCE: 188

Glu Val Lys Leu Gln Glu Ser Gly Pro Ser Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Phe Pro Arg Asp Asn Asn Thr Lys Tyr Asn Glu Asn Phe
    50                  55                  60

Lys Gly Lys Ala Thr Leu Thr Val Asp Thr Ser Ser Thr Ala Tyr
65                  70                  75                  80

Met Glu Leu His Ser Leu Thr Ser Glu Asp Ser Ala Val Tyr Phe Cys
                85                  90                  95

Thr Lys Glu Asn Trp Val Gly Asp Phe Asp Tyr Trp Gly Gln Gly Thr
            100                 105                 110

Thr Leu Thr Leu Ser Ser
        115

<210> SEQ ID NO 189
<211> LENGTH: 114
<212> TYPE: PRT
<213> ORGANISM: Artificial Sequence
<220> FEATURE:
<223> OTHER INFORMATION: chemically synthesized

<400> SEQUENCE: 189

Glu Val Gln Leu Gln Gln Ser Gly Pro Asp Leu Val Thr Pro Gly Ala
1               5                   10                  15

Ser Val Arg Ile Ser Cys Gln Ala Ser Gly Tyr Thr Phe Pro Asp Tyr
            20                  25                  30

Tyr Met Asn Trp Val Lys Gln Ser His Gly Lys Ser Leu Glu Trp Ile
        35                  40                  45

Gly Asp Ile Asp Pro Asn Tyr Gly Gly Thr Thr Tyr Asn Gln Lys Phe
    50                  55                  60

Lys Gly Lys Ala Ile Leu Thr Val Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ala Leu Thr Asp Trp Gly Gln Gly Thr Ser Leu Thr Val
            100                 105                 110

Ser Ser

<210> SEQ ID NO 190
<211> LENGTH: 106
<212> TYPE: PRT
<213> ORGANISM: Artificial Sequence
<220> FEATURE:
<223> OTHER INFORMATION: chemically synthesized

<400> SEQUENCE: 190

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Ser Ser Val Ser Tyr Ile
            20                  25                  30

Tyr Trp Phe Gln Gln Lys Pro Gly Gln Ser Pro Arg Pro Leu Ile Tyr
        35                  40                  45

Ala Ala Phe Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 191
<211> LENGTH: 114
<212> TYPE: PRT
<213> ORGANISM: Artificial Sequence
<220> FEATURE:
<223> OTHER INFORMATION: chemically synthesized

<400> SEQUENCE: 191

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Gly Leu Glu Trp Met
        35                  40                  45

Gly Asp Ile Asp Pro Asn Tyr Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 192
<211> LENGTH: 114
<212> TYPE: PRT
<213> ORGANISM: Artificial Sequence
<220> FEATURE:
<223> OTHER INFORMATION: chemically synthesized

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Ser Leu Glu Trp Met
        35                  40                  45

Gly Asp Ile Asp Pro Asn Tyr Gly Gly Thr Asn Tyr Asn Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

-continued

Ala Arg Gly Ala Leu Thr Asp Trp Gly Gln Gly Thr Met Val Thr Val
            100                 105                 110
Ser Ser

<210> SEQ ID NO 193
<211> LENGTH: 114
<212> TYPE: PRT
<213> ORGANISM: Artificial Sequence
<220> FEATURE:
<223> OTHER INFORMATION: chemically synthesized

<400> SEQUENCE: 193

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Ser Leu Glu Trp Met
            35                  40                  45

Gly Asp Ile Asp Pro Asn Tyr Gly Gly Thr Asn Tyr Asn Gln Lys Phe
        50                  55                  60

Gln Gly Arg Val Thr Met Thr Val Asp Arg Ser Ser Thr Ala Tyr
65                  70                  75                  80

Met Glu Leu Ser Arg Leu Arg Ser Asp Thr Ala Val Tyr Tyr Cys
            85                  90                  95

Ala Arg Gly Ala Leu Thr Asp Trp Gly Gln Gly Thr Met Val Thr Val
            100                 105                 110
Ser Ser

<210> SEQ ID NO 194
<211> LENGTH: 114
<212> TYPE: PRT
<213> ORGANISM: Artificial Sequence
<220> FEATURE:
<223> OTHER INFORMATION: chemically synthesized

<400> SEQUENCE: 194

Glu Val Gln Leu Val Glu Ser Gly Gly Gly Leu Val Gln Pro Gly Arg
1               5                   10                  15

Ser Leu Arg Leu Ser Cys Thr Ala Ser Gly Tyr Thr Phe Pro Asp Tyr
            20                  25                  30

Tyr Met Asn Trp Val Arg Gln Ala Pro Gly Lys Gly Leu Glu Trp Val
            35                  40                  45

Gly Asp Ile Asp Pro Asn Tyr Gly Gly Thr Thr Tyr Ala Ala Ser Val
        50                  55                  60

Lys Gly Arg Phe Thr Ile Ser Val Asp Arg Ser Lys Ser Ile Ala Tyr
65                  70                  75                  80

Leu Gln Met Ser Ser Leu Lys Thr Glu Asp Thr Ala Val Tyr Tyr Cys
            85                  90                  95

Thr Arg Gly Ala Leu Thr Asp Trp Gly Gln Gly Thr Met Val Thr Val
            100                 105                 110
Ser Ser

<210> SEQ ID NO 195
<211> LENGTH: 114
<212> TYPE: PRT
<213> ORGANISM: Artificial Sequence
<220> FEATURE:
<223> OTHER INFORMATION: chemically synthesized

```
<400> SEQUENCE: 195

Glu Val Gln Leu Val Glu Ser Gly Gly Leu Val Gln Pro Gly Arg
1               5                   10                  15

Ser Leu Arg Leu Ser Cys Thr Ala Ser Gly Tyr Thr Phe Pro Asp Tyr
            20                  25                  30

Tyr Met Asn Trp Val Arg Gln Ala Pro Gly Lys Gly Leu Glu Trp Val
        35                  40                  45

Gly Asp Ile Asp Pro Asn Tyr Gly Gly Thr Thr Tyr Asn Ala Ser Val
    50                  55                  60

Lys Gly Arg Phe Thr Ile Ser Val Asp Arg Ser Lys Ser Ile Ala Tyr
65                  70                  75                  80

Leu Gln Met Ser Ser Leu Lys Thr Glu Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 196
<211> LENGTH: 107
<212> TYPE: PRT
<213> ORGANISM: Artificial Sequence
<220> FEATURE:
<223> OTHER INFORMATION: chemically synthesized

<400> SEQUENCE: 196

Asp Ile Val Met Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Asp Ser Ser Tyr Pro Leu
                85                  90                  95

Thr Phe Gly Ala Gly Thr Lys Val Glu Leu Lys
            100                 105

<210> SEQ ID NO 197
<211> LENGTH: 107
<212> TYPE: PRT
<213> ORGANISM: Artificial Sequence
<220> FEATURE:
<223> OTHER INFORMATION: chemically synthesized

<400> SEQUENCE: 197

Asp Ile Val Thr Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
```

65                  70                  75                  80
Glu Asp Leu Ala Asp Tyr Phe Cys Gln Gln Asp Ser Ser Tyr Pro Leu
                85                  90                  95

Thr Phe Gly Ala Gly Thr Lys Val Glu Leu Lys
            100                 105

<210> SEQ ID NO 198
<211> LENGTH: 113
<212> TYPE: PRT
<213> ORGANISM: Artificial Sequence
<220> FEATURE:
<223> OTHER INFORMATION: chemically synthesized

<400> SEQUENCE: 198

Asp Ile Val Met Thr Gln Ser Pro Ser Leu Ala Val Ser Val Gly
1               5                   10                  15

Glu Lys Val Ser Met Gly Cys Lys Ser Ser Gln Ser Leu Leu Tyr Ser
                20                  25                  30

Ser Asn Gln Lys Asn Ser Leu Ala Trp Tyr Gln Lys Pro Gly Gln
            35                  40                  45

Ser Pro Lys Leu Leu Ile Asp Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
            100                 105                 110

Lys

<210> SEQ ID NO 199
<211> LENGTH: 106
<212> TYPE: PRT
<213> ORGANISM: Artificial Sequence
<220> FEATURE:
<223> OTHER INFORMATION: chemically synthesized

<400> SEQUENCE: 199

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Ile Arg Tyr Met
                20                  25                  30

His Trp Tyr Gln Gln Lys Pro Gly Thr Ser Pro Lys Arg Trp Ile Ser
            35                  40                  45

Asp Thr Ser Lys Leu Thr Ser Gly Val Pro Ala Arg Phe Ser Gly Ser
50                  55                  60

Gly Ser Gly Thr Ser Tyr Ala Leu Thr Ile Ser Ser Met Glu Ala Glu
65                  70                  75                  80

Asp Ala Ala Thr Tyr Tyr Cys His Gln Arg Ser Ser Tyr Pro Trp Thr
                85                  90                  95

Phe Gly Gly Gly Thr Lys Leu Glu Ile Lys
            100                 105

<210> SEQ ID NO 200
<211> LENGTH: 106
<212> TYPE: PRT
<213> ORGANISM: Artificial Sequence
<220> FEATURE:
<223> OTHER INFORMATION: chemically synthesized

<400> SEQUENCE: 200

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

Tyr Trp Phe Gln Gln Lys Pro Gly Ser Ser Pro Lys Pro Trp Ile Tyr
        35                  40                  45

Ala Thr Phe Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Thr Glu
65                  70                  75                  80

Asp Ala Ala Thr Tyr Tyr Cys Gln Gln Trp Ser Asn Asn Pro Leu Thr
                85                  90                  95

Phe Gly Ala Gly Thr Lys Leu Glu Leu Lys
            100                 105
```

<210> SEQ ID NO 201
<211> LENGTH: 106
<212> TYPE: PRT
<213> ORGANISM: Artificial Sequence
<220> FEATURE:
<223> OTHER INFORMATION: chemically synthesized

<400> SEQUENCE: 201

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Ile
            20                  25                  30

Tyr Trp Phe Gln Gln Lys Pro Gly Gln Ala Pro Arg Leu Leu Ile Tyr
        35                  40                  45

Ala Ala Phe Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105
```

<210> SEQ ID NO 202
<211> LENGTH: 106
<212> TYPE: PRT
<213> ORGANISM: Artificial Sequence
<220> FEATURE:
<223> OTHER INFORMATION: chemically synthesized

<400> SEQUENCE: 202

```
Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Ile
            20                  25                  30

Tyr Trp Phe Gln Gln Lys Pro Gly Gln Ser Pro Arg Pro Leu Ile Tyr
        35                  40                  45

Ala Thr Phe Asn Leu Ala Ser Gly Ile Pro Ala Arg Phe Ser Gly Ser
    50                  55                  60

Gly Ser Gly Thr Ser Tyr Thr Leu Thr Ile Ser Arg Leu Glu Pro Glu
65                  70                  75                  80
```

```
Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 203
<211> LENGTH: 106
<212> TYPE: PRT
<213> ORGANISM: Artificial Sequence
<220> FEATURE:
<223> OTHER INFORMATION: chemically synthesized

<400> SEQUENCE: 203

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Ser Gly Val Ser Tyr Ile
                20                  25                  30

Tyr Trp Phe Gln Gln Lys Pro Gly Lys Ala Pro Lys Leu Leu Ile Tyr
            35                  40                  45

Ala Ala Phe Asn Leu Ala Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 204
<211> LENGTH: 106
<212> TYPE: PRT
<213> ORGANISM: Artificial Sequence
<220> FEATURE:
<223> OTHER INFORMATION: chemically synthesized

<400> SEQUENCE: 204

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Ser Gly Val Ser Tyr Ile
                20                  25                  30

Tyr Trp Phe Gln Gln Lys Pro Gly Lys Ala Pro Lys Pro Leu Ile Tyr
            35                  40                  45

Ala Ala Phe Asn Leu Ala Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 205
<211> LENGTH: 106
<212> TYPE: PRT
<213> ORGANISM: Artificial Sequence
<220> FEATURE:
<223> OTHER INFORMATION: chemically synthesized

<400> SEQUENCE: 205
```

```
Asp Ile Gln Leu Thr Gln Ser Pro Ser Ile Leu Ser Ala Ser Val Gly
1               5                   10                  15

Asp Arg Val Thr Ile Thr Cys Arg Ala Ser Ser Val Ser Tyr Ile
            20                  25                  30

Tyr Trp Phe Gln Gln Lys Pro Gly Lys Ala Pro Lys Pro Leu Ile Tyr
        35                  40                  45

Ala Thr Phe Asn Leu Ala Ser Gly Val Pro Ser Arg Phe Ser Gly Ser
    50                  55                  60

Gly Ser Gly Thr Ser Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105
```

<210> SEQ ID NO 206
<211> LENGTH: 124
<212> TYPE: PRT
<213> ORGANISM: Artificial Sequence
<220> FEATURE:
<223> OTHER INFORMATION: chemically synthesized

<400> SEQUENCE: 206

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Leu Pro Ser Gly Thr Ile Leu Val Gly Gly Trp Phe Asp
            100                 105                 110

Pro Trp Gly Gln Gly Thr Leu Val Thr Val Ser Ser
        115                 120
```

<210> SEQ ID NO 207
<211> LENGTH: 124
<212> TYPE: PRT
<213> ORGANISM: Artificial Sequence
<220> FEATURE:
<223> OTHER INFORMATION: chemically synthesized

<400> SEQUENCE: 207

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Ser Ala Ile Ser Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Asp Val Phe Pro Glu Thr Phe Ser Met Asn Tyr Gly Met Asp
            100                 105                 110

Val Trp Gly Gln Gly Thr Leu Val Thr Val Ser Ser
        115                 120
```

<210> SEQ ID NO 208
<211> LENGTH: 128
<212> TYPE: PRT
<213> ORGANISM: Artificial Sequence
<220> FEATURE:
<223> OTHER INFORMATION: chemically synthesized

<400> SEQUENCE: 208

```
Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Val Leu Leu Pro Cys Ser Ser Thr Ser Cys Tyr Gly Ser Val
            100                 105                 110

Gly Ala Phe Asp Ile Trp Gly Gln Gly Thr Thr Val Thr Val Ser Ser
        115                 120                 125
```

<210> SEQ ID NO 209
<211> LENGTH: 117
<212> TYPE: PRT
<213> ORGANISM: Artificial Sequence
<220> FEATURE:
<223> OTHER INFORMATION: chemically synthesized

<400> SEQUENCE: 209

```
Gln Val Gln Leu Val Gln Ser Gly Gly Ser Val Val Arg Pro Gly Glu
1               5                   10                  15

Ser Leu Arg Leu Ser Cys Val Ala Ser Gly Phe Ile Phe Asp Asn Tyr
            20                  25                  30

Asp Met Ser Trp Val Arg Gln Val Pro Gly Lys Gly Leu Glu Trp Val
        35                  40                  45

Ser Arg Val Asn Trp Asn Gly Gly Ser Thr Thr Tyr Ala Asp Ala Val
    50                  55                  60

Lys Gly Arg Phe Thr Ile Ser Arg Asp Asn Thr Lys Asn Ser Leu Tyr
65                  70                  75                  80

Leu Gln Met Asn Asn Leu Arg Ala Glu Asp Thr Ala Val Tyr Tyr Cys
                85                  90                  95

Val Arg Glu Phe Val Gly Ala Tyr Asp Leu Trp Gly Gln Gly Thr Thr
            100                 105                 110

Val Thr Val Ser Ser
        115
```

-continued

```
<210> SEQ ID NO 210
<211> LENGTH: 121
<212> TYPE: PRT
<213> ORGANISM: Artificial Sequence
<220> FEATURE:
<223> OTHER INFORMATION: chemically synthesized

<400> SEQUENCE: 210
```

Gln Val Gln Leu Val Gln Ser Gly Ala Glu Val Lys Pro Gly Ala
1               5                   10                  15

Thr Val Lys Val Ser Cys Lys Val Phe Gly Asp Thr Phe Arg Gly Leu
            20                  25                  30

Tyr Ile His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Leu Arg Trp Gly Ile Trp Gly Trp Phe Asp Pro Trp Gly
            100                 105                 110

Gln Gly Thr Leu Val Thr Val Ser Ser
        115                 120

```
<210> SEQ ID NO 211
<211> LENGTH: 121
<212> TYPE: PRT
<213> ORGANISM: Artificial Sequence
<220> FEATURE:
<223> OTHER INFORMATION: chemically synthesized

<400> SEQUENCE: 211
```

Glu Val Gln Leu Val Gln Ser Gly Ala Glu Leu Lys Lys Pro Gly Ser
1               5                   10                  15

Ser Val Lys Val Ser Cys Lys Ala Phe Gly Gly Thr Phe Ser Asp Asn
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Lys Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Val Leu Ser Ser Leu Arg Ser Glu Asp Thr Ala Val Tyr Tyr Cys
                85                  90                  95

Ala Arg Thr Met Val Arg Gly Phe Leu Gly Val Met Asp Val Trp Gly
            100                 105                 110

Gln Gly Thr Thr Val Thr Val Ser Ser
        115                 120

```
<210> SEQ ID NO 212
<211> LENGTH: 125
<212> TYPE: PRT
<213> ORGANISM: Artificial Sequence
<220> FEATURE:
<223> OTHER INFORMATION: chemically synthesized

<400> SEQUENCE: 212
```

Gln Val Gln Leu Val Gln Ser Gly Gly Gly Leu Val Gln Pro Gly Gly
1               5                   10                  15

-continued

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Phe Val Thr Ile Phe Gly Val Pro Arg Tyr Gly Met
            100                 105                 110

Asp Val Trp Gly Gln Gly Thr Thr Val Thr Val Ser Ser
        115                 120                 125
```

<210> SEQ ID NO 213
<211> LENGTH: 120
<212> TYPE: PRT
<213> ORGANISM: Artificial Sequence
<220> FEATURE:
<223> OTHER INFORMATION: chemically synthesized

<400> SEQUENCE: 213

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Pro
            100                 105                 110

Gly Thr Leu Val Thr Val Ser Ser
        115                 120
```

<210> SEQ ID NO 214
<211> LENGTH: 118
<212> TYPE: PRT
<213> ORGANISM: Artificial Sequence
<220> FEATURE:
<223> OTHER INFORMATION: chemically synthesized

<400> SEQUENCE: 214

```
Glu Val Gln Leu Val Glu Ser Gly Ala Glu Val Lys Lys Pro Gly Ser
1               5                   10                  15

Ser Val Lys Val Ser Cys Lys Val Ser Gly Gly Thr Phe Gly Thr Tyr
            20                  25                  30

Ala Leu Asn Trp Val Arg Gln Ala Pro Gly Gln Gly Leu Glu Trp Met
        35                  40                  45

Gly Arg Ile Val Pro Leu Ile Gly Leu Val Asn Tyr Ala His Asn Phe
    50                  55                  60

Glu Gly Arg Ile Ser Ile Thr Ala Asp Lys Ser Thr Gly Thr Ala Tyr
```

```
                65                  70                  75                  80
Met Glu Leu Ser Asn Leu Arg Ser Asp Asp Thr Ala Val Tyr Tyr Cys
                    85                  90                  95

Ala Arg Glu Val Tyr Gly Gly Asn Ser Asp Tyr Trp Gly Gln Gly Thr
                    100                 105                 110

Leu Val Thr Val Ser Ser
        115

<210> SEQ ID NO 215
<211> LENGTH: 120
<212> TYPE: PRT
<213> ORGANISM: Artificial Sequence
<220> FEATURE:
<223> OTHER INFORMATION: chemically synthesized

<400> SEQUENCE: 215

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Leu Ser Ser His
                20                  25                  30

Gly Ile Thr Trp Val Arg Gln Ala Pro Gly Gln Gly Leu Glu Trp Met
            35                  40                  45

Gly Trp Ile Ser Ala His Asn Gly His Ala Ser Asn Ala Gln Lys Val
    50                  55                  60

Glu Asp Arg Val Thr Met Thr Thr Asp Thr Ser Thr Asn Thr Ala Tyr
65                  70                  75                  80

Met Glu Leu Arg Ser Leu Thr Ala Asp Asp Thr Ala Val Tyr Tyr Cys
                    85                  90                  95

Ala Arg Val His Ala Ala Leu Tyr Tyr Gly Met Asp Val Trp Gly Gln
                    100                 105                 110

Gly Thr Leu Val Thr Val Ser Ser
            115                 120

<210> SEQ ID NO 216
<211> LENGTH: 121
<212> TYPE: PRT
<213> ORGANISM: Artificial Sequence
<220> FEATURE:
<223> OTHER INFORMATION: chemically synthesized

<400> SEQUENCE: 216

Gln Val Gln Leu Gln Glu Ser Gly Gly Gly Val Val Gln Pro Gly Arg
1               5                   10                  15

Ser Leu Arg Leu Ser Cys Ser Ala Ser Gly Phe Thr Phe Ser Arg His
                20                  25                  30

Gly Met His Trp Val Arg Gln Ala Pro Gly Lys Gly Leu Glu Trp Val
            35                  40                  45

Ala Val Ile Ser His Asp Gly Ser Val Lys Tyr Tyr Ala Asp Ser Met
    50                  55                  60

Lys Gly Arg Phe Ser Ile Ser Arg Asp Asn Ser Asn Asn Thr Leu Tyr
65                  70                  75                  80

Leu Gln Met Asp Ser Leu Arg Ala Asp Asp Thr Ala Val Tyr Tyr Cys
                    85                  90                  95

Ala Arg Gly Leu Ser Tyr Gln Val Ser Gly Trp Phe Asp Pro Trp Gly
                    100                 105                 110

Gln Gly Thr Leu Val Thr Val Ser Ser
            115                 120
```

<210> SEQ ID NO 217
<211> LENGTH: 110
<212> TYPE: PRT
<213> ORGANISM: Artificial Sequence
<220> FEATURE:
<223> OTHER INFORMATION: chemically synthesized

<400> SEQUENCE: 217

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Lys Asp Glu Ala Asp Tyr Tyr Cys Gln Ser Tyr Asp Gly
                85                  90                  95

Ile Thr Val Ile Phe Gly Gly Gly Thr Lys Leu Thr Val Leu
            100                 105                 110

<210> SEQ ID NO 218
<211> LENGTH: 111
<212> TYPE: PRT
<213> ORGANISM: Artificial Sequence
<220> FEATURE:
<223> OTHER INFORMATION: chemically synthesized

<400> SEQUENCE: 218

Asn Phe Met Leu Thr Gln Pro His Ser Val Ser Gly Ser Pro Gly Lys
1               5                   10                  15

Thr Val Thr Leu Pro Cys Thr Arg Ser Ser Gly Ser Ile Ala Ser His
            20                  25                  30

Tyr Val Gln Trp Tyr Gln Gln Arg Pro Gly Ser Ala Pro Thr Thr Val
        35                  40                  45

Ile Tyr Glu Asp Asn Lys Arg Pro Ser Gly Val Pro Asp Arg Phe Ser
    50                  55                  60

Gly Ser Ile Asp Ser Ser Ser Asn Ser Ala Ser Leu Ser Ile Ser Gly
65                  70                  75                  80

Leu Lys Thr Glu Asp Glu Ala Asp Tyr Tyr Cys Gln Ser Tyr Asp Ser
                85                  90                  95

Ser Asn Arg Trp Val Phe Gly Gly Gly Thr Lys Leu Thr Val Leu
            100                 105                 110

<210> SEQ ID NO 219
<211> LENGTH: 115
<212> TYPE: PRT
<213> ORGANISM: Artificial Sequence
<220> FEATURE:
<223> OTHER INFORMATION: chemically synthesized

<400> SEQUENCE: 219

Leu Pro Val Leu Thr Gln Pro Ala Ser Leu Ser Ala Ser Pro Gly Ala
1               5                   10                  15

Ser Ala Ser Leu Thr Cys Thr Leu Arg Ser Gly Leu Asn Val Gly Ser
            20                  25                  30

Tyr Arg Ile Tyr Trp Tyr Gln Gln Lys Pro Gly Ser Arg Pro Gln Tyr

```
              35                  40                  45
Leu Leu Asn Tyr Lys Ser Asp Ser Asn Lys Gln Gln Ala Ser Gly Val
         50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp Tyr Ser Ser Ala Val Val Phe Gly Gly Gly Thr Lys Leu
                100                 105                 110

Thr Val Leu
        115

<210> SEQ ID NO 220
<211> LENGTH: 111
<212> TYPE: PRT
<213> ORGANISM: Artificial Sequence
<220> FEATURE:
<223> OTHER INFORMATION: chemically synthesized

<400> SEQUENCE: 220

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Asn Ile Ala Ser Asn
             20                  25                  30

Tyr Val Gln Trp Tyr Gln Gln Arg Pro Gly Ser Ala Pro Thr Thr Val
         35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn Leu Trp Val Phe Gly Gly Gly Thr Lys Leu Thr Val Leu
                100                 105                 110

<210> SEQ ID NO 221
<211> LENGTH: 108
<212> TYPE: PRT
<213> ORGANISM: Artificial Sequence
<220> FEATURE:
<223> OTHER INFORMATION: chemically synthesized

<400> SEQUENCE: 221

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Tyr Val Phe Gly Thr Gly Thr Lys Val Thr Val Leu
                100                 105
```

<210> SEQ ID NO 222
<211> LENGTH: 108
<212> TYPE: PRT
<213> ORGANISM: Artificial Sequence
<220> FEATURE:
<223> OTHER INFORMATION: chemically synthesized

<400> SEQUENCE: 222

```
Leu Pro Val Leu Thr Gln Ala Pro Ser Val Ser Val Ala Pro Gly Lys
1               5                   10                  15

Thr Ala Arg Ile Thr Cys Gly Gly Ser Asp Ile Gly Arg Lys Ser Val
            20                  25                  30

His Trp Tyr Gln Gln Lys Pro Gly Gln Ala Pro Ala Leu Val Ile Tyr
        35                  40                  45

Ser Asp Arg Asp Arg Pro Ser Gly Ile Ser Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asn Asn Ser Asp His
                85                  90                  95

Tyr Val Phe Gly Ala Gly Thr Glu Leu Ile Val Leu
            100                 105
```

<210> SEQ ID NO 223
<211> LENGTH: 109
<212> TYPE: PRT
<213> ORGANISM: Artificial Sequence
<220> FEATURE:
<223> OTHER INFORMATION: chemically synthesized

<400> SEQUENCE: 223

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Leu Pro Phe Gly Gly Gly Thr Lys Leu Thr Val Leu
            100                 105
```

<210> SEQ ID NO 224
<211> LENGTH: 107
<212> TYPE: PRT
<213> ORGANISM: Artificial Sequence
<220> FEATURE:
<223> OTHER INFORMATION: chemically synthesized

<400> SEQUENCE: 224

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asn Ser
            20                  25                  30

Leu Ala Trp Tyr Gln Gln Lys Pro Gly Gln Ala Pro Arg Leu Leu Met
```

```
                35                  40                  45
Tyr Gly Ala Ser Ser Arg Ala Thr Gly Ile Pro Asp Arg Phe Ser Gly
         50                  55                  60

Ser Gly Ala Gly Thr Asp Phe Thr Leu Thr Ile Ser Ser Leu Glu Pro
 65                  70                  75                  80

Glu Asp Phe Ala Thr Tyr Tyr Cys Gln Gln His Thr Ile Pro Thr Phe
                 85                  90                  95

Ser Phe Gly Pro Gly Thr Lys Val Glu Val Lys
            100                 105
```

<210> SEQ ID NO 225
<211> LENGTH: 107
<212> TYPE: PRT
<213> ORGANISM: Artificial Sequence
<220> FEATURE:
<223> OTHER INFORMATION: chemically synthesized

<400> SEQUENCE: 225

```
Asp Ile Val Met Thr Gln Thr Pro Ser Phe Leu Ser Ala Ser Ile Gly
  1               5                  10                  15

Asp Arg Val Thr Ile Thr Cys Arg Ala Ser Gln Gly Ile Gly Ser Tyr
             20                  25                  30

Leu Ala Trp Tyr Gln Gln Arg Pro Gly Glu Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Gln Gln Leu Asn Asn Tyr Pro Ile
                 85                  90                  95

Thr Phe Gly Gln Gly Thr Arg Leu Glu Ile Lys
            100                 105
```

<210> SEQ ID NO 226
<211> LENGTH: 105
<212> TYPE: PRT
<213> ORGANISM: Artificial Sequence
<220> FEATURE:
<223> OTHER INFORMATION: chemically synthesized

<400> SEQUENCE: 226

```
Gln Ser Ala Leu Thr Gln Pro Pro Ser Val Ser Val Ser Pro Gly Gln
  1               5                  10                  15

Thr Ala Asn Ile Pro Cys Ser Gly Asp Lys Leu Gly Asn Lys Tyr Ala
             20                  25                  30

Tyr Trp Tyr Gln Gln Lys Pro Gly Gln Ser Pro Val Leu Leu Ile Tyr
         35                  40                  45

Gln Asp Ile Lys Arg Pro Ser Arg Ile Pro Glu Arg Phe Ser Gly Ser
     50                  55                  60

Asn Ser Ala Asp Thr Ala Thr Leu Thr Ile Ser Gly Thr Gln Ala Met
 65                  70                  75                  80

Asp Glu Ala Asp Tyr Tyr Cys Gln Thr Trp Asp Asn Ser Val Val Phe
                 85                  90                  95

Gly Gly Gly Thr Lys Leu Thr Val Leu
            100                 105
```

<210> SEQ ID NO 227
<211> LENGTH: 112

<212> TYPE: PRT
<213> ORGANISM: Artificial Sequence
<220> FEATURE:
<223> OTHER INFORMATION: chemically synthesized

<400> SEQUENCE: 227

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Arg His Val Ile Phe Gly Gly Gly Thr Lys Leu Thr Val Leu
            100                 105                 110

<210> SEQ ID NO 228
<211> LENGTH: 110
<212> TYPE: PRT
<213> ORGANISM: Artificial Sequence
<220> FEATURE:
<223> OTHER INFORMATION: chemically synthesized

<400> SEQUENCE: 228

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Gly Thr Asn
            20                  25                  30

Tyr Val Gln Trp Tyr Gln Gln Arg Pro Gly Ser Ala Pro Val Ala Leu
        35                  40                  45

Ile Tyr Glu Asp Tyr Arg Arg Pro Ser Gly Val Pro Asp Arg Phe Ser
    50                  55                  60

Gly Ser Ile Asp Ser Ser Ser Asn Ser Ala Ser Leu Ile Ile Ser Gly
65                  70                  75                  80

Leu Lys Pro Glu Asp Glu Ala Asp Tyr Tyr Cys Gln Ser Tyr His Ser
                85                  90                  95

Ser Gly Trp Glu Phe Gly Gly Gly Thr Lys Leu Thr Val Leu
            100                 105                 110

<210> SEQ ID NO 229
<211> LENGTH: 108
<212> TYPE: PRT
<213> ORGANISM: Artificial Sequence
<220> FEATURE:
<223> OTHER INFORMATION: chemically synthesized

<400> SEQUENCE: 229

Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser

```
                 50                  55                  60
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Trp Val Phe Gly Gly Gly Thr Lys Leu Thr Val Leu
            100                 105

<210> SEQ ID NO 230
<211> LENGTH: 111
<212> TYPE: PRT
<213> ORGANISM: Artificial Sequence
<220> FEATURE:
<223> OTHER INFORMATION: chemically synthesized

<400> SEQUENCE: 230

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                 20                  25                  30

Tyr Val Gln Trp Tyr Gln Gln Arg Pro Gly Ser Ala Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Thr Thr Pro Ser Val Phe Gly Gly Gly Thr Lys Leu Thr Val Leu
            100                 105                 110

<210> SEQ ID NO 231
<211> LENGTH: 120
<212> TYPE: PRT
<213> ORGANISM: Artificial Sequence
<220> FEATURE:
<223> OTHER INFORMATION: chemically synthesized

<400> SEQUENCE: 231

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Thr Ser Pro His Asn Gly Leu Thr Ala Phe Ala Gln Ile Leu
 50                  55                  60

Glu Gly Arg Val Thr Met Thr Thr Asp Thr Ser Thr Asn Thr Ala Tyr
 65                  70                  75                  80

Met Glu Leu Arg Asn Leu Thr Phe Asp Asp Thr Ala Val Tyr Phe Cys
                 85                  90                  95

Ala Lys Val His Pro Val Phe Ser Tyr Ala Leu Asp Val Trp Gly Gln
            100                 105                 110

Gly Thr Leu Val Thr Val Ser Ser
            115                 120

<210> SEQ ID NO 232
<211> LENGTH: 118
```

```
<212> TYPE: PRT
<213> ORGANISM: Artificial Sequence
<220> FEATURE:
<223> OTHER INFORMATION: chemically synthesized

<400> SEQUENCE: 232

Glu Val Gln Leu Val Glu Ser Gly Ala Glu Val Met Asn Pro Gly Ser
1               5                   10                  15

Ser Val Arg Val Ser Cys Arg Gly Ser Gly Gly Asp Phe Ser Thr Tyr
            20                  25                  30

Ala Phe Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Tyr Gly Ser Asp Pro Val Leu Trp Gly Gln Gly Thr
            100                 105                 110

Leu Val Thr Val Ser Ser
        115

<210> SEQ ID NO 233
<211> LENGTH: 118
<212> TYPE: PRT
<213> ORGANISM: Artificial Sequence
<220> FEATURE:
<223> OTHER INFORMATION: chemically synthesized

<400> SEQUENCE: 233

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Val
    50                  55                  60

Gln Gly Arg Val Thr Met Thr Thr Asp Thr Ser Thr Ser Thr Gly Tyr
65                  70                  75                  80

Met Glu Leu Arg Ser Leu Arg Ser Asp Asp Thr Ala Val Tyr Tyr Cys
                85                  90                  95

Ala Arg Gly Asp Phe Arg Lys Pro Phe Asp Tyr Trp Gly Gln Gly Thr
            100                 105                 110

Leu Val Thr Val Ser Ser
        115

<210> SEQ ID NO 234
<211> LENGTH: 115
<212> TYPE: PRT
<213> ORGANISM: Artificial Sequence
<220> FEATURE:
<223> OTHER INFORMATION: chemically synthesized

<400> SEQUENCE: 234

Glu Val Gln Leu Val Gln Ser Gly Pro Glu Leu Lys Lys Pro Gly Ala
1               5                   10                  15

Ser Val Lys Met Ser Cys Lys Ala Ser Gly Tyr Thr Phe Thr Ser Tyr
```

```
                20                  25                  30
Val Met His Trp Val Lys Gln Ala Pro Gly Gln Arg Leu Glu Trp Ile
            35                  40                  45
Gly Tyr Val Asn Pro Phe Asn Asp Gly Thr Lys Tyr Asn Glu Met Phe
        50                  55                  60
Lys Gly Arg Ala Thr Leu Thr Ser Asp Lys Ser Thr Ser Thr Ala Tyr
65                  70                  75                  80
Met Glu Leu Ser Ser Leu Arg Ser Glu Asp Ser Ala Val Tyr Tyr Cys
                85                  90                  95
Ala Arg Gln Ala Trp Gly Tyr Pro Trp Gly Gln Gly Thr Leu Val Thr
                100                 105                 110
Val Ser Ser
        115

<210> SEQ ID NO 235
<211> LENGTH: 115
<212> TYPE: PRT
<213> ORGANISM: Artificial Sequence
<220> FEATURE:
<223> OTHER INFORMATION: chemically synthesized

<400> SEQUENCE: 235

Glu Val Gln Leu Val Gln Ser Gly Ala Glu Val Lys Lys Pro Gly Ala
1               5                   10                  15
Ser Val Lys Met Ser Cys Lys Ala Ser Gly Tyr Thr Phe Thr Ser Tyr
                20                  25                  30
Val Met His Trp Val Lys Gln Ala Pro Gly Gln Arg Leu Glu Trp Ile
            35                  40                  45
Gly Tyr Val Asn Pro Phe Asn Asp Gly Thr Lys Tyr Asn Glu Met Phe
        50                  55                  60
Lys Gly Arg Ala Thr Leu Thr Ser Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gln Ala Trp Gly Tyr Pro Trp Gly Gln Gly Thr Leu Val Thr
                100                 105                 110
Val Ser Ser
        115

<210> SEQ ID NO 236
<211> LENGTH: 115
<212> TYPE: PRT
<213> ORGANISM: Artificial Sequence
<220> FEATURE:
<223> OTHER INFORMATION: chemically synthesized

<400> SEQUENCE: 236

Glu Val Gln Leu Val Gln Ser Gly Ala Glu Val Lys Lys Pro Gly Ala
1               5                   10                  15
Ser Val Lys Met Ser Cys Lys Ala Ser Gly Tyr Thr Phe Thr Ser Tyr
                20                  25                  30
Val Met His Trp Val Arg Gln Ala Pro Gly Gln Arg Leu Glu Trp Ile
            35                  40                  45
Gly Tyr Val Asn Pro Phe Asn Asp Gly Thr Lys Tyr Asn Glu Met Phe
        50                  55                  60
Lys Gly Arg Ala Thr Leu Thr Ser Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115

<210> SEQ ID NO 237
<211> LENGTH: 115
<212> TYPE: PRT
<213> ORGANISM: Artificial Sequence
<220> FEATURE:
<223> OTHER INFORMATION: chemically synthesized

<400> SEQUENCE: 237

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115

<210> SEQ ID NO 238
<211> LENGTH: 115
<212> TYPE: PRT
<213> ORGANISM: Artificial Sequence
<220> FEATURE:
<223> OTHER INFORMATION: chemically synthesized

<400> SEQUENCE: 238

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115

<210> SEQ ID NO 239
```

```
<211> LENGTH: 111
<212> TYPE: PRT
<213> ORGANISM: Artificial Sequence
<220> FEATURE:
<223> OTHER INFORMATION: chemically synthesized

<400> SEQUENCE: 239

Asp Ile Val Leu Thr Gln Ser Pro Ala Ser Leu Ala Leu Ser Pro Gly
1               5                   10                  15

Glu Arg Ala Thr Leu Ser Cys Arg Ala Thr Glu Ser Val Glu Tyr Tyr
            20                  25                  30

Gly Thr Ser Leu Val Gln Trp Tyr Gln Gln Lys Pro Gly Gln Pro Pro
        35                  40                  45

Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Glu Glu Asp Ala Ala Met Tyr Phe Cys Gln Gln Ser Arg
                85                  90                  95

Arg Val Pro Tyr Thr Phe Gly Gln Gly Thr Lys Leu Glu Ile Lys
            100                 105                 110

<210> SEQ ID NO 240
<211> LENGTH: 111
<212> TYPE: PRT
<213> ORGANISM: Artificial Sequence
<220> FEATURE:
<223> OTHER INFORMATION: chemically synthesized

<400> SEQUENCE: 240

Asp Ile Val Leu Thr Gln Ser Pro Ala Thr Leu Ser Leu Ser Pro Gly
1               5                   10                  15

Glu Arg Ala Thr Leu Ser Cys Arg Ala Thr Glu Ser Val Glu Tyr Tyr
            20                  25                  30

Gly Thr Ser Leu Val Gln Trp Tyr Gln Gln Lys Pro Gly Gln Pro Pro
        35                  40                  45

Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Met Tyr Phe Cys Gln Gln Ser Arg
                85                  90                  95

Arg Val Pro Tyr Thr Phe Gly Gln Gly Thr Lys Leu Glu Ile Lys
            100                 105                 110

<210> SEQ ID NO 241
<211> LENGTH: 111
<212> TYPE: PRT
<213> ORGANISM: Artificial Sequence
<220> FEATURE:
<223> OTHER INFORMATION: chemically synthesized

<400> SEQUENCE: 241

Glu Ile Val Leu Thr Gln Ser Pro Ala Thr Leu Ser Leu Ser Pro Gly
1               5                   10                  15

Glu Arg Ala Thr Leu Ser Cys Arg Ala Thr Glu Ser Val Glu Tyr Tyr
            20                  25                  30

Gly Thr Ser Leu Val Gln Trp Tyr Gln Gln Lys Pro Gly Gln Pro Pro
        35                  40                  45
```

```
Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Met Tyr Phe Cys Gln Gln Ser Arg
                85                  90                  95

Arg Val Pro Tyr Thr Phe Gly Gln Gly Thr Lys Leu Glu Ile Lys
                100                 105                 110

<210> SEQ ID NO 242
<211> LENGTH: 111
<212> TYPE: PRT
<213> ORGANISM: Artificial Sequence
<220> FEATURE:
<223> OTHER INFORMATION: chemically synthesized

<400> SEQUENCE: 242

Asp Ile Val Leu Thr Gln Ser Pro Ala Thr Leu Ser Leu Ser Pro Gly
1               5                   10                  15

Glu Arg Ala Thr Leu Ser Cys Arg Ala Thr Glu Ser Val Glu Tyr Tyr
                20                  25                  30

Gly Thr Ser Leu Val Gln Trp Tyr Gln Gln Lys Pro Gly Gln Pro Pro
            35                  40                  45

Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Phe Cys Gln Gln Ser Arg
                85                  90                  95

Arg Val Pro Tyr Thr Phe Gly Gln Gly Thr Lys Leu Glu Ile Lys
                100                 105                 110

<210> SEQ ID NO 243
<211> LENGTH: 123
<212> TYPE: PRT
<213> ORGANISM: Artificial Sequence
<220> FEATURE:
<223> OTHER INFORMATION: chemically synthesized

<400> SEQUENCE: 243

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Ile Tyr Asp Ser Ser Gly Tyr Ser Phe Asp Tyr
                100                 105                 110

Trp Gly Gln Gly Thr Leu Val Thr Val Ser Ser
        115                 120

<210> SEQ ID NO 244
```

<211> LENGTH: 124
<212> TYPE: PRT
<213> ORGANISM: Artificial Sequence
<220> FEATURE:
<223> OTHER INFORMATION: chemically synthesized

<400> SEQUENCE: 244

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Ser Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
        115                 120

<210> SEQ ID NO 245
<211> LENGTH: 118
<212> TYPE: PRT
<213> ORGANISM: Artificial Sequence
<220> FEATURE:
<223> OTHER INFORMATION: chemically synthesized

<400> SEQUENCE: 245

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ala Val Pro Gly Ala Phe Asp Ile Trp Gly Gln Gly Thr
            100                 105                 110

Met Val Thr Val Ser Ser
        115

<210> SEQ ID NO 246
<211> LENGTH: 116
<212> TYPE: PRT
<213> ORGANISM: Artificial Sequence
<220> FEATURE:
<223> OTHER INFORMATION: chemically synthesized

<400> SEQUENCE: 246

Glu Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Ala Val Ile
        35                  40                  45

Ser Tyr Asp Gly Ser Asn Lys Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Arg Gly
                85                  90                  95

Gln Trp Leu Val Thr Glu Leu Asp Tyr Trp Gly Gln Gly Thr Leu Val
            100                 105                 110

Thr Val Ser Ser
        115

<210> SEQ ID NO 247
<211> LENGTH: 122
<212> TYPE: PRT
<213> ORGANISM: Artificial Sequence
<220> FEATURE:
<223> OTHER INFORMATION: chemically synthesized

<400> SEQUENCE: 247

Glu Val Gln Leu Val Glu Ser Gly Ser Glu Val Glu Lys Pro Gly Ser
1               5                   10                  15

Ser Val Lys Val Ser Cys Lys Ala Ser Gly Gly Thr Phe Ser Asp Ser
            20                  25                  30

Gly Ile Ser Trp Val Arg Gln Ala Pro Gly Gln Gly Leu Glu Trp Met
        35                  40                  45

Gly Gly Ile Ile Pro Met Phe Ala Thr Pro Tyr Tyr Ala Gln Lys Phe
    50                  55                  60

Gln Asp Arg Val Thr Ile Thr Ala Asp Glu Ser Thr Ser Thr Val Tyr
65                  70                  75                  80

Met Glu Leu Ser Gly Leu Arg Ser Asp Asp Thr Ala Val Phe Tyr Cys
                85                  90                  95

Ala Arg Asp Arg Gly Arg Gly His Leu Pro Trp Tyr Phe Asp Leu Trp
            100                 105                 110

Gly Arg Gly Thr Leu Val Thr Val Ser Ser
        115                 120

<210> SEQ ID NO 248
<211> LENGTH: 119
<212> TYPE: PRT
<213> ORGANISM: Artificial Sequence
<220> FEATURE:
<223> OTHER INFORMATION: chemically synthesized

<400> SEQUENCE: 248

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Ala Pro Tyr Tyr Tyr Tyr Met Asp Val Trp Gly Gln Gly
            100                 105                 110

Thr Thr Val Thr Val Ser Ser
        115

<210> SEQ ID NO 249
<211> LENGTH: 124
<212> TYPE: PRT
<213> ORGANISM: Artificial Sequence
<220> FEATURE:
<223> OTHER INFORMATION: chemically synthesized

<400> SEQUENCE: 249

Glu Val Gln Leu Leu Glu Ser Gly Ala Glu Val Lys Lys Pro Gly Ser
1               5                   10                  15

Ser Val Lys Val Ser Cys Lys Ala Ser Gly Gly Thr Leu Ser Arg Tyr
            20                  25                  30

Ala Leu Ser Trp Val Arg Gln Ala Pro Gly Gln Gly Pro Glu Trp Val
        35                  40                  45

Gly Ala Ile Ile Pro Ile Phe Gly Thr Pro His Tyr Ser Lys Lys Phe
    50                  55                  60

Gln Asp Arg Val Ile Ile Thr Val Asp Thr Ser Thr Asn Thr Ala Phe
65                  70                  75                  80

Met Glu Leu Ser Ser Leu Arg Phe Glu Asp Thr Ala Leu Tyr Phe Cys
                85                  90                  95

Ala Arg Gly His Asp Glu Tyr Asp Ile Ser Gly Tyr His Arg Leu Asp
            100                 105                 110

Tyr Trp Gly Gln Gly Thr Leu Val Thr Val Ser Ser
        115                 120

<210> SEQ ID NO 250
<211> LENGTH: 121
<212> TYPE: PRT
<213> ORGANISM: Artificial Sequence
<220> FEATURE:
<223> OTHER INFORMATION: chemically synthesized

<400> SEQUENCE: 250

Gln Val Gln Leu Val Gln Ser Gly Ser Glu Leu Lys Lys Pro Gly Ser
1               5                   10                  15

Ser Val Lys Val Ser Cys Lys Ala Ser Gly Tyr Ser Phe Ser Gly Tyr
            20                  25                  30

Tyr Ile His Trp Val Arg Gln Ala Pro Gly Gln Gly Leu Glu Trp Met
        35                  40                  45

Gly Trp Ile Asp Pro Asn Ser Gly Val Thr Asn Tyr Val Arg Arg Phe
    50                  55                  60

Gln Gly Arg Val Thr Met Thr Arg Asp Thr Ser Leu Ser Thr Ala Tyr
65                  70                  75                  80

Met Glu Leu Ser Gly Leu Thr Ala Asp Thr Ala Val Tyr Tyr Cys
                85                  90                  95

Ala Arg Asp Glu Asn Leu Trp Gln Phe Gly Tyr Leu Asp Tyr Trp Gly
            100                 105                 110

Gln Gly Thr Leu Val Thr Val Ser Ser
        115                 120
```

```
<210> SEQ ID NO 251
<211> LENGTH: 120
<212> TYPE: PRT
<213> ORGANISM: Artificial Sequence
<220> FEATURE:
<223> OTHER INFORMATION: chemically synthesized

<400> SEQUENCE: 251

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Arg Tyr
            20                  25                  30

Gly Val His Trp Val Arg Gln Ala Pro Gly Gln Gly Leu Glu Trp Met
        35                  40                  45

Gly Arg Leu Ile Pro Ile Val Ser Met Thr Asn Tyr Ala Gln Lys Phe
    50                  55                  60

Gln Asp Arg Val Ser Ile Thr Thr Asp Lys Ser Thr Gly Thr Ala Tyr
65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln
            100                 105                 110

Gly Thr Leu Val Thr Val Ser Ser
        115                 120

<210> SEQ ID NO 252
<211> LENGTH: 118
<212> TYPE: PRT
<213> ORGANISM: Artificial Sequence
<220> FEATURE:
<223> OTHER INFORMATION: chemically synthesized

<400> SEQUENCE: 252

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 253
<211> LENGTH: 118
<212> TYPE: PRT
<213> ORGANISM: Artificial Sequence
<220> FEATURE:
<223> OTHER INFORMATION: chemically synthesized

<400> SEQUENCE: 253

Glu Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 254
<211> LENGTH: 121
<212> TYPE: PRT
<213> ORGANISM: Artificial Sequence
<220> FEATURE:
<223> OTHER INFORMATION: chemically synthesized

<400> SEQUENCE: 254

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Pro Pro Gly Lys Gly Leu Glu Trp Leu
            35                  40                  45

Ala Val Ile Ser Tyr Asp Gly Ser Tyr Lys Ile His Ala Asp Ser Val
    50                  55                  60

Gln Gly Arg Phe Thr Ile Ser Arg Asp Asn Ala Lys Asn Ser Val Phe
65                  70                  75                  80

Leu Gln Met Asn Ser Leu Lys Thr Glu Asp Thr Ala Val Tyr Tyr Cys
                85                  90                  95

Thr Thr Asp Arg Lys Trp Leu Ala Trp His Gly Met Asp Val Trp Gly
            100                 105                 110

Gln Gly Thr Thr Val Thr Val Ser Ser
        115                 120

<210> SEQ ID NO 255
<211> LENGTH: 118
<212> TYPE: PRT
<213> ORGANISM: Artificial Sequence
<220> FEATURE:
<223> OTHER INFORMATION: chemically synthesized

<400> SEQUENCE: 255

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Asp Gly Ile Val Ala Asp Phe Gln His Trp Gly Gln Gly Thr
                100                 105                 110

Leu Val Thr Val Ser Ser
        115

<210> SEQ ID NO 256
<211> LENGTH: 121
<212> TYPE: PRT
<213> ORGANISM: Artificial Sequence
<220> FEATURE:
<223> OTHER INFORMATION: chemically synthesized

<400> SEQUENCE: 256

Glu Val Gln Leu Val Glu Ser Gly Ala Glu Val Lys Lys Pro Gly Ala
1               5                   10                  15

Ser Val Lys Val Ser Cys Lys Ala Ser Gly Asp Thr Phe Ser Arg Tyr
                20                  25                  30

Gly Ile Thr Trp Val Arg Gln Ala Pro Gly Arg Gly Leu Glu Trp Met
            35                  40                  45

Gly Asn Ile Val Pro Phe Phe Gly Ala Thr Asn Tyr Ala Gln Lys Phe
        50                  55                  60

Gln Gly Arg Leu Thr Ile Thr Ala Asp Lys Ser Ser Tyr Thr Ser Tyr
65                  70                  75                  80

Met Asp Leu Ser Ser Leu Arg Ser Asp Thr Ala Val Tyr Tyr Cys
                    85                  90                  95

Ala Arg Asp His Phe Tyr Gly Ser Gly Gly Tyr Phe Asp Tyr Trp Gly
                100                 105                 110

Gln Gly Thr Leu Val Thr Val Ser Ser
            115                 120

<210> SEQ ID NO 257
<211> LENGTH: 121
<212> TYPE: PRT
<213> ORGANISM: Artificial Sequence
<220> FEATURE:
<223> OTHER INFORMATION: chemically synthesized

<400> SEQUENCE: 257

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Asn Ser Tyr
                20                  25                  30

Asp Ile Asn Trp Val Arg Gln Ala Pro Gly Gln Gly Leu Glu Trp Met
            35                  40                  45

Gly Gly Ile Ile Pro Val Phe Gly Thr Ala Asn Tyr Ala Glu Ser Phe
        50                  55                  60

Gln Gly Arg Val Thr Met Thr Ala Asp His Ser Thr Ser Thr Ala Tyr
65                  70                  75                  80

Met Glu Leu Asn Asn Leu Arg Ser Glu Asp Thr Ala Val Tyr Tyr Cys
                    85                  90                  95

Ala Arg Asp Arg Trp His Tyr Glu Ser Arg Pro Met Asp Val Trp Gly
                100                 105                 110

Gln Gly Thr Thr Val Thr Val Ser Ser
            115                 120
```

```
<210> SEQ ID NO 258
<211> LENGTH: 119
<212> TYPE: PRT
<213> ORGANISM: Artificial Sequence
<220> FEATURE:
<223> OTHER INFORMATION: chemically synthesized

<400> SEQUENCE: 258

Glu Val Gln Leu Val Glu Ser Gly Gly Gly Leu Val Arg Pro Gly Gly
1               5                   10                  15

Ser Leu Arg Leu Ala Cys Ala Ala Ser Gly Phe Ser Phe Ser Asp Tyr
                20                  25                  30

Tyr Met Thr Trp Ile Arg Gln Ala Pro Gly Arg Gly Leu Glu Trp Ile
            35                  40                  45

Ala Tyr Ile Ser Asp Ser Gly Gln Thr Val His Tyr Ala Asp Ser Val
        50                  55                  60

Lys Gly Arg Phe Thr Ile Ser Arg Asp Asn Thr Lys Asn Ser Leu Phe
65                  70                  75                  80

Leu Gln Val Asn Thr Leu Arg Ala Glu Asp Thr Ala Val Tyr Tyr Cys
                85                  90                  95

Ala Arg Glu Asp Leu Leu Gly Tyr Tyr Leu Gln Ser Trp Gly Gln Gly
                100                 105                 110

Thr Leu Val Thr Val Ser Ser
        115

<210> SEQ ID NO 259
<211> LENGTH: 131
<212> TYPE: PRT
<213> ORGANISM: Artificial Sequence
<220> FEATURE:
<223> OTHER INFORMATION: chemically synthesized

<400> SEQUENCE: 259

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Glu Pro Arg Ala Val Ala Gly Ser Gln Ala
                100                 105                 110

Tyr Tyr Tyr Tyr Gly Met Asp Val Trp Gly Gln Gly Thr Thr Val Thr
            115                 120                 125

Val Ser Ser
    130

<210> SEQ ID NO 260
<211> LENGTH: 124
<212> TYPE: PRT
<213> ORGANISM: Artificial Sequence
<220> FEATURE:
<223> OTHER INFORMATION: chemically synthesized
```

```
<400> SEQUENCE: 260

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asp Gly Ser Thr Ser Tyr Ala Gln Lys Phe
    50                  55                  60

Gln Gly Arg Val Thr Met Thr Arg Asp Thr Ser Thr Ser Thr Val His
65                  70                  75                  80

Met Glu Leu Ser Ser Leu Arg Ser Glu Asp Thr Ala Val Tyr Tyr Cys
                85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
        115                 120

<210> SEQ ID NO 261
<211> LENGTH: 118
<212> TYPE: PRT
<213> ORGANISM: Artificial Sequence
<220> FEATURE:
<223> OTHER INFORMATION: chemically synthesized

<400> SEQUENCE: 261

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 262
<211> LENGTH: 118
<212> TYPE: PRT
<213> ORGANISM: Artificial Sequence
<220> FEATURE:
<223> OTHER INFORMATION: chemically synthesized

<400> SEQUENCE: 262

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45
```

```
Ala Val Ile Ser Phe Asp Gly Ser Asn Lys Tyr Tyr Ala Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Gly Trp Leu Asp Arg Asp Ile Asp Tyr Trp Gly Gln Gly Thr
            100                 105                 110

Leu Val Thr Val Ser Ser
            115

<210> SEQ ID NO 263
<211> LENGTH: 110
<212> TYPE: PRT
<213> ORGANISM: Artificial Sequence
<220> FEATURE:
<223> OTHER INFORMATION: chemically synthesized

<400> SEQUENCE: 263

Gln Ser Val Leu Thr Gln Pro Pro Ser Val Ser Ala Ala Pro Gly Gln
 1               5                  10                  15

Lys Val Thr Ile Ser Cys Ser Gly Asn Ser Asn Ile Ala Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Tyr Arg Pro Ser Gly Ile Pro Asp Arg Phe Ser
 50                  55                  60

Gly Ser Lys Ser Gly Thr Ser Ala Thr Leu Asp Ile Thr Gly Leu Gln
 65                  70                  75                  80

Thr Gly Asp Glu Ala Asp Tyr Tyr Cys Gly Val Trp Asp Gly Ser Leu
                 85                  90                  95

Thr Thr Gly Val Phe Gly Gly Gly Thr Lys Leu Thr Val Leu
            100                 105                 110

<210> SEQ ID NO 264
<211> LENGTH: 107
<212> TYPE: PRT
<213> ORGANISM: Artificial Sequence
<220> FEATURE:
<223> OTHER INFORMATION: chemically synthesized

<400> SEQUENCE: 264

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
             20                  25                  30

Leu Ala Trp Tyr Gln Gln Lys Pro Gly Lys Val Pro Lys Leu Leu Ile
         35                  40                  45

Tyr Ala Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Gln Leu His Thr Phe Pro Leu
                 85                  90                  95

Thr Phe Gly Gly Gly Thr Lys Val Glu Ile Lys
            100                 105

<210> SEQ ID NO 265
```

```
<211> LENGTH: 111
<212> TYPE: PRT
<213> ORGANISM: Artificial Sequence
<220> FEATURE:
<223> OTHER INFORMATION: chemically synthesized

<400> SEQUENCE: 265

Gln Pro Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Phe Val Ser Trp Tyr Arg Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Thr
                85                  90                  95

Asn Ser Leu Gly Ile Phe Gly Thr Gly Thr Lys Leu Thr Val Leu
            100                 105                 110

<210> SEQ ID NO 266
<211> LENGTH: 111
<212> TYPE: PRT
<213> ORGANISM: Artificial Sequence
<220> FEATURE:
<223> OTHER INFORMATION: chemically synthesized

<400> SEQUENCE: 266

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asp Ile Gly Asn His
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Asn Ser Leu
                85                  90                  95

Ser Pro His Leu Leu Phe Gly Gly Gly Thr Lys Leu Thr Val Leu
            100                 105                 110

<210> SEQ ID NO 267
<211> LENGTH: 110
<212> TYPE: PRT
<213> ORGANISM: Artificial Sequence
<220> FEATURE:
<223> OTHER INFORMATION: chemically synthesized

<400> SEQUENCE: 267

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Met Gly Asn Asn
            20                  25                  30

Tyr Val Ser Trp Tyr Lys Gln Val Pro Gly Thr Ala Pro Lys Leu Leu
        35                  40                  45
```

Ile Tyr Glu Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Asn Ser Leu
                 85                  90                  95

Ser Gly Phe Val Phe Ala Ser Gly Thr Lys Val Thr Val Leu
            100                 105                 110

<210> SEQ ID NO 268
<211> LENGTH: 109
<212> TYPE: PRT
<213> ORGANISM: Artificial Sequence
<220> FEATURE:
<223> OTHER INFORMATION: chemically synthesized

<400> SEQUENCE: 268

Gln Ser Ala Leu Thr Gln Pro Ala Ser Val Ser Gly Ser Leu Gly Gln
 1               5                  10                  15

Ser Val Thr Ile Ser Cys Thr Gly Ser Ser Asp Val Gly Ser Tyr
                 20                  25                  30

Asn Leu Val Ser Trp Tyr Gln Gln His Pro Gly Lys Ala Pro Asn Leu
             35                  40                  45

Met Ile Tyr Asp Val Ser Lys Arg Ser Gly Val Ser Asn Arg Phe Ser
    50                  55                  60

Gly Ser Lys Ser Gly Asn Thr Ala Ser Leu Thr Ile Ser Gly Leu Gln
 65                  70                  75                  80

Ala Glu Asp Glu Ala Asp Tyr Tyr Cys Ser Ser Tyr Thr Gly Ile Ser
                 85                  90                  95

Thr Val Val Phe Gly Gly Gly Thr Lys Leu Thr Val Leu
            100                 105

<210> SEQ ID NO 269
<211> LENGTH: 110
<212> TYPE: PRT
<213> ORGANISM: Artificial Sequence
<220> FEATURE:
<223> OTHER INFORMATION: chemically synthesized

<400> SEQUENCE: 269

Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                 20                  25                  30

Asn Leu Val Ser Trp Tyr Gln Gln His Pro Gly Lys Ala Pro Lys Leu
             35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Gly Gly Phe
                 85                  90                  95

Asn Asn Leu Leu Phe Gly Gly Gly Thr Lys Leu Thr Val Leu
            100                 105                 110

<210> SEQ ID NO 270
<211> LENGTH: 107
<212> TYPE: PRT
<213> ORGANISM: Artificial Sequence

```
<220> FEATURE:
<223> OTHER INFORMATION: chemically synthesized

<400> SEQUENCE: 270

Asp Ile Val Met Thr Gln Ser Pro Ser Ser Leu Ser Ala Ser Ile Gly
1               5                   10                  15

Asp Arg Val Thr Ile Thr Cys Arg Ala Ser Gln Arg Ile Ser Ala Tyr
            20                  25                  30

Val Asn Trp Tyr Gln Gln Lys Pro Gly Lys Ala Pro Lys Val Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ser Pro Trp
                85                  90                  95

Thr Phe Gly Gln Gly Thr Lys Val Glu Ile Lys
            100                 105

<210> SEQ ID NO 271
<211> LENGTH: 112
<212> TYPE: PRT
<213> ORGANISM: Artificial Sequence
<220> FEATURE:
<223> OTHER INFORMATION: chemically synthesized

<400> SEQUENCE: 271

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asp Ser Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ile Phe Phe Tyr Val Phe Gly Thr Gly Thr Lys Val Thr Val Leu
            100                 105                 110

<210> SEQ ID NO 272
<211> LENGTH: 110
<212> TYPE: PRT
<213> ORGANISM: Artificial Sequence
<220> FEATURE:
<223> OTHER INFORMATION: chemically synthesized

<400> SEQUENCE: 272

Leu Pro Val Leu Thr Gln Pro Ala Ser Val Ser Gly Ser Pro Gly Gln
1               5                   10                  15

Ser Ile Thr Ile Ser Cys Thr Gly Thr Thr Ser Asp Ile Gly Gly Tyr
            20                  25                  30

Asp Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr His Val Phe Gly Thr Gly Thr Lys Leu Thr Val Leu
            100                 105                 110

<210> SEQ ID NO 273
<211> LENGTH: 111
<212> TYPE: PRT
<213> ORGANISM: Artificial Sequence
<220> FEATURE:
<223> OTHER INFORMATION: chemically synthesized

<400> SEQUENCE: 273

Gln Ser Ala Leu Thr Gln Pro Ala Ser Val Ser Gly Ser Pro Gly Gln
1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Arg Ser Ser
                 85                  90                  95

Thr Leu Gly Pro Val Phe Gly Gly Gly Thr Lys Leu Thr Val Leu
            100                 105                 110

<210> SEQ ID NO 274
<211> LENGTH: 110
<212> TYPE: PRT
<213> ORGANISM: Artificial Sequence
<220> FEATURE:
<223> OTHER INFORMATION: chemically synthesized

<400> SEQUENCE: 274

Gln Ala Gly Leu Thr Gln Pro Pro Ser Val Ser Glu Ala Pro Arg Gln
1               5                  10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Leu Thr Val Leu
            100                 105                 110

<210> SEQ ID NO 275
<211> LENGTH: 110
<212> TYPE: PRT
<213> ORGANISM: Artificial Sequence
<220> FEATURE:
<223> OTHER INFORMATION: chemically synthesized
```

```
<400> SEQUENCE: 275

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Thr His Val Phe Gly Thr Gly Thr Lys Val Thr Val Leu
            100                 105                 110

<210> SEQ ID NO 276
<211> LENGTH: 110
<212> TYPE: PRT
<213> ORGANISM: Artificial Sequence
<220> FEATURE:
<223> OTHER INFORMATION: chemically synthesized

<400> SEQUENCE: 276

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Val Trp Val Phe Gly Gly Gly Thr Gln Leu Thr Val Leu
            100                 105                 110

<210> SEQ ID NO 277
<211> LENGTH: 112
<212> TYPE: PRT
<213> ORGANISM: Artificial Sequence
<220> FEATURE:
<223> OTHER INFORMATION: chemically synthesized

<400> SEQUENCE: 277

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Arg Ala Pro Arg Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

```
Gln Ala Glu Asp Glu Gly Asp Tyr Tyr Cys Ser Ser Tyr Thr Ser Gly
                85                  90                  95

Gly Thr Leu Gly Pro Val Phe Gly Gly Gly Thr Lys Leu Thr Val Leu
            100                 105                 110

<210> SEQ ID NO 278
<211> LENGTH: 110
<212> TYPE: PRT
<213> ORGANISM: Artificial Sequence
<220> FEATURE:
<223> OTHER INFORMATION: chemically synthesized

<400> SEQUENCE: 278

Gln Ala Gly Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 279
<211> LENGTH: 107
<212> TYPE: PRT
<213> ORGANISM: Artificial Sequence
<220> FEATURE:
<223> OTHER INFORMATION: chemically synthesized

<400> SEQUENCE: 279

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Arg Pro Gly Lys Ala Pro Asn Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Ser Thr Pro Tyr
                85                  90                  95

Thr Phe Gly Gln Gly Thr Lys Leu Glu Ile Lys
            100                 105

<210> SEQ ID NO 280
<211> LENGTH: 111
<212> TYPE: PRT
<213> ORGANISM: Artificial Sequence
<220> FEATURE:
<223> OTHER INFORMATION: chemically synthesized

<400> SEQUENCE: 280

Gln Ser Val Leu Thr Gln Pro Ala Ser Val Ser Gly Ser Pro Gly Gln
```

```
          1               5                  10                 15
Ser Ile Thr Ile Ser Cys Thr Gly Thr Ser Ser Asp Val Gly Gly Tyr
               20                 25                 30

Asn Tyr Val Ser Trp Tyr Arg Gln His Pro Gly Lys Ala Pro Lys Leu
               35                 40                 45

Met Ile Tyr Asp Val Ser Tyr Arg Pro Ser Gly Val Ser Asn Arg Phe
    50                 55                 60

Ser Gly Ser Lys Ser Gly Asn Thr Ala Ser Leu Thr Ile Ser Gly Leu
65                  70                 75                 80

Gln Ala Glu Asp Glu Ala Asp Tyr Tyr Cys Ser Ser Tyr Thr Asp Ser
                85                 90                 95

Ser Thr Arg Tyr Val Phe Gly Thr Gly Thr Lys Leu Thr Val Leu
               100                105                110

<210> SEQ ID NO 281
<211> LENGTH: 110
<212> TYPE: PRT
<213> ORGANISM: Artificial Sequence
<220> FEATURE:
<223> OTHER INFORMATION: chemically synthesized

<400> SEQUENCE: 281

Gln Pro Val Leu Thr Gln Pro Pro Ser Ala Ser Gly Thr Pro Gly Gln
1               5                  10                 15

Arg Val Ala Ile Ser Cys Ser Gly Ser Arg Ser Asn Ile Glu Ile Asn
               20                 25                 30

Ser Val Asn Trp Tyr Gln Gln Leu Pro Gly Thr Ala Pro Lys Leu Leu
               35                 40                 45

Ile Tyr Asp Asn Asn Lys Arg Pro Ser Gly Ile Pro Asp Arg Phe Ser
    50                 55                 60

Gly Ser Lys Ser Gly Thr Ser Ala Thr Leu Gly Ile Thr Gly Leu Gln
65                  70                 75                 80

Thr Gly Asp Glu Ala Asp Tyr Tyr Cys Gly Ser Trp Asp Ser Ser Leu
                85                 90                 95

Ser Ala Asp Val Phe Gly Thr Gly Thr Lys Leu Thr Val Leu
               100                105                110

<210> SEQ ID NO 282
<211> LENGTH: 110
<212> TYPE: PRT
<213> ORGANISM: Artificial Sequence
<220> FEATURE:
<223> OTHER INFORMATION: chemically synthesized

<400> SEQUENCE: 282

Gln Ser Val Leu Thr Gln Pro Pro Ser Val Ser Ala Ala Pro Gly Lys
1               5                  10                 15

Lys Val Thr Ile Ser Cys Ser Gly Ser Ser Ser Asn Ile Gly Asn Asn
               20                 25                 30

Tyr Val Ser Trp Tyr Gln Gln Leu Pro Gly Thr Ala Pro Lys Leu Leu
               35                 40                 45

Ile Tyr Arg Asn Asn Gln Arg Pro Ser Gly Val Pro Asp Arg Phe Ser
    50                 55                 60

Gly Ser Lys Ser Gly Thr Ser Ala Ser Leu Ala Ile Ser Gly Leu Gln
65                  70                 75                 80

Ser Glu Asp Glu Ala Asp Tyr Tyr Cys Ala Thr Trp Asp Asp Ser Leu
                85                 90                 95
```

```
Asn Gly Trp Val Phe Gly Gly Gly Thr Lys Leu Thr Val Leu
            100                 105                 110
```

<210> SEQ ID NO 283
<211> LENGTH: 111
<212> TYPE: PRT
<213> ORGANISM: Artificial Sequence
<220> FEATURE:
<223> OTHER INFORMATION: chemically synthesized

<400> SEQUENCE: 283

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Arg His Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Glu Phe Phe Cys Gly Thr Trp Asp Ser Arg
                85                  90                  95

Leu Thr Thr Tyr Val Phe Gly Ser Gly Thr Lys Leu Thr Val Leu
            100                 105                 110
```

<210> SEQ ID NO 284
<211> LENGTH: 110
<212> TYPE: PRT
<213> ORGANISM: Artificial Sequence
<220> FEATURE:
<223> OTHER INFORMATION: chemically synthesized

<400> SEQUENCE: 284

```
Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110
```

<210> SEQ ID NO 285
<211> LENGTH: 103
<212> TYPE: PRT
<213> ORGANISM: Artificial Sequence
<220> FEATURE:
<223> OTHER INFORMATION: chemically synthesized

<400> SEQUENCE: 285

```
Val Ile Trp Met Thr Gln Ser Pro Ser Leu Ser Ala Ser Val Gly
1               5                   10                  15

Asp Arg Val Thr Ile Thr Cys Ala Ala Ser Ser Leu Gln Ser Trp Tyr
```

```
                     20                  25                  30
Gln Gln Lys Pro Gly Lys Ala Pro Lys Leu Leu Ile Tyr Glu Ala Ser
             35                  40                  45

Thr Leu Glu Ser Gly Val Pro Ser Arg Phe Ser Gly Ser Gly Ser Gly
 50                  55                  60

Thr Glu Phe Thr Leu Thr Ile Ser Ser Leu Gln Pro Glu Asp Phe Ala
 65                  70                  75                  80

Thr Tyr Tyr Cys Gln Gln Ser Tyr Ser Thr Pro Tyr Thr Phe Gly Gln
                 85                  90                  95

Gly Thr Lys Leu Glu Ile Lys
            100

<210> SEQ ID NO 286
<211> LENGTH: 110
<212> TYPE: PRT
<213> ORGANISM: Artificial Sequence
<220> FEATURE:
<223> OTHER INFORMATION: chemically synthesized

<400> SEQUENCE: 286

Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
             20                  25                  30

Tyr Val Ser Trp Tyr Gln Gln Val Pro Gly Thr Ala Pro Lys Leu Leu
             35                  40                  45

Ile Tyr Asp Asn Asn Lys Arg Pro Ser Gly Ile Pro Asp Arg Phe Ser
     50                  55                  60

Gly Ser Asn Ser Asp Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Trp Val Phe Gly Gly Gly Thr Lys Leu Thr Val Leu
            100                 105                 110

<210> SEQ ID NO 287
<211> LENGTH: 112
<212> TYPE: PRT
<213> ORGANISM: Artificial Sequence
<220> FEATURE:
<223> OTHER INFORMATION: chemically synthesized

<400> SEQUENCE: 287

Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
             20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Gly Ser Val Val Phe Gly Gly Gly Thr Lys Leu Thr Val Leu
            100                 105                 110
```

```
<210> SEQ ID NO 288
<211> LENGTH: 108
<212> TYPE: PRT
<213> ORGANISM: Artificial Sequence
<220> FEATURE:
<223> OTHER INFORMATION: chemically synthesized

<400> SEQUENCE: 288

Ser Tyr Glu Leu Met Gln Pro Pro Ser Val Ser Val Ala Pro Gly Lys
1               5                   10                  15
Thr Ala Thr Ile Ala Cys Gly Gly Glu Asn Ile Gly Arg Lys Thr Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Leu Val Trp Asp Ser Ser Ser Asp His
                85                  90                  95
Arg Ile Phe Gly Gly Gly Thr Lys Leu Thr Val Leu
            100                 105

<210> SEQ ID NO 289
<211> LENGTH: 108
<212> TYPE: PRT
<213> ORGANISM: Artificial Sequence
<220> FEATURE:
<223> OTHER INFORMATION: chemically synthesized

<400> SEQUENCE: 289

Ser Tyr Glu Leu Met Gln Pro Pro Ser Val Ser Val Ala Pro Gly Lys
1               5                   10                  15
Thr Ala Thr Ile Ala Cys Gly Gly Glu Asn Ile Gly Arg Lys Thr Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95
Arg Ile Phe Gly Gly Gly Thr Lys Leu Thr Val Leu
            100                 105

<210> SEQ ID NO 290
<211> LENGTH: 108
<212> TYPE: PRT
<213> ORGANISM: Artificial Sequence
<220> FEATURE:
<223> OTHER INFORMATION: chemically synthesized

<400> SEQUENCE: 290

Ser Tyr Glu Leu Met Gln Pro Pro Ser Val Ser Val Ala Pro Gly Lys
1               5                   10                  15
Thr Ala Thr Ile Ala Cys Gly Gly Glu Asn Ile Gly Arg Lys Thr Val
            20                  25                  30
His Trp Tyr Gln Gln Lys Pro Gly Gln Ala Pro Val Leu Val Ile Tyr
```

```
                35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Arg Ile Phe Gly Gly Gly Thr Lys Leu Thr Val Leu
                100                 105

<210> SEQ ID NO 291
<211> LENGTH: 108
<212> TYPE: PRT
<213> ORGANISM: Artificial Sequence
<220> FEATURE:
<223> OTHER INFORMATION: chemically synthesized

<400> SEQUENCE: 291

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Arg Ile Phe Gly Gly Gly Thr Lys Leu Thr Val Leu
                100                 105

<210> SEQ ID NO 292
<211> LENGTH: 447
<212> TYPE: PRT
<213> ORGANISM: Artificial Sequence
<220> FEATURE:
<223> OTHER INFORMATION: chemically synthesized

<400> SEQUENCE: 292

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125
```

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 293
<211> LENGTH: 440
<212> TYPE: PRT
<213> ORGANISM: Artificial Sequence
<220> FEATURE:
<223> OTHER INFORMATION: chemically synthesized

<400> SEQUENCE: 293

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
                35                  40                  45

```
Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 294
<211> LENGTH: 218
<212> TYPE: PRT
```

<213> ORGANISM: Artificial Sequence
<220> FEATURE:
<223> OTHER INFORMATION: chemically synthesized

<400> SEQUENCE: 294

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
                20                  25                  30
Gly Tyr Ser Tyr Leu His Trp Tyr Gln Gln Lys Pro Gly Gln Ala Pro
            35                  40                  45
Arg Leu Leu Ile Tyr Leu Ala Ser Tyr Leu Glu Ser Gly Val Pro Ala
        50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 295
<211> LENGTH: 214
<212> TYPE: PRT
<213> ORGANISM: Artificial Sequence
<220> FEATURE:
<223> OTHER INFORMATION: chemically synthesized

<400> SEQUENCE: 295

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Ser Ser Asn Trp Pro Arg
                85                  90                  95
Thr Phe Gly Gln Gly Thr Lys Val Glu Ile Lys Arg Thr Val Ala Ala
            100                 105                 110
```

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 296
<211> LENGTH: 122
<212> TYPE: PRT
<213> ORGANISM: Artificial Sequence
<220> FEATURE:
<223> OTHER INFORMATION: chemically synthesized

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
            115                 120

<210> SEQ ID NO 297
<211> LENGTH: 118
<212> TYPE: PRT
<213> ORGANISM: Artificial Sequence
<220> FEATURE:
<223> OTHER INFORMATION: chemically synthesized

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 298
<211> LENGTH: 447
<212> TYPE: PRT
<213> ORGANISM: Artificial Sequence
<220> FEATURE:
<223> OTHER INFORMATION: chemically synthesized

<400> SEQUENCE: 298

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 299
<211> LENGTH: 108
<212> TYPE: PRT
<213> ORGANISM: Artificial Sequence
<220> FEATURE:
<223> OTHER INFORMATION: chemically synthesized

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 300
<211> LENGTH: 214
<212> TYPE: PRT
<213> ORGANISM: Artificial Sequence
<220> FEATURE:
<223> OTHER INFORMATION: chemically synthesized

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Leu Tyr His Pro Ala
                    85                  90                  95

Thr Phe Gly Gln Gly Thr Lys Val Glu Ile Lys Arg Thr Val Ala Ala
                    100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 301
<211> LENGTH: 121
<212> TYPE: PRT
<213> ORGANISM: Artificial Sequence
<220> FEATURE:
<223> OTHER INFORMATION: chemically synthesized

<400> SEQUENCE: 301

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
                20                  25                  30

Trp Met Ser Trp Val Arg Gln Ala Pro Gly Lys Gly Leu Glu Trp Val
                35                  40                  45

Ala Asn Ile Asn Gln Asp Gly Thr Glu Lys Tyr Tyr Val Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
                    85                  90                  95

Ala Asn Thr Tyr Tyr Asp Phe Trp Ser Gly His Phe Asp Tyr Trp Gly
                    100                 105                 110

Gln Gly Thr Leu Val Thr Val Ser Ser
            115                 120

<210> SEQ ID NO 302
<211> LENGTH: 121
<212> TYPE: PRT
<213> ORGANISM: Artificial Sequence
<220> FEATURE:
<223> OTHER INFORMATION: chemically synthesized

<400> SEQUENCE: 302

Gln Glu His Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Asn Phe
                20                  25                  30
```

```
Gly Met His Trp Val Arg Gln Ala Pro Gly Lys Gly Leu Glu Trp Val
            35                  40                  45

Ala Ala Leu Trp Ser Asp Gly Ser Asn Lys Tyr Ala Asp Ser Val
 50                  55                  60

Lys Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Gly Ala Pro Gly Ile Pro Ile Phe Gly Tyr Trp Gly
            100                 105                 110

Gln Gly Thr Leu Val Thr Val Ser Ser
            115                 120

<210> SEQ ID NO 303
<211> LENGTH: 130
<212> TYPE: PRT
<213> ORGANISM: Artificial Sequence
<220> FEATURE:
<223> OTHER INFORMATION: chemically synthesized

<400> SEQUENCE: 303

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Arg Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu His Leu Gln Met Asn Ser Leu Lys Thr Glu Asp Thr Ala Val Tyr
                 85                  90                  95

Tyr Cys Thr Thr Asp Asp Ile Val Val Pro Ala Val Met Arg Glu
            100                 105                 110

Tyr Tyr Phe Gly Met Asp Val Trp Gly Gln Gly Thr Thr Val Thr Val
            115                 120                 125

Ser Ser
    130

<210> SEQ ID NO 304
<211> LENGTH: 121
<212> TYPE: PRT
<213> ORGANISM: Artificial Sequence
<220> FEATURE:
<223> OTHER INFORMATION: chemically synthesized

<400> SEQUENCE: 304

Gln Val Gln Leu Val Gln Ser Gly Ala Glu Val Lys Lys Pro Gly Ala
 1               5                  10                  15

Ser Val Gln Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Met
            35                  40                  45

Gly Trp Ile Asn Pro Asn Ser Gly Thr Lys Tyr Ala His Lys Phe
 50                  55                  60

Gln Gly Arg Val Thr Met Thr Arg Asp Thr Ser Ile Asp Thr Ala Tyr
 65                  70                  75                  80
```

Met Ile Leu Ser Ser Leu Ile Ser Asp Asp Thr Ala Val Tyr Tyr Cys
            85                  90                  95

Ala Arg Asp Glu Asp Trp Asn Phe Gly Ser Trp Phe Asp Ser Trp Gly
            100                 105                 110

Gln Gly Thr Leu Val Thr Val Ser Ser
        115                 120

<210> SEQ ID NO 305
<211> LENGTH: 121
<212> TYPE: PRT
<213> ORGANISM: Artificial Sequence
<220> FEATURE:
<223> OTHER INFORMATION: chemically synthesized

<400> SEQUENCE: 305

Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly His Gly Leu Glu Trp Met
        35                  40                  45

Gly Trp Leu Asn Pro Asn Thr Gly Thr Thr Lys Tyr Ile Gln Asn Phe
    50                  55                  60

Gln Gly Arg Val Thr Met Thr Arg Asp Thr Ser Ser Thr Ala Tyr
65                  70                  75                  80

Met Glu Leu Thr Arg Leu Arg Ser Asp Asp Thr Ala Val Tyr Tyr Cys
            85                  90                  95

Ala Arg Asp Glu Asp Trp Asn Tyr Gly Ser Trp Phe Asp Thr Trp Gly
            100                 105                 110

Gln Gly Thr Leu Val Thr Val Ser Ser
        115                 120

<210> SEQ ID NO 306
<211> LENGTH: 120
<212> TYPE: PRT
<213> ORGANISM: Artificial Sequence
<220> FEATURE:
<223> OTHER INFORMATION: chemically synthesized

<400> SEQUENCE: 306

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Arg Gly Leu Glu Trp Val
        35                  40                  45

Ser Gly Ile His Trp His Gly Lys Arg Thr Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Lys Gly Glu Asp Thr Ala Leu Tyr His Cys
            85                  90                  95

Val Arg Gly Gly Met Ser Thr Gly Asp Trp Phe Asp Pro Trp Gly Gln
            100                 105                 110

Gly Thr Leu Val Ile Val Ser Ser
        115                 120

<210> SEQ ID NO 307
<211> LENGTH: 120
<212> TYPE: PRT
<213> ORGANISM: Artificial Sequence
<220> FEATURE:
<223> OTHER INFORMATION: chemically synthesized

<400> SEQUENCE: 307

```
Glu Val Gln Leu Val Glu Ser Gly Gly Gly Val Val Arg Pro Gly Gly
1               5                  10                  15

Ser Leu Arg Leu Ser Cys Ala Ala Ser Gly Phe Thr Phe Asp Asp Tyr
            20                  25                  30

Gly Met Thr Trp Val Arg Gln Val Pro Gly Lys Gly Leu Glu Trp Val
        35                  40                  45

Ser Gly Ile His Trp Ser Gly Arg Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Met Ser Thr Gly Asp Trp Phe Asp Pro Trp Gly Gln
            100                 105                 110

Gly Thr Leu Val Thr Val Ser Ser
        115                 120
```

<210> SEQ ID NO 308
<211> LENGTH: 115
<212> TYPE: PRT
<213> ORGANISM: Artificial Sequence
<220> FEATURE:
<223> OTHER INFORMATION: chemically synthesized

<400> SEQUENCE: 308

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Val Gly Ser Asn
            20                  25                  30

Tyr Met Asn Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Leu Thr Ser Lys Asn Thr Leu Tyr Leu
65                  70                  75                  80

Gln Met Ser Ser Leu Arg Pro Glu Asp Thr Ala Val Tyr Tyr Cys Ala
                85                  90                  95

Arg Gly Ile Arg Gly Leu Asp Val Trp Gly Gln Gly Thr Thr Val Thr
            100                 105                 110

Val Ser Ser
        115
```

<210> SEQ ID NO 309
<211> LENGTH: 115
<212> TYPE: PRT
<213> ORGANISM: Artificial Sequence
<220> FEATURE:
<223> OTHER INFORMATION: chemically synthesized

<400> SEQUENCE: 309

```
Glu Glu Arg Leu Val Glu Ser Gly Gly Asp Leu Val Gln Pro Gly Gly
1               5                  10                  15
```

Ser Leu Arg Leu Ser Cys Ala Ala Ser Gly Ile Thr Val Gly Thr Asn
            20                  25                  30

Tyr Met Asn Trp Val Arg Gln Ala Pro Gly Lys Gly Leu Glu Trp Val
        35                  40                  45

Ser Val Ile Ser Ser Gly Gly Asn Thr His Tyr Ala Asp Ser Val Lys
    50                  55                  60

Gly Arg Phe Ile Met Ser Arg Gln Thr Ser Lys Asn Thr Leu Tyr Leu
65                  70                  75                  80

Gln Met Asn Ser Leu Glu Thr Glu Asp Thr Ala Val Tyr Tyr Cys Ala
                85                  90                  95

Arg Gly Ile Arg Gly Leu Asp Val Trp Gly Gln Gly Thr Met Val Thr
            100                 105                 110

Val Ser Ser
        115

<210> SEQ ID NO 310
<211> LENGTH: 118
<212> TYPE: PRT
<213> ORGANISM: Artificial Sequence
<220> FEATURE:
<223> OTHER INFORMATION: chemically synthesized

<400> SEQUENCE: 310

Gln Val Gln Leu Val Gln Ser Gly Ala Glu Val Lys Met Pro Gly Ser
1               5                   10                  15

Ser Val Arg Val Ser Cys Lys Ala Ser Gly Gly Ile Phe Ser Ser Ser
            20                  25                  30

Thr Ile Ser Trp Val Arg Gln Ala Pro Gly Gln Gly Leu Glu Trp Met
        35                  40                  45

Gly Glu Ile Ile Pro Val Phe Gly Thr Val Asn Tyr Ala Gln Lys Phe
    50                  55                  60

Gln Asp Arg Val Ile Phe Thr Ala Asp Glu Ser Thr Thr Thr Ala Tyr
65                  70                  75                  80

Met Glu Leu Ser Ser Leu Lys Ser Gly Asp Thr Ala Val Tyr Phe Cys
                85                  90                  95

Ala Arg Asn Trp Gly Leu Gly Ser Phe Tyr Ile Trp Gly Gln Gly Thr
            100                 105                 110

Met Val Thr Val Ser Ser
        115

<210> SEQ ID NO 311
<211> LENGTH: 115
<212> TYPE: PRT
<213> ORGANISM: Artificial Sequence
<220> FEATURE:
<223> OTHER INFORMATION: chemically synthesized

<400> SEQUENCE: 311

Glu Val Gln Leu Val Glu Ser Gly Gly Asp Leu Val His Pro Gly Arg
1               5                   10                  15

Ser Leu Arg Leu Ser Cys Ala Ala Ser Gly Phe Pro Phe Asp Glu Tyr
            20                  25                  30

Ala Met His Trp Val Arg Gln Val Pro Gly Lys Gly Leu Glu Trp Val
        35                  40                  45

Ser Gly Ile Ser Trp Ser Asn Asn Ile Gly Tyr Ala Asp Ser Val
    50                  55                  60

Lys Gly Arg Phe Thr Ile Ser Arg Asp Asn Ala Lys Asn Ser Leu Tyr

```
                 65                  70                  75                  80

Leu Gln Met Asn Ser Leu Arg Pro Glu Asp Thr Ala Phe Tyr Tyr Cys
                 85                  90                  95

Ala Lys Ser Gly Ile Phe Asp Ser Trp Gly Gln Gly Thr Leu Val Thr
                100                 105                 110

Val Ser Ser
        115

<210> SEQ ID NO 312
<211> LENGTH: 118
<212> TYPE: PRT
<213> ORGANISM: Artificial Sequence
<220> FEATURE:
<223> OTHER INFORMATION: chemically synthesized

<400> SEQUENCE: 312

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Thr Leu Ile Ser Tyr Glu Gly Arg Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Thr Leu Tyr Gly Met Asp Val Trp Gly Gln Gly Thr
                100                 105                 110

Thr Val Thr Val Ser Ser
            115

<210> SEQ ID NO 313
<211> LENGTH: 121
<212> TYPE: PRT
<213> ORGANISM: Artificial Sequence
<220> FEATURE:
<223> OTHER INFORMATION: chemically synthesized

<400> SEQUENCE: 313

Gln Val Thr Leu Arg Glu Ser Gly Pro Ala Leu Val Lys Thr Thr Gln
1               5                   10                  15

Thr Leu Thr Leu Thr Cys Thr Phe Ser Gly Phe Ser Leu Ser Thr Asn
                20                  25                  30

Arg Met Cys Val Thr Trp Ile Arg Gln Pro Pro Gly Lys Ala Leu Glu
                35                  40                  45

Trp Leu Ala Arg Ile Asp Trp Asp Gly Val Lys Tyr Tyr Asn Thr Ser
            50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Phe Tyr
                85                  90                  95

Cys Ala Arg Ser Thr Ser Leu Thr Phe Tyr Tyr Phe Asp Tyr Trp Gly
                100                 105                 110

Gln Gly Thr Leu Val Thr Val Ser Ser
            115                 120
```

<210> SEQ ID NO 314
<211> LENGTH: 115
<212> TYPE: PRT
<213> ORGANISM: Artificial Sequence
<220> FEATURE:
<223> OTHER INFORMATION: chemically synthesized

<400> SEQUENCE: 314

```
Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Val Gly Thr Asn
            20                  25                  30

His Met Asn Trp Val Arg Gln Ala Pro Gly Lys Gly Leu Glu Trp Val
        35                  40                  45

Ser Val Ile Tyr Ser Gly Gly Asn Thr Phe Tyr Ala Asp Ser Val Lys
    50                  55                  60

Gly Arg Phe Thr Ile Ser Arg His Thr Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Gly Leu Gly Gly Met Asp Val Trp Gly Gln Gly Thr Thr Val Thr
            100                 105                 110

Val Ser Ser
        115
```

<210> SEQ ID NO 315
<211> LENGTH: 120
<212> TYPE: PRT
<213> ORGANISM: Artificial Sequence
<220> FEATURE:
<223> OTHER INFORMATION: chemically synthesized

<400> SEQUENCE: 315

```
Glu Val Gln Leu Val Glu Ser Gly Gly Gly Leu Val Gln Arg Gly Glu
1               5                   10                  15

Ser Leu Arg Leu Tyr Cys Ala Ala Ser Gly Phe Thr Phe Ser Lys Tyr
            20                  25                  30

Trp Met Asn Trp Val Arg Gln Ala Pro Gly Lys Gly Leu Glu Trp Val
        35                  40                  45

Ala Asn Ile Lys Gly Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Trp Gly Ser Gly Tyr Tyr Phe Asp Phe Trp Gly Gln
            100                 105                 110

Gly Thr Leu Val Thr Val Ser Ser
        115                 120
```

<210> SEQ ID NO 316
<211> LENGTH: 130
<212> TYPE: PRT
<213> ORGANISM: Artificial Sequence
<220> FEATURE:
<223> OTHER INFORMATION: chemically synthesized

<400> SEQUENCE: 316

```
Glu Val Gln Leu Val Glu Ser Gly Gly Gly Leu Val Gln Ser Gly Gly
```

```
                1               5                  10                 15
            Ser Leu Arg Leu Ser Cys Ala Ala Ser Gly Phe Thr Phe Ser Ser Tyr
                            20                  25                 30

Trp Met Ser Trp Val Arg Gln Ala Pro Gly Lys Gly Leu Glu Trp Val
                            35                  40                 45

Ala Asn Ile Lys Gln Asp Gly Ser Glu Lys Tyr Tyr Val Asp Ser Val
                            50                  55                 60

Lys Gly Arg Phe Thr Ile Ser Arg Asp Asn Ala Lys Asn Ser Leu Tyr
             65                  70                  75                 80

Leu Gln Met Asn Ser Leu Arg Ala Asp Asp Thr Ala Val Tyr Tyr Cys
                            85                  90                 95

Ala Arg Asp Asp Ile Val Val Pro Ala Pro Met Gly Tyr Tyr
                            100                 105                110

Tyr Tyr Phe Gly Met Asp Val Trp Gly Gln Gly Thr Thr Val Thr Val
                            115                 120                125

Ser Ser
              130

<210> SEQ ID NO 317
<211> LENGTH: 123
<212> TYPE: PRT
<213> ORGANISM: Artificial Sequence
<220> FEATURE:
<223> OTHER INFORMATION: chemically synthesized

<400> SEQUENCE: 317

Glu Val Gln Leu Val Glu Ser Gly Gly Gly Leu Val Gln Pro Gly Arg
             1               5                  10                 15

Ser Leu Arg Leu Ser Cys Ala Ala Ser Gly Phe Thr Phe Asp Asp Phe
                            20                  25                 30

Ala Met His Trp Val Arg Gln Ala Pro Gly Lys Gly Leu Glu Trp Val
                            35                  40                 45

Ser Gly Ile Ser Trp Thr Gly Gly Asn Met Asp Tyr Ala Asn Ser Val
                            50                  55                 60

Lys Gly Arg Phe Thr Ile Ser Arg Glu Asp Ala Lys Asn Ser Leu Tyr
             65                  70                  75                 80

Leu Gln Met Asn Ser Leu Arg Ala Ala Asp Thr Ala Leu Tyr Tyr Cys
                            85                  90                 95

Val Lys Asp Ile Arg Gly Ile Val Ala Thr Gly Gly Ala Phe Asp Ile
                            100                 105                110

Trp Gly Arg Gly Thr Met Val Thr Val Ser Ser
                            115                 120

<210> SEQ ID NO 318
<211> LENGTH: 115
<212> TYPE: PRT
<213> ORGANISM: Artificial Sequence
<220> FEATURE:
<223> OTHER INFORMATION: chemically synthesized

<400> SEQUENCE: 318

Glu Val Gln Leu Val Glu Ser Gly Gly Gly Leu Val Gln Pro Gly Gly
             1               5                  10                 15

Ser Leu Arg Leu Ser Cys Ala Ala Ser Gly Phe Thr Val Gly Thr Asn
                            20                  25                 30

Tyr Met Asn Trp Val Arg Gln Ala Pro Gly Lys Gly Leu Glu Trp Ile
                            35                  40                 45
```

```
Ser Val Ile Tyr Ser Gly Gly Ser Thr Phe Tyr Ala Asp Ser Val Lys
 50                  55                  60

Gly Arg Phe Thr Ile Ser Arg Gln Thr Ser Gln Asn Thr Leu Tyr Leu
 65                  70                  75                  80

Gln Met Asn Ser Leu Arg Pro Glu Asp Thr Ala Val Tyr Tyr Cys Ala
                 85                  90                  95

Arg Gly Ile Arg Gly Phe Asp Ile Trp Gly Gln Gly Thr Met Val Thr
                100                 105                 110

Val Ser Ser
        115
```

<210> SEQ ID NO 319
<211> LENGTH: 115
<212> TYPE: PRT
<213> ORGANISM: Artificial Sequence
<220> FEATURE:
<223> OTHER INFORMATION: chemically synthesized

<400> SEQUENCE: 319

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Ser Thr Asn
                 20                  25                  30

Tyr Met Asn Trp Val Arg Gln Ala Pro Gly Lys Gly Leu Glu Trp Val
             35                  40                  45

Ala Val Ile Tyr Ser Ser Gly Ser Thr Tyr Tyr Ile Asp Ser Val Lys
 50                  55                  60

Gly Arg Phe Thr Ile Ser Arg Leu Thr Ser Lys Asn Thr Val Tyr Leu
 65                  70                  75                  80

Gln Met Ser Ser Leu Asn Ser Glu Asp Thr Ala Val Tyr Tyr Cys Ala
                 85                  90                  95

Arg Gly Ile Arg Gly Phe Asp Ile Trp Gly Gln Gly Thr Met Val Thr
                100                 105                 110

Val Ser Ser
        115
```

<210> SEQ ID NO 320
<211> LENGTH: 124
<212> TYPE: PRT
<213> ORGANISM: Artificial Sequence
<220> FEATURE:
<223> OTHER INFORMATION: chemically synthesized

<400> SEQUENCE: 320

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Ile Asp Asp Ser
                 20                  25                  30

Ala Met His Trp Val Arg Gln Thr Pro Gly Lys Gly Leu Glu Trp Val
             35                  40                  45

Ser Gly Ile Ser Trp Lys Ser Ser Ile Gly Tyr Ala Asp Ser Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
                 85                  90                  95

Val Lys Asp Ile Arg Gly Asn Trp Asn Tyr Gly Gly Asn Trp Phe Asp
                100                 105                 110
```

```
Pro Trp Gly Gln Gly Thr Leu Val Thr Val Ser Ser
        115                 120
```

<210> SEQ ID NO 321
<211> LENGTH: 115
<212> TYPE: PRT
<213> ORGANISM: Artificial Sequence
<220> FEATURE:
<223> OTHER INFORMATION: chemically synthesized

<400> SEQUENCE: 321

```
Glu Val Gln Leu Val Glu Ser Gly Gly Leu Val Gln Pro Gly Gly
1               5                   10                  15

Ser Leu Arg Leu Ser Cys Glu Ala Ser Gly Phe Thr Val Gly Val Asn
            20                  25                  30

His Met Asn Trp Val Arg Gln Ala Pro Gly Lys Gly Leu Glu Trp Val
                35                  40                  45

Ser Val Ile Phe Ser Ser Gly Arg Thr Phe Tyr Gly Asp Tyr Val Lys
        50                  55                  60

Gly Arg Leu Thr Ile Phe Arg Gln Thr Ser Gln Asn Thr Val Tyr Leu
65                  70                  75                  80

Gln Met Asn Ser Leu Arg Ser Glu Asp Thr Ala Ile Tyr Tyr Cys Ala
                85                  90                  95

Arg Gly Ile Gly Gly Leu Asp Ile Trp Gly Arg Gly Thr Met Val Thr
            100                 105                 110

Val Ser Ser
        115
```

<210> SEQ ID NO 322
<211> LENGTH: 123
<212> TYPE: PRT
<213> ORGANISM: Artificial Sequence
<220> FEATURE:
<223> OTHER INFORMATION: chemically synthesized

<400> SEQUENCE: 322

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
                35                  40                  45

Ser Gly Ile Ser Trp Thr Gly Thr Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Thr Glu Asp Thr Ala Ile Tyr Tyr Cys
                85                  90                  95

Thr Arg Asp Ile Arg Gly Asn Trp Lys Tyr Gly Gly Trp Phe Asp Pro
            100                 105                 110

Trp Gly Gln Gly Thr Leu Val Thr Val Ser Ser
        115                 120
```

<210> SEQ ID NO 323
<211> LENGTH: 120
<212> TYPE: PRT
<213> ORGANISM: Artificial Sequence
<220> FEATURE:
<223> OTHER INFORMATION: chemically synthesized

<400> SEQUENCE: 323

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Met His Trp Val Arg Gln Ala Pro Gly Gln Gly Leu Asp Trp Met
        35                  40                  45

Gly Trp Ile Ser Pro Asn Ser Gly Phe Thr Asn Tyr Ala Gln Lys Phe
    50                  55                  60

Gln Gly Arg Val Thr Met Thr Arg Asp Thr Ser Ile Asn Thr Phe Tyr
65                  70                  75                  80

Met Glu Leu Ser Gly Leu Arg Ser Asp Asp Thr Ala Val Tyr Tyr Cys
                85                  90                  95

Ala Arg Glu Gly Ser Thr His His Asn Ser Phe Asp Pro Trp Gly Gln
            100                 105                 110

Gly Thr Leu Val Thr Val Ser Ser
        115                 120

<210> SEQ ID NO 324
<211> LENGTH: 114
<212> TYPE: PRT
<213> ORGANISM: Artificial Sequence
<220> FEATURE:
<223> OTHER INFORMATION: chemically synthesized

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Gly Thr Asn
            20                  25                  30

Phe Met Asn Trp Val Arg Gln Ala Pro Gly Lys Gly Leu Glu Trp Val
        35                  40                  45

Ser Ala Ile Tyr Ser Gly Gly Thr Ala Asn Tyr Ala Asp Ser Val Lys
    50                  55                  60

Gly Arg Phe Thr Ile Ser Arg Asp Thr Ser Arg Asn Thr Leu Tyr Leu
65                  70                  75                  80

Gln Met Asn Ser Leu Arg Thr Glu Asp Thr Ala Val Tyr Tyr Cys Ala
                85                  90                  95

Arg Gly Gly Gly Met Asp Val Trp Gly Gln Gly Thr Thr Val Thr Val
            100                 105                 110

Ser Ser

<210> SEQ ID NO 325
<211> LENGTH: 118
<212> TYPE: PRT
<213> ORGANISM: Artificial Sequence
<220> FEATURE:
<223> OTHER INFORMATION: chemically synthesized

<400> SEQUENCE: 325

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Thr Tyr
            20                  25                  30

Val Leu Ser Trp Val Arg Gln Ala Pro Gly Gln Gly Leu Glu Trp Met
        35                  40                  45

```
Gly Glu Ile Ile Pro Ile Leu Gly Ala Ala Asn Tyr Ala Gln Asn Phe
 50                  55                  60

Gln Gly Arg Val Thr Phe Thr Thr Asp Glu Ser Thr Asn Thr Ala Tyr
 65                  70                  75                  80

Met Asp Leu Ser Ser Leu Arg Ser Glu Asp Thr Ala Val Tyr Tyr Cys
                 85                  90                  95

Ala Arg Asp Arg Thr Ser Gly Gly Phe Asp Pro Trp Gly Gln Gly Thr
                100                 105                 110

Leu Val Thr Val Ser Ser
            115

<210> SEQ ID NO 326
<211> LENGTH: 119
<212> TYPE: PRT
<213> ORGANISM: Artificial Sequence
<220> FEATURE:
<223> OTHER INFORMATION: chemically synthesized

<400> SEQUENCE: 326

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Thr His Tyr
                 20                  25                  30

Gly Ile Ser Trp Val Arg Gln Ala Pro Gly Gln Gly Leu Glu Trp Val
             35                  40                  45

Gly Trp Ile Ser Pro Tyr Asn Gly Tyr Thr Asp Tyr Ala Gln Lys Leu
 50                  55                  60

Gln Gly Arg Val Thr Leu Thr Thr Asp Thr Ser Thr Thr Thr Ala Tyr
 65                  70                  75                  80

Met Glu Leu Arg Asn Leu Arg Ser Asp Asp Thr Ala Met Tyr Tyr Cys
                 85                  90                  95

Ser Arg Gly Arg Gly Pro Tyr Trp Ser Phe Asp Leu Trp Gly Arg Gly
                100                 105                 110

Thr Leu Val Thr Val Ser Ser
            115

<210> SEQ ID NO 327
<211> LENGTH: 106
<212> TYPE: PRT
<213> ORGANISM: Artificial Sequence
<220> FEATURE:
<223> OTHER INFORMATION: chemically synthesized

<400> SEQUENCE: 327

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr His Ser Tyr Ser Tyr
                 85                  90                  95

Thr Phe Gly Gln Gly Thr Lys Glu Ile Lys
                100                 105
```

```
<210> SEQ ID NO 328
<211> LENGTH: 107
<212> TYPE: PRT
<213> ORGANISM: Artificial Sequence
<220> FEATURE:
<223> OTHER INFORMATION: chemically synthesized

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Ala Ile Lys
            100                 105

<210> SEQ ID NO 329
<211> LENGTH: 107
<212> TYPE: PRT
<213> ORGANISM: Artificial Sequence
<220> FEATURE:
<223> OTHER INFORMATION: chemically synthesized

<400> SEQUENCE: 329

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Tyr
                85                  90                  95

Thr Phe Gly Gln Gly Thr Lys Leu Glu Ile Lys
            100                 105

<210> SEQ ID NO 330
<211> LENGTH: 112
<212> TYPE: PRT
<213> ORGANISM: Artificial Sequence
<220> FEATURE:
<223> OTHER INFORMATION: chemically synthesized

<400> SEQUENCE: 330

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Thr Leu Val His Gly
            20                  25                  30
```

Asp Gly Asn Thr Tyr Leu Ser Trp Ile Gln Gln Arg Pro Gly Gln Pro
              35                  40                  45

Pro Arg Leu Leu Ile Tyr Lys Val Ser Asn Gln Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Leu Tyr Phe Cys Met Gln Ala
                 85                  90                  95

Thr His Phe Pro Ile Thr Phe Gly Gln Gly Thr Arg Leu Glu Ile Lys
            100                 105                 110

<210> SEQ ID NO 331
<211> LENGTH: 112
<212> TYPE: PRT
<213> ORGANISM: Artificial Sequence
<220> FEATURE:
<223> OTHER INFORMATION: chemically synthesized

<400> SEQUENCE: 331

Asp Ile Val Met Thr Gln Thr Pro Leu Ser Ser Pro Val Thr Leu Gly
 1               5                  10                  15

Gln Pro Ala Ser Ile Ser Cys Arg Ser Ser Pro Ser Leu Val His Ser
             20                  25                  30

Asp Gly Asn Thr Tyr Leu Ser Trp Leu Gln Gln Arg Pro Gly Gln Pro
             35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr His Phe Pro Ile Thr Phe Gly Gln Gly Thr Arg Leu Glu Ile Arg
            100                 105                 110

<210> SEQ ID NO 332
<211> LENGTH: 108
<212> TYPE: PRT
<213> ORGANISM: Artificial Sequence
<220> FEATURE:
<223> OTHER INFORMATION: chemically synthesized

<400> SEQUENCE: 332

Asp Ile Gln Met Thr Gln Ser Pro Ser Ser Leu Ser Ala Ser Leu Gly
 1               5                  10                  15

Asp Arg Val Thr Ile Thr Cys Arg Ala Ser Gln Ser Ile Asn Ser Tyr
             20                  25                  30

Leu Asn Trp Tyr Gln Gln Lys Pro Gly Lys Ala Pro Lys Leu Leu Ile
             35                  40                  45

Tyr Val Ala Ser Ser Leu Gln Ser Gly Val Pro Ser Arg Phe Ser Gly
     50                  55                  60

Ser Gly Ser Gly Thr Glu Phe Thr Leu Thr Ile Ser Asn Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105

<210> SEQ ID NO 333

```
<211> LENGTH: 108
<212> TYPE: PRT
<213> ORGANISM: Artificial Sequence
<220> FEATURE:
<223> OTHER INFORMATION: chemically synthesized

<400> SEQUENCE: 333

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 334
<211> LENGTH: 108
<212> TYPE: PRT
<213> ORGANISM: Artificial Sequence
<220> FEATURE:
<223> OTHER INFORMATION: chemically synthesized

<400> SEQUENCE: 334

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Ile Tyr
            20                  25                  30

Leu Asn Trp Tyr Gln Gln Lys Pro Gly Arg Ala Pro Arg Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Ser Tyr Ser Thr Pro Pro
                85                  90                  95

Ile Thr Phe Gly Gln Gly Thr Arg Leu Glu Ile Lys
            100                 105

<210> SEQ ID NO 335
<211> LENGTH: 108
<212> TYPE: PRT
<213> ORGANISM: Artificial Sequence
<220> FEATURE:
<223> OTHER INFORMATION: chemically synthesized

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Met Ser Ser Tyr
            20                  25                  30

Leu Asn Trp Tyr Gln Gln Lys Pro Gly Arg Ala Pro Lys Leu Leu Ile
        35                  40                  45
```

Phe Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105

<210> SEQ ID NO 336
<211> LENGTH: 108
<212> TYPE: PRT
<213> ORGANISM: Artificial Sequence
<220> FEATURE:
<223> OTHER INFORMATION: chemically synthesized

<400> SEQUENCE: 336

Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Phe Asn Phe Asn
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Asn Arg Leu Glu
 65                  70                  75                  80

Pro Glu Asp Phe Gly Val Phe Tyr Cys Gln Gln Tyr Glu Ser Ala Pro
                 85                  90                  95

Trp Thr Phe Gly Gln Gly Thr Lys Val Glu Ile Lys
            100                 105

<210> SEQ ID NO 337
<211> LENGTH: 105
<212> TYPE: PRT
<213> ORGANISM: Artificial Sequence
<220> FEATURE:
<223> OTHER INFORMATION: chemically synthesized

<400> SEQUENCE: 337

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Leu Leu Ile Tyr Ala Ala
             35                  40                  45

Ser Ser Leu Gln Ser Gly Val Pro Ser Arg Phe Ser Gly Gly Gly Ser
 50                  55                  60

Gly Thr Asp Phe Thr Leu Thr Ile Ser Ser Leu Arg Pro Glu Asp Phe
 65                  70                  75                  80

Ala Thr Tyr Tyr Cys Gln Gln Ser Tyr Cys Thr Pro Pro Ile Thr Phe
                 85                  90                  95

Gly Gln Gly Thr Arg Leu Glu Ile Lys
            100                 105

<210> SEQ ID NO 338
<211> LENGTH: 108
<212> TYPE: PRT
<213> ORGANISM: Artificial Sequence

```
<220> FEATURE:
<223> OTHER INFORMATION: chemically synthesized

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 339
<211> LENGTH: 91
<212> TYPE: PRT
<213> ORGANISM: Artificial Sequence
<220> FEATURE:
<223> OTHER INFORMATION: chemically synthesized

<400> SEQUENCE: 339

Asp Arg Val Thr Ile Thr Cys Arg Ala Ser Gln Val Ile Ser Asn Tyr
1               5                   10                  15

Leu Ala Trp Tyr Gln Gln Lys Pro Gly Lys Val Pro Arg Leu Leu Ile
            20                  25                  30

Tyr Ala Ala Ser Thr Leu Gln Ser Gly Val Pro Ser Arg Phe Ser Gly
        35                  40                  45

Ser Gly Ser Gly Thr Asp Phe Thr Leu Thr Ile Ser Ser Leu Gln Pro
    50                  55                  60

Glu Asp Val Ala Thr Tyr Tyr Cys Gln Lys Tyr Asn Ser Ala Pro Arg
65                  70                  75                  80

Thr Phe Gly Gln Gly Thr Lys Val Glu Ile Lys
                85                  90

<210> SEQ ID NO 340
<211> LENGTH: 107
<212> TYPE: PRT
<213> ORGANISM: Artificial Sequence
<220> FEATURE:
<223> OTHER INFORMATION: chemically synthesized

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Phe Gln Asn Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Asn Thr Pro Leu
                85                  90                  95

Thr Phe Gly Gly Gly Thr Lys Val Glu Ile Lys
            100                 105

<210> SEQ ID NO 341
<211> LENGTH: 107
<212> TYPE: PRT
<213> ORGANISM: Artificial Sequence
<220> FEATURE:
<223> OTHER INFORMATION: chemically synthesized

<400> SEQUENCE: 341

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 342
<211> LENGTH: 108
<212> TYPE: PRT
<213> ORGANISM: Artificial Sequence
<220> FEATURE:
<223> OTHER INFORMATION: chemically synthesized

<400> SEQUENCE: 342

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 343
<211> LENGTH: 115
<212> TYPE: PRT
<213> ORGANISM: Artificial Sequence
<220> FEATURE:
<223> OTHER INFORMATION: chemically synthesized

<400> SEQUENCE: 343

Gln Ser Leu Glu Glu Ser Gly Gly Arg Leu Val Lys Pro Asp Glu Thr
```

```
1               5                   10                  15
Leu Thr Ile Thr Cys Thr Val Ser Gly Ile Asp Leu Ser Ser Asn Gly
                20                  25                  30

Leu Thr Trp Val Arg Gln Ala Pro Gly Glu Gly Leu Glu Trp Ile Gly
            35                  40                  45

Thr Ile Asn Lys Asp Ala Ser Ala Tyr Tyr Ala Ser Trp Ala Lys Gly
        50                  55                  60

Arg Leu Thr Ile Ser Lys Pro Ser Ser Thr Val Asp Leu Lys Ile
65                  70                  75                  80

Thr Ser Pro Thr Thr Glu Asp Thr Ala Thr Tyr Phe Cys Gly Arg Ile
                85                  90                  95

Ala Phe Lys Thr Gly Thr Ser Ile Trp Gly Pro Gly Thr Leu Val Thr
                100                 105                 110

Val Ser Ser
        115

<210> SEQ ID NO 344
<211> LENGTH: 112
<212> TYPE: PRT
<213> ORGANISM: Artificial Sequence
<220> FEATURE:
<223> OTHER INFORMATION: chemically synthesized

<400> SEQUENCE: 344

Ala Ile Val Met Thr Gln Thr Pro Ser Pro Val Ser Ala Ala Val Gly
1               5                   10                  15

Gly Thr Val Thr Ile Asn Cys Gln Ala Ser Glu Ser Val Tyr Ser Asn
                20                  25                  30

Asn Tyr Leu Ser Trp Phe Gln Gln Lys Pro Gly Gln Pro Pro Lys Leu
            35                  40                  45

Leu Ile Tyr Leu Ala Ser Thr Leu Ala Ser Gly Val Pro Ser Arg Phe
        50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ile Gly Gly Lys Ser Ser
                85                  90                  95

Ser Thr Asp Gly Asn Ala Phe Gly Gly Gly Thr Glu Val Val Val Arg
                100                 105                 110

<210> SEQ ID NO 345
<211> LENGTH: 121
<212> TYPE: PRT
<213> ORGANISM: Artificial Sequence
<220> FEATURE:
<223> OTHER INFORMATION: chemically synthesized

<400> SEQUENCE: 345

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Asn Ile Val Ala Thr Ile Thr Pro Leu Asp Tyr Trp Gly
            100                 105                 110

Gln Gly Thr Leu Val Thr Val Ser Ser
        115                 120

<210> SEQ ID NO 346
<211> LENGTH: 110
<212> TYPE: PRT
<213> ORGANISM: Artificial Sequence
<220> FEATURE:
<223> OTHER INFORMATION: chemically synthesized

<400> SEQUENCE: 346

Gln Pro Val Leu Thr Gln Pro Pro Ser Val Ser Ala Ala Pro Gly Gln
1               5                   10                  15

Lys Val Thr Ile Ser Cys Ser Gly Ser Ser Asn Ile Ala Asn Asn
            20                  25                  30

Tyr Val Ser Trp Tyr Gln Gln Leu Pro Gly Thr Ala Pro Lys Leu Leu
            35                  40                  45

Ile Phe Ala Asn Asn Lys Arg Pro Ser Gly Ile Pro Asp Arg Phe Ser
50                  55                  60

Gly Ser Lys Ser Gly Thr Ser Ala Ala Leu Asp Ile Thr Gly Leu Gln
65                  70                  75                  80

Thr Gly Asp Glu Ala Asp Tyr Tyr Cys Gly Thr Trp Asp Ser Asp Leu
                85                  90                  95

Arg Ala Gly Val Phe Gly Gly Gly Thr Lys Leu Thr Val Leu
            100                 105                 110

<210> SEQ ID NO 347
<211> LENGTH: 123
<212> TYPE: PRT
<213> ORGANISM: Artificial Sequence
<220> FEATURE:
<223> OTHER INFORMATION: chemically synthesized

<400> SEQUENCE: 347

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Ile Tyr Asp Ser Ser Gly Tyr Ser Phe Asp Tyr
            100                 105                 110

Trp Gly Gln Gly Thr Leu Val Thr Val Ser Ser
            115                 120

<210> SEQ ID NO 348
<211> LENGTH: 118
<212> TYPE: PRT
<213> ORGANISM: Artificial Sequence
```

-continued

```
<220> FEATURE:
<223> OTHER INFORMATION: chemically synthesized

<400> SEQUENCE: 348

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 349
<211> LENGTH: 118
<212> TYPE: PRT
<213> ORGANISM: Artificial Sequence
<220> FEATURE:
<223> OTHER INFORMATION: chemically synthesized

<400> SEQUENCE: 349

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 350
<211> LENGTH: 118
<212> TYPE: PRT
<213> ORGANISM: Artificial Sequence
<220> FEATURE:
<223> OTHER INFORMATION: chemically synthesized

<400> SEQUENCE: 350

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
            115

<210> SEQ ID NO 351
<211> LENGTH: 118
<212> TYPE: PRT
<213> ORGANISM: Artificial Sequence
<220> FEATURE:
<223> OTHER INFORMATION: chemically synthesized

<400> SEQUENCE: 351

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
            115

<210> SEQ ID NO 352
<211> LENGTH: 118
<212> TYPE: PRT
<213> ORGANISM: Artificial Sequence
<220> FEATURE:
<223> OTHER INFORMATION: chemically synthesized

<400> SEQUENCE: 352

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

```
Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 353
<211> LENGTH: 118
<212> TYPE: PRT
<213> ORGANISM: Artificial Sequence
<220> FEATURE:
<223> OTHER INFORMATION: chemically synthesized

<400> SEQUENCE: 353

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 354
<211> LENGTH: 120
<212> TYPE: PRT
<213> ORGANISM: Artificial Sequence
<220> FEATURE:
<223> OTHER INFORMATION: chemically synthesized

<400> SEQUENCE: 354

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Gly Val His Trp Val Arg Gln Ala Pro Gly Gln Gly Leu Glu Trp Met
        35                  40                  45

Gly Arg Leu Ile Pro Ile Val Ser Met Thr Asn Tyr Ala Gln Lys Phe
    50                  55                  60

Gln Asp Arg Val Ser Ile Thr Thr Asp Lys Ser Thr Gly Thr Ala Tyr
65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln
            100                 105                 110

Gly Thr Leu Val Thr Val Ser Ser
        115                 120

<210> SEQ ID NO 355
<211> LENGTH: 118
<212> TYPE: PRT
```

<213> ORGANISM: Artificial Sequence
<220> FEATURE:
<223> OTHER INFORMATION: chemically synthesized

<400> SEQUENCE: 355

Gln Met Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 356
<211> LENGTH: 118
<212> TYPE: PRT
<213> ORGANISM: Artificial Sequence
<220> FEATURE:
<223> OTHER INFORMATION: chemically synthesized

<400> SEQUENCE: 356

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 357
<211> LENGTH: 121
<212> TYPE: PRT
<213> ORGANISM: Artificial Sequence
<220> FEATURE:
<223> OTHER INFORMATION: chemically synthesized

<400> SEQUENCE: 357

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Tyr Ser Trp Val Arg Gln Ala Pro Gly Gln Gly Leu Glu Trp Met
            35                  40                  45

Gly Gly Ile Ile Pro Ser Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
                100                 105                 110

Gln Gly Thr Leu Val Thr Val Ser Ser
            115                 120

<210> SEQ ID NO 358
<211> LENGTH: 121
<212> TYPE: PRT
<213> ORGANISM: Artificial Sequence
<220> FEATURE:
<223> OTHER INFORMATION: chemically synthesized

<400> SEQUENCE: 358

Gln Met Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Tyr Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
                100                 105                 110

Gln Gly Thr Leu Val Thr Val Ser Ser
            115                 120

<210> SEQ ID NO 359
<211> LENGTH: 121
<212> TYPE: PRT
<213> ORGANISM: Artificial Sequence
<220> FEATURE:
<223> OTHER INFORMATION: chemically synthesized

<400> SEQUENCE: 359

Gln Met Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Tyr Ser Trp Val Arg Gln Ala Pro Gly Gln Gly Leu Glu Trp Met
            35                  40                  45

Gly Gly Ile Ile Pro Ser Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
```

85                  90                  95

Ala Arg Gly Pro Ile Val Ala Thr Ile Thr Pro Leu Asp Tyr Trp Gly
                100                 105                 110

Gln Gly Thr Leu Val Thr Val Ser Ser
            115                 120

<210> SEQ ID NO 360
<211> LENGTH: 121
<212> TYPE: PRT
<213> ORGANISM: Artificial Sequence
<220> FEATURE:
<223> OTHER INFORMATION: chemically synthesized

<400> SEQUENCE: 360

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ala Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
                100                 105                 110

Gln Gly Thr Leu Val Thr Val Ser Ser
            115                 120

<210> SEQ ID NO 361
<211> LENGTH: 108
<212> TYPE: PRT
<213> ORGANISM: Artificial Sequence
<220> FEATURE:
<223> OTHER INFORMATION: chemically synthesized

<400> SEQUENCE: 361

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Ile Phe Gly Gly Gly Thr Lys Leu Thr Val Leu
                100                 105

<210> SEQ ID NO 362
<211> LENGTH: 107
<212> TYPE: PRT
<213> ORGANISM: Artificial Sequence
<220> FEATURE:

<223> OTHER INFORMATION: chemically synthesized

<400> SEQUENCE: 362

```
Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Thr Thr Ser Ser Leu Lys Ser Gly Val Pro Ser Arg Phe Ser Gly
50                  55                  60

Ser Gly Ser Gly Thr Asp Phe Thr Leu Thr Ile Ser Arg Leu Gln Pro
65                  70                  75                  80

Glu Asp Phe Ala Thr Tyr Tyr Cys Gln Gln Ser Tyr Ser Ser Thr Trp
                85                  90                  95

Thr Phe Gly Arg Gly Thr Lys Val Glu Ile Lys
            100                 105
```

<210> SEQ ID NO 363
<211> LENGTH: 110
<212> TYPE: PRT
<213> ORGANISM: Artificial Sequence
<220> FEATURE:
<223> OTHER INFORMATION: chemically synthesized

<400> SEQUENCE: 363

```
Gln Ser Val Leu Thr Gln Pro Pro Ser Val Ser Ala Ala Pro Gly Gln
1               5                   10                  15

Lys Val Thr Ile Ser Cys Ser Gly Asn Asn Ser Asn Ile Ala Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Tyr Arg Pro Ser Gly Ile Pro Asp Arg Phe Ser
50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Val Trp Asp Gly Ser Leu
                85                  90                  95

Thr Thr Gly Val Phe Gly Gly Gly Thr Lys Leu Thr Val Leu
            100                 105                 110
```

<210> SEQ ID NO 364
<211> LENGTH: 110
<212> TYPE: PRT
<213> ORGANISM: Artificial Sequence
<220> FEATURE:
<223> OTHER INFORMATION: chemically synthesized

<400> SEQUENCE: 364

```
Leu Pro Val Leu Thr Gln Pro Ala Ser Val Ser Gly Ser Pro Gly Gln
1               5                   10                  15

Ser Ile Thr Ile Ser Cys Thr Gly Thr Ser Asp Ile Gly Gly Tyr
            20                  25                  30

Asp Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
```

```
                65                  70                  75                  80
Gln Ala Glu Asp Glu Ala Asp Tyr Tyr Cys Ser Ser Tyr Thr Ser Ser
                    85                  90                  95

Ser Thr His Val Phe Gly Thr Gly Thr Lys Leu Thr Val Leu
                100                 105                 110

<210> SEQ ID NO 365
<211> LENGTH: 111
<212> TYPE: PRT
<213> ORGANISM: Artificial Sequence
<220> FEATURE:
<223> OTHER INFORMATION: chemically synthesized

<400> SEQUENCE: 365

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ser
                    85                  90                  95

Thr Leu Gly Pro Val Phe Gly Gly Gly Thr Lys Leu Thr Val Leu
                100                 105                 110

<210> SEQ ID NO 366
<211> LENGTH: 110
<212> TYPE: PRT
<213> ORGANISM: Artificial Sequence
<220> FEATURE:
<223> OTHER INFORMATION: chemically synthesized

<400> SEQUENCE: 366

Gln Ala Gly Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                    85                  90                  95

Asn Gly Tyr Val Phe Gly Thr Gly Thr Lys Leu Thr Val Leu
                100                 105                 110

<210> SEQ ID NO 367
<211> LENGTH: 110
<212> TYPE: PRT
<213> ORGANISM: Artificial Sequence
<220> FEATURE:
<223> OTHER INFORMATION: chemically synthesized

<400> SEQUENCE: 367
```

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Thr Thr His Val Phe Gly Thr Gly Thr Lys Val Thr Val Leu
            100                 105                 110

<210> SEQ ID NO 368
<211> LENGTH: 110
<212> TYPE: PRT
<213> ORGANISM: Artificial Sequence
<220> FEATURE:
<223> OTHER INFORMATION: chemically synthesized

<400> SEQUENCE: 368

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65              70                  75                  80

Thr Gly Asp Glu Ala Asp Tyr Tyr Cys Gly Thr Trp Asp Ser Ser Leu
                85                  90                  95

Ser Val Trp Val Phe Gly Gly Gly Thr Gln Leu Thr Val Leu
            100                 105                 110

<210> SEQ ID NO 369
<211> LENGTH: 112
<212> TYPE: PRT
<213> ORGANISM: Artificial Sequence
<220> FEATURE:
<223> OTHER INFORMATION: chemically synthesized

<400> SEQUENCE: 369

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Arg Ala Pro Arg Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Gly Asp Tyr Tyr Cys Ser Ser Tyr Thr Ser Gly

```
                85                  90                  95
Gly Thr Leu Gly Pro Val Phe Gly Gly Gly Thr Lys Leu Thr Val Leu
            100                 105                 110

<210> SEQ ID NO 370
<211> LENGTH: 110
<212> TYPE: PRT
<213> ORGANISM: Artificial Sequence
<220> FEATURE:
<223> OTHER INFORMATION: chemically synthesized

<400> SEQUENCE: 370

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 371
<211> LENGTH: 110
<212> TYPE: PRT
<213> ORGANISM: Artificial Sequence
<220> FEATURE:
<223> OTHER INFORMATION: chemically synthesized

<400> SEQUENCE: 371

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Val Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Asn Ser Asp Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 372
<211> LENGTH: 112
<212> TYPE: PRT
<213> ORGANISM: Artificial Sequence
<220> FEATURE:
<223> OTHER INFORMATION: chemically synthesized

<400> SEQUENCE: 372

Gln Ser Val Val Thr Gln Pro Pro Ser Val Ser Ala Ala Pro Gly Gln
1               5                   10                  15
```

```
Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Ser Val Val Phe Gly Gly Gly Thr Lys Leu Thr Val Leu
            100                 105                 110

<210> SEQ ID NO 373
<211> LENGTH: 108
<212> TYPE: PRT
<213> ORGANISM: Artificial Sequence
<220> FEATURE:
<223> OTHER INFORMATION: chemically synthesized

<400> SEQUENCE: 373

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Leu Val Trp Asp Ser Ser Ser Asp His
                85                  90                  95

Arg Ile Phe Gly Gly Gly Thr Lys Leu Thr Val Leu
            100                 105

<210> SEQ ID NO 374
<211> LENGTH: 108
<212> TYPE: PRT
<213> ORGANISM: Artificial Sequence
<220> FEATURE:
<223> OTHER INFORMATION: chemically synthesized

<400> SEQUENCE: 374

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Ile Phe Gly Gly Gly Thr Lys Leu Thr Val Leu
```

<210> SEQ ID NO 375
<211> LENGTH: 108
<212> TYPE: PRT
<213> ORGANISM: Artificial Sequence
<220> FEATURE:
<223> OTHER INFORMATION: chemically synthesized

<400> SEQUENCE: 375

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Ile Phe Gly Gly Gly Thr Lys Leu Thr Val Leu
            100                 105

<210> SEQ ID NO 376
<211> LENGTH: 108
<212> TYPE: PRT
<213> ORGANISM: Artificial Sequence
<220> FEATURE:
<223> OTHER INFORMATION: chemically synthesized

<400> SEQUENCE: 376

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Ile Phe Gly Gly Gly Thr Lys Leu Thr Val Leu
            100                 105

<210> SEQ ID NO 377
<211> LENGTH: 122
<212> TYPE: PRT
<213> ORGANISM: Artificial Sequence
<220> FEATURE:
<223> OTHER INFORMATION: chemically synthesized

<400> SEQUENCE: 377

Gln Val Gln Leu Val Gln Ser Gly Ser Glu Val Lys Lys Ser Gly Ser
1               5                   10                  15

Ser Val Lys Val Ser Cys Lys Thr Ser Gly Gly Thr Phe Ser Ile Thr
            20                  25                  30

Asn Tyr Ala Ile Asn Trp Val Arg Gln Ala Pro Gly Gln Gly Leu Glu
            35                  40                  45

Trp Met Gly Gly Ile Leu Pro Ile Phe Gly Ala Ala Lys Tyr Ala Gln
    50                  55                  60

Lys Phe Gln Asp Arg Val Thr Ile Thr Ala Asp Glu Ser Thr Asn Thr
65                  70                  75                  80

Ala Tyr Leu Glu Leu Ser Ser Leu Thr Ser Glu Asp Thr Ala Met Tyr
                85                  90                  95

Tyr Cys Ala Arg Gly Lys Arg Trp Leu Gln Ser Asp Leu Gln Tyr Trp
            100                 105                 110

Gly Gln Gly Thr Leu Val Thr Val Ser Ser
            115                 120

<210> SEQ ID NO 378
<211> LENGTH: 110
<212> TYPE: PRT
<213> ORGANISM: Artificial Sequence
<220> FEATURE:
<223> OTHER INFORMATION: chemically synthesized

<400> SEQUENCE: 378

Gln Pro Val Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Ser Tyr
            20                  25                  30

Asp Leu Val Ser Trp Tyr Gln Gln Ser Pro Gly Lys Val Pro Lys Leu
        35                  40                  45

Leu Ile Tyr Glu Gly Val Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Thr
                85                  90                  95

Arg Asn Phe Val Phe Gly Gly Gly Thr Gln Leu Thr Val Leu
            100                 105                 110

<210> SEQ ID NO 379
<211> LENGTH: 121
<212> TYPE: PRT
<213> ORGANISM: Artificial Sequence
<220> FEATURE:
<223> OTHER INFORMATION: chemically synthesized

<400> SEQUENCE: 379

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Ser Thr Gly Gly Ala Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ala Gly Gln Ser Arg Pro Gly Phe Asp Tyr Trp Gly 100                 105                 110

Gln Gly Thr Leu Val Thr Val Ser Ser
        115                 120

<210> SEQ ID NO 380
<211> LENGTH: 121
<212> TYPE: PRT
<213> ORGANISM: Artificial Sequence
<220> FEATURE:
<223> OTHER INFORMATION: chemically synthesized

<400> SEQUENCE: 380

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Ser Thr Gly Gly Ala Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ala Gly Gln Ser Trp Pro Gly Phe Asp Tyr Trp Gly
            100                 105                 110

Gln Gly Thr Leu Val Thr Val Ser Ser
        115                 120

<210> SEQ ID NO 381
<211> LENGTH: 121
<212> TYPE: PRT
<213> ORGANISM: Artificial Sequence
<220> FEATURE:
<223> OTHER INFORMATION: chemically synthesized

<400> SEQUENCE: 381

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Ser Thr Gly Gly Ala Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ala Gly Gln Ser Phe Pro Gly Phe Asp Tyr Trp Gly
            100                 105                 110

Gln Gly Thr Leu Val Thr Val Ser Ser
        115                 120

<210> SEQ ID NO 382
<211> LENGTH: 116
<212> TYPE: PRT
<213> ORGANISM: Artificial Sequence
<220> FEATURE:

<223> OTHER INFORMATION: chemically synthesized

<400> SEQUENCE: 382

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Ser Thr Gly Gly Ala Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Ala Phe Asp Tyr Trp Gly Gln Gly Thr Leu Val
            100                 105                 110

Thr Val Ser Ser
        115

<210> SEQ ID NO 383
<211> LENGTH: 116
<212> TYPE: PRT
<213> ORGANISM: Artificial Sequence
<220> FEATURE:
<223> OTHER INFORMATION: chemically synthesized

<400> SEQUENCE: 383

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Ser Thr Gly Gly Ala Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Gly Tyr Asp Tyr Trp Gly Gln Gly Thr Leu Val
            100                 105                 110

Thr Val Ser Ser
        115

<210> SEQ ID NO 384
<211> LENGTH: 116
<212> TYPE: PRT
<213> ORGANISM: Artificial Sequence
<220> FEATURE:
<223> OTHER INFORMATION: chemically synthesized

<400> SEQUENCE: 384

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45
Ser Ser Ile Tyr Ser Thr Gly Gly Ala Thr Ala Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Trp Ser Lys Gly Phe Asp Tyr Trp Gly Gln Gly Thr Leu Val
            100                 105                 110
Thr Val Ser Ser
            115

<210> SEQ ID NO 385
<211> LENGTH: 113
<212> TYPE: PRT
<213> ORGANISM: Artificial Sequence
<220> FEATURE:
<223> OTHER INFORMATION: chemically synthesized

<400> SEQUENCE: 385

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ser Ile Trp Lys Gln Gly Ile Val Thr Val Tyr Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Lys Ser Ser Ala Gly Phe Asp Tyr Trp Gly Gln Gly Thr Leu Val Thr
            100                 105                 110
Val

<210> SEQ ID NO 386
<211> LENGTH: 115
<212> TYPE: PRT
<213> ORGANISM: Artificial Sequence
<220> FEATURE:
<223> OTHER INFORMATION: chemically synthesized

<400> SEQUENCE: 386

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ser Ile Trp Arg Asn Gly Ile Val Thr Val Tyr Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Lys Ser Ser Ala Gly Phe Asp Tyr Trp Gly Gln Gly Thr Leu Val Thr
```

-continued

```
                100                 105                 110

Val Ser Ser
        115

<210> SEQ ID NO 387
<211> LENGTH: 115
<212> TYPE: PRT
<213> ORGANISM: Artificial Sequence
<220> FEATURE:
<223> OTHER INFORMATION: chemically synthesized

<400> SEQUENCE: 387

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Trp Lys Gln Gly Met Val Thr Val Tyr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Ser Ala Gly Phe Asp Tyr Trp Gly Gln Gly Thr Leu Val Thr
            100                 105                 110

Val Ser Ser
        115

<210> SEQ ID NO 388
<211> LENGTH: 115
<212> TYPE: PRT
<213> ORGANISM: Artificial Sequence
<220> FEATURE:
<223> OTHER INFORMATION: chemically synthesized

<400> SEQUENCE: 388

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Gln Gly Leu Ala Thr Ala Tyr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Ser Ala Gly Phe Asp Tyr Trp Gly Gln Gly Thr Leu Val Thr
            100                 105                 110

Val Ser Ser
        115

<210> SEQ ID NO 389
<211> LENGTH: 115
<212> TYPE: PRT
<213> ORGANISM: Artificial Sequence
<220> FEATURE:
```

<223> OTHER INFORMATION: chemically synthesized

<400> SEQUENCE: 389

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Glu Ile Val Ala Thr Gly Ile Leu Thr Ser Tyr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Ser Ala Gly Phe Asp Tyr Trp Gly Gln Gly Thr Leu Val Thr
            100                 105                 110

Val Ser Ser
        115
```

<210> SEQ ID NO 390
<211> LENGTH: 115
<212> TYPE: PRT
<213> ORGANISM: Artificial Sequence
<220> FEATURE:
<223> OTHER INFORMATION: chemically synthesized

<400> SEQUENCE: 390

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Arg Gln Gly Leu Ile Thr Val Tyr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Ser Ala Gly Phe Asp Tyr Trp Gly Gln Gly Thr Leu Val Thr
            100                 105                 110

Val Ser Ser
        115
```

<210> SEQ ID NO 391
<211> LENGTH: 115
<212> TYPE: PRT
<213> ORGANISM: Artificial Sequence
<220> FEATURE:
<223> OTHER INFORMATION: chemically synthesized

<400> SEQUENCE: 391

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
            35                  40                  45

Ser Ser Ile Trp Tyr Gln Gly Leu Val Thr Val Tyr Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ser Ser Ala Gly Phe Asp Tyr Trp Gly Gln Gly Thr Leu Val Thr
            100                 105                 110

Val Ser Ser
        115

<210> SEQ ID NO 392
<211> LENGTH: 114
<212> TYPE: PRT
<213> ORGANISM: Artificial Sequence
<220> FEATURE:
<223> OTHER INFORMATION: chemically synthesized

<400> SEQUENCE: 392

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Asp Ile Trp Lys Gln Gly Phe Ala Thr Ala Asp Ser Val Lys Gly
    50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
                 85                  90                  95

Ser Ser Ala Gly Phe Asp Tyr Trp Gly Gln Gly Thr Leu Val Thr Val
            100                 105                 110

Ser Ser

<210> SEQ ID NO 393
<211> LENGTH: 115
<212> TYPE: PRT
<213> ORGANISM: Artificial Sequence
<220> FEATURE:
<223> OTHER INFORMATION: chemically synthesized

<400> SEQUENCE: 393

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ser Ile Trp Lys Gln Gly Ile Val Thr Val Tyr Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ser Ser Ala Gly Phe Asp Tyr Trp Gly Gln Gly Thr Leu Val Thr
```

Val Ser Ser
    115

<210> SEQ ID NO 394
<211> LENGTH: 115
<212> TYPE: PRT
<213> ORGANISM: Artificial Sequence
<220> FEATURE:
<223> OTHER INFORMATION: chemically synthesized

<400> SEQUENCE: 394

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Gln Gly Leu Ala Thr Ala Tyr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Ser Ala Gly Phe Asp Tyr Trp Gly Gln Gly Thr Leu Val Thr
            100                 105                 110

Val Ser Ser
    115

<210> SEQ ID NO 395
<211> LENGTH: 116
<212> TYPE: PRT
<213> ORGANISM: Artificial Sequence
<220> FEATURE:
<223> OTHER INFORMATION: chemically synthesized

<400> SEQUENCE: 395

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Ala Phe Asp Tyr Trp Gly Gln Gly Thr Leu Val
            100                 105                 110

Thr Val Ser Ser
    115

<210> SEQ ID NO 396
<211> LENGTH: 116
<212> TYPE: PRT
<213> ORGANISM: Artificial Sequence
<220> FEATURE:

<223> OTHER INFORMATION: chemically synthesized

<400> SEQUENCE: 396

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Gly Tyr Asp Tyr Trp Gly Gln Gly Thr Leu Val
            100                 105                 110

Thr Val Ser Ser
            115

<210> SEQ ID NO 397
<211> LENGTH: 116
<212> TYPE: PRT
<213> ORGANISM: Artificial Sequence
<220> FEATURE:
<223> OTHER INFORMATION: chemically synthesized

<400> SEQUENCE: 397

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Lys Gly Phe Asp Tyr Trp Gly Gln Gly Thr Leu Val
            100                 105                 110

Thr Val Ser Ser
            115

<210> SEQ ID NO 398
<211> LENGTH: 120
<212> TYPE: PRT
<213> ORGANISM: Artificial Sequence
<220> FEATURE:
<223> OTHER INFORMATION: chemically synthesized

<400> SEQUENCE: 398

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Glu Thr Ser Trp Val Arg Gln Ala Pro Gly Lys Gly Leu Glu

```
                35                  40                  45
Trp Val Ser Ser Ile Trp Tyr Gln Gly Leu Val Thr Val Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Trp Ser Ala Ala Phe Asp Tyr Trp Gly Gln
            100                 105                 110

Gly Thr Leu Val Thr Val Ser Ser
            115                 120

<210> SEQ ID NO 399
<211> LENGTH: 116
<212> TYPE: PRT
<213> ORGANISM: Artificial Sequence
<220> FEATURE:
<223> OTHER INFORMATION: chemically synthesized

<400> SEQUENCE: 399

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
                35                  40                  45

Ser Ser Ile Trp Tyr Gln Gly Leu Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Gly Tyr Asp Tyr Trp Gly Gln Gly Thr Leu Val
            100                 105                 110

Thr Val Ser Ser
            115

<210> SEQ ID NO 400
<211> LENGTH: 116
<212> TYPE: PRT
<213> ORGANISM: Artificial Sequence
<220> FEATURE:
<223> OTHER INFORMATION: chemically synthesized

<400> SEQUENCE: 400

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
                35                  40                  45

Ser Ser Ile Trp Tyr Gln Gly Leu Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Trp Ser Lys Gly Phe Asp Tyr Trp Gly Gln Gly Thr Leu Val
            100                 105                 110

Thr Val Ser Ser
        115

<210> SEQ ID NO 401
<211> LENGTH: 108
<212> TYPE: PRT
<213> ORGANISM: Artificial Sequence
<220> FEATURE:
<223> OTHER INFORMATION: chemically synthesized

<400> SEQUENCE: 401

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asn Gly Tyr Pro Ser
                85                  90                  95

Thr Phe Gly Gln Gly Thr Lys Val Glu Ile Lys Arg
            100                 105

<210> SEQ ID NO 402
<211> LENGTH: 108
<212> TYPE: PRT
<213> ORGANISM: Artificial Sequence
<220> FEATURE:
<223> OTHER INFORMATION: chemically synthesized

<400> SEQUENCE: 402

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asn Gly Tyr Pro Ser
                85                  90                  95

Thr Phe Gly Gln Gly Thr Lys Val Glu Ile Lys Arg
            100                 105

<210> SEQ ID NO 403
<211> LENGTH: 108
<212> TYPE: PRT
<213> ORGANISM: Artificial Sequence
<220> FEATURE:
<223> OTHER INFORMATION: chemically synthesized

<400> SEQUENCE: 403

Asp Ile Gln Met Thr Gln Ser Pro Ser Ser Leu Ser Ala Ser Val Gly
```

```
                1               5                   10                  15
            Asp Arg Val Thr Ile Thr Cys Arg Ala Ser Gln Ser Ile Ser Ser Tyr
                            20                  25                  30

Leu Asn Trp Tyr Gln Gln Lys Pro Gly Lys Ala Pro Lys Leu Leu Ile
                            35                  40                  45

Tyr Ala Ala Ser Ser Leu Gln Ser Gly Val Pro Ser Arg Phe Ser Gly
                            50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Gln Gln Asp Asn Gly Tyr Pro Ser
                            85                  90                  95

Thr Phe Gly Gly Gly Thr Lys Val Glu Ile Lys Arg
                            100                 105

<210> SEQ ID NO 404
<211> LENGTH: 240
<212> TYPE: PRT
<213> ORGANISM: Artificial Sequence
<220> FEATURE:
<223> OTHER INFORMATION: chemically synthesized

<400> SEQUENCE: 404

Glu Val Gln Leu Leu Glu Ser Gly Gly Gly Leu Val Gln Pro Gly Gly
            1               5                   10                  15

Ser Leu Arg Leu Ser Cys Ala Ala Ser Gly Phe Thr Phe Ser Ser Tyr
                            20                  25                  30

Ala Met Ser Trp Val Arg Gln Ala Pro Gly Lys Gly Leu Glu Trp Val
                            35                  40                  45

Ser Asp Ile Thr Ala Ser Gly Gln Arg Thr Thr Tyr Ala Asp Ser Val
                            50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                            85                  90                  95

Ala Arg Ser Lys Ile Ala Phe Asp Tyr Trp Gly Gln Gly Thr Leu Val
                            100                 105                 110

Thr Val Ser Ser Gly Gly Gly Ser Gly Gly Gly Ser Gly Gly
                            115                 120                 125

Gly Gly Ser Thr Asp Ile Gln Met Thr Gln Ser Pro Ser Ser Leu Ser
                        130                 135                 140

Ala Ser Val Gly Asp Arg Val Thr Ile Thr Cys Arg Ala Ser Gln Ser
            145                 150                 155                 160

Ile Ser Ser Tyr Leu Asn Trp Tyr Gln Gln Lys Pro Gly Lys Ala Pro
                            165                 170                 175

Lys Leu Leu Ile Tyr Lys Ala Ser Arg Leu Gln Ser Gly Val Pro Ser
                            180                 185                 190

Arg Phe Ser Gly Ser Gly Ser Gly Thr Asp Phe Thr Leu Thr Ile Ser
                            195                 200                 205

Ser Leu Gln Pro Glu Asp Phe Ala Thr Tyr Tyr Cys Gln Gln Arg Ala
                            210                 215                 220

Leu Lys Pro Val Thr Phe Gly Gln Gly Thr Lys Val Glu Ile Lys Arg
            225                 230                 235                 240

<210> SEQ ID NO 405
<211> LENGTH: 240
<212> TYPE: PRT
```

<213> ORGANISM: Artificial Sequence
<220> FEATURE:
<223> OTHER INFORMATION: chemically synthesized

<400> SEQUENCE: 405

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asn Lys Asp Gly His Tyr Thr Ser Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asn Leu Asp Glu Phe Asp Tyr Trp Gly Gln Gly Thr Leu Val
        100                 105                 110

Thr Val Ser Ser Gly Gly Gly Gly Ser Gly Gly Gly Gly Ser Gly Gly
    115                 120                 125

Gly Gly Ser Thr Asp Ile Gln Met Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
            165                 170                 175

Lys Leu Leu Ile Tyr Ala Ala Ser Ser Leu Gln Ser Gly Val Pro Ser
        180                 185                 190

Arg Phe Ser Gly Ser Gly Ser Gly Thr Asp Phe Thr Leu Thr Ile Ser
    195                 200                 205

Ser Leu Gln Pro Glu Asp Phe Ala Thr Tyr Tyr Cys Gln Gln Ser Tyr
210                 215                 220

Ser Thr Pro Asn Thr Phe Gly Gln Gly Thr Lys Val Glu Ile Lys Arg
225                 230                 235                 240
```

<210> SEQ ID NO 406
<211> LENGTH: 240
<212> TYPE: PRT
<213> ORGANISM: Artificial Sequence
<220> FEATURE:
<223> OTHER INFORMATION: chemically synthesized

<400> SEQUENCE: 406

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Met Ala Thr Gly Ala Gly Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95
```

Ala Lys Asp Gly Ala Gly Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Thr Asp Ile Gln Met Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ser Ala Ser Gln Leu Gln Ser Gly Val Pro Ser
            180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Ala Asn
        210                 215                 220

Ser Arg Pro Ser Thr Phe Gly Gln Gly Thr Lys Val Glu Ile Lys Arg
225                 230                 235                 240

<210> SEQ ID NO 407
<211> LENGTH: 240
<212> TYPE: PRT
<213> ORGANISM: Artificial Sequence
<220> FEATURE:
<223> OTHER INFORMATION: chemically synthesized

<400> SEQUENCE: 407

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Gln Trp Val
        35                  40                  45

Ser Thr Ile Thr Ser Ser Gly Ala Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Tyr Thr Gly Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Asn Ala Ser Ser Leu Gln Ser Gly Val Pro Ser
            180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Tyr Thr
        210                 215                 220

Tyr Gly Pro Gly Thr Phe Gly Gln Gly Thr Lys Val Glu Ile Lys Arg
225                 230                 235                 240

<210> SEQ ID NO 408
<211> LENGTH: 240
<212> TYPE: PRT
<213> ORGANISM: Artificial Sequence
<220> FEATURE:
<223> OTHER INFORMATION: chemically synthesized

<400> SEQUENCE: 408

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Ser Thr Gly Gly Ala Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ala Gly Phe Asp Tyr Trp Gly Gln Gly Thr Leu Val
            100                 105                 110

Thr Val Ser Ser Gly Gly Gly Gly Ser Gly Gly Gly Ser Gly Gly
        115                 120                 125

Gly Gly Ser Thr Asp Ile Gln Met Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Tyr Ala Ser Thr Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Asp Asn
    210                 215                 220

Gly Tyr Pro Ser Thr Phe Gly Gln Gly Thr Lys Val Glu Ile Lys Arg
225                 230                 235                 240

<210> SEQ ID NO 409
<211> LENGTH: 122
<212> TYPE: PRT
<213> ORGANISM: Artificial Sequence
<220> FEATURE:
<223> OTHER INFORMATION: chemically synthesized

<400> SEQUENCE: 409

Gln Leu Gln Leu Gln Glu Ser Gly Gly Gly Leu Val Gln Ala Gly Gly
1               5                   10                  15

Ser Leu Arg Leu Ser Cys Ala Ala Ser Gly Ile Met Phe Tyr Ile Ser
            20                  25                  30

Asp Met Gly Trp Tyr Arg Gln Ala Pro Gly Lys Gln Arg Glu Phe Val
        35                  40                  45

Ala Thr Ile Thr Ser Gly Gly Thr Thr Asn Tyr Ala Asp Ser Val Glu
    50                  55                  60

Gly Arg Phe Ser Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Thr
                85                  90                  95

Ala His Gly Pro Thr Tyr Gly Ser Thr Trp Asp Asp Leu Trp Gly Gln
            100                 105                 110

Gly Thr Gln Val Thr Val Lys Pro Gly Gly
        115                 120

<210> SEQ ID NO 410
<211> LENGTH: 8
<212> TYPE: PRT
<213> ORGANISM: Artificial Sequence
<220> FEATURE:
<223> OTHER INFORMATION: chemically synthesized

<400> SEQUENCE: 410

Gly Ile Met Phe Tyr Ile Ser Asp
1               5

<210> SEQ ID NO 411
<211> LENGTH: 10
<212> TYPE: PRT
<213> ORGANISM: Artificial Sequence
<220> FEATURE:
<223> OTHER INFORMATION: chemically synthesized

<400> SEQUENCE: 411

Thr Ile Thr Ser Gly Gly Thr Thr Asn Tyr
1               5                   10

<210> SEQ ID NO 412
<211> LENGTH: 14
<212> TYPE: PRT
<213> ORGANISM: Artificial Sequence
<220> FEATURE:
<223> OTHER INFORMATION: chemically synthesized

<400> SEQUENCE: 412

Thr Ala His Gly Pro Thr Tyr Gly Ser Thr Trp Asp Asp Leu
1               5                   10

<210> SEQ ID NO 413
<211> LENGTH: 113
<212> TYPE: PRT
<213> ORGANISM: Artificial Sequence
<220> FEATURE:
<223> OTHER INFORMATION: chemically synthesized

<400> SEQUENCE: 413

Gln Val Gln Leu Gln Glu Ser Gly Gly Gly Leu Val Gln Ala Gly Gly
1               5                   10                  15

Ser Leu Arg Leu Ser Cys Ala Ala Ser Glu Thr Phe Gly Val Val Phe
            20                  25                  30

Thr Leu Gly Trp Tyr Arg Gln Thr Pro Gly Lys Gln Arg Glu Phe Val
        35                  40                  45

Ala Arg Val Thr Gly Thr Asp Thr Val Asp Tyr Ala Asp Ser Val Lys
    50                  55                  60

Gly Arg Phe Thr Ile Ser Ser Asp Phe Ala Arg Asn Thr Val Tyr Leu
65                  70                  75                  80

Gln Met Asn Asn Leu Lys Pro Glu Asp Thr Ala Val Tyr Tyr Cys Asn
                85                  90                  95

Thr Gly Ala Tyr Trp Gly Gln Gly Thr Gln Val Thr Val Lys Pro Gly
            100                 105                 110
Gly

<210> SEQ ID NO 414
<211> LENGTH: 7
<212> TYPE: PRT
<213> ORGANISM: Artificial Sequence
<220> FEATURE:
<223> OTHER INFORMATION: chemically synthesized

<400> SEQUENCE: 414

Thr Phe Gly Val Val Phe Thr
1               5

<210> SEQ ID NO 415
<211> LENGTH: 7
<212> TYPE: PRT
<213> ORGANISM: Artificial Sequence
<220> FEATURE:
<223> OTHER INFORMATION: chemically synthesized

<400> SEQUENCE: 415

Val Thr Gly Thr Asp Thr Val
1               5

<210> SEQ ID NO 416
<211> LENGTH: 5
<212> TYPE: PRT
<213> ORGANISM: Artificial Sequence
<220> FEATURE:
<223> OTHER INFORMATION: chemically synthesized

<400> SEQUENCE: 416

Asn Thr Gly Ala Tyr
1               5

<210> SEQ ID NO 417
<211> LENGTH: 119
<212> TYPE: PRT
<213> ORGANISM: Artificial Sequence
<220> FEATURE:
<223> OTHER INFORMATION: chemically synthesized

<400> SEQUENCE: 417

Gln Val Gln Leu Val Gln Ser Gly Gly Leu Val Gln Thr Gly Gly
1               5                   10                  15

Ser Leu Arg Leu Ser Cys Ala Ala Ser Gly Arg Thr Ala Ser Thr Tyr
                20                  25                  30

Ser Met Gly Trp Phe Arg Gln Ala Pro Gly Lys Glu Arg Gln Phe Val
            35                  40                  45

Ala Arg Ile Ile Trp Ser Thr Gly Ser Thr Tyr Tyr Thr Asn Ser Val
        50                  55                  60

Glu Gly Arg Phe Thr Ile Ser Arg Asp Ile Ala Lys Asn Thr Leu Tyr
65                  70                  75                  80

Leu Gln Met Asn Ser Leu Glu Pro Glu Asp Thr Ala Val Tyr Tyr Cys
                85                  90                  95

Thr Ala Arg Glu Pro Thr Gly Tyr Asp Tyr Trp Gly Gln Gly Thr Gln
            100                 105                 110

Val Thr Val Lys Pro Gly Gly
        115

<210> SEQ ID NO 418
<211> LENGTH: 8
<212> TYPE: PRT
<213> ORGANISM: Artificial Sequence
<220> FEATURE:
<223> OTHER INFORMATION: chemically synthesized

<400> SEQUENCE: 418

Gly Arg Thr Ala Ser Thr Tyr Ser
1               5

<210> SEQ ID NO 419
<211> LENGTH: 7
<212> TYPE: PRT
<213> ORGANISM: Artificial Sequence
<220> FEATURE:
<223> OTHER INFORMATION: chemically synthesized

<400> SEQUENCE: 419

Ile Trp Ser Thr Gly Ser Thr
1               5

<210> SEQ ID NO 420
<211> LENGTH: 10
<212> TYPE: PRT
<213> ORGANISM: Artificial Sequence
<220> FEATURE:
<223> OTHER INFORMATION: chemically synthesized

<400> SEQUENCE: 420

Thr Ala Arg Glu Pro Thr Gly Tyr Asp Tyr
1               5                   10

<210> SEQ ID NO 421
<211> LENGTH: 122
<212> TYPE: PRT
<213> ORGANISM: Artificial Sequence
<220> FEATURE:
<223> OTHER INFORMATION: chemically synthesized

<400> SEQUENCE: 421

Gln Leu Gln Leu Gln Glu Ser Gly Gly Gly Leu Val Gln Ala Gly Gly
1               5                   10                  15

Ser Leu Gly Leu Ser Cys Ala Ala Ser Gly Ser Ile Phe Arg Phe Gly
            20                  25                  30

Ala Arg Gly Trp Tyr Arg Gln Ala Pro Gly Lys Gln Arg Glu Leu Val
        35                  40                  45

Ala Ile Ile Thr Ser Gly Gly Ser Thr Asn Tyr Ala Asp Ser Val Gln
    50                  55                  60

Gly Arg Phe Thr Ile Ser Arg Asp Asn Ala Lys Asn Met Val Tyr Leu
65                  70                  75                  80

Gln Met Asn Gly Leu Lys Ser Gly Asp Thr Ala Val Tyr Tyr Cys Ala
                85                  90                  95

Ala Asp Arg Ser Asp Ala Val Gly Val Gly Trp Asp Tyr Trp Gly Gln
            100                 105                 110

Gly Thr Gln Val Thr Val Lys Pro Gly Gly
        115                 120

<210> SEQ ID NO 422
<211> LENGTH: 8
<212> TYPE: PRT
<213> ORGANISM: Artificial Sequence
<220> FEATURE:

<223> OTHER INFORMATION: chemically synthesized

<400> SEQUENCE: 422

Gly Ser Ile Phe Arg Phe Gly Ala
1               5

<210> SEQ ID NO 423
<211> LENGTH: 7
<212> TYPE: PRT
<213> ORGANISM: Artificial Sequence
<220> FEATURE:
<223> OTHER INFORMATION: chemically synthesized

<400> SEQUENCE: 423

Ile Thr Ser Gly Gly Ser Thr
1               5

<210> SEQ ID NO 424
<211> LENGTH: 14
<212> TYPE: PRT
<213> ORGANISM: Artificial Sequence
<220> FEATURE:
<223> OTHER INFORMATION: chemically synthesized

<400> SEQUENCE: 424

Ala Ala Asp Arg Ser Asp Ala Val Gly Val Gly Trp Asp Tyr
1               5                   10

<210> SEQ ID NO 425
<211> LENGTH: 119
<212> TYPE: PRT
<213> ORGANISM: Artificial Sequence
<220> FEATURE:
<223> OTHER INFORMATION: chemically synthesized

<400> SEQUENCE: 425

Gln Val Gln Leu Gln Gln Ser Gly Gly Leu Val Gln Thr Gly Gly
1               5                   10                  15

Ser Leu Arg Leu Ser Cys Ala Ala Ser Gly Arg Thr Ala Ser Thr Tyr
            20                  25                  30

Ser Met Gly Trp Phe Arg Gln Ala Pro Gly Lys Glu Arg Gln Phe Val
        35                  40                  45

Ala Arg Ile Ile Trp Ser Thr Gly Ser Thr Tyr Tyr Thr Asn Ser Val
    50                  55                  60

Glu Gly Arg Phe Thr Ile Ser Arg Asp Ile Ala Lys Asn Thr Leu Tyr
65                  70                  75                  80

Leu Gln Met Asn Ser Leu Glu Pro Glu Asp Thr Ala Val Tyr Tyr Cys
                85                  90                  95

Thr Ala Arg Asp Pro Thr Gly Tyr Asp Tyr Trp Gly Gln Gly Thr Gln
            100                 105                 110

Val Thr Val Lys Pro Gly Gly
        115

<210> SEQ ID NO 426
<211> LENGTH: 8
<212> TYPE: PRT
<213> ORGANISM: Artificial Sequence
<220> FEATURE:
<223> OTHER INFORMATION: chemically synthesized

<400> SEQUENCE: 426

Ile Ile Trp Ser Thr Gly Ser Thr
1               5

<210> SEQ ID NO 427
<211> LENGTH: 10
<212> TYPE: PRT
<213> ORGANISM: Artificial Sequence
<220> FEATURE:
<223> OTHER INFORMATION: chemically synthesized

<400> SEQUENCE: 427

Thr Ala Arg Asp Pro Thr Gly Tyr Asp Tyr
1               5                   10

<210> SEQ ID NO 428
<211> LENGTH: 121
<212> TYPE: PRT
<213> ORGANISM: Artificial Sequence
<220> FEATURE:
<223> OTHER INFORMATION: chemically synthesized

<400> SEQUENCE: 428

Gln Leu Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asp
            20                  25                  30

Ala Thr Ala Trp Tyr Arg Gln Ala Pro Gly Lys Gln Arg Glu Leu Val
        35                  40                  45

Ala Ile Ile Thr Ser Ser Gly Ser Thr Asn Tyr Pro Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Asn Pro Glu Asp Thr Ala Leu Tyr Ser Cys Asn
                85                  90                  95

Ala Ile Thr Arg Met Gly Gly Ser Thr Tyr Asp Phe Trp Gly Gln Gly
            100                 105                 110

Thr Gln Val Thr Val Lys Pro Gly Gly
        115                 120

<210> SEQ ID NO 429
<211> LENGTH: 8
<212> TYPE: PRT
<213> ORGANISM: Artificial Sequence
<220> FEATURE:
<223> OTHER INFORMATION: chemically synthesized

<400> SEQUENCE: 429

Gly Ser Ile Phe Ser Ile Asp Ala
1               5

<210> SEQ ID NO 430
<211> LENGTH: 7
<212> TYPE: PRT
<213> ORGANISM: Artificial Sequence
<220> FEATURE:
<223> OTHER INFORMATION: chemically synthesized

<400> SEQUENCE: 430

Ile Thr Ser Ser Gly Ser Thr
1               5

<210> SEQ ID NO 431
<211> LENGTH: 13
<212> TYPE: PRT
<213> ORGANISM: Artificial Sequence
<220> FEATURE:
<223> OTHER INFORMATION: chemically synthesized

<400> SEQUENCE: 431

Asn Ala Ile Thr Arg Met Gly Gly Ser Thr Tyr Asp Phe
1               5                   10

<210> SEQ ID NO 432
<211> LENGTH: 117
<212> TYPE: PRT
<213> ORGANISM: Artificial Sequence
<220> FEATURE:
<223> OTHER INFORMATION: chemically synthesized

<400> SEQUENCE: 432

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Pro Ala Gly Asp Gly Ser Thr Lys Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Phe Cys
                85                  90                  95

Ala Lys Ser Arg Gly Trp Ser Thr Val Asp Asp Met Asp Tyr Trp Gly
            100                 105                 110

Lys Gly Thr Gln Val
        115

<210> SEQ ID NO 433
<211> LENGTH: 8
<212> TYPE: PRT
<213> ORGANISM: Artificial Sequence
<220> FEATURE:
<223> OTHER INFORMATION: chemically synthesized

<400> SEQUENCE: 433

Gly Phe Thr Phe Ser Ser Tyr Ala
1               5

<210> SEQ ID NO 434
<211> LENGTH: 8
<212> TYPE: PRT
<213> ORGANISM: Artificial Sequence
<220> FEATURE:
<223> OTHER INFORMATION: chemically synthesized

<400> SEQUENCE: 434

Ile Pro Ala Gly Asp Gly Ser Thr
1               5

<210> SEQ ID NO 435
<211> LENGTH: 14
<212> TYPE: PRT
<213> ORGANISM: Artificial Sequence
<220> FEATURE:
<223> OTHER INFORMATION: chemically synthesized

<400> SEQUENCE: 435

Ala Lys Ser Arg Gly Trp Ser Thr Val Asp Asp Met Asp Tyr

<210> SEQ ID NO 436
<211> LENGTH: 117
<212> TYPE: PRT
<213> ORGANISM: Artificial Sequence
<220> FEATURE:
<223> OTHER INFORMATION: chemically synthesized

<400> SEQUENCE: 436

Gln Val Gln Leu Val Gln Ser Gly Gly Gly Leu Val Gln Pro Gly Gly
1               5                   10                  15
Ser Leu Arg Leu Ser Cys Val Val Ser Gly Phe Thr Phe Arg Ser Tyr
            20                  25                  30
Ala Met Ser Trp Val Arg Gln Ala Pro Gly Lys Gly Leu Glu Trp Val
        35                  40                  45
Ser Thr Ile Asn Ser Gly Glu Ser Ser Thr Lys Tyr Ala Asp Ser Val
    50                  55                  60
Lys Gly Arg Phe Thr Ile Ser Arg Asp Asp Ala Lys Asn Thr Leu Tyr
65                  70                  75                  80
Leu Gln Met Ser Asp Leu Lys Pro Glu Asp Thr Ala Val Tyr Phe Cys
                85                  90                  95
Ala Lys His Arg Gly Trp Ser Thr Val Asp Asp Ile Asn Tyr Trp Gly
            100                 105                 110
Lys Gly Thr Gln Val
        115

<210> SEQ ID NO 437
<211> LENGTH: 8
<212> TYPE: PRT
<213> ORGANISM: Artificial Sequence
<220> FEATURE:
<223> OTHER INFORMATION: chemically synthesized

<400> SEQUENCE: 437

Gly Phe Thr Phe Arg Ser Tyr Ala
1               5

<210> SEQ ID NO 438
<211> LENGTH: 8
<212> TYPE: PRT
<213> ORGANISM: Artificial Sequence
<220> FEATURE:
<223> OTHER INFORMATION: chemically synthesized

<400> SEQUENCE: 438

Ile Asn Ser Gly Glu Ser Ser Thr
1               5

<210> SEQ ID NO 439
<211> LENGTH: 14
<212> TYPE: PRT
<213> ORGANISM: Artificial Sequence
<220> FEATURE:
<223> OTHER INFORMATION: chemically synthesized

<400> SEQUENCE: 439

Ala Lys His Arg Gly Trp Ser Thr Val Asp Asp Ile Asn Tyr
1               5                   10

<210> SEQ ID NO 440
<211> LENGTH: 119
<212> TYPE: PRT

```
<213> ORGANISM: Artificial Sequence
<220> FEATURE:
<223> OTHER INFORMATION: chemically synthesized

<400> SEQUENCE: 440

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp His
            20                  25                  30

Ala Met Ser Trp Val Arg Gln Ala Pro Gly Lys Gly Leu Glu Trp Val
        35                  40                  45

Ser Ala Ile Ser Trp Asn Gly His Tyr Thr Tyr Tyr Ala Glu Ser Met
    50                  55                  60

Lys Gly Arg Phe Ala Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Lys Gly Trp Arg Gly Ser Tyr Thr Arg Asp Arg Pro Phe Ala Ser
            100                 105                 110

Trp Gly Gln Gly Thr Gln Val
        115

<210> SEQ ID NO 441
<211> LENGTH: 8
<212> TYPE: PRT
<213> ORGANISM: Artificial Sequence
<220> FEATURE:
<223> OTHER INFORMATION: chemically synthesized

<400> SEQUENCE: 441

Gly Phe Thr Phe Asp Asp His Ala
1               5

<210> SEQ ID NO 442
<211> LENGTH: 8
<212> TYPE: PRT
<213> ORGANISM: Artificial Sequence
<220> FEATURE:
<223> OTHER INFORMATION: chemically synthesized

<400> SEQUENCE: 442

Ile Ser Trp Asn Gly His Tyr Thr
1               5

<210> SEQ ID NO 443
<211> LENGTH: 16
<212> TYPE: PRT
<213> ORGANISM: Artificial Sequence
<220> FEATURE:
<223> OTHER INFORMATION: chemically synthesized

<400> SEQUENCE: 443

Val Lys Gly Trp Arg Gly Ser Tyr Thr Arg Asp Arg Pro Phe Ala Ser
1               5                   10                  15

<210> SEQ ID NO 444
<211> LENGTH: 118
<212> TYPE: PRT
<213> ORGANISM: Artificial Sequence
<220> FEATURE:
<223> OTHER INFORMATION: chemically synthesized

<400> SEQUENCE: 444
```

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ser Thr Asn Thr Gly Gly Ser Thr Tyr Tyr Ala Tyr
    50                  55                  60

Ala Asp Ser Val Lys Gly Arg Phe Thr Ile Ser Arg Asp Asn Ala Lys
65                  70                  75                  80

Asn Thr Leu Tyr Leu Glu Met Asn Ser Leu Lys Pro Glu Asp Thr Ala
                85                  90                  95

Gln Tyr Tyr Cys Val Arg Thr Arg Trp Glu Gly Val Tyr Asp Tyr Trp
            100                 105                 110

Gly Leu Gly Thr Gln Val
        115
```

<210> SEQ ID NO 445
<211> LENGTH: 8
<212> TYPE: PRT
<213> ORGANISM: Artificial Sequence
<220> FEATURE:
<223> OTHER INFORMATION: chemically synthesized

<400> SEQUENCE: 445

```
Gly Phe Thr Phe Ser Ser Tyr Tyr
1               5
```

<210> SEQ ID NO 446
<211> LENGTH: 10
<212> TYPE: PRT
<213> ORGANISM: Artificial Sequence
<220> FEATURE:
<223> OTHER INFORMATION: chemically synthesized

<400> SEQUENCE: 446

```
Ile Ser Thr Asn Thr Gly Gly Gly Ser Thr
1               5                   10
```

<210> SEQ ID NO 447
<211> LENGTH: 11
<212> TYPE: PRT
<213> ORGANISM: Artificial Sequence
<220> FEATURE:
<223> OTHER INFORMATION: chemically synthesized

<400> SEQUENCE: 447

```
Val Arg Thr Arg Trp Glu Gly Val Tyr Asp Tyr
1               5                   10
```

<210> SEQ ID NO 448
<211> LENGTH: 482
<212> TYPE: PRT
<213> ORGANISM: Artificial Sequence
<220> FEATURE:
<223> OTHER INFORMATION: chemically synthesized

<400> SEQUENCE: 448

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Ser Phe Ser Ile Asn
            20                  25                  30
```

-continued

Ala Met Gly Trp Tyr Arg Gln Ala Pro Gly Lys Arg Glu Phe Val
          35                  40                  45

Ala Ala Ile Glu Ser Gly Arg Asn Thr Val Tyr Ala Glu Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro Gly Gly Gly Asp Lys Thr
        115                 120                 125

His Thr Cys Pro Pro Cys Pro Ala Pro Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Ser Gly Gly Gly
            340                 345                 350

Gly Ser Gly Gly Gly Ser Glu Val Gln Leu Leu Glu Ser Gly Gly
        355                 360                 365

Gly Glu Val Gln Pro Gly Gly Ser Leu Arg Leu Ser Cys Ala Ala Ser
    370                 375                 380

Gly Phe Ser Phe Ser Ile Asn Ala Met Gly Trp Tyr Arg Gln Ala Pro
385                 390                 395                 400

Gly Lys Arg Arg Glu Phe Val Ala Ala Ile Glu Ser Gly Arg Asn Thr
                405                 410                 415

Val Tyr Ala Glu Ser Val Lys Gly Arg Phe Thr Ile Ser Arg Asp Asn
            420                 425                 430

Ala Lys Asn Thr Val Tyr Leu Gln Met Ser Ser Leu Arg Ala Glu Asp
        435                 440                 445

Thr Ala Val Tyr Tyr Cys Gly Leu Leu Lys Gly Asn Arg Val Val Ser

```
                450            455            460
Pro Ser Val Ala Tyr Trp Gly Gln Gly Thr Leu Val Thr Val Lys Pro
465                 470                 475                 480

Gly Gly

<210> SEQ ID NO 449
<211> LENGTH: 466
<212> TYPE: PRT
<213> ORGANISM: Artificial Sequence
<220> FEATURE:
<223> OTHER INFORMATION: chemically synthesized

<400> SEQUENCE: 449

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

Ser Thr Thr Thr Ser Ser Gly Ala Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro Gly
            100                 105                 110

Gly Ser Gly Gly Ser Glu Val Gln Leu Leu Glu Ser Gly Gly Gly Glu
        115                 120                 125

Val Gln Pro Gly Gly Ser Leu Arg Leu Ser Cys Ala Ala Ser Gly Phe
130                 135                 140

Ser Phe Ser Ile Asn Ala Met Gly Trp Tyr Arg Gln Ala Pro Gly Lys
145                 150                 155                 160

Arg Arg Glu Phe Val Ala Ala Ile Glu Ser Gly Arg Asn Thr Val Tyr
                165                 170                 175

Ala Glu Ser Val Lys Gly Arg Phe Thr Ile Ser Arg Asp Asn Ala Lys
            180                 185                 190

Asn Thr Val Tyr Leu Gln Met Ser Ser Leu Arg Ala Glu Asp Thr Ala
        195                 200                 205

Val Tyr Tyr Cys Gly Leu Leu Lys Gly Asn Arg Val Val Ser Pro Ser
    210                 215                 220

Val Ala Tyr Trp Gly Gln Gly Thr Leu Val Thr Val Lys Pro Gly Gly
225                 230                 235                 240

Gly Gly Asp Lys Thr His Thr Cys Pro Pro Cys Pro Ala Pro Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335
```

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Arg Asp Glu Leu Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
                450                 455                 460

Gly Lys
465

<210> SEQ ID NO 450
<211> LENGTH: 466
<212> TYPE: PRT
<213> ORGANISM: Artificial Sequence
<220> FEATURE:
<223> OTHER INFORMATION: chemically synthesized

<400> SEQUENCE: 450

Glu Val Gln Leu Leu Glu Ser Gly Gly Gly Val Gln Pro Gly Gly
1               5                   10                  15

Ser Leu Arg Leu Ser Cys Ala Ala Ser Gly Gly Ile Phe Ala Ile Lys
                20                  25                  30

Pro Ile Ser Trp Tyr Arg Gln Ala Pro Gly Lys Gln Arg Glu Trp Val
            35                  40                  45

Ser Thr Thr Thr Ser Ser Gly Ala Thr Asn Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro Gly
                100                 105                 110

Gly Ser Gly Gly Ser Glu Val Gln Leu Leu Glu Ser Gly Gly Gly Glu
            115                 120                 125

Val Gln Pro Gly Gly Ser Leu Arg Leu Ser Cys Ala Ala Ser Gly Phe
        130                 135                 140

Ser Phe Ser Ile Asn Ala Met Gly Trp Tyr Arg Gln Ala Pro Gly Lys
145                 150                 155                 160

Arg Arg Glu Phe Val Ala Ala Ile Tyr Ser Gly Arg Asn Thr Val Tyr
                165                 170                 175

Ala Glu Ser Val Lys Gly Arg Phe Thr Ile Ser Arg Asp Asn Ala Lys
            180                 185                 190

Asn Thr Val Tyr Leu Gln Met Ser Ser Leu Arg Ala Glu Asp Thr Ala
        195                 200                 205

Val Tyr Tyr Cys Gly Leu Leu Lys Gly Asn Arg Val Val Ser Pro Ser
210                 215                 220

```
Val Ala Tyr Trp Gly Gln Gly Thr Leu Val Thr Val Lys Pro Gly Gly
225                 230                 235                 240

Gly Gly Asp Lys Thr His Thr Cys Pro Pro Cys Pro Ala Pro Gly Gly
            245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Asp Val Ser His Glu
    275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 451
<211> LENGTH: 466
<212> TYPE: PRT
<213> ORGANISM: Artificial Sequence
<220> FEATURE:
<223> OTHER INFORMATION: chemically synthesized

<400> SEQUENCE: 451

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

Ser Thr Thr Thr Ser Ser Gly Ala Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro Gly
            100                 105                 110
```

Gly Ser Gly Gly Ser Glu Val Gln Leu Leu Glu Ser Gly Gly Glu
            115                 120                 125

Val Gln Pro Gly Gly Ser Leu Arg Leu Ser Cys Ala Ala Ser Gly Phe
        130                 135                 140

Ser Phe Ser Ile Asn Ala Met Gly Trp Tyr Arg Gln Ala Pro Gly Lys
145                 150                 155                 160

Arg Arg Glu Phe Val Ala Ala Ile Tyr Ser Gly Ser Ser Thr Val Tyr
                165                 170                 175

Ala Glu Ser Val Lys Gly Arg Phe Thr Ile Ser Arg Asp Asn Ala Lys
            180                 185                 190

Asn Thr Val Tyr Leu Gln Met Ser Ser Leu Arg Ala Glu Asp Thr Ala
        195                 200                 205

Val Tyr Tyr Cys Gly Leu Leu Lys Gly Asn Arg Val Val Ser Pro Ser
210                 215                 220

Val Ala Tyr Trp Gly Gln Gly Thr Leu Val Thr Val Lys Pro Gly Gly
225                 230                 235                 240

Gly Gly Asp Lys Thr His Thr Cys Pro Pro Cys Pro Ala Pro Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
            290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 452
<211> LENGTH: 481
<212> TYPE: PRT
<213> ORGANISM: Artificial Sequence
<220> FEATURE:
<223> OTHER INFORMATION: chemically synthesized

<400> SEQUENCE: 452

-continued

```
Glu Val Gln Leu Leu Glu Ser Gly Gly Gly Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

Ser Thr Thr Thr Ser Ser Gly Ala Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
            85                  90                  95

Val Phe Glu Tyr Trp Gly Gln Gly Thr Leu Val Thr Val Lys Pro Gly
        100                 105                 110

Gly Ser Gly Gly Ser Glu Val Gln Leu Leu Glu Ser Gly Gly Gly Glu
    115                 120                 125

Val Gln Leu Leu Glu Ser Gly Gly Glu Val Gln Pro Gly Gly Ser
    130                 135                 140

Leu Arg Leu Ser Cys Ala Ala Ser Gly Trp Ala Phe Gly Asn Tyr Gly
145                 150                 155                 160

Met Ala Trp Phe Arg Gln Ala Pro Gly Lys Glu Arg Glu Phe Val Ser
            165                 170                 175

Arg Leu Ala Trp Gln Gly Gly Ser Thr Asp Tyr Val Glu Ser Val Lys
        180                 185                 190

Gly Arg Phe Thr Ile Ser Arg Asp Asn Ala Lys Asn Thr Leu Tyr Leu
            195                 200                 205

Gln Met Ser Ser Leu Arg Ala Glu Asp Thr Ala Val Tyr Tyr Cys Ala
    210                 215                 220

Arg Gln Arg Ser Tyr Ser Arg Tyr Asp Ile Arg Thr Pro Gln Thr Tyr
225                 230                 235                 240

Asp Tyr Trp Gly Gln Gly Thr Leu Val Thr Val Lys Pro Gly Gly Gly
        245                 250                 255

Gly Asp Lys Thr His Thr Cys Pro Pro Cys Pro Ala Pro Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Glu
        340                 345                 350

Tyr Lys Cys Lys Val Ser Asn Lys Ala Leu Pro Ala Pro Ile Glu Lys
    355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
            405                 410                 415
```

Ser Asn Gly Gln Pro Glu Asn Asn Tyr Lys Thr Thr Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 453
<211> LENGTH: 481
<212> TYPE: PRT
<213> ORGANISM: Artificial Sequence
<220> FEATURE:
<223> OTHER INFORMATION: chemically synthesized

<400> SEQUENCE: 453

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

Ser Thr Thr Ser Ser Gly Ala Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro Gly
            100                 105                 110

Gly Ser Gly Gly Ser Glu Val Gln Leu Leu Glu Ser Gly Gly Gly Glu
        115                 120                 125

Val Gln Leu Leu Glu Ser Gly Gly Gly Glu Val Gln Pro Gly Gly Ser
    130                 135                 140

Leu Arg Leu Ser Cys Ala Ala Ser Gly Trp Ala Phe Gly Asn Tyr Gly
145                 150                 155                 160

Met Ala Trp Phe Arg Gln Ala Pro Gly Lys Glu Arg Glu Phe Val Ser
                165                 170                 175

Arg Leu Ala Trp Gly Gly Gly Ser Thr Asp Tyr Val Glu Ser Val Lys
            180                 185                 190

Gly Arg Phe Thr Ile Ser Arg Asp Asn Ala Lys Asn Thr Leu Tyr Leu
        195                 200                 205

Gln Met Ser Ser Leu Arg Ala Glu Asp Thr Ala Val Tyr Tyr Cys Ala
    210                 215                 220

Arg Gln Arg Ser Tyr Ser Arg Tyr Asp Ile Arg Thr Pro Gln Thr Tyr
225                 230                 235                 240

Asp Tyr Trp Gly Gln Gly Thr Leu Val Thr Val Lys Pro Gly Gly Gly
                245                 250                 255

Gly Asp Lys Thr His Thr Cys Pro Pro Cys Pro Ala Pro Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp

```
            290                 295                 300
Pro Glu Val Lys Phe Asn Trp Tyr Val Asp Gly Val Glu Val His Asn
305                 310                 315                 320

Ala Lys Thr Lys Pro Arg Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
                355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 454
<211> LENGTH: 481
<212> TYPE: PRT
<213> ORGANISM: Artificial Sequence
<220> FEATURE:
<223> OTHER INFORMATION: chemically synthesized

<400> SEQUENCE: 454

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

Ser Thr Thr Thr Ser Ser Gly Ala Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro Gly
            100                 105                 110

Gly Ser Gly Gly Ser Glu Val Gln Leu Leu Glu Ser Gly Gly Gly Glu
        115                 120                 125

Val Gln Leu Leu Glu Ser Gly Gly Gly Glu Val Gln Pro Gly Gly Ser
    130                 135                 140

Leu Arg Leu Ser Cys Ala Ala Ser Gly Trp Ala Phe Ser Asn Tyr Gly
145                 150                 155                 160

Met Ala Trp Phe Arg Gln Ala Pro Gly Lys Glu Arg Glu Phe Val Ser
                165                 170                 175
```

Arg Leu Ala Trp Gly Gly Ser Thr Asp Tyr Val Glu Ser Val Lys
            180                 185                 190

Gly Arg Phe Thr Ile Ser Arg Asp Asn Ala Lys Asn Thr Leu Tyr Leu
        195                 200                 205

Gln Met Ser Ser Leu Arg Ala Glu Asp Thr Ala Val Tyr Tyr Cys Ala
210                 215                 220

Arg Gln Arg Ser Tyr Ser Arg Tyr Asp Ile Arg Thr Pro Gln Thr Tyr
225                 230                 235                 240

Asp Tyr Trp Gly Gln Gly Thr Leu Val Thr Val Lys Pro Gly Gly Gly
                245                 250                 255

Gly Asp Lys Thr His Thr Cys Pro Pro Cys Pro Ala Pro Gly Gly Pro
            260                 265                 270

Ser Val Phe Leu Phe Pro Pro Lys Pro Lys Asp Thr Leu Met Ile Ser
                275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Glu
                340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
        370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 455
<211> LENGTH: 481
<212> TYPE: PRT
<213> ORGANISM: Artificial Sequence
<220> FEATURE:
<223> OTHER INFORMATION: chemically synthesized

<400> SEQUENCE: 455

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

```
Ser Thr Thr Thr Ser Ser Gly Ala Thr Asn Tyr Ala Glu Ser Val Lys
    50              55                  60

Gly Arg Phe Thr Ile Ser Arg Asp Asn Ala Lys Asn Thr Leu Tyr Leu
 65              70              75                      80

Gln Met Ser Ser Leu Arg Ala Glu Asp Thr Ala Val Tyr Tyr Cys Asn
                85              90                  95

Val Phe Glu Tyr Trp Gly Gln Gly Thr Leu Val Thr Val Lys Pro Gly
            100             105             110

Gly Ser Gly Gly Ser Glu Val Gln Leu Leu Glu Ser Gly Gly Gly Glu
            115             120             125

Val Gln Leu Leu Glu Ser Gly Gly Glu Val Gln Pro Gly Gly Ser
130             135             140

Leu Arg Leu Ser Cys Ala Ala Ser Gly Trp Ala Phe Gly Asn Tyr Gly
145             150             155             160

Met Ala Trp Phe Arg Gln Ala Pro Gly Lys Glu Arg Glu Phe Val Ser
                165             170             175

Arg Leu Ala Trp Ser Gly Gly Ser Thr Asp Tyr Val Glu Ser Val Lys
            180             185             190

Gly Arg Phe Thr Ile Ser Arg Asp Asn Ala Lys Asn Thr Leu Tyr Leu
            195             200             205

Gln Met Ser Ser Leu Arg Ala Glu Asp Thr Ala Val Tyr Tyr Cys Ala
    210             215             220

Arg Gln Arg Ser Tyr Ser Arg Tyr Asp Ile Arg Thr Pro Gln Thr Tyr
225             230             235             240

Asp Tyr Trp Gly Gln Gly Thr Leu Val Thr Val Lys Pro Gly Gly Gly
            245             250             255

Gly Asp Lys Thr His Thr Cys Pro Pro Cys Pro Ala Pro Gly Gly Pro
            260             265             270

Ser Val Phe Leu Phe Pro Pro Lys Pro Lys Asp Thr Leu Met Ile Ser
            275             280             285

Arg Thr Pro Glu Val Thr Cys Val Val Val Asp Val Ser His Glu Asp
    290             295             300

Pro Glu Val Lys Phe Asn Trp Tyr Val Asp Gly Val Glu Val His Asn
305             310             315             320

Ala Lys Thr Lys Pro Arg Glu Glu Gln Tyr Asn Ser Thr Tyr Arg Val
            325             330             335

Val Ser Val Leu Thr Val Leu His Gln Asp Trp Leu Asn Gly Lys Glu
            340             345             350

Tyr Lys Cys Lys Val Ser Asn Lys Ala Leu Pro Ala Pro Ile Glu Lys
            355             360             365

Thr Ile Ser Lys Ala Lys Gly Gln Pro Arg Glu Pro Gln Val Tyr Thr
    370             375             380

Leu Pro Pro Ser Arg Asp Glu Leu Thr Lys Asn Gln Val Ser Leu Thr
385             390             395             400

Cys Leu Val Lys Gly Phe Tyr Pro Ser Asp Ile Ala Val Glu Trp Glu
            405             410             415

Ser Asn Gly Gln Pro Glu Asn Asn Tyr Lys Thr Thr Pro Pro Val Leu
            420             425             430

Asp Ser Asp Gly Ser Phe Phe Leu Tyr Ser Lys Leu Thr Val Asp Lys
            435             440             445

Ser Arg Trp Gln Gln Gly Asn Val Phe Ser Cys Ser Val Met His Glu
    450             455             460

Ala Leu His Asn His Tyr Thr Gln Lys Ser Leu Ser Leu Ser Pro Gly
```

<210> SEQ ID NO 456
<211> LENGTH: 481
<212> TYPE: PRT
<213> ORGANISM: Artificial Sequence
<220> FEATURE:
<223> OTHER INFORMATION: chemically synthesized

<400> SEQUENCE: 456

```
Glu Val Gln Leu Leu Glu Ser Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

Ser Thr Thr Thr Ser Ser Gly Ala Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro Gly
            100                 105                 110

Gly Ser Gly Gly Ser Glu Val Gln Leu Leu Glu Ser Gly Gly Gly Glu
        115                 120                 125

Val Gln Leu Leu Glu Ser Gly Gly Glu Val Gln Pro Gly Gly Ser
    130                 135                 140

Leu Arg Leu Ser Cys Ala Ala Ser Gly Trp Ala Phe Ser Asn Tyr Gly
145                 150                 155                 160

Met Ala Trp Phe Arg Gln Ala Pro Gly Lys Glu Arg Glu Phe Val Ser
                165                 170                 175

Arg Leu Ala Trp Ser Gly Gly Ser Thr Asp Tyr Val Glu Ser Val Lys
            180                 185                 190

Gly Arg Phe Thr Ile Ser Arg Asp Asn Ala Lys Asn Thr Leu Tyr Leu
        195                 200                 205

Gln Met Ser Ser Leu Arg Ala Glu Asp Thr Ala Val Tyr Tyr Cys Ala
    210                 215                 220

Arg Gln Arg Ser Tyr Ser Arg Tyr Asp Ile Arg Thr Pro Gln Thr Tyr
225                 230                 235                 240

Asp Tyr Trp Gly Gln Gly Thr Leu Val Thr Val Lys Pro Gly Gly Gly
                245                 250                 255

Gly Asp Lys Thr His Thr Cys Pro Pro Cys Pro Ala Pro Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350
```

```
Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
                420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```